(12) United States Patent
Gasser et al.

(10) Patent No.: US 11,773,424 B2
(45) Date of Patent: Oct. 3, 2023

(54) CARBON-SOURCE REGULATED PROTEIN PRODUCTION IN A RECOMBINANT HOST CELL

(71) Applicant: LONZA LTD, Visp (CH)

(72) Inventors: Brigitte Gasser, Vienna (AT); Corinna Rebnegger, Vienna (AT); Mirelle Citiali Flores Villegas, Perchtoldsdorf (AT); Diethard Mattanovich, Vienna (AT)

(73) Assignee: LONZA LTD, Visp (CH)

( * ) Notice: Subject to any disclaimer, the term of this patent is extended or adjusted under 35 U.S.C. 154(b) by 0 days.

(21) Appl. No.: 17/421,619

(22) PCT Filed: Jan. 10, 2020

(86) PCT No.: PCT/EP2020/050517
§ 371 (c)(1),
(2) Date: Jul. 8, 2021

(87) PCT Pub. No.: WO2020/144313
PCT Pub. Date: Jul. 16, 2020

(65) Prior Publication Data
US 2022/0042064 A1 Feb. 10, 2022

(30) Foreign Application Priority Data
Jan. 11, 2019 (EP) .................................... 19151376

(51) Int. Cl.
*C12N 15/81* (2006.01)
*C12P 21/00* (2006.01)
*C12P 21/02* (2006.01)
*C12N 15/63* (2006.01)

(52) U.S. Cl.
CPC .............. *C12P 21/02* (2013.01); *C12N 15/81* (2013.01); *C12N 15/63* (2013.01)

(58) Field of Classification Search
CPC .... C12N 15/81; C12N 15/63; C12N 2830/15; C12N 15/09; C12N 2800/22; C12P 21/00
USPC .......................... 435/254.2, 320.1, 69.1, 473
See application file for complete search history.

(56) References Cited

U.S. PATENT DOCUMENTS 6,153,424 A 11/2000 Raymond et al.

FOREIGN PATENT DOCUMENTS

| EP | 2258855 A1 | 12/2010 |
|---|---|---|
| EP | 2669375 A1 | 12/2013 |
| EP | 2952584 A1 | 12/2015 |
| JP | 2014-530016 A | 11/2014 |
| JP | 2017-511147 A | 4/2017 |
| JP | 2017-511148 A | 4/2017 |
| WO | 1992/017595 A1 | 10/1992 |
| WO | 2008/128701 A2 | 10/2008 |
| WO | 2010/099195 A1 | 9/2010 |
| WO | 2012/152823 A1 | 11/2012 |
| WO | 2013/050551 A1 | 4/2013 |
| WO | 2014/067926 A1 | 5/2014 |
| WO | 2015/158800 A1 | 10/2015 |
| WO | 2015/158808 A2 | 10/2015 |
| WO | 2017/021541 A1 | 2/2017 |

OTHER PUBLICATIONS

Devos et al., Proteins: Structure, Function and Genetics, 2000, vol. 41: 98-107.*
Whisstock et al., Quarterly Reviews of Biophysics 2003, vol. 36 (3): 307-340.*
Witkowski et al., Biochemistry 38:11643-11650, 1999.*
Kisselev L., Structure, 2002, vol. 10: 8-9.*
Benjamini et al., "The control of the false discovery rate in multiple testing under dependency," The Annals of Statistics 29(4):1165-1188 (2001).
Doneanu et al., "Analysis of host-cell proteins in biotherapeutic proteins by comprehensive online two-dimensional liquid chromatography/mass spectrometry," mAbs 4(1):24-44 (2012).
Gaj et al., "ZFN, TALEN, and CRISPR/Cas-based methods for genome engineering," Trends in Biotechnology 31 (7):397-405 (2013).
Gasser et al., "Pichia pastoris: protein production host and model organism for biomedical research," Future Microbiol. 8(2):191-208 (2013).
Graf et al., "Novel insights into the unfolded protein response using Pichia pastoris specific DNA microarrays," BMC Genomics 9(1):1-13 (2008).
Heiss et al., "Identification and deletion of the major secreted protein of Pichia pastoris," Appl Microbiol Biotechnol 97:1241-1249 (2013).
Heiss et al., "Multistep processing of the secretion leader of the extracellular protein Epx1 in Pichia pastoris and implications for protein localization," Microbiology 161 (7):1356-1368 (2015).
Kim et al., "Two distinct domains of Flo8 activator mediates its role in transcriptional activation and the physical interaction with Mss11," Biochemical and biophysical research communications 449(2):202-207 (2014).
Kurtzman, "Biotechnological strains of Komagataella (Pichia) pastoris are Komagataella phaYi as determined from multigene sequence analysis," J Ind Microbiol Biotechnol 36:1435-1438 (2009).

(Continued)

*Primary Examiner* — Robert B Mondesi
*Assistant Examiner* — Mohammad Y Meah
(74) *Attorney, Agent, or Firm* — MEDLER, FERRO, WOODHOUSE & MILLS PLLC

(57) ABSTRACT

A recombinant host cell comprising an endogenous gene encoding a FLO8 protein comprising the amino acid sequence identified as SEQ ID NO:1 or a homologue thereof, which host cell is engineered by one or more genetic modifications to reduce expression of said gene compared to the host cell prior to said one or more genetic modifications, and which host cell comprises a heterologous expression cassette comprising a gene of interest (GO!) under the control of an expression cassette promoter (ECP) which ECP is repressible by a non-methanol carbon source, and a method of producing a protein of interest using said recombinant host cell.

30 Claims, 15 Drawing Sheets

Specification includes a Sequence Listing.

(56) References Cited

OTHER PUBLICATIONS

Marx et al., "Overexpression of the riboflavin biosynthetic pathway in Pichia pastoris," Microbial Cell Factories 7(1):1-11 (2008).
Mateja et al., "The Dimerization Mechanism of LIS1 and its Implication for Proteins Containing the LisH Motif," J Mol Biol. 357(2):621-631 (2006).
Mattanovich et al., "Genome, secretome and glucose transport highlight unique features of the protein production host Pichia pastoris," Microbial Cell Factories 8(1):1-13 (2009).
Pothoulakis et al., "Synthetic gene regulation for independent external induction of the *Saccharomyces cerevisiae* pseudohyphal growth phenotype", Communications Biology 1(1):1-11 (2018).
Prielhofer et al., "Induction without methanol: novel regulated promoters enable high-level expression in Pichia pastoris", Microbial Cell Factories 12(1):1-10 (2013).
Prielhofer et al., "Superior protein titers in half the fermentation time: Promoter and process engineering for the glucose-regulated GTH1 promoter of Pichia pastoris," Biotechnology and Bioengineering 115(10):2479-2488 (2018).
Rebnegger et al., "Pichia pastoris exhibits high viability and low maintenance energy requirement at near zero specific growth rates", Applied and Environmental Microbiology 82(15):4570-4583 (2016).
Robinson et al., "edgeR: a Bioconductor package for differential expression analysis of digital gene expression data," Bioinformatics 26(1):139-140 (2010).
Stadlmayr et al., "Identification and characterisation of novel Pichia pastoris promoters for heterologous protein production," J Biotechnol. 150(4):519-529 (2010).
Weninger et al., "Combinatorial optimization of CRISPR/Cas9 expression enables precision genome engineering in the methylotrophic yeast Pichia pastoris," Journal of Biotechnology 235:139-149 (2016).
Hartner et al., "Promoter library designed for fine-tuned gene expression in Pichia pastoris," Nucleic Acids Research 36(12):e76 (2008).
Suppi et al., "Repression vs. activation of MOX, FMD, MPP1 and MAL1 promoters by sugars in Hansenula polymorpha: the outcome depends on cell's ability to phosphorylate sugar," FEMS Yeast Research 13(2):219-232 (2013).
Wang et al., "Methanol-Independent Protein Expression by AOX1 Promoter with trans-Acting Elements Engineering and Glucose-Glycerol-Shift Induction in Pichia pastoris," Scientific Reports 7:41850 (2017).
Weinhandl et al., "Carbon source dependent promoters in yeasts," Microbial Cell Factories 13:5 (2014).

\* cited by examiner

Fig. 1:

Amino acid sequence, FLO8 Protein *Komagataella phaffii*, SEQ ID NO:1

```
>XP_002494151/PP7435_Chr4-0252/PAS_chr4_0711 (Flo8_Komagataella phaffii
CBS7435/GS115) LisH domain underlined MNKPNGSEQQPPSRGMKQESGGPVTSSTTPGTNTGLENSHSMGADMEPDVGATSPRHLLNGYIYDYLVKSNMQNLA
DQFAQETELLETDLTVPMDTPSGYLLEWWMVFWDLFNARLKQRGSQKAHQYIQLNMLRQQQQRTMRNTARVQKVPL
RPHTQSSPSMSQTFIPQQPQQQAQGQQHAQAQAQVQAHQQAQHHAQAQVPVQPQQHQLGGQTQQQQSINTGSPAGP
NAINSRVQHLAQQQMNHLRQQATATTQQPIPQQNIPSNQQGPTGPYPTSPSRRPRLLSNESGASAPSVMTKSQLQG
VPPSQQPHQQQGQQVGPPNQHQGQSSSFYSGMPPQGVVVPHQFNPQQYANMLARQQHVQAQQQVQLQQVQHVQQRQ
QQDQQQHRLSAGSPGHPSFGVFQQPPPMSNHNQVMINQGETFFDPHSPYAQPNGYPQPQQQQQQQQQQQQQQQPQ
QQQQQQQQKQQPPPPPRQPQRQQAMAMAPLPHSTSAAGTPHSSTTPRFSQPGPVYQQPLPASQPQHSPPSSIQQP
ELVPTPGSQHQQIAQPQSQSQHQQSQQSQSSASKIVGIQEYQKELMMLEKQNKQRHDMACKKGSGHFSNFDPIPEH
TPPEPKFNVNVMLPPQNSAVVTKNTPGTSPGTQTQNTAHSTGNTSAGSTPNNVAPVRKKKEPAKKKAKKATEPPTP
TTPQTPIAARTHQNSTGGIPGNNAATKRRKREPLVDQTVSPNLNEASKSTKTGKISSQTDFTGSDNGFLQDFGDGT
GPPTGTDDMEFDFNSFLNNETGEPNSSTIHFDNVFNWGEGTEAGDL
```

Nucleotide sequence, *flo8* gene *Komagataella phaffii*, SEQ ID NO:2

```
>XM_002494106.1 Komagataella phaffii GS115 Hypothetical protein
(PAS_chr4_0711), partial mRNA ATGAACAAGCCAAACGGGTCTGAACAACAACCACCGTCACGCGGAATGAAGCAAGAGTCAGGAGGCCCAG
TTACTTCATCTACGACGCCGGGTACCAATACTGGCCTAGAAAACTCTCATTCCATGGGGCGGATATGGA
GCCTGATGTTGGTGCTACCTCTCCTCGCCATCTTCTTAATGGGTACATTTACGATTATTTAGTCAAATCT
AACATGCAAAATTTGGCTGATCAATTTGCCCAAGAGACGGAGCTCTTAGAAACAGACTTGACAGTACCAA
TGGATACGCCTTCAGGCTATCTTCTAGAATGGTGGATGGTATTCTGGGACCTTTTCAATGCCCGCCTAAA
GCAACGGGGTTCACAGAAGGCCCACCAGTATATTCAGTTGAACATGCTACGACAACAGCAACAGAGGACC
ATGCGAAATACAGCCCGTGTTCAAAAAGTCCCGTTGAGGCCACACACCCAATCATCTCCTTCAATGTCAC
AGACTTTTATTCCACAGCAGCCTCAACAGCAAGCACAGGGACAACAGCACGCCCAGGCTCAAGCCCAAGT
GCAAGCACATCAGCAAGCCCAACACCACGCGCAGGCACAAGTGCCAGTGCAACCGCAACAGCACCAGCTA
GGAGGCCAAACTCAACAGCAGCAATCCATTAACACTGGGTCTCCTGCGGGTCCAAATGCTATCAACTCGC
GTGTTCAACACTTAGCACAACAACAGATGAATCACCTTCGCCAGCAGGCGACTGCCACTACGCAACAACC
TATCCCGCAACAGAATATCCCATCAAACCAACAGGGTCCTACAGGCCCTTATCCTACTTCCCCTTCAAGA
AGACCGAGATTACTGTCTAACGAATCGGGTGCAAGTGCACCCTCTGTAATGACAAAGTCACAGCTCCAAG
GAGTCCCTCCCTCACAACAACCACACCAGCAGCAAGGTCAGCAGGTAGGCCCCCCTAATCAACATCAAGG
TCAATCTTCTTCCTTTTATTCGGGCATGCCTCCTCAAGGGGTCGTGGTTCCTCATCAGTTCAATCCTCAG
CAGTATGCCAATATGCTAGCAAGACAACAGCATGTACAAGCTCAACAACAGGTTCAGTTACAACAGGTCC
AACATGTACAACAGAGACAACAGCAAGACCAACAACAACACCGCCTGTCCGCCGGTTCACCGGGGCACCC
TTCATTTGGCGTTTTTCAACAACCTCCTCCGATGTCAAACCATAATCAGGTCATGATCAATCAGCAGGGA
GAAACTTTTTTTGATCCACATTCTCCATATGCTCAACCTAACGGGTACCCCAGCCACAGCAACAACAAC
AACAACAGCAACAACAACAACAACAGCAGCAACCGCAACAGCAGCAGCAGCAGCAGCAACAGAAGCA
GCAACCACCACCACCACCACGACAGCCTCAGCGCCAACAAGCGATGGCCATGGCTCCTCTGCCTCACTCT
ACTTCTGCCGCCGGTACTCCTCACTCGTCCACCACACCTAGATTCTCGCAACCTGGTCCTGTTTATCAGC
AGCCTTTACCTGCATCTCAACCGCAACATTCTCCGCCTTCTTCTATTCAGCAGCCGGAGCTAGTTCCAAC
TCCAGGGTCACAACATCAGCAAATAGCACAACCACAATCACAGAGCCAACACCAGCAATCGCAACAGTCT
CAATCAAGTGCTTCTAAAATTGTAGGTATACAGGAGTATCAGAAAGAGCTAATGATGCTTGAGAAACAGA
ACAAACAGCGTCATGACATGGCATGTAAGAAGGGAAGCGGGCATTTTCTAACTTTGATCCAATTCCAGA
GCACACACCGCCCGAACCAAAATTTAATGTGAATGTAATGCTCCCTCCCCAGAACTCTGCAGTGGTCACG
AAGAATACTCCCGGAACTTCACCTGGTACACAAACTCAAAACACTGCACATAGTACTGGTAACACTTCTG
CGGGGTCTACACCAAATAATGTCGCACCTGTACGAAAGAAAAAGGAGCCAGCTAAAAGAAGGCAAAGAA
AGCTACTGAGCCCCCGACTCCCACTACTCCACAGACTCCAATTGCAGCTAGGACACATCAAAACTCTACA
GGCGGCATTCCTGGTAATAATGCTGCTACTAAGCGACGAAAACGGGAGCCGCTGGTTGATCAAACTGTTT
CACCTAACCTTAACGAAGCTTCCAAGTCAACAAAGACCGGAAAAATTTCATCTCAAACTGACTTTACAGG
TTCTGACAATGGATTCTTACAGGATTTTGGCGATGGAACTGGTCCTCCCACTGGAACCGATGATATGGAA
TTTGATTTTAACAGTTTTCTTAATAACGAAACTGGCGAACCTAATAGTTCAACCATTCATTTTGACAATG
TATTCAATTGGGGAGAAGGTACCGAAGCCGGAGATTTATAG
```

Fig. 1 (continued)

Amino acid sequence, FLO8 Protein *Komagataella pastoris*, SEQ ID NO:3

\>ANZ77695.1 BA75_04606T0 [Komagataella pastoris] LisH domain underlined

MNKPNGSGQQPPSRGMKQDPGGPVTSSTTPGTNTGFENSHSMGADVEPDVGAASPRHI<u>LNGYIHDYLVKSNMQNLA
DQFAQES</u>DLLETDLTVPMDTPTGYLLEWWMVFWDLFNARLKQRGSQKAHQYIQLNMLRQQQQRTMRNTARVQKVPL
RPHTQSSPSMSQTFIPQQPQQQAQAQAQQHAQAQAQVQAHQQAQHHAQAQVPMQSQPHQQGGQTQQQQPINTGSPA
GPNAINSRVQHLAQQQMNHLRQQATATTQQPIPQQNIPSNQQGPAGPYPTSPSRRPRLLSNESGASAPSVMTKSQL
QGGPPSQQPHQQQAQQVGPPNQHQGQSSSFYSGMPPQGVVVPHQFNPQQYANMLARQQHVQAQQQVQLQQVPHVQQ
RQQQDQQQHRLSAGSPGHPSFGVFQQPPPMSNHNQVMINQQGETFFDPHSPYAQPNGYPQPQQQQQQQQQQQQQQQ
QQQQQQQQKQQQPPPRQPQRQQAMATAPLPHSTSASGTPHTATTPRFSQPGPVYQQPLPASQPQHSPPTSIQQQEP
IPTPGSQHQQIAQPQSQNQHQQPQQPQASASKMVGIQEYQKELMMLEKQNKQRHDMAIKKGSGHFSNFDPIPEHTQ
TEPKFNVNVMLPPQNSAVATKNTPGTSPGTQTQNTAHSTGNTSAGSTPNNVVPVRKKKEPSKKKSKKATEPPTPTT
PQTPIAARAHQNSTGGISGNNAATKRRKREPLVDQTVSPNLNEASKSTKPGKISSQNDFTGSDNGFLQDFGDGTGP
PTGTDDMEFDFNSFLNNETGEPNSSTIHFDNVFNWGEGTEAGDL

Nucleotide sequence, FLO8 Protein *Komagataella pastoris*, SEQ ID NO :4
\>CP014587.1:1153190-1155604 Komagataella pastoris strain ATCC 28485
chromosome 4 sequence ATGAACAAGCCAAACGGGTCTGGACAACAACCACCGTCACGCGGAATGAAGCAAGACCCAGGAGGCCCAG
TTACCTCATCTACGACACCCGGTACCAATACTGGCTTTGAAAACTCTCATTCCATGGGAGCGGATGTGGA
GCCTGATGTTGGTGCCGCCTCTCCTCGCCATATTCTTAATGGGTACATTCATGATTACTTAGTCAAATCT
AATATGCAAAATTTGGCCGATCAATTTGCTCAAGAGTCGGATCTCTTAGAAACAGACCTAACGGTACCAA
TGGATACACCTACAGGCTATCTTTTAGAGTGGTGGATGGTATTTTGGGACCTTTTCAATGCCCGCCTAAA
GCAACGAGGTTCACAGAAGGCTCATCAGTATATTCAGTTGAACATGCTACGACAACAACAGCAGAGGACT
ATGCGAAATACAGCCCGTGTTCAGAAAGTCCCGTTGAGACCACACACCCAATCATCTCCTTCAATGTCAC
AGACCTTTATTCCACAGCAGCCTCAACAGCAAGCACAGGCACAGGCACAGCAGCACGCCCAAGCTCAAGC
GCAAGTCCAGGCTCATCAGCAAGCACAGCATCATGCGCAGGCTCAAGTGCCAATGCAATCGCAACCACAT
CAGCAAGGAGGCCAAACTCAACAACAGCAACCCATTAACACTGGGTCTCCTGCGGGCCAAATGCTATCA
ACTCTCGTGTGCAACACTTAGCGCAACAACAGATGAATCATCTTCGCCAGCAGGCAACTGCCACTACCCA
GCAACCTATCCCGCAACAGAATATTCCATCAAACCAGCAGGGCCCTGCGGGCCCTTATCCTACATCGCCT
TCAAGAAGACCGAGATTACTGTCTAACGAATCGGGTGCAAGTGCACCCTCTGTAATGACGAAGTCACAGC
TCCAAGGAGGTCCTCCATCACAACAACCACACCAACAGCAAGCTCAGCAGGTAGGACCCCCCAATCAACA
TCAAGGCCAGTCCTCTTCCTTTTATTCGGGCATGCCTCCTCAAGGAGTTGTGGTTCCTCATCAGTTCAAT
CCTCAGCAGTATGCCAATATGCTAGCAAGACAACAGCATGTGCAAGCTCAACAACAGGTTCAGTTACAGC
AGGTTCCACATGTGCAACAAAGACAACAGCAAGACCAACAACAACACCGCTTGTCAGCGGTTCACCAGG
GCATCCTTCATTTGGCGTTTTTCAACAACCTCCTCCGATGTCAAACCATAATCAGGTCATGATCAACCAG
CAGGGAGAAACCTTTTTTGATCCTCATTCACCATATGCTCAACCTAATGGGTACCCCCAGCCACAGCAAC
AACAACAACAGCAGCAACAACAACAACAACAACAGCAGCAGCAGCAGCAACAACAGAAGCAGCA
ACAGCCACCACCAAGACAGCCTCAGCGCCAACAAGCGATGGCTACGGCTCCTTTGCCTCATTCTACTTCT
GCCTCGGGTACTCCTCACACGGCCACCACACCTAGATTCTCCCAGCCTGGTCCTGTTTATCAGCAGCCTT
TACCTGCATCTCAACCGCAACATTCTCCGCCTACTTCTATTCAGCAACAGGAACCAATTCCAACTCCTGG
GTCACAACATCAGCAAATAGCACAACCGCAATCACAGAATCAACACCAGCAACCGCAGCAACCTCAAGCA
AGTGCTTCTAAAATGGTGGGTATACAGGAGTACCAGAAAGAGTTAATGATGCTTGAGAAGCAGAACAAAC
AACGTCATGACATGGCAATTAAGAAGGGAAGCGGACATTTCTCTAATTTTGATCCAATTCCAGAGCACAC
ACAGACTGAACCAAAATTCAATGTGAACGTAATGCTCCCTCCCCAGAACTCTGCAGTGGCCACGAAGAAT
ACTCCTGGAACTTCTCCTGGTACGCAAACTCAAAACACTGCACACAGTACTGGCAACACTTCTGCTGGGT
CTACACCGAATAATGTTGTACCAGTTCGAAAAAAGAAGGAGCCATCTAAAAAGAAATCAAAGAAGGCTAC
CGAACCTCCAACTCCTACTACTCCACAGACACCAATTGCAGCTAGGGCACATCAAAACTCTACGGGCGGC
ATTTCAGGTAATAATGCTGCTACTAAGCGACGAAAAGGGAGCCGCTGGTCGACCAAACAGTTTCACCTA
ACCTTAACGAAGCTTCGAAATCAACAAAGCCTGGGAAAATCTCATCTCAAAATGACTTTACAGGTTCTGA
CAATGGATTTTTACAGGATTTTGGCGATGGAACAGGTCCCCCCACTGGAACTGACGATATGGAGTTTGAT
TTTAACAGTTTTCTCAACAACGAAACTGGTGAACCTAATAGTTCAACCATTCATTTTGACAATGTATTTA
ATTGGGGGGAGGGTACTGAAGCCGGGGATCTATAG

Fig. 1 (continued)

FLO8 ortholog of *S. cerevisiae* (strain ATCC 204508 / S288c), SEQ ID NO:5

```
>sp|P40068|FLO8_YEAST Transcriptional activator FLO8 OS=Saccharomyces
cerevisiae (strain ATCC 204508 / S288c) OX=559292 GN=FLO8 PE=5 SV=2
LisH domain underlined MSYKVNSSYPDSIPPTEQPYMASQYKQDLQSNIAMATNSEQQRQQQQQQQQQQQQWINQPTAENSDLKEKMNCKNT
LNEYIFDFLTKSSLKNTAAAFAQDAHLDRDKGQNPVDGPKSKENNGNQNTFSKVVDTPQGFLYEWWQIFWDIFNTS
SSRGGSEFAQQYYQLVLQEQRQEQIYRSLAVHAARLQHDAERRGEYSNEDIDPMHLAAMMLGNPMAPAVQMRNVNM
NPIPIPMVGNPIVNNFSIPPYNNANPTTGATAVAPTAPPSGDFTNVGPTQNRSQNVTGWPVYNYPMQPTTENPVGN
PCNNNTTNNTTNNKSPVNQPKSLKTMHSTDKPNNVPTSKSTRSRSATSKAKGKVKAGLVAKRRRKNNTATVSAGST
NACSPNITTPGSTTSEPAMVGSRVNKTPRSDIATNFRNQAIIFGEEDIYSNSKSSPSLDGASPSALASKQPTKVRK
NTKKASTSAFPVESTNKLGGNSVVTGKKRSPPNTRVSRRKSTPSVILNADATKDENNMLRTFSNTIAPNIHSAPPT
KTANSLPFPGINLGSFNKPAVSSPLSSVTESCFDPESGKIAGKNGPKRAVNSKVSASSPLSIATPRSGDAQKQRSS
KVPGNVVIKPPHGFSTTNLNITLKNSKIITSQNNTVSQELPNGGNILEAQVGNDSRSSKGNRNTLSTPEEKKPSSN
NQGYDFDALKNSSSLLFPNQAYASNNRTPNENSNVADETSASTNSGDNDNTLIQPSSNVGTTLGPQQTSTNENQNV
HSQNLKFGNIGMVEDQGPDYDLNLLDTNENDFNFINWEG
```

FLO8 ortholog of *S. cerevisiae* (CEN.PK113-7D), SEQ ID NO:6

```
>EIW10903.1 Flo8p [Saccharomyces cerevisiae CEN.PK113-7D]
LisH domain underlined MSYKVNSSYPDSIPPTEQPYMASQYKQDLQSNIAMATNSEQQRQQQQWINQPTAENSDLKEKMNCKNTLNEYIFDF
LTKSSLKNTAAAFAQDAHLDRDKGQNPIDGPKSKENNGNQNTFSKVVDTPQGFLYEWWQIFWDIFNTSSRGGSEF
AQQYYQLVLQEQRQEQIYRSLAAHAARLQHDAERRGEYSNEDIDPMHLAAMMLGNPMAPAVQMRNVNMNPIPIPMV
GNPIVNNFSIPPYNNANPTTGATAVAPTAPPSGDFANVGPTQNRSQNVTGWPVYNYPMQPTTENPVGNPCNNNTTN
NTTNNKSPVNQPKSLKTMHSTDKPNNVPTSKSTRSRSATSKAKGKVKAGLVAKRRRKNNTATVSAGSTNAGSPNIT
TPGSTTSEPAMVGSRVNKTPRSDIATNFRNQAIIFGEEDIYSNSKSSPSLDGASPSALVSKQPTKVRKNTKKASTS
AFPVESANKLGGNSVVTGKKRSPPNTRVLRRKSTPSVILNADATKDENNMLRTFSNTTAPNIHSAPPTKTANSLPF
PGINLGSFNKPAVSSPLSSVTESCFDPESGKIAGKNGPKRAVNSKVSASSPLSIATPPSGDAQEQRSSNVPGNVVI
KPPHGFSTTNLNITLKSSKIITSQNNTAFQELPNGGNILEAQVGNDSRSSKGNRDTLSTPEEKKPSSNNQGYDFDA
LKNSSSLLFPNQAYASNNRTPNENSNVADETSASTNNGDNDNTLIQPSSNVGTTLGPQQTSTNENQNVHSQNLKFG
NIGMVEDQGPDYDLNLLDTNENDFNFINWEG
```

FLO8 ortholog of *Yarrowia lipolytica* (CLIB122), SEQ ID NO:7

```
>XP_503484.1 YALI0E03102p [Yarrowia lipolytica CLIB122]
LisH domain underlined MPAKSDKELLNAYIYDYLLKHNMHDSARTFGAEAKVVPNVKKEDDKDLPKPLIPIDAPQGFLYEWWALFWDIYSAR
GSKGGGSVPAQQYVQGTMRLRQEHAARAQLQQQHQAQQHAQAQAAAQVQGQAQGQGQGQNPTQGPQPQGHMGMPGQ
GPHQPGGPFMNGNMMFPPGQMRMGQLPQHLQQQGTVAGANPSDDSSSPGGTSPAKRQRLSPDMGGQSHPEQQGQH
MMGTPNPNNPVFNSQVMQQLKASQGQMPNLQQQQQAQLQQYSNTLSLAQQRAMMNAKGGPNGQPGQPGQPGQPGQP
GQPGQPGQPGQPLPMGYEGMEPGFMGGNGLIINAQQMRQQQAGSGGAAGSGQLNGNSNALHDYQMQLMLLEQQNKK
RLMVARQEQQEGQPRAEGQAAAAGANPGARMSGQFKRPGSSPVVGNIGDRRVTPKLPNQPSPLIDANRASPLQSN
FNGQGDFNVVVGPSGQMMRMQQPQQQGGPPQQQGQQQGGPGQQQGGPGQQPQQGQQQGQQGGPQGGQHRFDDPQQL
PQSQNGGPQPGSAPGQLPQTQGGPQRPPSRVSQMPPPGVQGGQRTQPSSPGQASNPGSGGSSGSAPGGTTPTQANK
QLKGKKAEPKKRAKKGNQPVTPKAVSESPTPTTPATPSAASNQSLLSKATNFAANNKQAQAAAHAQAQAQAAAQAQ
SQMHMGGMGGSSSGLELDVNGGMGLDNDSSSFLNDFSTGNEGDVGDMDFDFNSFLNTDDNAAGALKFDSGSAFGWG
EGVEAMNE
```

Fig. 1 (continued)

FLO8 ortholog of *Ogataea polymorpha*, SEQ ID NO:8

```
>XP_018209309.1 hypothetical protein OGAPODRAFT_77715 [Ogataea polymorpha]
LisH domain underlined
```

MSQNATPQTTEGHMSMNDQQSNSSSGTNNTEHPSSSSVSSVPTVSDSTAVNS<u>RELLNAYVYDFILKSGFTATASAF
FKEANI</u>PVIHSEKRPTNSPSSSATGTSDLPASFMTMDAPQGFLYEWWQIFWDVFNARTQRGGTTNATQYYHYVNLK
QKQDHLMSQQAAAVAAASTVMNGNNTSMSGAPVTSAAQDIGVLMPQQQQQQQQAQMAHPPQQVPMAQQQRVNARMQ
QPQQQQSQSMPMHPQAAAQAQMNTLRQQQIAQQAQAAQVAAQAVSQRGSPSKRQRMDAAGNGSATEINQTSSPNIA
MNSQQQQQQQHPPMPMPQGMMIPNQFGVPQQYAMFAAAQAAQQGQSQQKFNQYMIPNFQNQPQQPQQQMLMHQQM
HQQSVHMQHDQQHPPPPPPNVPQHSQTFSNPNDFFHEMPKQNNPGTARVNDTAIKDYEKQLRLMESQNRRRLDVHR
NVSDSKDPNSPGSAQFTEYSAMLNQMPPQHAAASIMQQRASPATKASPTTKSPANGAPPANGKQKKAPRKARKNSS
SVPATPLTPANNQPTPQTNIPPTPQNTTPQQTPQSSAAAASQVMAGKKGIKRKNRGRAIYPIEYSR

FLO8 ortholog of *Aspergillus niger* (CBS 513.88), SEQ ID NO:9

Aspergillus niger

```
>XP_001395127.2 cAMP-dependent protein kinase pathway protein (Som1)
[Aspergillus niger CBS 513.88]
LisH domain underlined
```

MNQMNQMNMAGMNPGAGGPVGGVPMINNGSAAPRNEQNINNIPENM<u>INNLNTYIYDYFLKRGYHDCARALVKDESI
KLNTEPPIKTSPGHRRDADVNGVDGDTMMTDGKDGDKLKIPDDLPRPNLPSEGQQSSFLLDWFSLFWDFFWAQRKK</u>
GNSNDVRSYLTHTQNMMRLREQHQNQLLRQQPLMNGQMGQMNIRRNGMVPPNLQKTVLQNNTTGLSQQQLAQMHKN
QQVQMMQQMQREHSDMDMNGHRPQSPASAENAPSPSKRPRLEGGPMNGQQLAPNGRGQAQGIPGQPTPQALLMQNG
LNRAMNPNQFQAFQQSGPAAQQKQMQGMPNGMMNPANVMANPQTEMVSIPEGQVYPINGDYYGANGQMAQVRTGMQ
TPGGQHGNHALQDYQMQLMLLEQQNKRRLMMARQEQDSMARPDGQPQMPGQQLPPGTSPQGSRAGTSPNPNDQMKR
GTPKMPQTGLPGSPSAADAMAQGRGSPASMNFPGGQMPPEMAGPQFFVKNMADGMAAPNGMRPPSSNPAFSTPQMG
QPIQAGANRMPNGGWQPQQGAQGQPMAPQQSPATQPQSTGTPQERNAMPPPQAPPAPGANVGRTQPPSPQTAAPPT
PQQGNKPAPKKKETKDSRKRPKKGAAAAAAAAQANTAATPSSEAEHPPTPTPSTPITPQHPNSFNKTGANATTSAP
QQPTSAPAPPPLVQQPPDQTQQPFNELSIPDASAFNLDFSALENPDILENFDFDTFLNTDADTAGFGFDPNTSYPT
DGVETGAGDGL

Fig. 1 (continued)

SEQ ID NO:10 [pG1-3, pGTH1-D1240]
T motifs: italic and underlined; first and second core regulatory regions: italic, double underlined, spacer core region between first and second core regulatory region: italic; translation initiation site: dotted line; bold: repeated regulatory region;

```
CAAACATTTGCTCCCCCTAGTCTCCAGGGAAATGTAAAATATACTGCTAATAGAAAACAGTAAGACGCTCAGTTGT
CAGGATAATTACGTTCGACTGTAGTAAAACAGGAATCTGTATTGTTAGAAAGAACGAGAGTTTTTTACGGCGCCGC
CATATTGGGCCGTGTGAAAACAGCTTGAAACCCCACTACTTTCAAAGGTTCTGTTGCTATACACGAACCATGTTTA
ACCAACCTCGCTTTTGACTTGACTGAAGTCATCGGTTAACAATCAAGTACCCTAGTCTGTCTGAATGCTCCTTTCC
ATATTCAGTAGGTGTTTCTTGCACTTTTGCATGCACTGCGGAAGAATTAGCCAATAGCGCGTTTCATATGCGCTTT
TACCCCCTCTTTTGTCAAGCGCAAAATGCCTGTAAGATTTGGTGGGGGTGTGAGCCGTTAGCTGAAGTACAACAGG
CTAATTCCCTGAAAAAACTGCAGCTCAGGGATTCCCACTATTTGGTATTCTGATATGTTTTTCCTGATATGCATCA
AAACTCTAATCTAAAACCTGAATCTCCGC*TATTTTTTTTTTTTTT*GATGACCCGTTTTCGTGACAAATTAATTT
CCAACGGGGTCTTGT**CCGGATAAGAGAATTTTGTTTGATTATCCGTTCGG*ATAAATGGA*CGCCTGCTC*CATATTTT*
*TCCGGTT*ATTACCCCACCTGGAAGTGCCCAGAATTTTCCGGGGATTACGGATAATA**CGGTGGTCTGGATTAATTAA
TACGAGATCTCAGGGATTCCCACTATTTGGTATTCTGATATGTTTTTCCTGATATGCATCAAAACTCTAATCTAAA
ACCTGAATCTCCGC*TATTTTTTTTTTTTTT*GATGACCCGTTTTCGTGACAAATTAATTTCCAACGGGGTCTTGT
**CCGGATAAGAGAATTTTGTTTGATTATCCGTTCGG*ATAAATGGA*CGCCTGCTC*CATATTTTTCCGGTT*ATTACCCC
ACCTGGAAGTGCCCAGAATTTTCCGGGGATTACGGATAATAC**GGTGGTCTGGATTAATTAATACGCCAAGTCTTAC
ATTTTGTTGCAGTCTCGTGCGAGTATGTGCAATAATAAACAAGATGAGCCAATTTATTGGATTAGTTGCAGCTTGA
CCCCGCCATAGCTAGGCATAGCCAAGTGCTATGGGTGTTAGATGATGCACTTGGATGCAGTGAGTTTTGGAGTATA
AAAGATCCTTAAAATTCCACCCTT
```

SEQ ID NO:11 [pG1-D1427, pG1-4 (PG1-D1427-2xTA(T)14]:
Example comprising two T motifs which are (T)n (n=14), each extended by preceding TA (extending the T motif at its 5'-end to become a TA(T)n motif)]
T motifs: italic and underlined; first and second core regulatory regions: italic, double underlined, spacer core region between first and second core regulatory region: italic; translation initiation site: dotted line; bold: repeated regulatory region;

```
CAAACATTTGCTCCCCCTAGTCTCCAGGGAAATGTAAAATATACTGCTAATAGAAAACAGTAAGACGCTCAGTTGT
CAGGATAATTACGTTCGACTGTAGTAAAACAGGAATCTGTATTGTTAGAAAGAACGAGAGTTTTTTACGGCGCCGC
CATATTGGGCCGTGTGAAAACAGCTTGAAACCCCACTACTTTCAAAGGTTCTGTTGCTATACACGAACCATGTTTA
ACCAACCTCGCTTTTGACTTGACTGAAGTCATCGGTTAACAATCAAGTACCCTAGTCTGTCTGAATGCTCCTTTCC
ATATTCAGTAGGTGTTTCTTGCACTTTTGCATGCACTGCGGAAGAATTAGCCAATAGCGCGTTTCATATGCGCTTT
TACCCCCTCTTTTGTCAAGCGCAAAATGCCTGTAAGATTTGGTGGGGGTGTGAGCCGTTAGCTGAAGTACAACAGG
CTAATTCCCTGAAAAAACTGCAGCTCAGGGATTCCCACTATTTGGTATTCTGATATGTTTTTCCTGATATGCATCA
AAACTCTAATCTAAAACCTGAATCTCCGC*TATTTTTTTTTTTTTT*GATGACCCGTTTTCGTGACAAATTAATTTC
CAACGGGGTCTTGT**CCGGATAAGAGAATTTTGTTTGATTATCCGTTCGG*ATAAATGGACGCCTGCTC*CATATTTTT*
*CCGGTT*ATTACCCCACCTGGAAGTGCCCAGAATTTTCCGGGGATTACGGATAATA**CGGTGGTCTGGATTAATTAAT
ACGCCAAGTCTTACATTTTGTTGCAGTCTCGTGCGAGTATGTGCAATAATAAACAAGATGAGCCAATTTATTGGAT
TAGTTGCAGCTTGACCCCGCCATAGCTAGGCATAGCCAAGTGCTATGGGTGTTAGATGATGCACTTGGATGCAGTG
AGTTTTGGAGTATAAAAGATCCTTAAAATTCCACCCTTAGATCTCAGGGATTCCCACTATTTGGTATTCTGATATG
TTTTTCCTGATATGCATCAAAACTCTAATCTAAAACCTGAATCTCCGC*TATTTTTTTTTTTTTT*GATGACCCGTT
TTCGTGACAAATTAATTTCCAACGGGGTCTTGT**CCGGATAAGAGAATTTTGTTTGATTATCCGTTCGG*ATAAATGG
ACGCCTGCTC*CATATTTTTCCGGTT*ATTACCCCACCTGGAAGTGCCCAGAATTTTCCGGGGATTACGGATAATA**CG
GTGGTCTGGATTAATTAATACGCCAAGTCTTACATTTTGTTGCAGTCTCGTGCGAGTATGTGCAATAATAAACAAG
ATGAGCCAATTTATTGGATTAGTTGCAGCTTGACCCCGCCATAGCTAGGCATAGCCAAGTGCTATGGGTGTTAGAT
GATGCACTTGGATGCAGTGAGTTTTGGAGTATAAAAGATCCTTAAAATTCCACCCTT
```

Fig. 1 (continued)

pG1, SEQ ID NO:12

CAAACATTTGCTCCCCCTAGTCTCCAGGGAAATGTAAAATATACTGCTAATAGAAAACAGTAAGACGCTCAGTTGT
CAGGATAATTACGTTCGACTGTAGTAAAACAGGAATCTGTATTGTTAGAAAGAACGAGAGTTTTTTACGGCGCCGC
CATATTGGGCCGTGTGAAAACAGCTTGAAACCCCACTACTTTCAAAGGTTCTGTTGCTATACACGAACCATGTTTA
ACCAACCTCGCTTTTGACTTGACTGAAGTCATCGGTTAACAATCAAGTACCCTAGTCTGTCTGAATGCTCCTTTCC
ATATTCAGTAGGTGTTTCTTGCACTTTTGCATGCACTGCGGAAGAATTAGCCAATAGCGCGTTTCATATGCGCTTT
TACCCCCTCTTTTGTCAAGCGCAAATGCCTGTAAGATTTGGTGGGGGTGTGAGCCGTTAGCTGAAGTACAACAGG
CTAATTCCCTGAAAAAACTGCAGATAGACTTCAAGATCTCAGGGATTCCCACTATTTGGTATTCTGATATGTTTTT
CCTGATATGCATCAAAACTCTAATCTAAAACCTGAATCTCCGCTATTTTTTTTTTTTTnnGATGACCCCGTTTTC
GTGACAAATTAATTTCCAACGGGGTCTTGTCCGGATAAGAGAATTTTGTTTGATTATCCGTTCGGATAAATGGACG
CCTGCTCCATATTTTTCCGGTTATTACCCCACCTGGAAGTGCCCAGAATTTTCCGGGGATTACGGATAATACGGTG
GTCTGGATTAATTAATACGCCAAGTCTTACATTTTGTTGCAGTCTCGTGCGAGTATGTGCAATAATAAACAAGATG
AGCCAATTTATTGGATTAGTTGCAGCTTGACCCCGCCATAGCTAGGCATAGCCAAGTGCTATGGGTGTTAGATGAT
GCACTTGGATGCAGTGAGTTTTGGAGTATAAAAGATCCTTAAAATTCCACCCTT wherein n at positions 592 and 593 is T or absent pG3, SEQ ID NO:13

GTAAATAGCGGCAGCAATCCAGTAACCTTTTCTGAATAGCAGAGCCTTAACTAAAATAATGGCCAGGGTAAAAAAT
TCGAAATTTGACACCAAAAATAAAGACTTGTCGTTATAAGTCTTAACAAAGTCCGCAATTTTGGAGCTAACGGTGG
CGGTTGCTGGGATATTCAATAATGGTAGAATGTTGCTGCGGGTATATGACAGAGCGTGAAACACACTGAACAAGGT
AAATGGAACAACAGCAATTGCAATATGGGGAGGATAGTCAAGAACAAAGCAGCAATGGCAAAGTACTGAATATTC
TCCAAAGCCAAAAGGTCCAGTGGTTTCAACGACAAAGTCTTGTTGGTATAGCTTTGGAACAAAAGGACACCGAAAG
ACTCGACAGCGCCCACAAATACAGCGTTGTAGAAGAACGAATTGATTGCTCCAGAGCTTCTAATAGTCAGAAGATA
CCCCAAACCTCCGAGCAACGTTAGCACATGACCTAAGAACCAGGCGAAGTGAAGAGTCTGGAATAACGACACCCAG
TCAGTTTTTCCTGAGCTCCTGGTGGGATTGGTAGAAGCATTTGATTTGCTTGGAGTGGTTTTATTTGAAGATGGTG
TTGAAGCCATTGTTGCTAAAGAGTCGGAGTTTTGCTTTTAGGGTTTGTTAAGCAAAGGAGGAAAAACTGCGCCGTT
TGAAGTCCCAGGTAGTTTCGCGTGTGAGGCCAGCCAGGGAAAGCTTCCTTCGGTACTTTTTTTCTTTTGCAGGTT
CCGGACGGATTAAGCTTCGGGTTATGAGGGGGGCGGTAGCCAATTCCGGACACAATATTGCGTCGCAGCTAGTCAC
CCCGCCATAAATATACGCAGGATTGAGGTAATAACATCGATAGTCTTAGTAATTAATACAATTCAGTGGCGAATTT
GGCAACATGACGTAAGGCCCACTGTTGTCTATAAAAGGGGATGAATTTTCATGTTTTTGAGGCCTCCCGGACAATT
TATTGAACTCAA pG4, SEQ ID NO:14

TGGACTGTTCAATTTGAAGTCGATGCTGACGATGTCAAGAGAGATGCTCAATTATATTTGTCATTTGCTGGTTACA
CTGGAAACGCTACTTTTGTTGGCGGAAACTCTACCAGTTTGGCCGTCCATGTAAACGATGTCGTTCTGGGCCGTGA
CCGTTTCAACACGAACATAACCAATGACAAATCCACTTACAGGTCTAGTTCATATGGAGGCAATTGGTACCTTACT
TCTTTGGATGTCCCAAGTGGGGCTTTAACGTCTGGTACTAACAATGTCTCGTTTGTCACTACAAACTCCGAGGTAA
ATAAAGGATTCTTGTGGGATTCTCTCAAGTTTGTTTGGAAGTTGTAACAGGTTTATAAGCATATCGTGCGCTTGTC
CACAATTGAATCATTTATTGTTGCGAGATACATGAACAAAGTGTGAACTGGGACCCATTACTACAATTCCCACGCA
ACGTTGTTTCAAAGCCCATATTTTTTGACAATTGTTTCGTTACACCCCAGTTTGATGTACATCGCTTGCAATGA
TGTGTGTCCCGGAGTATTTTCCATATTCAGCTTGAATTCGTATACTCAACCAATATCTGGGGTATACTTTTATGT
AACCTATACAAATCAACTATACTATTTCACCTTTCGACCAATCATCTCCCATCTTGTTAAGTTTTGCTTCCTATAT
CCCTGACCCTGACATCACCCATGATTCCGCTCAACGGTTCTCCTCTACATCGTCCTCTTTTGGAGAGGGTGTTCA
GTTTGACATTCAAATTACCCCCGCCATCACGCGCAACCGAGACCGCACCCCCGAATTTTCACAAATTACCCCACA
CCCTATACTCCACCACTATGAGGGTTATTAGAACTGATCACGTATAAATACCACCGCAAGTTCCCAAGGGATCGTG
TTCTTCTTCTCCAATTGCAATCATATTTCTGACTCTTTCTAGTTCAGATTAATTCCTTTACACTTGCTTTTTTCCC
TTACCTTTATCC

Fig. 1 (continued)

pG6, SEQ ID NO:15

AGACCAGCAGTTTAACTACGCAAATCCACAGGAATTTCTACATCACAATACCAATGGTAATACCACGACGTCAAGG
AATGGAAACGACGACTTGGAGGAAGACTTCGTCAACCTCTTGCGGAGTACCCGAGGCTAAGACAATAAGAAGAAAA
AAAAAAGAAAAGCGGTGGGGGAGGGATTATTAAATAAGGATTATGTAACCCCAGGGTACCGTTCTATACATATTTA
AGGATTATTTAGGACAATCGATGAAATCGGCATCAAACTGGATGGGAGTATAGTGTCCGGATAATCGGATAAATCA
TCTTGCGAGGAGCCGCTTGGTTGGTTGGTGAGAGGAGTGAAATATGTGTCTCCTCACCCAAGAATCGCGATATCAG
CACCCTGTGGGGGACACTATTGGCCTCCCTCCCAAACCTTCGATGTGGTAGTGCTTTATTATATTGATTACATTGA
TTACATAGCTAAACCCTGCCTGGTTGCAAGTTGAGCTCCGAATTCCAATATTAGTAAAATGCCTGCAAGATAACCT
CGGTATGGCGTCCGACCCCGCTTAATTATTTTAACTCCTTTCCAACGAGGACTTCGTAATTTTTGATTAGGGAGTT
GAGAAACGGGGGGTCTTGATACCTCCTCGATTTCAGATCCCACCCCCTCTCAGTCCCAAGTGGGACCCCCCTCGGC
CGTGAAATGCGCGCACTTTAGTTTTTTTCGCATGTAAACGCCGGTGTCCGTCAATTAAAAGTCGCAGACTAGGGTG
AACTTTACCATTTTTGTCGCACTCCGTCTCCTCGGAATAGGGGTGTAGTAATTCTGCAGTAGTGCAATTTTTACCC
CGCCAAGGGGGGGCGAAAAGAGACGACCTCATCACGCATTCTCCAGTCGCTCTCTACGCCTACAGCACCGACGTAG
TTAACTTTCTCCCATATATAAAGCAATTGCCATTCCCCTGAAAACTTTAACCTCTGCTTTTTCTTGATTTTTCCTT
GCCCAAAGAAAAG pG8, SEQ ID NO:16

CTGCACAACCATTGCCAGTAAGGACGAAGAGAAGGCCCCACTACCCAAAATTCAGGATAACGTCTTCATACCATGC
AGCGACGCCTACAAGACGCTGTCAAGACATGCCAACTTCAACGAAGTGAACTTTAACACATTGATCGGGAAATTGA
CCACCAAGGGAATGCTGGTTGAGGCTGGAAGCGTTGCCAGTGTCCTGAGGGAACTGGACCGAAAGTTTAGTAATGC
ATAAGAGGATATATATAGGAATGCAGTAATAATATTAGTACCCATTAAGTGGGCTAAGCCATTGGAAGGCCGTCTG
ACTGATGGTGGTGTTCTTCTCATTTAGATAGTGCATTTGCAACTACCGTCTGAGATTGAGTTTGATGTGAAGCTCC
AGCGCCAAAACAGTATAAGAACCTTATCTCCGCATTATTGTTCTTGCGTAAAAGTTTGTGTGAAGAAACAGGGGTA
GTTGCGCAGATTAGTTGTAATATGCGCATAGGATGGGTCATTGACTTCTTTCCTCGAAAGAGCCACACCGTTAGCT
AAAAAAGGACGCGCATCTACCCCAAAATAGAATGTGGGGAAATAGGACGCGCAACTTCCTCTCAATCACTGGACGT
CAGAAAAACAAATGCGCAATCGAGTCACCCTCCGTGATACCCTCCGTGATACCCCTCTCCGTCTATTCTGACAGC
GTCTCCCCATGACGTTTCAATCTACTTAGAAAAGATTTCGTTTTTTTTCCTTCAATTACACGATCTCATCTTCTG
CAAGGGTCTGGAGGACATCACCAATCTGCGACTCCATAACTTAGTCCTGAGTTTATATTTACGCTTCATCTGATGA
GTAGGAAGAAAAGTTTCACGAAATTCCCCGCCAACTTGCCCTTCGGAATAAGCAGCCACTCTCCTTCTGCCCAT
AGTAAGCTTGCGCGAGGCCCCAACTTGGCCAGAAACTTTAAATATGCCAAACAATCTCCCCCAATCTAAGTTCTCC
CTCTTCTAAAAA first core regulatory region, SEQ ID NO:17

ATAAATGGA second core regulatory region, SEQ ID NO:18:

CATATTTTTCCGGTT

Fig. 1 (continued)

T motif identified by any of SEQ ID NO:19-34
- TA(T)$_{13}$: SEQ ID NO:19: *TATTTTTTTTTTTTT*
- (T)$_{15}$ : SEQ ID NO:20 *TTTTTTTTTTTTTTT*
- TA(T)$_{14}$: SEQ ID NO:21: *TATTTTTTTTTTTTTT*
- (T)$_{16}$ : SEQ ID NO:22: *TTTTTTTTTTTTTTTT*
- TA(T)$_{15}$: SEQ ID NO:23: *TATTTTTTTTTTTTTTT*
- (T)$_{17}$ : SEQ ID NO:24: *TTTTTTTTTTTTTTTTT*
- TA(T)$_{16}$: SEQ ID NO:25: *TATTTTTTTTTTTTTTTT*
- (T)$_{18}$ : SEQ ID NO:26: *TTTTTTTTTTTTTTTTTT*
- TA(T)$_{17}$: SEQ ID NO:27: *TATTTTTTTTTTTTTTTTT*
- (T)$_{19}$ : SEQ ID NO:28: *TTTTTTTTTTTTTTTTTTT*
- TA(T)$_{18}$: SEQ ID NO:29: *TATTTTTTTTTTTTTTTTTT*
- (T)$_{20}$ : SEQ ID NO:30: *TTTTTTTTTTTTTTTTTTTT*
- TA(T)$_{19}$: SEQ ID NO:31: *TATTTTTTTTTTTTTTTTTTT*
- (T)$_{21}$ : SEQ ID NO:32: *TTTTTTTTTTTTTTTTTTTTT*
- TA(T)$_{20}$: SEQ ID NO:33: *TATTTTTTTTTTTTTTTTTTTT*
- (T)$_{22}$ : SEQ ID NO:34: *TTTTTTTTTTTTTTTTTTTTTT*

Main regulatory region: (SEQ ID NO:35): <u>ATAAATGGA</u>CGCCTGCTC<u>CATATTTTTCCGGTT</u>
(including the first and second core region, SEQ ID NO:17 and 18, underlined)

Spacer core region: (SEQ ID NO:36): CGCCTGCTC

Spacer main region: (SEQ ID NO:37): [incl. a T16 motif, italic and underlined]
ATTACCCCACCTGGAAGTGCCCAGAATTTTCCGGGGATTACGGATAATACGGTGGTCTGGATTAATTAATACGA
GATCTCAGGGATTCCCACTATTTGGTATTCTGATATGTTTTTCCTGATATGCATCAAAACTCTAATCTAAAACCTGA
ATCTCCGC*<u>TTTTTTTTTTTTTTTT</u>*GATGACCCCGTTTTCGTGACAAATTAATTTCCAACGGGGTCTTGT**CCGGATAA
GAGAATTTTGTTTGATTATCCGTTCGG**

Exemplary translation initiation site (of pG1): (SEQ ID NO:38): TTCCACCCTT

Exemplary translation initiation site (of pAOX1): (SEQ ID NO:39): TTCGAAACG

Fig. 1 (continued)

Exemplary translation initiation site (consensus sequence of eukaryotes):

(SEQ ID NO:40):

gccgccRcc wherein R at position 7 is A or G, preferably A
[upper-case letters indicate highly conserved bases; R=purine (A or G, with A being more frequent here), see also Kozak M (1987). "An analysis of 5'-noncoding sequences from 699 vertebrate messenger RNAs". Nucleic Acids Res. 15 (20): 8125–8148.]

Exemplary translation initiation site (e.g. used in pPUZZLE vectors):

(SEQ ID NO:85): CCTGCAGGCC

Exemplary translation initiation site (consensus sequence of *P. pastoris*):

(SEQ ID NO:86):

nnnnnnAnn wherein
n at positions 1-6 is any nucleic acid, preferably A;
n at positions 8-9 is any nucleic acid, preferably A pG1a (SEQ ID NO:41)

```
GGAATCTGTATTGTTAGAAAGAACGAGAGTTTTTTACGGCGCCGCCATATTGGGCCGTGTGAAAACAGCTTGAAAC
CCCACTACTTTCAAAGGTTCTGTTGCTATACACGAACCATGTTTAACCAACCTCGCTTTTGACTTGACTGAAGTCA
TCGGTTAACAATCAAGTACCCTAGTCTGTCTGAATGCTCCTTTCCATATTCAGTAGGTGTTTCTTGCACTTTTGCA
TGCACTGCGGAAGAATTAGCCAATAGCGCGTTTCATATGCGCTTTTACCCCCTCTTTTGTCAAGCGCAAAATGCCT
GTAAGATTTGGTGGGGGTGTGAGCCGTTAGCTGAAGTACAACAGGCTAATTCCCTGAAAAAACTGCAGATAGACTT
CAAGATCTCAGGGATTCCCACTATTTGGTATTCTGATATGTTTTCCTGATATGCATCAAAACTCTAATCTAAAAC
CTGAATCTCCGCTATTTTTTTTTTTTTTTGATGACCCCGTTTTCGTGACAAATTAATTTCCAACGGGGTCTTGTC
CGGATAAGAGAATTTTGTTTGATTATCCGTTCGGATAAATGGACGCCTGCTCCATATTTTCCGGTTATTACCCCA
CCTGGAAGTGCCCAGAATTTTCCGGGGATTACGGATAATACGGTGGTCTGGATTAATTAATACGCCAAGTCTTACA
TTTTGTTGCAGTCTCGTGCGAGTATGTGCAATAATAAACAAGATGAGCCAATTTATTGGATTAGTTGCAGCTTGAC
CCCGCCATAGCTAGGCATAGCCAAGTGCTATGGGTGTTAGATGATGCACTTGGATGCAGTGAGTTTTGGAGTATAA
AAGATCCTTAAAATTCCACCCTT
``` pG1b (SEQ ID NO:42)

```
CCATATTCAGTAGGTGTTTCTTGCACTTTTGCATGCACTGCGGAAGAATTAGCCAATAGCGCGTTTCATATGCGCT
TTTACCCCCTCTTTTGTCAAGCGCAAAATGCCTGTAAGATTTGGTGGGGGTGTGAGCCGTTAGCTGAAGTACAACA
GGCTAATTCCCTGAAAAAACTGCAGATAGACTTCAAGATCTCAGGGATTCCCACTATTTGGTATTCTGATATGTTT
TCCTGATATGCATCAAAACTCTAATCTAAAACCTGAATCTCCGCTATTTTTTTTTTTTTTGATGACCCCGTTT
TCGTGACAAATTAATTTCCAACGGGGTCTTGTCCGGATAAGAGAATTTTGTTTGATTATCCGTTCGGATAAATGGA
CGCCTGCTCCATATTTTCCGGTTATTACCCCACCTGGAAGTGCCCAGAATTTTCCGGGGATTACGGATAATACGG
TGGTCTGGATTAATTAATACGCCAAGTCTTACATTTTGTTGCAGTCTCGTGCGAGTATGTGCAATAATAAACAAGA
TGAGCCAATTTATTGGATTAGTTGCAGCTTGACCCCGCCATAGCTAGGCATAGCCAAGTGCTATGGGTGTTAGATG
ATGCACTTGGATGCAGTGAGTTTTGGAGTATAAAAGATCCTTAAAATTCCACCCTT
```

Fig. 1 (continued)

pG1c (SEQ ID NO:43)

CTGCAGATAGACTTCAAGATCTCAGGGATTCCCACTATTTGGTATTCTGATATGTTTTTCCTGATATGCATCAAAA
CTCTAATCTAAAACCTGAATCTCCGCTATTTTTTTTTTTTTTTGATGACCCCGTTTTCGTGACAAATTAATTTCC
AACGGGGTCTTGTCCGGATAAGAGAATTTTGTTTGATTATCCGTTCGGATAAATGGACGCCTGCTCCATATTTTTC
CGGTTATTACCCCACCTGGAAGTGCCCAGAATTTTCCGGGGATTACGGATAATACGGTGGTCTGGATTAATTAATA
CGCCAAGTCTTACATTTTGTTGCAGTCTCGTGCGAGTATGTGCAATAATAAACAAGATGAGCCAATTTATTGGATT
AGTTGCAGCTTGACCCCGCCATAGCTAGGCATAGCCAAGTGCTATGGGTGTTAGATGATGCACTTGGATGCAGTGA
GTTTTGGAGTATAAAAGATCCTTAAAATTCCACCCTT pG1d (SEQ ID NO:44)

GACCCCGTTTTCGTGACAAATTAATTTCCAACGGGGTCTTGTCCGGATAAGAGAATTTTGTTTGATTATCCGTTCG
GATAAATGGACGCCTGCTCCATATTTTTCCGGTTATTACCCCACCTGGAAGTGCCCAGAATTTTCCGGGGATTACG
GATAATACGGTGGTCTGGATTAATTAATACGCCAAGTCTTACATTTTGTTGCAGTCTCGTGCGAGTATGTGCAATA
ATAAACAAGATGAGCCAATTTATTGGATTAGTTGCAGCTTGACCCCGCCATAGCTAGGCATAGCCAAGTGCTATGG
GTGTTAGATGATGCACTTGGATGCAGTGAGTTTTGGAGTATAAAAGATCCTTAAAATTCCACCCTT pG1e (SEQ ID NO:45)

CCGGATAAGAGAATTTTGTTTGATTATCCGTTCGGATAAATGGACGCCTGCTCCATATTTTTCCGGTTATTACCCC
ACCTGGAAGTGCCCAGAATTTTCCGGGGATTACGGATAATACGGTGGTCTGGATTAATTAATACGCCAAGTCTTAC
ATTTTGTTGCAGTCTCGTGCGAGTATGTGCAATAATAAACAAGATGAGCCAATTTATTGGATTAGTTGCAGCTTGA
CCCCGCCATAGCTAGGCATAGCCAAGTGCTATGGGTGTTAGATGATGCACTTGGATGCAGTGAGTTTTGGAGTATA
AAAGATCCTTAAAATTCCACCCTT

Native pGAP promoter sequence of P. pastoris (GS115): SEQ ID NO:46

CTGCTACTCTGGTCCCAAGTGAACCACCTTTTGGACCCTATTGACCGGACCTTAACTTGCCAAACCTAAACGCTTA
ATGCCTCAGACGTTTTAATGCCTCTCAACACCTCCAAGGTTGCTTTCTTGAGCATGCCTACTAGGAACTTTAACGA
ACTGTGGGGTTGCAGACAGTTTCAGGCGTGTCCCGACCAATATGGCCTACTAGACTCTCTGAAAAATCACAGTTTT
CCAGTAGTTCCGATCAAATTACCATCGAAATGGTCCCATAAACGGACATTTGACATCCGTTCCTGAATTATAGTCT
TCCACCGTGGATCATGGTGTTCCTTTTTTTCCCAAAGAATATCAGCATCCCTTAACTACGTTAGGTCAGTGATGAC
AATGGACCAAATTGTTGCAAGGTTTTTCTTTTTCTTTCATCGGCACATTTCAGCCTCACATGCGACTATTATCGAT
CAATGAAATCCATCAAGATTGAAATCTTAAAATTGCCCCTTTCACTTGACAGGATCCTTTTTTGTAGAAATGTCTT
GGTGTCCTCGTCCAATCAGGTAGCCATCTCTGAAATATCTGGCTCCGTTGCAACTCCGAACGACCTGCTGGCAACG
TAAAATTCTCCGGGGTAAAACTTAAATGTGGAGTAATGGAACCAGAAACGTCTCTTCCCTTCTCTCTCCTTCCACC
GCCCGTTACCGTCCCTAGGAAATTTTACTCTGCTGGAGAGCTTCTTCTACGGCCCCTTGCAGCAATGCTCTTCCC
AGCATTACGTTGCGGGTAAAACGGAGGTCGTGTACCCGACCTAGCAGCCCAGGGATGGAAAAGTCCCGGCCGTCGC
TGGCAATAATAGCGGGCGGACGCATGTCATGAGATTATTGGAAACCACCAGAATCGAATATAAAAGGCGAACACCT
TTCCCAATTTTGGTTTCTCCTGACCCAAAGACTTTAAATTTAATTTATTTGTCCCTATTTCAATCAATTGAACAAC
TATCAAAACACA

Fig. 1 (continued)

Rgt1 of *P. pastoris* (PAS_chr1-3_0233): SEQ ID NO:47

```
MIPTIDPKDPELVSEDTAQSASARKRSKVSRACDECRRKKIKCDATFLANSNTLLKPCTNCYKYNCSCSFTRVPLK
RGPSKGFARDGSGYERRRSSSVHSVSSSQSVTSPVPSHASLPIPPANPVSLPRLNVPGDGLLSPKAVPPTNLFWKV
PYELPSFSDRRSSVASADSFRRPSIYQSDSEDDFYSATGSQRNSISQAPRQRNLSPALSVSSTSSLNNRIKSLNMV
ASTLESNIHNYYSQGFNSSLPILPLDERILSTLLSNVSNGSSSASWDAIRSPILELFDKSILMLLRSYESQFNFND
LLDHVTEMQSIYPRIRSHLLSDELLKLIFLMSGVLTDYALILTGQPYSTGLSITVSVFNDWKTYENVQRVLVINRA
GSLDLDYDSLPFLFARCYLSLATLDLIYSLSFSSPRLISSFANLPILDIVQKCGITKDAKLDETPLPVLDQFLNCF
LPGDTYPTALNTLKTGLVLLDFTNNRSTTLRFPFINIHDDNHMTGLSHLLSNVSDFMSQFTEVHSDSKDSQLLFLR
CIWAFWEIGSVLSELIDHFISSSANSQVGDKDASFFYEHQLKVTTLLGTFSNIASAFLTSSTTAASHPPPSISPFH
IISMVESFKMVQFLNKLIASFISLNEKLEKRELEDELSKCKEELNNLNERFQAVSSVQTLPVVHVLFRDLVFSSNR
LDTQRDRASSVVSATTTTSTATTTATTKKSSFGNLLHSDEENILPTVIDWCKEQKHSAEMFLNKNDLNGWLY
```

Cat8-1 of *P. pastoris* (PAS_chr2-1_0757): SEQ ID NO:48

```
MMPEEQVTSPQRKHQKSKAKTIRAPGSSIERVAQACDRCRSKKTRCDGKRPQCSQCAAVGFECKISDKLSRRAFPR
GYTETLEERIRELEFENKKLHKLIDLKNEQVEIKNRIDQESTLTNENLTLLNKEQEVSHSGNIHHHADGEPCNCAN
SVSARPVSIAGSVDIDTTDLSDEDDSLYSAASYNAKYHQTGTSGPEMVRLSQRYSSGNFNDPLSFEQSNAPGAAAA
ISIQNKMRTQTFVNLANLVAMSIPRTTEETLFIASLLAKICNVHGFQSKAPILTAKSIALLKDKYNYGNDEVFANI
TLKNVNFNKLTSQQSQQFFQSLNLPNQVNLDLFITTFFNTWNNFIPIINRHIFMSSYIKFNKSRETMFTDNSMFGN
EKFGEILLLITTMVMLSQERNNNREAVPSSSYKKDSTPHPHRPDASSQSNVEILQYYDHLIHEFIKSNISDDCSLP
TLESLSLQLLYCLAIGDLTTSYELRGKIITMGQQLRLHRCPSAVLGTNGSKVSQMQQGERRILFWCIYILDTFSAL
ILGVPRLLKDYEIECALPFSNESNNANVKGSIENTTNTVIINNIKLSLAGKVSDCALAVMRYSKVLGNILDSIFQR
SSINNPSVVSKSTNITEETCLLHEHALDLWRRELSPHINVDLDKSPGGVEYERLSDNQLTILFLYYHAKILIYLPL
MANESSQSRSSASYINIQQSTTSILAIANTLATKERNFYFLPLPVNLSREKVRLAFLSAKGSLEYARGGALFQESK
ILLASVINELKIETSIGMLGCLSVPCMEAVDNAMEQIMALPGKVSSVNGSNSEMKRSSSKRKSSPLRQDISGDERK
SHNIEVSDSRTPSVQSSLYPQPNQMHHPNIIKSENNEQMIPENDTPGAINDIFTSHSPPGTVTSMKEEDLPIKVPI
LLQTQQRQIYNNNPNHSLFSQQPGTQVLSGQQMPGPSSTDQQFKRITTPDGLDSLMMQDFGVDASLGLPMLDFDFN
FDFENVQNNYSQSNVSPPNSESVPSSIQGTHSNDPKDSQVSAGSLFGL
```

Cat8-2 of *P. pastoris* (PAS_chr4_0540): SEQ ID NO:49

```
MKENQASNKFNLIKNPITGKPRISQACDRCRIKKIKCDGTLPSCTNCSKIGFVCKISDRLTRSSFPKGYTKNLEQK
LIDMELDRNRLMLELNRIKKEGFDGTNNNIAMASSVSSSENLKSDDSSECQSVTVSLSSTSGPSLSPEPKQDDFRF
RVGMDGSFVLNQFLQSPLMDYIKSLNVLQFNGCANFDQSFNDDPLVLNKYHMNLNRFLNLIFYKLLLPLIHRNSNT
LNEKFAEDNNSLDSLIWKFFTNYNKLIPILEFDSFYKDYLQFIHKYYSNNQVFVDGFRKYFEFSEFEQCFIVKLIL
ILKFTLPVIHDTSVPSEIYRLISMDSLQRLFGNIDFLKPSTDKVSILLLVLHYMVLYESPKSLLDTQDEAQKYDEF
IGNLLSTAVHHITSLRLHIDPRKLQFPRPLPSNGNRLRIKLSWCYKLISKLFRVIYNIDNDSLYSLDDSHLPELQS
ISILHEELDVTIQFNNLLNLIPNNFHSLRDKQSLSKIKTQLLEWHKNFNTEFVEHFNLNDTDSDELSAEKINVLRS
KLISLNRLNCYNSYFQLVIELQLKENLDSVVSGIFGLSNEMLIDNKSSTELLNTLQQTPIIHQSSILVSLCYRIQT
GNLQDEICSILVNNYEKLLQCNDAGLPIKILPQLVHYFKGKISTNLSNSAAHEDLMNMFTLNDNLSTTTTDLDSFI
IPPKRKQDQTLPIGTKRSKSASTSSVISSDDCSLFSNSLSVPTTFSGSSISVGMDNPPSSLFGSYKRPSSIVKQEP
TINPRSNGTNTDSNLFDTFNDSIKGSLNNGLKKLKDIRCNSVVERSHSSQRNDFLMDQEDSITKETINFSELFTCG
TPTASQSIDRSPKSLLLNDLAIAPDTLVIKPDAEDLDRLKNKIRSVKSTVH
```

LisH domain of the FLO8 protein of *K. phaffii* (SEQ ID NO:50)

```
LLNGYIYDYLVKSNMQNLADQFAQET
```

LisH domain of the FLO8 protein of *K. pastoris* (SEQ ID NO:51)

```
LNGYIHDYLVKSNMQNLADQFAQES
BLASTp: 96% identity to SEQ ID NO :50 (23/24 aa)
```

Fig. 1 (continued)

**LisH domain of the FLO8 ortholog of *S. cerevisiae* (strain ATCC 204508 / S288c) (SEQ ID NO:52)**

```
LNEYIFDFLTKSSLKNTAAAFAQDA
BLASTp: 54% identity to SEQ ID NO :50 (13/24 aa)
```

**LisH domain of the FLO8 ortholog of *S. cerevisiae* (CEN.PK113-7D), (SEQ ID NO:53)**

```
LNEYIFDFLTKSSLKNTAAAFAQDA
BLASTp: 54% identity to SEQ ID NO :50 (13/24 aa)
```

**LisH domain of the FLO8 ortholog of *Yarrowia lipolytica* (CLIB122), (SEQ ID NO:54)**

```
ELLNAYIYDYLLKHNMHDSARTFGAEA
BLASTp: 71% identity to SEQ ID NO :50 (12/17 aa)
```

**LisH domain of the FLO8 ortholog of *Ogataea polymorpha*, (SEQ ID NO:55)**

```
ELLNAYVYDFILKSGFTATASAFFKEA
BLASTp: 62% identity to SEQ ID NO :50 (8/13 aa)
```

**LisH domain of the FLO8 ortholog of *Aspergillus niger* (CBS 513.88) (SEQ ID NO:56)**

```
NNLNTYIYDYFLKRGYHDCARALVKD
BLASTp: 73% identity to SEQ ID NO :50 (8/11 aa)
```

Sequence scR (SEQ ID NO:57):
```
CAGGAACAACTAATGGAGTCTGGGGGTGGTTTGGTTACCCTGGGTGGTTCTCTTAAGCTTTCATGTAAGGCCTCTG
GTATTGATTTTTCGCACTACGGTATCTCCTGGGTTAGACAAGCTCCTGGAAAAGGTCTGGAATGGATCGCTTACAT
TTACCCAAATTACGGTTCTGTTGACTATGCCTCCTGGGTCAATGGTAGGTTCACTATTTCCCTTGACAACGCTCAG
AACACGGTATTCCTACAGATGATCTCCCTAACCGCTGCTGATACTGCAACCTACTTCTGTGCTCGTGACAGAGGTT
ACTACTCTGGCTCTCGTGGAACTAGACTTGACTTATGGGGACAAGGTACTCTCGTTACCATCTCTAGTGGTGGAGG
TGGTTCTGGAGGAGGAGGTTCCGGCGGAGGTGGTAGCGAGCTGGTCATGACTCAAACCCCTCCATCCCTATCTGCA
TCAGTCGGTGAAACCGTTAGAATTAGATGCCTTGCATCTGAGTTCTTGTTCAACGGTGTGTCCTGGTATCAACAAA
AGCCTGGTAAGCCTCCAAAGTTTCTCATTTCTGGTGCCTCAAACCTCGAATCTGGAGTGCCACCAAGATTTTCCGG
ATCTGGCTCTGGTACTGACTACACTCTGACAATTGGTGGTGTTCAAGCTGAGGATGTTGCTACCTACTATTGTCTC
GGTGGTTACTCAGGATCTTCCGGCCTAACTTTCGGTGCCGGTACAAACGTCGAGATCAAAGGTGGACATCACCACC
ACCATCACTAATAG
```

Sequence vHH (SEQ ID NO:58):
```
CAGGTTCAGCTGCAGGAGTCCGGTGGTGGTCTGGTTCAAGCCGGTGGTTCATTAAGATTGTCCTGTGCTGCCTCTG
GTAGAACTTTCACTTCTTTCGCAATGGGTTGGTTTAGACAAGCACCTGGAAAAGAGAGAGTTTGTTGCTTCTAT
CTCCAGATCCGGTACTTTAACTAGATACGCTGACTCTGCCAAGGGTAGATTCACTATTTCTGTTGACAACGCCAAG
AACACTGTTTCTTTGCAAATGGACAACCTTAACCCAGATGACACCGCAGTCTATTACTGTGCCGCTGACTTGCACA
GACCATACGGTCCAGGAACCCAAAGATCCGATGAGTACGATTCTTGGGGTCAGGGAACTCAAGTCACTGTCTCTTC
AGGTGGTGGATCTGGTGGTGGAGGTTCAGGTGGTGGAGGATCCGGTGGTGGTGGTTCTGGTGGTGGTGGATCTGGT
GGAGGTGAAGTTCAACTTGTCGAATCCGGTGGTGCACTTGTCCAACCTGGTGGATCTCTTAGACTTTCTTGTGCCG
CCTCCGGTTTTCCTGTTAACCGTTACTCTATGCGTTGGTACAGACAAGCCCCTGGAAAAGAACGTGAATGGGTTGC
CGGAATGTCCTCAGCTGGTGACAGATCCTCCTACGAAGATTCTGTGAAGGGACGTTTCACCATCTCCAGAGATGAC
GCCCGTAACACCGTTTACCTTCAAATGAACTCCCTTAAGCCTGAGGATACTGCCGTCTACTATTGTAACGTGAATG
TCGGATTTGAATACTGGGGACAGGGAACCCAAGTTACTGTCTCTTCCGGTGGACATCACCACCACCATCACTAATA
G
```

Fig. 1 (continued)

Signal sequence (SEQ ID NO:59):

MKXSTNLILAIAAASXVVSA, wherein
X at position 3 is either F or L; and
X at position 16 is either A or T.

Leader sequence (SEQ ID NO:60):

MKXSTNLILAIAAASXVVSAAPVAPAEEAANHLHKR, wherein
X at position 3 is either F or L
X at position 16 is either A or T Signal sequence, aMF, *S. cerevisiae* (SEQ ID NO:61):

MRFPSIFTAVLFAASSALAAPVNTTTEDETAQIPAEAVIGYSDLEGDFDVAVLPFSNSTNNGLLFINTTIASIAAK
EEGVSLEKR.

Helper factor 1, *Komagataella pastoris* (SEQ ID NO:62):
MSSDAVEQLE NFQLIKFDRF DPSTQSTIRI ARSPKPIPVK VVIVGDGGCG
KTCLLNVFAT GTFPEAYVPT IIENVVITLV TPTGQIAAVT LWDTAGQEEY
DRLRPLSYSD VDVVLLCYSI DNLSTFHNVA DKWYPEVAHF CPNTPIILVG
TKSDMRRHQK SQPHFVSPQD SSQLARQMGA VMNIECSAKE VSNVNIVFDA
AVSYCLSNSR PKTRGDNDNN RSNRRLSRAK RASMFIRGKD VSSTSGNSRE
ELVEYDQDGL AIIPDRKKRK CSII Helper factor 2, *Komagataella pastoris* (SEQ ID NO:63):
MLNKLFIAIL IVITAVIGET TTSSTTASLS ESPTLVWVTG TDASGRLATT
QSAYTQQFSQ LYSSIASPSS GSIGLGTIQG TVGIVRTYET ITLAS Helper factor 3, *Komagataella pastoris* (SEQ ID NO:64):
MSTAIPGGQR TLAKRRAANL DKKQDEPTSA RSAGAGGSSS TMLKLYTDEA
QGLKVDPLIV LVLAVGFIFS VIGLHVVAKL TGKLIN Helper factor 4, *Komagataella pastoris* (SEQ ID NO:65):
MTPRSHIFFD ISINNQPAGR IIFELFNDIV PKTAENFRAL STGEKGIGKS
GKPLHYKGST FHRIIKDFMV QGGDFTNGNG TGGESIYGEK FEDENFQLTH
DKPFLLSMAN AGPGTNGSQF FITTVPTPHL DNKHVVFGKV IAGKATVRKI
ERNSEGEAPI EPVVIEDCGE LPEDADLTIS DETGDKYEEV LKDNENIDID
DFEQVYQAIT EIKELGTKYF KNGDTKIAFE KYQKAANYLL EYIPSDLSEE
QSSKLELLKT SVFSNVALAG LKVSKFKDTI KYATLVIEDE SADAKAKSKG
YYRRGSAYSS LKDEDSAISD FQKALELSPG DPAISQSLQR TTKARKDRLA
KEKAALSKFF E Helper factor 5, *Komagataella pastoris* (SEQ ID NO:66):
MTNWKAILTP AQYQVLRLGG TERPYTGQYV NFKKNGTYLC SGCQTPLYKS
GTKFDSSCGW PAFYEALPGA VKRIEDNSLG MRRIEIRCSK CDGHLGHVFE
GEGFDTPTDS RHCVNSISLK FQGEEEN

Fig. 1 (continued)

**Helper factor 6, *Komagataella pastoris* (SEQ ID NO:67):**
MSHLLLRDSF WGRTIYHLSK HRYFSFPEEK DGFIAPEKYY LNMDQVSIHA
ESEKNIVEGL VDTSNSSLEE VKTTRVIVDW DEYDQKENPQ NWSSLLKCFV
VFEVGILTVA VYMGSAIYTP GIEDIMRDLN VSRTVATLPL TLFVIGYAVG
PMIFSPMSEH PAIGRTTIYV WTLFIFAILQ IPTALTTNIA GFCILRFIGG
FFASPALATG PASVGDVIAI PHLPVGLGLW SICAVCGPSL GPLFGAIFSQ
LVSWRWCFWF LLITSGTLFI VLGFTLPETY VPTLLYRKAR RLRALTKNEL
IISKGELDIQ DRTAKEVLIE CLWRPVDISF RDPVVLMINL YISMVYSIWY
IWFEAFPIVF LEIYGFSLIG MGASFAGILI GVLICSACYC YACHVTFARR
IIANETIHPE FFVPGAIIGG CIMPTGIFIL GWTATKSVHW IVPIIGSGLF
AAGGYLIFQT LFNYLAMSFP RYMASAFAGN DLFRSFSASV FPLFGHALYA
NLGSEKFPVG WGSSVLGFIT VAMIAIPVTF MRYGPRLRAN SRYAGP

**Helper factor 7, *Komagataella pastoris* (SEQ ID NO:68):**
MTDYVTSKRP DNVLNWTSIH VSSWIGETIP EIDPSLLQNF LEHDIAGDVL
PYLKSEDLKE IGINELKHRI SIKKNIHELL VSNEKHIDTS ILSDTATELG
TLILTNKFIT QMANRKNVVD DSTHHSNNRR LTEQFNKLRK DLLPIFKWIK
ETQPLPTPEN THFANMGSVP ASPVEHTSGE STLSNPSLST INAGEGVNSA
VAGQSLGRKP TLSSRRQSHA LSPTGEHLNV SSSSPSTGNF ETLNGERPNL
RSASSGSQEH TENELLKPLR VKADEPCYKV IQNAMKRHGL SVDDWRKYAL
VICYGDEERV LGLHEKPGSI FKELKDQKQN PAIMLRQIDT NNDDQNHIET
PGGRL

**Helper factor 8, *Komagataella pastoris* (SEQ ID NO:69):**
MTTNGQKRQK TRKPLLINAF VMGCAGLQNP GLWKHPKDSS HRFNQIDHWT
YLAKLAEKGK FNALFIADVL GGYDVYKGPE NLATPAVAGA QWPVTEPSAV
VSAMAAVTTN LAFGVTFSTI SEAPYHFARR LSTLDHLTKG RIGWNVVSSY
LESAARNLLN GEKLDEHDQR YLKAEEYIQI VYELLLSSWR DDAVVLDKKA
GVYTDPTRFR KINFEGKFFK VPGPHIVDPT PQRLPVILQA GTSKVGKEFA
AKHAEIVFVI SFSPDDLKPK IAEVRQLAKE KFGRNHDDIK FVALATPVIG
ATHELAEEKY QELLSYGDIE GAQALFGGWT GIDLSQYGED EELGNVSSNA
MRGAVQNWTK AIPNEKRWTR KVIAKQITVG GLGPAFVGTP EEIADELEHW
SDHAGLDGFN FTYAVNPLSF EEIVEDLIPV LQRRGLAQKE YPNPETGSTF
RKNLFGTDFV PSTHPAYNLR WRAGVSKEEF EKSLNATTNW YSSFARSGAL
GELHNTCRIL YLQIVKYKYR LRVRSEGNSI PFAKMTKENE AKRQKTSQPK
AKKQLIINAF MSGSSGNQSP GLWSYPGDKS TEYTTLDYWV ELAQKLEKAK
FHSIFIADVL GGYDVYNGPG NYSAAAKSGA QFPMIEPSAA VTAMAAATKS
ITFGVTFSTI SEAPYHFARR LGTLDLLTNG RVGWNIVSSY LDSAARNLLN
GEPLPLHADR YKRAEEFLQV VYRLFLSSWR DDAYKLDKKT RTFADPKLIR
TIDHVGEFFN VPGPQFLPPT PQRLPLILQA GTSKVGMDYA AKHAEVVFLA
SFDPESLQEK IKTVRDIAET KYNRPRDSIK FLILITVVIA DTHEDAVKRY
EDLASYADLE GAQALFSGWT GIDIGKYGED EPLEHVESNA IKSHVKNWTK
FKDNKPRARK DIAKQIGVGG SGPLLVGSVQ EIADELERWA EVSDLDGFNF
AYADYPQTFD DIIEKLLPEL NKRGVFWDDY KIPGGTFRES VFGRKFVDKD
HPAYDLRWRS DQTREEFEKK LAELEKK

**Helper factor 9, *Komagataella pastoris* (SEQ ID NO:70):**
MRFSNVVLTA IAAAGVQADE ALYTVFYNDV TENAQEYLSY IQANTAAGFT
DLLSLYTELA TYTDDSYTSI FTEEDFPASE LSSFVVNLPW YSSRIEPQVA
AAETGESEEE SETGESEEES ETGEETETET GSESESESES ETSATGTGTG
TSASESAETE TSTDAAVSID HPKSTLLMGL TAAVVSITFG VFAL

Fig. 1 (continued)

Helper factor 10, *Komagataella pastoris* (SEQ ID NO:71):
MSSFRVLDLV KPFTPFLPEV ISPERKVPFQ QKLMWTGVTL LIFLVMSEIP
LYGITSSDSS DPLFWLRMML ASNRGTLMEL GISPIVTSGM VFQLLQGIQI
LDVNMENKAD RELFQTAQKV FAILLSIGQA TVYVLTGMYG PPGELGVGVC
LLLVLQLVFA GIVVILLDEL LQKGYGLGSG ISLFMATNIC EQIFWKTFAP
TTVNRGRGKE FEGAFISFFH LILTKKDKKR ALLESFYRDN APNMFQVIAT
LVVFFTVVYL QGFRLEIPVK STRQRGPYGT YPIRLFYTSN MPIMLQSALT
SNIFIISQML YSHFPDNAFV KLIGTWEAQP GSAQLFAASG LAYYMQPPMS
LSQALLDPIK TVVYVVFVLT TCAIFSKTWI EISGSSPRDV AKQFKDQGLV
IAGHRDATVY KELKKIIPTA AAFGGATIGA LSVVSDLLGT LGSGTSILLA
VTTIYGYYEL AVKEGGFSKG GPSGFVDL

SEQUENCE LISTING

<160> NUMBER OF SEQ ID NOS: 86

<210> SEQ ID NO 1
<211> LENGTH: 806
<212> TYPE: PRT
<213> ORGANISM: Komagataella phaffii

<400> SEQUENCE: 1

```
Met Asn Lys Pro Asn Gly Ser Glu Gln Gln Pro Pro Ser Arg Gly Met
1               5                   10                  15

Lys Gln Glu Ser Gly Gly Pro Val Thr Ser Thr Thr Pro Gly Thr
                20                  25                  30

Asn Thr Gly Leu Glu Asn Ser His Ser Met Gly Ala Asp Met Glu Pro
                35                  40                  45

Asp Val Gly Ala Thr Ser Pro Arg His Leu Leu Asn Gly Tyr Ile Tyr
            50                  55                  60

Asp Tyr Leu Val Lys Ser Asn Met Gln Asn Leu Ala Asp Gln Phe Ala
65                  70                  75                  80

Gln Glu Thr Glu Leu Leu Glu Thr Asp Leu Thr Val Pro Met Asp Thr
                85                  90                  95

Pro Ser Gly Tyr Leu Leu Glu Trp Trp Met Val Phe Trp Asp Leu Phe
                100                 105                 110

Asn Ala Arg Leu Lys Gln Arg Gly Ser Gln Lys Ala His Gln Tyr Ile
            115                 120                 125

Gln Leu Asn Met Leu Arg Gln Gln Gln Arg Thr Met Arg Asn Thr
        130                 135                 140

Ala Arg Val Gln Lys Val Pro Leu Arg Pro His Thr Gln Ser Ser Pro
145                 150                 155                 160

Ser Met Ser Gln Thr Phe Ile Pro Gln Gln Pro Gln Gln Ala Gln
                165                 170                 175

Gly Gln Gln His Ala Gln Ala Gln Ala Gln Val Gln Ala His Gln Gln
            180                 185                 190

Ala Gln His His Ala Gln Ala Gln Val Pro Val Gln Pro Gln Gln His
            195                 200                 205

Gln Leu Gly Gly Gln Thr Gln Gln Gln Ser Ile Asn Thr Gly Ser
        210                 215                 220

Pro Ala Gly Pro Asn Ala Ile Asn Ser Arg Val Gln His Leu Ala Gln
225                 230                 235                 240

Gln Gln Met Asn His Leu Arg Gln Gln Ala Thr Ala Thr Thr Gln Gln
                245                 250                 255

Pro Ile Pro Gln Gln Asn Ile Pro Ser Asn Gln Gln Gly Pro Thr Gly
                260                 265                 270

Pro Tyr Pro Thr Ser Pro Ser Arg Arg Pro Arg Leu Leu Ser Asn Glu
            275                 280                 285

Ser Gly Ala Ser Ala Pro Ser Val Met Thr Lys Ser Gln Leu Gln Gly
        290                 295                 300

Val Pro Pro Ser Gln Gln Pro His Gln Gln Gly Gln Gln Val Gly
305                 310                 315                 320

Pro Pro Asn Gln His Gln Gly Gln Ser Ser Ser Phe Tyr Ser Gly Met
                325                 330                 335

Pro Pro Gln Gly Val Val Pro His Gln Phe Asn Pro Gln Gln Tyr
            340                 345                 350

Ala Asn Met Leu Ala Arg Gln Gln His Val Gln Ala Gln Gln Val
        355                 360                 365
```

Gln Leu Gln Gln Val Gln His Val Gln Gln Arg Gln Gln Asp Gln
    370                 375                 380

Gln Gln His Arg Leu Ser Ala Gly Ser Pro Gly His Pro Ser Phe Gly
385                 390                 395                 400

Val Phe Gln Gln Pro Pro Met Ser Asn His Asn Gln Val Met Ile
                405                 410                 415

Asn Gln Gln Gly Glu Thr Phe Phe Asp Pro His Ser Pro Tyr Ala Gln
            420                 425                 430

Pro Asn Gly Tyr Pro Gln Pro Gln Gln Gln Gln Gln Gln Gln Gln
            435                 440                 445

Gln Gln Gln Gln Gln Pro Gln Gln Gln Gln Gln Gln Gln Gln
    450                 455                 460

Gln Lys Gln Gln Pro Pro Pro Arg Gln Pro Gln Arg Gln Gln
465                 470                 475                 480

Ala Met Ala Met Ala Pro Leu Pro His Ser Thr Ser Ala Ala Gly Thr
                485                 490                 495

Pro His Ser Ser Thr Thr Pro Arg Phe Ser Gln Pro Gly Pro Val Tyr
            500                 505                 510

Gln Gln Pro Leu Pro Ala Ser Gln Pro Gln His Ser Pro Pro Ser Ser
    515                 520                 525

Ile Gln Gln Pro Glu Leu Val Pro Thr Pro Gly Ser Gln His Gln Gln
    530                 535                 540

Ile Ala Gln Pro Gln Ser Gln Ser His Gln Gln Ser Gln Gln Ser
545                 550                 555                 560

Gln Ser Ser Ala Ser Lys Ile Val Gly Ile Gln Glu Tyr Gln Lys Glu
                565                 570                 575

Leu Met Met Leu Glu Lys Gln Asn Lys Gln Arg His Asp Met Ala Cys
            580                 585                 590

Lys Lys Gly Ser Gly His Phe Ser Asn Phe Asp Pro Ile Pro Glu His
            595                 600                 605

Thr Pro Pro Glu Pro Lys Phe Asn Val Asn Val Met Leu Pro Pro Gln
    610                 615                 620

Asn Ser Ala Val Val Thr Lys Asn Thr Pro Gly Thr Ser Pro Gly Thr
625                 630                 635                 640

Gln Thr Gln Asn Thr Ala His Ser Thr Gly Asn Thr Ser Ala Gly Ser
                645                 650                 655

Thr Pro Asn Asn Val Ala Pro Val Arg Lys Lys Glu Pro Ala Lys
            660                 665                 670

Lys Lys Ala Lys Lys Ala Thr Glu Pro Pro Thr Pro Thr Pro Gln
            675                 680                 685

Thr Pro Ile Ala Ala Arg Thr His Gln Asn Ser Thr Gly Gly Ile Pro
    690                 695                 700

Gly Asn Asn Ala Ala Thr Lys Arg Arg Lys Arg Glu Pro Leu Val Asp
705                 710                 715                 720

Gln Thr Val Ser Pro Asn Leu Asn Glu Ala Ser Lys Ser Thr Lys Thr
                725                 730                 735

Gly Lys Ile Ser Ser Gln Thr Asp Phe Thr Gly Ser Asp Asn Gly Phe
            740                 745                 750

Leu Gln Asp Phe Gly Asp Gly Thr Gly Pro Pro Thr Gly Thr Asp Asp
            755                 760                 765

Met Glu Phe Asp Phe Asn Ser Phe Leu Asn Asn Glu Thr Gly Glu Pro
    770                 775                 780

Asn Ser Ser Thr Ile His Phe Asp Asn Val Phe Asn Trp Gly Glu Gly

Thr Glu Ala Gly Asp Leu
            805

<210> SEQ ID NO 2
<211> LENGTH: 2421
<212> TYPE: DNA
<213> ORGANISM: Komagataella phaffii

<400> SEQUENCE: 2

| | | | | | | |
|---|---|---|---|---|---|---|
| atgaacaagc | caaacgggtc | tgaacaacaa | ccaccgtcac | gcggaatgaa | gcaagagtca | 60 |
| ggaggcccag | ttacttcatc | tacgacgccg | ggtaccaata | ctggcctaga | aaactctcat | 120 |
| tccatggggg | cggatatgga | gcctgatgtt | ggtgctacct | ctcctcgcca | tcttcttaat | 180 |
| gggtacattt | acgattattt | agtcaaatct | aacatgcaaa | atttggctga | tcaatttgcc | 240 |
| caagagacgg | agctcttaga | aacagacttg | acagtaccaa | tggatacgcc | ttcaggctat | 300 |
| cttctagaat | ggtggatggt | attctgggac | cttttcaatg | cccgcctaaa | gcaacggggt | 360 |
| tcacagaagg | cccaccagta | tattcagttg | aacatgctac | gacaacagca | acagaggacc | 420 |
| atgcgaaata | cagcccgtgt | caaaaagtc | ccgttgaggc | cacacaccca | atcatctcct | 480 |
| tcaatgtcac | agactttat | tccacagcag | cctcaacagc | aagcacaggg | acaacagcac | 540 |
| gcccaggctc | aagcccaagt | gcaagcacat | cagcaagccc | aacaccacgc | gcaggcacaa | 600 |
| gtgccagtgc | aaccgcaaca | gcaccagcta | ggaggccaaa | ctcaacagca | gcaatccatt | 660 |
| aacactgggt | ctcctgcggg | tccaaatgct | atcaactcgc | gtgttcaaca | cttagcacaa | 720 |
| caacagatga | atcaccttcg | ccagcaggcg | actgccacta | cgcaacaacc | tatcccgcaa | 780 |
| cagaatatcc | catcaaacca | acagggtcct | caggcccctt | atcctacttc | cccttcaaga | 840 |
| agaccgagat | tactgtctaa | cgaatcgggt | gcaagtgcac | cctctgtaat | gacaaagtca | 900 |
| cagctccaag | gagtccctcc | ctcacaacaa | ccacaccagc | agcaaggtca | gcaggtaggc | 960 |
| cccctaatc | aacatcaagg | tcaatcttct | tccttttatt | cgggcatgcc | tcctcaaggg | 1020 |
| gtcgtggttc | ctcatcagtt | caatcctcag | cagtatgcca | atatgctagc | aagacaacag | 1080 |
| catgtacaag | ctcaacaaca | ggttcagtta | caacaggtcc | aacatgtaca | acagagacaa | 1140 |
| cagcaagacc | aacaacaaca | ccgcctgtcc | gccggttcac | cggggcaccc | ttcatttggc | 1200 |
| gtttttcaac | aacctcctcc | gatgtcaaac | cataatcagg | tcatgatcaa | tcagcaggga | 1260 |
| gaaactttt | ttgatccaca | ttctccatat | gctcaaccta | cgggtacccc | ccagccacag | 1320 |
| caacaacaac | aacaacagca | acaacaacaa | caacagcagc | aaccgcaaca | gcagcagcag | 1380 |
| cagcagcagc | aacagaagca | gcaaccacca | ccaccaccac | gacagcctca | gcgccaacaa | 1440 |
| gcgatggcca | tggctcctct | gcctcactct | acttctgccg | ccgtactcc | tcactcgtcc | 1500 |
| accacaccta | gattctcgca | acctggtcct | gtttatcagc | agcctttacc | tgcatctcaa | 1560 |
| ccgcaacatt | ctccgccttc | ttctattcag | cagccggagc | tagttccaac | tccagggtca | 1620 |
| caacatcagc | aaatagcaca | accacaatca | cagagccaac | accagcaatc | gcaacagtct | 1680 |
| caatcaagtg | cttctaaaat | tgtaggtata | caggagtatc | agaaagagct | aatgatgctt | 1740 |
| gagaaacaga | caaacagcg | tcatgacatg | gcatgtaaga | agggaagcgg | gcatttttct | 1800 |
| aactttgatc | caattccaga | gcacacaccg | cccgaaccaa | aatttaatgt | gaatgtaatg | 1860 |
| ctccctcccc | agaactctgc | agtggtcacg | aagaatactc | ccggaacttc | acctggtaca | 1920 |
| caaactcaaa | acactgcaca | tagtactggt | aacacttctg | cggggtctac | accaaataat | 1980 |

-continued

```
gtcgcacctg tacgaaagaa aaaggagcca gctaaaaaga aggcaaagaa agctactgag    2040
cccccgactc ccactactcc acagactcca attgcagcta ggacacatca aaactctaca    2100
ggcggcattc ctggtaataa tgctgctact aagcgacgaa aacgggagcc gctggttgat    2160
caaactgttt cacctaacct taacgaagct tccaagtcaa caaagaccgg aaaaatttca    2220
tctcaaactg actttacagg ttctgacaat ggattcttac aggattttgg cgatggaact    2280
ggtcctccca ctggaaccga tgatatgaaa tttgatttta acagttttct taataacgaa    2340
actggcgaac ctaatagttc aaccattcat tttgacaatg tattcaattg gggagaaggt    2400
accgaagccg gagatttata g                                              2421
```

<210> SEQ ID NO 3
<211> LENGTH: 804
<212> TYPE: PRT
<213> ORGANISM: Komagataella pastoris

<400> SEQUENCE: 3

```
Met Asn Lys Pro Asn Gly Ser Gly Gln Gln Pro Pro Ser Arg Gly Met
1               5                   10                  15

Lys Gln Asp Pro Gly Gly Pro Val Thr Ser Thr Thr Pro Gly Thr
            20                  25                  30

Asn Thr Gly Phe Glu Asn Ser His Ser Met Gly Ala Asp Val Glu Pro
        35                  40                  45

Asp Val Gly Ala Ala Ser Pro Arg His Ile Leu Asn Gly Tyr Ile His
    50                  55                  60

Asp Tyr Leu Val Lys Ser Asn Met Gln Asn Leu Ala Asp Gln Phe Ala
65                  70                  75                  80

Gln Glu Ser Asp Leu Leu Glu Thr Asp Leu Thr Val Pro Met Asp Thr
                85                  90                  95

Pro Thr Gly Tyr Leu Leu Glu Trp Trp Met Val Phe Trp Asp Leu Phe
            100                 105                 110

Asn Ala Arg Leu Lys Gln Arg Gly Ser Gln Lys Ala His Gln Tyr Ile
        115                 120                 125

Gln Leu Asn Met Leu Arg Gln Gln Gln Arg Thr Met Arg Asn Thr
    130                 135                 140

Ala Arg Val Gln Lys Val Pro Leu Arg Pro His Thr Gln Ser Ser Pro
145                 150                 155                 160

Ser Met Ser Gln Thr Phe Ile Pro Gln Gln Pro Gln Gln Ala Gln
                165                 170                 175

Ala Gln Ala Gln Gln His Ala Gln Ala Gln Ala Gln Val Gln Ala His
            180                 185                 190

Gln Gln Ala Gln His His Ala Gln Ala Gln Val Pro Met Gln Ser Gln
        195                 200                 205

Pro His Gln Gln Gly Gly Gln Thr Gln Gln Gln Pro Ile Asn Thr
    210                 215                 220

Gly Ser Pro Ala Gly Pro Asn Ala Ile Asn Ser Arg Val Gln His Leu
225                 230                 235                 240

Ala Gln Gln Gln Met Asn His Leu Arg Gln Gln Ala Thr Ala Thr Thr
                245                 250                 255

Gln Gln Pro Ile Pro Gln Gln Asn Ile Pro Ser Asn Gln Gly Pro
            260                 265                 270

Ala Gly Pro Tyr Pro Thr Ser Pro Ser Arg Arg Pro Arg Leu Leu Ser
        275                 280                 285

Asn Glu Ser Gly Ala Ser Ala Pro Ser Val Met Thr Lys Ser Gln Leu
```

```
            290                 295                 300
Gln Gly Gly Pro Pro Ser Gln Pro His Gln Gln Ala Gln Gln
305                 310                 315                 320

Val Gly Pro Pro Asn Gln His Gln Gly Gln Ser Ser Phe Tyr Ser
                325                 330                 335

Gly Met Pro Pro Gln Gly Val Val Pro His Gln Phe Asn Pro Gln
                340                 345                 350

Gln Tyr Ala Asn Met Leu Ala Arg Gln Gln His Val Gln Ala Gln
                355                 360                 365

Gln Val Gln Leu Gln Gln Val Pro His Val Gln Gln Arg Gln Gln
370                 375                 380

Asp Gln Gln Gln His Arg Leu Ser Ala Gly Ser Pro Gly His Pro Ser
385                 390                 395                 400

Phe Gly Val Phe Gln Gln Pro Pro Met Ser Asn His Asn Gln Val
                405                 410                 415

Met Ile Asn Gln Gln Gly Glu Thr Phe Phe Asp Pro His Ser Pro Tyr
                420                 425                 430

Ala Gln Pro Asn Gly Tyr Pro Gln Pro Gln Gln Gln Gln Gln Gln
                435                 440                 445

Gln Gln Gln Gln Gln Gln Gln Gln Gln Gln Gln Gln Gln Gln
450                 455                 460

Lys Gln Gln Gln Pro Pro Arg Gln Pro Gln Arg Gln Gln Ala Met
465                 470                 475                 480

Ala Thr Ala Pro Leu Pro His Ser Thr Ser Ala Ser Gly Thr Pro His
                485                 490                 495

Thr Ala Thr Thr Pro Arg Phe Ser Gln Pro Gly Pro Val Tyr Gln Gln
                500                 505                 510

Pro Leu Pro Ala Ser Gln Pro Gln His Ser Pro Pro Thr Ser Ile Gln
                515                 520                 525

Gln Gln Glu Pro Ile Pro Thr Pro Gly Ser Gln His Gln Gln Ile Ala
530                 535                 540

Gln Pro Gln Ser Gln Asn Gln His Gln Gln Pro Gln Gln Pro Gln Ala
545                 550                 555                 560

Ser Ala Ser Lys Met Val Gly Ile Gln Glu Tyr Gln Lys Glu Leu Met
                565                 570                 575

Met Leu Glu Lys Gln Asn Lys Gln Arg His Asp Met Ala Ile Lys Lys
                580                 585                 590

Gly Ser Gly His Phe Ser Asn Phe Asp Pro Ile Pro Glu His Thr Gln
                595                 600                 605

Thr Glu Pro Lys Phe Asn Val Asn Val Met Leu Pro Pro Gln Asn Ser
610                 615                 620

Ala Val Ala Thr Lys Asn Thr Pro Gly Thr Ser Pro Gly Thr Gln Thr
625                 630                 635                 640

Gln Asn Thr Ala His Ser Thr Gly Asn Thr Ser Ala Gly Ser Thr Pro
                645                 650                 655

Asn Asn Val Val Pro Val Arg Lys Lys Glu Pro Ser Lys Lys Lys
                660                 665                 670

Ser Lys Lys Ala Thr Glu Pro Pro Thr Pro Thr Thr Pro Gln Thr Pro
                675                 680                 685

Ile Ala Ala Arg Ala His Gln Asn Ser Thr Gly Gly Ile Ser Gly Asn
                690                 695                 700

Asn Ala Ala Thr Lys Arg Arg Lys Arg Glu Pro Leu Val Asp Gln Thr
705                 710                 715                 720
```

```
Val Ser Pro Asn Leu Asn Glu Ala Ser Lys Ser Thr Lys Pro Gly Lys
            725                 730                 735

Ile Ser Ser Gln Asn Asp Phe Thr Gly Ser Asp Asn Gly Phe Leu Gln
            740                 745                 750

Asp Phe Gly Asp Gly Thr Gly Pro Pro Thr Gly Thr Asp Asp Met Glu
            755                 760                 765

Phe Asp Phe Asn Ser Phe Leu Asn Asn Glu Thr Gly Glu Pro Asn Ser
    770                 775                 780

Ser Thr Ile His Phe Asp Asn Val Phe Asn Trp Gly Glu Gly Thr Glu
785                 790                 795                 800

Ala Gly Asp Leu

<210> SEQ ID NO 4
<211> LENGTH: 2415
<212> TYPE: DNA
<213> ORGANISM: Komagataella pastoris

<400> SEQUENCE: 4
atgaacaagc caaacgggtc tggacaacaa ccaccgtcac gcggaatgaa gcaagaccca      60
ggaggcccag ttacctcatc tacgacaccc ggtaccaata ctggctttga aaactctcat     120
tccatgggag cggatgtgga gcctgatgtt ggtgccgcct ctcctcgcca tattcttaat     180
gggtacattc atgattactt agtcaaatct aatatgcaaa atttggccga tcaatttgct     240
caagagtcgg atctcttaga aacagaccta acggtaccaa tggatacacc tacaggctat     300
cttttagagt ggtggatggt attttgggac ctttttcaatg cccgcctaaa gcaacgaggt     360
tcacagaagg ctcatcagta tattcagttg aacatgctac gacaacaaca gcagaggact     420
atgcgaaata cagcccgtgt tcagaaagtc ccgttgagac cacacaccca atcatctcct     480
tcaatgtcac agaccttat tccacagcag cctcaacagc aagcacaggc acaggcacag     540
cagcacgccc aagctcaagc gcaagtccag gctcatcagc aagcacagca tcatgcgcag     600
gctcaagtgc aatgcaatgc aaccacat cagcaaggag ccaaactca acaacagcaa         660
cccattaaca ctgggtctcc tgcggggcca aatgctatca actctcgtgt gcaacactta     720
gcgcaacaac agatgaatca tcttcgccag caggcaactg ccactaccca gcaacctatc     780
ccgcaacaga atattccatc aaaccagcag ggccctgcgg gcccttatcc tacatcgcct     840
tcaagaagac cgagattact gtctaacgaa tcgggtgcaa gtgcaccctc tgtaatgacg     900
aagtcacagc tccaaggagg tcctccatca acaaccac accaacagca agctcagcag       960
gtaggacccc ccaatcaaca tcaaggccag tcctcttcct tttattcggg catgcctcct    1020
caaggagttg tggttcctca tcagttcaat cctcagcagt atgccaatat gctagcaaga    1080
caacagcatg tgcaagctca acaacaggtt cagttacagc aggttccaca tgtgcaacaa    1140
agacaacagc aagaccaaca acaacaccgc ttgtcagccg ttcaccagg gcatccttca    1200
tttggcgttt ttcaacaacc tcctccgatg tcaaaccata atcaggtcat gatcaaccag    1260
cagggagaaa cctttttttga tcctcattca ccatatgctc aacctaatgg gtaccccag     1320
ccacagcaac aacaacaaca gcagcaacaa caacaacaac aacaacaaca gcagcagcag    1380
cagcaacaac agaagcagca acagccacca ccaagacagc ctcagcgcca acaagcgatg    1440
gctacggctc ctttgcctca ttctactcct gcctcgggta ctcctcacac ggccaccaca    1500
cctagattct cccagcctgg tcctgtttat cagcagcctt tacctgcatc tcaaccgcaa    1560
cattctccgc ctacttctat tcagcaacag gaaccaattc aactcctgg gtcacaacat    1620
```

```
cagcaaatag cacaaccgca atcacagaat caacaccagc aaccgcagca acctcaagca      1680
agtgcttcta aaatggtggg tatacaggag taccagaaag agttaatgat gcttgagaag      1740
cagaacaaac aacgtcatga catggcaatt aagaagggaa gcggacattt ctctaatttt      1800
gatccaattc cagagcacac acagactgaa ccaaaattca atgtgaacgt aatgctccct      1860
ccccagaact ctgcagtggc cacgaagaat actcctggaa cttctcctgg tacgcaaact      1920
caaaacactg cacacagtac tggcaacact tctgctgggt ctacaccgaa taatgttgta      1980
ccagttcgaa aaagaagga gccatctaaa aagaaatcaa agaaggctac cgaacctcca      2040
actcctacta ctccacagac accaattgca gctagggcac atcaaaactc tacgggcggc      2100
atttcaggta ataatgctgc tactaagcga cgaaaaaggg agccgctggt cgaccaaaca      2160
gtttcaccta accttaacga agcttcgaaa tcaacaaagc ctgggaaaat ctcatctcaa      2220
aatgacttta caggttctga caatggattt ttacaggatt ttggcgatgg aacaggtccc      2280
cccactggaa ctgacgatat ggagtttgat tttaacagtt ttctcaacaa cgaaactggt      2340
gaacctaata gttcaaccat tcattttgac aatgtattta attgggggga gggtactgaa      2400
gccggggatc tatag                                                       2415

<210> SEQ ID NO 5
<211> LENGTH: 799
<212> TYPE: PRT
<213> ORGANISM: Saccharomyces cerevisiae

<400> SEQUENCE: 5

Met Ser Tyr Lys Val Asn Ser Ser Tyr Pro Asp Ser Ile Pro Pro Thr
1               5                   10                  15

Glu Gln Pro Tyr Met Ala Ser Gln Tyr Lys Gln Asp Leu Gln Ser Asn
            20                  25                  30

Ile Ala Met Ala Thr Asn Ser Glu Gln Gln Arg Gln Gln Gln Gln Gln
        35                  40                  45

Gln Gln Gln Gln Gln Gln Gln Trp Ile Asn Gln Pro Thr Ala Glu Asn
    50                  55                  60

Ser Asp Leu Lys Glu Lys Met Asn Cys Lys Asn Thr Leu Asn Glu Tyr
65                  70                  75                  80

Ile Phe Asp Phe Leu Thr Lys Ser Ser Leu Lys Asn Thr Ala Ala Ala
                85                  90                  95

Phe Ala Gln Asp Ala His Leu Asp Arg Asp Lys Gly Gln Asn Pro Val
            100                 105                 110

Asp Gly Pro Lys Ser Lys Glu Asn Asn Gly Asn Gln Asn Thr Phe Ser
        115                 120                 125

Lys Val Val Asp Thr Pro Gln Gly Phe Leu Tyr Glu Trp Trp Gln Ile
    130                 135                 140

Phe Trp Asp Ile Phe Asn Thr Ser Ser Arg Gly Gly Ser Glu Phe
145                 150                 155                 160

Ala Gln Gln Tyr Tyr Gln Leu Val Leu Gln Glu Arg Gln Glu Gln
                165                 170                 175

Ile Tyr Arg Ser Leu Ala Val His Ala Ala Arg Leu Gln His Asp Ala
            180                 185                 190

Glu Arg Arg Gly Glu Tyr Ser Asn Glu Asp Ile Asp Pro Met His Leu
        195                 200                 205

Ala Ala Met Met Leu Gly Asn Pro Met Ala Pro Ala Val Gln Met Arg
    210                 215                 220
```

-continued

```
Asn Val Asn Met Asn Pro Ile Pro Ile Pro Met Val Gly Asn Pro Ile
225                 230                 235                 240

Val Asn Asn Phe Ser Ile Pro Pro Tyr Asn Asn Ala Asn Pro Thr Thr
            245                 250                 255

Gly Ala Thr Ala Val Ala Pro Thr Ala Pro Pro Ser Gly Asp Phe Thr
            260                 265                 270

Asn Val Gly Pro Thr Gln Asn Arg Ser Gln Asn Val Thr Gly Trp Pro
            275                 280                 285

Val Tyr Asn Tyr Pro Met Gln Pro Thr Thr Glu Asn Pro Val Gly Asn
        290                 295                 300

Pro Cys Asn Asn Asn Thr Thr Asn Asn Thr Thr Asn Asn Lys Ser Pro
305                 310                 315                 320

Val Asn Gln Pro Lys Ser Leu Lys Thr Met His Ser Thr Asp Lys Pro
            325                 330                 335

Asn Asn Val Pro Thr Ser Lys Ser Thr Arg Ser Arg Ser Ala Thr Ser
            340                 345                 350

Lys Ala Lys Gly Lys Val Lys Ala Gly Leu Val Ala Lys Arg Arg Arg
            355                 360                 365

Lys Asn Asn Thr Ala Thr Val Ser Ala Gly Ser Thr Asn Ala Cys Ser
370                 375                 380

Pro Asn Ile Thr Thr Pro Gly Ser Thr Thr Ser Glu Pro Ala Met Val
385                 390                 395                 400

Gly Ser Arg Val Asn Lys Thr Pro Arg Ser Asp Ile Ala Thr Asn Phe
                405                 410                 415

Arg Asn Gln Ala Ile Ile Phe Gly Glu Glu Asp Ile Tyr Ser Asn Ser
            420                 425                 430

Lys Ser Ser Pro Ser Leu Asp Gly Ala Ser Pro Ser Ala Leu Ala Ser
            435                 440                 445

Lys Gln Pro Thr Lys Val Arg Lys Asn Thr Lys Lys Ala Ser Thr Ser
            450                 455                 460

Ala Phe Pro Val Glu Ser Thr Asn Lys Leu Gly Gly Asn Ser Val Val
465                 470                 475                 480

Thr Gly Lys Lys Arg Ser Pro Asn Thr Arg Val Ser Arg Arg Lys
            485                 490                 495

Ser Thr Pro Ser Val Ile Leu Asn Ala Asp Ala Thr Lys Asp Glu Asn
            500                 505                 510

Asn Met Leu Arg Thr Phe Ser Asn Thr Ile Ala Pro Asn Ile His Ser
            515                 520                 525

Ala Pro Pro Thr Lys Thr Ala Asn Ser Leu Pro Phe Pro Gly Ile Asn
            530                 535                 540

Leu Gly Ser Phe Asn Lys Pro Ala Val Ser Ser Pro Leu Ser Ser Val
545                 550                 555                 560

Thr Glu Ser Cys Phe Asp Pro Glu Ser Gly Lys Ile Ala Gly Lys Asn
            565                 570                 575

Gly Pro Lys Arg Ala Val Asn Ser Lys Val Ser Ala Ser Ser Pro Leu
            580                 585                 590

Ser Ile Ala Thr Pro Arg Ser Gly Asp Ala Gln Lys Gln Arg Ser Ser
            595                 600                 605

Lys Val Pro Gly Asn Val Val Ile Lys Pro Pro His Gly Phe Ser Thr
            610                 615                 620

Thr Asn Leu Asn Ile Thr Leu Lys Asn Ser Lys Ile Ile Thr Ser Gln
625                 630                 635                 640

Asn Asn Thr Val Ser Gln Glu Leu Pro Asn Gly Gly Asn Ile Leu Glu
```

```
                    645                 650                 655
Ala Gln Val Gly Asn Asp Ser Arg Ser Ser Lys Gly Asn Arg Asn Thr
                660                 665                 670

Leu Ser Thr Pro Glu Glu Lys Lys Pro Ser Ser Asn Asn Gln Gly Tyr
                675                 680                 685

Asp Phe Asp Ala Leu Lys Asn Ser Ser Ser Leu Leu Phe Pro Asn Gln
            690                 695                 700

Ala Tyr Ala Ser Asn Asn Arg Thr Pro Asn Glu Asn Ser Asn Val Ala
705                 710                 715                 720

Asp Glu Thr Ser Ala Ser Thr Asn Ser Gly Asp Asn Asp Asn Thr Leu
                725                 730                 735

Ile Gln Pro Ser Ser Asn Val Gly Thr Thr Leu Gly Pro Gln Gln Thr
                740                 745                 750

Ser Thr Asn Glu Asn Gln Asn Val His Ser Gln Asn Leu Lys Phe Gly
                755                 760                 765

Asn Ile Gly Met Val Glu Asp Gln Gly Pro Asp Tyr Asp Leu Asn Leu
                770                 775                 780

Leu Asp Thr Asn Glu Asn Asp Phe Asn Phe Ile Asn Trp Glu Gly
785                 790                 795

<210> SEQ ID NO 6
<211> LENGTH: 791
<212> TYPE: PRT
<213> ORGANISM: Saccharomyces cerevisiae

<400> SEQUENCE: 6

Met Ser Tyr Lys Val Asn Ser Ser Tyr Pro Asp Ser Ile Pro Pro Thr
1               5                   10                  15

Glu Gln Pro Tyr Met Ala Ser Gln Tyr Lys Gln Asp Leu Gln Ser Asn
                20                  25                  30

Ile Ala Met Ala Thr Asn Ser Glu Gln Gln Arg Gln Gln Gln Gln Trp
                35                  40                  45

Ile Asn Gln Pro Thr Ala Glu Asn Ser Asp Leu Lys Glu Lys Met Asn
            50                  55                  60

Cys Lys Asn Thr Leu Asn Glu Tyr Ile Phe Asp Phe Leu Thr Lys Ser
65                  70                  75                  80

Ser Leu Lys Asn Thr Ala Ala Ala Phe Ala Gln Asp Ala His Leu Asp
                85                  90                  95

Arg Asp Lys Gly Gln Asn Pro Ile Asp Gly Pro Lys Ser Lys Glu Asn
                100                 105                 110

Asn Gly Asn Gln Asn Thr Phe Ser Lys Val Val Asp Thr Pro Gln Gly
                115                 120                 125

Phe Leu Tyr Glu Trp Trp Gln Ile Phe Trp Asp Ile Phe Asn Thr Ser
            130                 135                 140

Ser Ser Arg Gly Gly Ser Glu Phe Ala Gln Gln Tyr Tyr Gln Leu Val
145                 150                 155                 160

Leu Gln Glu Gln Arg Gln Glu Gln Ile Tyr Arg Ser Leu Ala Ala His
                165                 170                 175

Ala Ala Arg Leu Gln His Asp Ala Glu Arg Arg Gly Glu Tyr Ser Asn
                180                 185                 190

Glu Asp Ile Asp Pro Met His Leu Ala Ala Met Met Leu Gly Asn Pro
            195                 200                 205

Met Ala Pro Ala Val Gln Met Arg Asn Val Asn Met Asn Pro Ile Pro
            210                 215                 220
```

-continued

```
Ile Pro Met Val Gly Asn Pro Ile Val Asn Asn Phe Ser Ile Pro Pro
225                 230                 235                 240

Tyr Asn Asn Ala Asn Pro Thr Thr Gly Ala Thr Ala Val Ala Pro Thr
            245                 250                 255

Ala Pro Pro Ser Gly Asp Phe Ala Asn Val Gly Pro Thr Gln Asn Arg
        260                 265                 270

Ser Gln Asn Val Thr Gly Trp Pro Val Tyr Asn Tyr Pro Met Gln Pro
    275                 280                 285

Thr Thr Glu Asn Pro Val Gly Asn Pro Cys Asn Asn Thr Thr Asn
290                 295                 300

Asn Thr Thr Asn Lys Ser Pro Val Asn Gln Pro Lys Ser Leu Lys
305                 310                 315                 320

Thr Met His Ser Thr Asp Lys Pro Asn Val Pro Thr Ser Lys Ser
            325                 330                 335

Thr Arg Ser Arg Ser Ala Thr Ser Lys Ala Lys Gly Lys Val Lys Ala
                340                 345                 350

Gly Leu Val Ala Lys Arg Arg Lys Asn Asn Thr Ala Thr Val Ser
        355                 360                 365

Ala Gly Ser Thr Asn Ala Gly Ser Pro Asn Ile Thr Thr Pro Gly Ser
370                 375                 380

Thr Thr Ser Glu Pro Ala Met Val Gly Ser Arg Val Asn Lys Thr Pro
385                 390                 395                 400

Arg Ser Asp Ile Ala Thr Asn Phe Arg Asn Gln Ala Ile Ile Phe Gly
                405                 410                 415

Glu Glu Asp Ile Tyr Ser Asn Ser Lys Ser Ser Pro Ser Leu Asp Gly
            420                 425                 430

Ala Ser Pro Ser Ala Leu Val Ser Lys Gln Pro Thr Lys Val Arg Lys
        435                 440                 445

Asn Thr Lys Lys Ala Ser Thr Ser Ala Phe Pro Val Glu Ser Ala Asn
    450                 455                 460

Lys Leu Gly Gly Asn Ser Val Val Thr Gly Lys Lys Arg Ser Pro Pro
465                 470                 475                 480

Asn Thr Arg Val Leu Arg Arg Lys Ser Thr Pro Ser Val Ile Leu Asn
                485                 490                 495

Ala Asp Ala Thr Lys Asp Glu Asn Asn Met Leu Arg Thr Phe Ser Asn
            500                 505                 510

Thr Thr Ala Pro Asn Ile His Ser Ala Pro Thr Lys Thr Ala Asn
        515                 520                 525

Ser Leu Pro Phe Pro Gly Ile Asn Leu Gly Ser Phe Asn Lys Pro Ala
    530                 535                 540

Val Ser Ser Pro Leu Ser Ser Val Thr Glu Ser Cys Phe Asp Pro Glu
545                 550                 555                 560

Ser Gly Lys Ile Ala Gly Lys Asn Gly Pro Lys Arg Ala Val Asn Ser
                565                 570                 575

Lys Val Ser Ala Ser Ser Pro Leu Ser Ile Ala Thr Pro Ser Gly
            580                 585                 590

Asp Ala Gln Glu Gln Arg Ser Ser Asn Val Pro Gly Asn Val Val Ile
        595                 600                 605

Lys Pro Pro His Gly Phe Ser Thr Thr Asn Leu Asn Ile Thr Leu Lys
    610                 615                 620

Ser Ser Lys Ile Ile Thr Ser Gln Asn Asn Thr Ala Phe Gln Glu Leu
625                 630                 635                 640

Pro Asn Gly Gly Asn Ile Leu Glu Ala Gln Val Gly Asn Asp Ser Arg
```

```
                645                 650                 655
Ser Ser Lys Gly Asn Arg Asp Thr Leu Ser Thr Pro Glu Glu Lys Lys
            660                 665                 670

Pro Ser Ser Asn Asn Gln Gly Tyr Asp Phe Asp Ala Leu Lys Asn Ser
            675                 680                 685

Ser Ser Leu Leu Phe Pro Asn Gln Ala Tyr Ala Ser Asn Asn Arg Thr
            690                 695                 700

Pro Asn Glu Asn Ser Asn Val Ala Asp Glu Thr Ser Ala Ser Thr Asn
705                 710                 715                 720

Asn Gly Asp Asn Asp Asn Thr Leu Ile Gln Pro Ser Ser Asn Val Gly
                725                 730                 735

Thr Thr Leu Gly Pro Gln Gln Thr Ser Thr Asn Glu Asn Gln Asn Val
            740                 745                 750

His Ser Gln Asn Leu Lys Phe Gly Asn Ile Gly Met Val Glu Asp Gln
            755                 760                 765

Gly Pro Asp Tyr Asp Leu Asn Leu Leu Asp Thr Asn Glu Asn Asp Phe
            770                 775                 780

Asn Phe Ile Asn Trp Glu Gly
785                 790

<210> SEQ ID NO 7
<211> LENGTH: 768
<212> TYPE: PRT
<213> ORGANISM: Yarrowia lipolytica

<400> SEQUENCE: 7

Met Pro Ala Lys Ser Asp Lys Glu Leu Leu Asn Ala Tyr Ile Tyr Asp
1               5                   10                  15

Tyr Leu Leu Lys His Asn Met His Asp Ser Ala Arg Thr Phe Gly Ala
                20                  25                  30

Glu Ala Lys Val Val Pro Asn Val Lys Lys Glu Asp Asp Lys Asp Leu
            35                  40                  45

Pro Lys Pro Leu Ile Pro Ile Asp Ala Pro Gln Gly Phe Leu Tyr Glu
        50                  55                  60

Trp Trp Ala Leu Phe Trp Asp Ile Tyr Ser Ala Arg Gly Ser Lys Gly
65                  70                  75                  80

Gly Gly Ser Val Pro Ala Gln Gln Tyr Val Gln Gly Thr Met Arg Leu
                85                  90                  95

Arg Gln Glu His Ala Ala Arg Ala Gln Leu Gln Gln Gln His Gln Ala
            100                 105                 110

Gln Gln His Ala Gln Ala Gln Ala Ala Gln Val Gln Gly Gln Ala
            115                 120                 125

Gln Gly Gln Gly Gln Gly Gln Asn Pro Thr Gln Gly Pro Gln Pro Gln
        130                 135                 140

Gly His Met Gly Met Pro Gly Gln Gly Pro His Gln Pro Gly Gly Pro
145                 150                 155                 160

Phe Met Asn Gly Asn Met Met Phe Pro Pro Gly Gln Met Arg Met Gly
                165                 170                 175

Gln Leu Pro Gln His Leu Gln Gln Gly Thr Gly Val Ala Gly Ala
            180                 185                 190

Asn Pro Ser Asp Asp Ser Ser Ser Pro Gly Gly Thr Ser Pro Ala Lys
        195                 200                 205

Arg Gln Arg Leu Ser Pro Asp Met Gly Gly Gln Ser His Pro Glu Gln
    210                 215                 220
```

-continued

```
Gln Gly Gln His Met Met Gly Thr Pro Asn Pro Asn Asn Pro Val Phe
225                 230                 235                 240

Asn Ser Gln Val Met Gln Gln Leu Lys Ala Ser Gln Gly Gln Met Pro
            245                 250                 255

Asn Leu Gln Gln Gln Gln Gln Ala Gln Leu Gln Gln Tyr Ser Asn Thr
            260                 265                 270

Leu Ser Leu Ala Gln Gln Arg Ala Met Met Asn Ala Lys Gly Gly Pro
        275                 280                 285

Asn Gly Gln Pro Gly Gln Pro Gly Gln Pro Gly Gln Pro Gly Gln Pro
    290                 295                 300

Gly Gln Pro Gly Gln Pro Gly Gln Pro Gly Gln Pro Leu Pro Met Gly
305                 310                 315                 320

Tyr Glu Gly Met Glu Pro Gly Phe Met Gly Gly Asn Gly Leu Ile Leu
                325                 330                 335

Asn Ala Gln Gln Met Arg Gln Gln Ala Gly Ser Gly Gly Ala Ala
                340                 345                 350

Gly Ser Gly Gln Leu Asn Gly Asn Ser Asn Ala Leu His Asp Tyr Gln
        355                 360                 365

Met Gln Leu Met Leu Leu Glu Gln Gln Asn Lys Lys Arg Leu Met Val
370                 375                 380

Ala Arg Gln Glu Gln Gln Gly Gln Pro Arg Ala Glu Gly Gln Ala
385                 390                 395                 400

Ala Ala Ala Gly Ala Asn Pro Gly Ala Arg Met Ser Gly Gln Phe Lys
                405                 410                 415

Arg Pro Gly Ser Ser Pro Val Val Gly Asn Ile Gly Asp Gly Arg Arg
            420                 425                 430

Val Thr Pro Lys Leu Pro Asn Gln Pro Ser Pro Leu Ile Asp Ala Asn
        435                 440                 445

Arg Ala Ser Pro Leu Gln Ser Asn Phe Asn Gly Gln Gly Asp Phe Asn
    450                 455                 460

Val Val Val Gly Pro Ser Gly Gln Met Met Arg Met Gln Gln Pro Gln
465                 470                 475                 480

Gln Gln Gly Gly Pro Pro Gln Gln Gln Gly Gln Gln Gln Gly Gly Pro
                485                 490                 495

Gly Gln Gln Gln Gly Gly Pro Gly Gln Pro Gln Gln Gly Gln Gln
            500                 505                 510

Gln Gly Gln Gln Gly Gly Pro Gln Gly Gln His Arg Phe Asp Asp
        515                 520                 525

Pro Gln Gln Leu Pro Gln Ser Gln Asn Gly Gly Pro Gln Pro Gly Ser
530                 535                 540

Ala Pro Gly Gln Leu Pro Gln Thr Gln Gly Pro Gln Arg Pro Pro
545                 550                 555                 560

Ser Arg Val Ser Gln Met Pro Pro Gly Val Gly Gly Gln Arg
                565                 570                 575

Thr Gln Pro Ser Ser Pro Gly Gln Ala Ser Asn Pro Gly Ser Gly Gly
            580                 585                 590

Ser Ser Gly Ser Ala Pro Gly Gly Thr Thr Pro Thr Gln Ala Asn Lys
        595                 600                 605

Gln Leu Lys Gly Lys Lys Ala Glu Pro Lys Lys Arg Ala Lys Lys Gly
    610                 615                 620

Asn Gln Pro Val Thr Pro Lys Ala Val Ser Glu Ser Pro Thr Pro Thr
625                 630                 635                 640

Thr Pro Ala Thr Pro Ser Ala Ala Ser Asn Gln Ser Leu Leu Ser Lys
```

```
            645                 650                 655
Ala Thr Asn Phe Ala Asn Asn Lys Gln Ala Gln Ala Ala His
            660                 665                 670

Ala Gln Ala Gln Ala Gln Ala Ala Gln Ala Gln Ser Gln Met His
        675                 680                 685

Met Gly Gly Met Gly Gly Ser Ser Gly Leu Glu Leu Asp Val Asn
    690                 695                 700

Gly Gly Met Gly Leu Asp Asn Asp Ser Ser Phe Leu Asn Asp Phe
705                 710                 715                 720

Ser Thr Gly Asn Glu Gly Asp Val Gly Met Asp Phe Asp Phe Asn
            725                 730                 735

Ser Phe Leu Asn Thr Asp Asp Asn Ala Ala Gly Ala Leu Lys Phe Asp
                740                 745                 750

Ser Gly Ser Ala Phe Gly Trp Gly Glu Gly Val Glu Ala Met Asn Glu
            755                 760                 765

<210> SEQ ID NO 8
<211> LENGTH: 598
<212> TYPE: PRT
<213> ORGANISM: Ogataea polymorpha

<400> SEQUENCE: 8

Met Ser Gln Asn Ala Thr Pro Gln Thr Thr Glu Gly His Met Ser Met
1               5                   10                  15

Asn Asp Gln Gln Ser Asn Ser Ser Gly Thr Asn Thr Glu His
            20                  25                  30

Pro Ser Ser Ser Val Ser Ser Val Pro Thr Val Ser Asp Ser Thr
        35                  40                  45

Ala Val Asn Ser Arg Glu Leu Leu Asn Ala Tyr Val Tyr Asp Phe Ile
    50                  55                  60

Leu Lys Ser Gly Phe Thr Ala Thr Ala Ser Ala Phe Phe Lys Glu Ala
65                  70                  75                  80

Asn Ile Pro Val Ile His Ser Glu Lys Arg Pro Thr Asn Ser Pro Ser
                85                  90                  95

Ser Ser Ala Thr Gly Thr Ser Asp Leu Pro Ala Ser Phe Met Thr Met
            100                 105                 110

Asp Ala Pro Gln Gly Phe Leu Tyr Glu Trp Trp Gln Ile Phe Trp Asp
        115                 120                 125

Val Phe Asn Ala Arg Thr Gln Arg Gly Gly Thr Thr Asn Ala Thr Gln
    130                 135                 140

Tyr Tyr His Tyr Val Asn Leu Lys Gln Lys Gln Asp His Leu Met Ser
145                 150                 155                 160

Gln Gln Ala Ala Ala Val Ala Ala Ala Ser Thr Val Met Asn Gly Asn
                165                 170                 175

Asn Thr Ser Met Ser Gly Ala Pro Val Thr Ser Ala Ala Gln Asp Ile
            180                 185                 190

Gly Val Leu Met Pro Gln Gln Gln Gln Gln Gln Ala Gln Met
        195                 200                 205

Ala His Pro Pro Gln Gln Val Pro Met Ala Gln Gln Arg Val Asn
    210                 215                 220

Ala Arg Met Gln Gln Pro Gln Gln Gln Ser Gln Ser Met Pro Met
225                 230                 235                 240

His Pro Gln Ala Ala Gln Ala Gln Met Asn Thr Leu Arg Gln Gln
                245                 250                 255
```

```
Gln Ile Ala Gln Ala Gln Ala Ala Gln Val Ala Gln Ala Val
            260                 265                 270

Ser Gln Arg Gly Ser Pro Ser Lys Arg Gln Arg Met Asp Ala Ala Gly
275                 280                 285

Asn Gly Ser Ala Thr Glu Ile Asn Gln Thr Ser Ser Pro Asn Ile Ala
            290                 295                 300

Met Asn Ser Gln Gln Gln Gln Gln Gln Gln His Pro Met Pro
305                 310                 315                 320

Met Pro Gln Gly Met Met Ile Pro Asn Gln Phe Gly Val Pro Gln Gln
                325                 330                 335

Tyr Ala Met Phe Ala Ala Ala Gln Ala Ala Gln Gln Gly Gln Ser Gln
            340                 345                 350

Gln Lys Phe Asn Gln Tyr Met Ile Pro Asn Phe Gln Asn Gln Pro Gln
            355                 360                 365

Gln Pro Gln Gln Gln Met Leu Met His Gln Gln Met His Gln Gln Ser
    370                 375                 380

Val His Met Gln His Asp Gln Gln His Pro Pro Pro Pro Pro Asn
385                 390                 395                 400

Val Pro Gln His Ser Gln Thr Phe Ser Asn Pro Asn Asp Phe Phe His
                405                 410                 415

Glu Met Pro Lys Gln Asn Asn Pro Gly Thr Ala Arg Val Asn Asp Thr
            420                 425                 430

Ala Ile Lys Asp Tyr Glu Lys Gln Leu Arg Leu Met Glu Ser Gln Asn
            435                 440                 445

Arg Arg Arg Leu Asp Val His Arg Asn Val Ser Asp Ser Lys Asp Pro
450                 455                 460

Asn Ser Pro Gly Ser Ala Gln Phe Thr Glu Tyr Ser Ala Met Leu Asn
465                 470                 475                 480

Gln Met Pro Pro Gln His Ala Ala Ser Ile Met Gln Arg Ala
                485                 490                 495

Ser Pro Ala Thr Lys Ala Ser Pro Thr Thr Lys Ser Pro Ala Asn Gly
            500                 505                 510

Ala Pro Pro Ala Asn Gly Lys Gln Lys Lys Ala Pro Arg Lys Ala Arg
            515                 520                 525

Lys Asn Ser Ser Ser Val Pro Ala Thr Pro Leu Thr Pro Ala Asn Asn
530                 535                 540

Gln Pro Thr Pro Gln Thr Asn Ile Pro Pro Thr Pro Gln Asn Thr Thr
545                 550                 555                 560

Pro Gln Gln Thr Pro Gln Ser Ser Ala Ala Ala Ser Gln Val Met
                565                 570                 575

Ala Gly Lys Lys Gly Ile Lys Arg Lys Asn Arg Gly Arg Ala Ile Tyr
            580                 585                 590

Pro Ile Glu Tyr Ser Arg
            595

<210> SEQ ID NO 9
<211> LENGTH: 771
<212> TYPE: PRT
<213> ORGANISM: Aspergillus niger

<400> SEQUENCE: 9

Met Asn Gln Met Asn Gln Met Asn Met Ala Gly Met Asn Pro Gly Ala
1               5                   10                  15

Gly Gly Pro Val Gly Gly Val Pro Met Ile Asn Asn Gly Ser Ala Ala
            20                  25                  30
```

-continued

```
Pro Arg Asn Glu Gln Asn Ile Asn Asn Ile Pro Glu Asn Met Ile Asn
         35                  40                  45

Asn Leu Asn Thr Tyr Ile Tyr Asp Tyr Phe Leu Lys Arg Gly Tyr His
     50                  55                  60

Asp Cys Ala Arg Ala Leu Val Lys Asp Glu Ser Ile Lys Leu Asn Thr
 65                  70                  75                  80

Glu Pro Pro Ile Lys Thr Ser Pro Gly His Arg Arg Asp Ala Asp Val
                 85                  90                  95

Asn Gly Val Asp Gly Asp Thr Met Met Thr Asp Gly Lys Asp Gly Asp
                100                 105                 110

Lys Leu Lys Ile Pro Asp Asp Leu Pro Arg Pro Asn Leu Pro Ser Glu
            115                 120                 125

Gly Gln Gln Ser Ser Phe Leu Leu Asp Trp Phe Ser Leu Phe Trp Asp
        130                 135                 140

Phe Phe Trp Ala Gln Arg Lys Lys Gly Asn Ser Asn Asp Val Arg Ser
145                 150                 155                 160

Tyr Leu Thr His Thr Gln Asn Met Met Arg Leu Arg Glu Gln His Gln
                165                 170                 175

Asn Gln Leu Leu Arg Gln Gln Pro Leu Met Asn Gly Gln Met Gly Gln
            180                 185                 190

Met Asn Ile Arg Arg Asn Gly Met Val Pro Pro Asn Leu Gln Lys Thr
        195                 200                 205

Val Leu Gln Asn Asn Thr Thr Gly Leu Ser Gln Gln Gln Leu Ala Gln
    210                 215                 220

Met His Lys Asn Gln Gln Val Gln Met Met Gln Gln Met Gln Arg Glu
225                 230                 235                 240

His Ser Asp Met Asp Met Asn Gly His Arg Pro Gln Ser Pro Ala Ser
                245                 250                 255

Ala Glu Asn Ala Pro Ser Pro Ser Lys Arg Pro Arg Leu Glu Gly Gly
            260                 265                 270

Pro Met Asn Gly Gln Gln Leu Ala Pro Asn Gly Arg Gly Gln Ala Gln
        275                 280                 285

Gly Ile Pro Gly Gln Pro Thr Pro Gln Ala Leu Leu Met Gln Asn Gly
    290                 295                 300

Leu Asn Arg Ala Met Asn Pro Asn Gln Phe Gln Ala Phe Gln Gln Ser
305                 310                 315                 320

Gly Pro Ala Ala Gln Gln Lys Gln Met Gln Gly Met Pro Asn Gly Met
                325                 330                 335

Met Asn Pro Ala Asn Val Met Ala Asn Pro Gln Thr Glu Met Val Ser
            340                 345                 350

Ile Pro Glu Gly Gln Val Tyr Pro Ile Asn Gly Asp Tyr Tyr Gly Ala
        355                 360                 365

Asn Gly Gln Met Ala Gln Val Arg Thr Gly Met Gln Thr Pro Gly Gly
    370                 375                 380

Gln His Gly Asn His Ala Leu Gln Asp Tyr Gln Met Gln Leu Met Leu
385                 390                 395                 400

Leu Glu Gln Gln Asn Lys Arg Arg Leu Met Met Ala Arg Gln Glu Gln
                405                 410                 415

Asp Ser Met Ala Arg Pro Asp Gly Gln Pro Gln Met Pro Gly Gln Gln
            420                 425                 430

Leu Pro Pro Gly Thr Ser Pro Gln Gly Ser Arg Ala Gly Thr Ser Pro
        435                 440                 445
```

Asn Pro Asn Asp Gln Met Lys Arg Gly Thr Pro Lys Met Pro Gln Thr
        450                 455                 460

Gly Leu Pro Gly Ser Pro Ser Ala Ala Asp Ala Met Ala Gln Gly Arg
465                 470                 475                 480

Gly Ser Pro Ala Ser Met Asn Phe Pro Gly Gly Gln Met Pro Pro Glu
                485                 490                 495

Met Ala Gly Pro Gln Phe Phe Val Lys Asn Met Ala Asp Gly Met Ala
                500                 505                 510

Ala Pro Asn Gly Met Arg Pro Ser Ser Asn Pro Ala Phe Ser Thr
            515                 520                 525

Pro Gln Met Gly Gln Pro Ile Gln Ala Gly Ala Asn Arg Met Pro Asn
530                 535                 540

Gly Gly Trp Gln Pro Gln Gln Gly Ala Gln Gly Gln Pro Met Ala Pro
545                 550                 555                 560

Gln Gln Ser Pro Ala Thr Gln Pro Gln Ser Thr Gly Thr Pro Gln Glu
                565                 570                 575

Arg Asn Ala Met Pro Pro Gln Ala Pro Pro Ala Pro Gly Ala Asn
                580                 585                 590

Val Gly Arg Thr Gln Pro Pro Ser Pro Gln Thr Ala Ala Pro Pro Thr
            595                 600                 605

Pro Gln Gln Gly Asn Lys Pro Ala Pro Lys Lys Lys Glu Thr Lys Asp
610                 615                 620

Ser Arg Lys Arg Pro Lys Lys Gly Ala Ala Ala Ala Ala Ala Ala
625                 630                 635                 640

Gln Ala Asn Thr Ala Ala Thr Pro Ser Ser Glu Ala Glu His Pro Pro
                645                 650                 655

Thr Pro Thr Pro Ser Thr Pro Ile Thr Pro Gln His Pro Asn Ser Phe
                660                 665                 670

Asn Lys Thr Gly Ala Asn Ala Thr Thr Ser Ala Pro Gln Gln Pro Thr
            675                 680                 685

Ser Ala Pro Ala Pro Pro Leu Val Gln Gln Pro Asp Gln Thr
            690                 695                 700

Gln Gln Pro Phe Asn Glu Leu Ser Ile Pro Asp Ala Ser Ala Phe Asn
705                 710                 715                 720

Leu Asp Phe Ser Ala Leu Glu Asn Pro Asp Ile Leu Glu Asn Phe Asp
                725                 730                 735

Phe Asp Thr Phe Leu Asn Thr Asp Ala Asp Thr Ala Gly Phe Gly Phe
            740                 745                 750

Asp Pro Asn Thr Ser Tyr Pro Asp Gly Val Glu Thr Gly Ala Gly
            755                 760                 765

Asp Gly Leu
    770

<210> SEQ ID NO 10
<211> LENGTH: 1240
<212> TYPE: DNA
<213> ORGANISM: Artificial Sequence
<220> FEATURE:
<223> OTHER INFORMATION: promoter

<400> SEQUENCE: 10
caaacatttg ctcccctag tctccaggga aatgtaaaat atactgctaa tagaaaacag      60
taagacgctc agttgtcagg ataattacgt tcgactgtag taaaacagga atctgtattg     120
ttagaaagaa cgagagtttt ttacggcgcc gccatattgg gccgtgtgaa aacagcttga    180

| | |
|---|---|
| aaccccacta ctttcaaagg ttctgttgct atacacgaac catgtttaac caacctcgct | 240 |
| tttgacttga ctgaagtcat cggttaacaa tcaagtaccc tagtctgtct gaatgctcct | 300 |
| ttccatattc agtaggtgtt tcttgcactt ttgcatgcac tgcggaagaa ttagccaata | 360 |
| gcgcgtttca tatgcgcttt taccccctct tttgtcaagc gcaaaatgcc tgtaagattt | 420 |
| ggtgggggtg tgagccgtta gctgaagtac aacaggctaa ttccctgaaa aaactgcagc | 480 |
| tcagggattc ccactatttg gtattctgat atgttttcc tgatatgcat caaaactcta | 540 |
| atctaaaacc tgaatctccg ctattttttt tttttttga tgaccccgtt ttcgtgacaa | 600 |
| attaatttcc aacggggtct tgtccggata agagaatttt gtttgattat ccgttcggat | 660 |
| aaatggacgc ctgctccata tttttccggt tattacccca cctggaagtg cccagaattt | 720 |
| tccggggatt acggataata cggtggtctg gattaattaa tacgagatct cagggattcc | 780 |
| cactatttgg tattctgata tgttttcct gatatgcatc aaaactctaa tctaaaacct | 840 |
| gaatctccgc tattttttt tttttttgat gaccccgttt tcgtgacaaa ttaatttcca | 900 |
| acggggtctt gtccggataa gagaattttg tttgattatc cgttcggata aatggacgcc | 960 |
| tgctccatat ttttccggtt attacccac ctggaagtgc ccagaatttt ccggggatta | 1020 |
| cggataatac ggtggtctgg attaattaat acgccaagtc ttacattttg ttgcagtctc | 1080 |
| gtgcgagtat gtgcaataat aaacaagatg agccaattta ttggattagt tgcagcttga | 1140 |
| ccccgccata gctaggcata gccaagtgct atgggtgtta gatgatgcac ttggatgcag | 1200 |
| tgagttttgg agtataaaag atccttaaaa ttccacccct | 1240 |

<210> SEQ ID NO 11
<211> LENGTH: 1425
<212> TYPE: DNA
<213> ORGANISM: Artificial Sequence
<220> FEATURE:
<223> OTHER INFORMATION: promoter

<400> SEQUENCE: 11

| | |
|---|---|
| caaacatttg ctcccctag tctccaggga aatgtaaaat atactgctaa tagaaaacag | 60 |
| taagacgctc agttgtcagg ataattacgt tcgactgtag taaaacagga atctgtattg | 120 |
| ttagaaagaa cgagagtttt ttacggcgcc gccatattgg gccgtgtgaa aacagcttga | 180 |
| aaccccacta ctttcaaagg ttctgttgct atacacgaac catgtttaac caacctcgct | 240 |
| tttgacttga ctgaagtcat cggttaacaa tcaagtaccc tagtctgtct gaatgctcct | 300 |
| ttccatattc agtaggtgtt tcttgcactt ttgcatgcac tgcggaagaa ttagccaata | 360 |
| gcgcgtttca tatgcgcttt taccccctct tttgtcaagc gcaaaatgcc tgtaagattt | 420 |
| ggtgggggtg tgagccgtta gctgaagtac aacaggctaa ttccctgaaa aaactgcagc | 480 |
| tcagggattc ccactatttg gtattctgat atgttttcc tgatatgcat caaaactcta | 540 |
| atctaaaacc tgaatctccg ctattttttt tttttttgat gaccccgttt tcgtgacaaa | 600 |
| ttaatttcca acggggtctt gtccggataa gagaattttg tttgattatc cgttcggata | 660 |
| aatggacgcc tgctccatat ttttccggtt attacccac ctggaagtgc ccagaatttt | 720 |
| ccggggatta cggataatac ggtggtctgg attaattaat acgccaagtc ttacattttg | 780 |
| ttgcagtctc gtgcgagtat gtgcaataat aaacaagatg agccaattta ttggattagt | 840 |
| tgcagcttga ccccgccata gctaggcata gccaagtgct atgggtgtta gatgatgcac | 900 |
| ttggatgcag tgagttttgg agtataaaag atccttaaaa ttccacccct agatctcagg | 960 |
| gattcccact atttggtatt ctgatatgtt tttcctgata tgcatcaaaa ctctaatcta | 1020 |

```
aaacctgaat ctccgctatt ttttttttt ttgatgaccc cgttttcgtg acaaattaat    1080
ttccaacggg gtcttgtccg gataagagaa ttttgtttga ttatccgttc ggataaatgg    1140
acgcctgctc catattttc cggttattac cccacctgga agtgcccaga attttccggg    1200
gattacggat aatacggtgg tctggattaa ttaatacgcc aagtcttaca ttttgttgca    1260
gtctcgtgcg agtatgtgca ataataaaca agatgagcca atttattgga ttagttgcag    1320
cttgaccccg ccatagctag gcatagccaa gtgctatggg tgttagatga tgcacttgga    1380
tgcagtgagt tttggagtat aaaagatcct taaaattcca ccctt                    1425

<210> SEQ ID NO 12
<211> LENGTH: 966
<212> TYPE: DNA
<213> ORGANISM: Artificial Sequence
<220> FEATURE:
<223> OTHER INFORMATION: promoter
<220> FEATURE:
<221> NAME/KEY: misc_feature
<222> LOCATION: (592)..(593)
<223> OTHER INFORMATION: n is T or absent

<400> SEQUENCE: 12
caaacatttg ctcccctag tctccaggga aatgtaaaat atactgctaa tagaaaacag     60
taagacgctc agttgtcagg ataattacgt tcgactgtag taaaacagga atctgtattg    120
ttagaaagaa cgagagtttt ttacggcgcc gccatattgg gccgtgtgaa acagcttga    180 aaccccacta ctttcaaagg ttctgttgct atacacgaac catgtttaac caacctcgct    240
tttgacttga ctgaagtcat cggttaacaa tcaagtaccc tagtctgtct gaatgctcct    300
ttccatattc agtaggtgtt tcttgcactt ttgcatgcac tgcggaagaa ttagccaata    360
gcgcgtttca tatgcgcttt taccccctct tttgtcaagc gcaaaatgcc tgtaagattt    420
ggtgggggtg tgagccgtta gctgaagtac aacaggctaa ttccctgaaa aaactgcaga    480
tagacttcaa gatctcaggg attcccacta tttggtattc tgatatgttt ttcctgatat    540
gcatcaaaac tctaatctaa aacctgaatc tccgctattt ttttttttt tnngatgacc    600 ccgttttcgt gacaaattaa tttccaacgg ggtcttgtcc ggataagaga attttgtttg    660
attatccgtt cggataaatg gacgcctgct ccatatttt ccggttatta ccccacctgg    720
aagtgcccag aattttccgg ggattacgga taatacggtg gtctggatta attaatacgc    780
caagtcttac attttgttgc agtctcgtgc gagtatgtgc aataataaac aagatgagcc    840
aatttattgg attagttgca gcttgacccc gccatagcta ggcatagcca agtgctatgg    900
gtgttagatg atgcacttgg atgcagtgag ttttggagta taaaagatcc ttaaaattcc    960
accctt                                                              966

<210> SEQ ID NO 13
<211> LENGTH: 1000
<212> TYPE: DNA
<213> ORGANISM: Artificial Sequence
<220> FEATURE:
<223> OTHER INFORMATION: promoter

<400> SEQUENCE: 13
gtaaatagcg gcagcaatcc agtaaccttt tctgaatagc agagccttaa ctaaaataat     60
ggccagggta aaaattcga aatttgacac caaaaataaa gacttgtcgt tataagtctt    120
aacaaagtcc gcaattttgg agctaacggt ggcggttgct gggatattca ataatggtag    180
```

```
aatgttgctg cgggtatatg acagagcgtg aaacacactg aacaaggtaa atggaacaac      240
agcaattgca atatggggga ggatagtcaa gaacaaagca gcaatggcaa agtactgaat      300
attctccaaa gccaaaaggt ccagtggttt caacgacaaa gtcttgttgg tatagctttg      360
gaacaaaagg acaccgaaag actcgacagc gcccacaaat acagcgttgt agaagaacga      420
attgattgct ccagagcttc taatagtcag aagataccc aaacctccga gcaacgttag        480
cacatgacct aagaaccagg cgaagtgaag agtctggaat aacgacaccc agtcagtttt      540
tcctgagctc ctggtgggat tggtagaagc atttgatttg cttggagtgg ttttatttga      600
agatggtgtt gaagccattg ttgctaaaga gtcggagttt tgcttttagg gtttgttaag      660
caaaggagga aaaactgcgc cgtttgaagt cccaggtagt ttcgcgtgtg aggccagcca      720
gggaaagctt ccttcggtac ttttttttct tttgcaggtt ccggacggat taagcttcgg      780
gttatgaggg gggcggtagc caattccgga cacaatattg cgtcgcagct agtcaccccg      840
ccataaatat acgcaggatt gaggtaataa catcgatagt cttagtaatt aatacaattc      900
agtggcgaat ttggcaacat gacgtaaggc ccactgttgt ctataaaagg ggatgaattt      960
tcatgttttt gaggcctccc ggacaattta ttgaactcaa                            1000

<210> SEQ ID NO 14
<211> LENGTH: 1000
<212> TYPE: DNA
<213> ORGANISM: Artificial Sequence
<220> FEATURE:
<223> OTHER INFORMATION: promoter

<400> SEQUENCE: 14
tggactgttc aatttgaagt cgatgctgac gatgtcaaga gagatgctca attatatttg       60
tcatttgctg gttacactgg aaacgctact tttgttggcg gaaactctac cagtttggcc      120
gtccatgtaa acgatgtcgt tctgggccgt gaccgtttca acacgaacat aaccaatgac      180
aaatccactt acaggtctag ttcatatgga ggcaattggt accttacttc tttggatgtc      240
ccaagtgggg ctttaacgtc tggtactaac aatgtctcgt ttgtcactac aaactccgag      300
gtaaataaag gattcttgtg ggattctctc aagtttgttt ggaagttgta acaggtttat      360
aagcatatcg tgcgcttgtc cacaattgaa tcatttattg ttgcgagata catgaacaaa      420
gtgtgaactg ggacccatta ctacaattcc cacgcaaccg ttgtttcaaa gcccatattt      480
tttgacaatt gtttcgttac accccagtt tgatgtacat cgcttgcaat gatgtgtgtc       540
ccggagtatt ttccatattc agcttgaatt cgtatactca accatatct gggggtatac        600 ttttatgtaa cctatacaaa tcaactatac tatttcacct ttcgaccaat catctcccat      660
cttgttaagt tttgcttcct atatccctga ccctgcatc acccatgatt ccgctcaacg        720
gttctcctct acatcgtccc tcttttggag agggtgttca gtttgacatt caaattaccc      780
cccgccatca cgcgcaaccg agaccgcacc cccgaatttt cacaaattac cccacaccct      840
atactccacc actatgaggg ttattagaac tgatcacgta taaataccac cgcaagttcc      900
caagggatcg tgttcttctt ctccaattgc aatcatattt ctgactcttt ctagttcaga      960
ttaattcctt tacacttgct ttttttccctt acctttatcc                           1000

<210> SEQ ID NO 15
<211> LENGTH: 1001
<212> TYPE: DNA
<213> ORGANISM: Artificial Sequence
<220> FEATURE:
<223> OTHER INFORMATION: promoter
```

<400> SEQUENCE: 15

```
agaccagcag tttaactacg caaatccaca ggaatttcta catcacaata ccaatggtaa    60
taccacgacg tcaaggaatg gaaacgacga cttggaggaa gacttcgtca acctcttgcg   120
gagtacccga ggctaagaca ataagaagaa aaaaaaaga aaagcggtgg gggagggatt   180
attaaataag gattatgtaa ccccagggta ccgttctata catatttaag gattatttag   240
gacaatcgat gaaatcggca tcaaactgga tgggagtata gtgtccggat aatcggataa   300
atcatcttgc gaggagccgc ttggttggtt ggtgagagga gtgaaatatg tgtctcctca   360
cccaagaatc gcgatatcag caccctgtgg gggacactat tggcctccct cccaaacctt   420
cgatgtggta gtgctttatt atattgatta cattgattac atagctaaac cctgcctggt   480
tgcaagttga gctccgaatt ccaatattag taaaatgcct gcaagataac ctcggtatgg   540
cgtccgaccc cgcttaatta ttttaactcc tttccaacga ggacttcgta attttttgatt   600
agggagttga gaaacggggg gtcttgatac ctcctcgatt tcagatccca ccccctctca   660
gtcccaagtg ggacccccct cggccgtgaa atgcgcgcac tttagttttt ttcgcatgta   720
aacgccggtg tccgtcaatt aaaagtcgca gactagggtg aactttacca tttttgtcgc   780
actccgtctc ctcggaatag gggtgtagta attctgcagt agtgcaattt ttaccccgcc   840
aagggggggc gaaagagac gacctcatca cgcattctcc agtcgctctc tacgcctaca   900
gcaccgacgt agttaacttt ctcccatata taagcaatt gccattcccc tgaaaacttt   960
aacctctgct ttttcttgat ttttccttgc ccaaagaaaa g                      1001
```

<210> SEQ ID NO 16
<211> LENGTH: 1000
<212> TYPE: DNA
<213> ORGANISM: Artificial Sequence
<220> FEATURE:
<223> OTHER INFORMATION: promoter

<400> SEQUENCE: 16

```
ctgcacaacc attgccagta aggacgaaga gaaggcccca ctacccaaaa ttcaggataa    60
cgtcttcata ccatgcagcg acgcctacaa gacgctgtca agacatgcca acttcaacga   120
agtgaacttt aacacattga tcgggaaatt gaccaccaag ggaatgctgg ttgaggctgg   180
aagcgttgcc agtgtcctga gggaactgga ccgaaagttt agtaatgcat aagaggatat   240
atataggaat gcagtaataa tattagtacc cattaagtgg gctaagccat tggaaggccg   300
tctgactgat ggtggtgttc ttctcattta gatagtgcat ttgcaactac cgtctgagat   360
tgagtttgat gtgaagctcc agcgccaaaa cagtataaga accttatctc cgcattattg   420
ttcttgcgta aaagtttgtg tgaagaaaca ggggtagttg cgcagattag ttgtaatatg   480
cgcataggat gggtcattga cttctttcct cgaaagagcc acaccgttag ctaaaaaagg   540
acgcgcatct acccccaaaat agaatgtggg gaaataggac gcgcaacttc ctctcaatca   600
ctggacgtca gaaaaacaaa tgcgcaatcg agtcaccctc cgtgataccc tccgtgatac   660
ccctctccg tctattctga cagcgtctcc ccatgacgtt tcaatctact tagaaaagat   720
ttcgtttttt tttccttcaa ttacacgatc tcatcttctg caagggtctg gaggacatca   780
ccaatctgcg actccataac ttagtcctga gtttatattt acgcttcatc tgatgagtag   840
gaagaaaaag tttcacgaaa ttccccgcc aacttgccct tcggaataag cagccactct   900
ccttctgccc atagtaagct tgcgcgaggc cccaacttgg ccagaaactt taaatatgcc   960
```

```
aaacaatctc ccccaatcta agttctccct cttctaaaaa                          1000
```

<210> SEQ ID NO 17
<211> LENGTH: 9
<212> TYPE: DNA
<213> ORGANISM: Artificial Sequence
<220> FEATURE:
<223> OTHER INFORMATION: regulatory region

<400> SEQUENCE: 17

```
ataaatgga                                                              9
```

<210> SEQ ID NO 18
<211> LENGTH: 15
<212> TYPE: DNA
<213> ORGANISM: Artificial Sequence
<220> FEATURE:
<223> OTHER INFORMATION: regulatory region

<400> SEQUENCE: 18

```
catattttc cggtt                                                       15
```

<210> SEQ ID NO 19
<211> LENGTH: 15
<212> TYPE: DNA
<213> ORGANISM: Artificial Sequence
<220> FEATURE:
<223> OTHER INFORMATION: motif

<400> SEQUENCE: 19

```
tattttttt ttttt                                                       15
```

<210> SEQ ID NO 20
<211> LENGTH: 15
<212> TYPE: DNA
<213> ORGANISM: Artificial Sequence
<220> FEATURE:
<223> OTHER INFORMATION: motif

<400> SEQUENCE: 20

```
ttttttttt ttttt                                                       15
```

<210> SEQ ID NO 21
<211> LENGTH: 16
<212> TYPE: DNA
<213> ORGANISM: Artificial Sequence
<220> FEATURE:
<223> OTHER INFORMATION: motif

<400> SEQUENCE: 21

```
tattttttt tttttt                                                      16
```

<210> SEQ ID NO 22
<211> LENGTH: 16
<212> TYPE: DNA
<213> ORGANISM: Artificial Sequence
<220> FEATURE:
<223> OTHER INFORMATION: motif

<400> SEQUENCE: 22

```
ttttttttt tttttt                                                      16
```

<210> SEQ ID NO 23
<211> LENGTH: 17
<212> TYPE: DNA
<213> ORGANISM: Artificial Sequence

```
<220> FEATURE:
<223> OTHER INFORMATION: motif

<400> SEQUENCE: 23 tattttttt tttttt                                                    17

<210> SEQ ID NO 24
<211> LENGTH: 17
<212> TYPE: DNA
<213> ORGANISM: Artificial Sequence
<220> FEATURE:
<223> OTHER INFORMATION: motif

<400> SEQUENCE: 24
tttttttttt ttttttt                                                  17

<210> SEQ ID NO 25
<211> LENGTH: 18
<212> TYPE: DNA
<213> ORGANISM: Artificial Sequence
<220> FEATURE:
<223> OTHER INFORMATION: motif

<400> SEQUENCE: 25 tattttttt ttttttt                                                   18

<210> SEQ ID NO 26
<211> LENGTH: 18
<212> TYPE: DNA
<213> ORGANISM: Artificial Sequence
<220> FEATURE:
<223> OTHER INFORMATION: motif

<400> SEQUENCE: 26
tttttttttt ttttttt                                                  18

<210> SEQ ID NO 27
<211> LENGTH: 19
<212> TYPE: DNA
<213> ORGANISM: Artificial Sequence
<220> FEATURE:
<223> OTHER INFORMATION: motif

<400> SEQUENCE: 27 tattttttt tttttttt                                                  19

<210> SEQ ID NO 28
<211> LENGTH: 19
<212> TYPE: DNA
<213> ORGANISM: Artificial Sequence
<220> FEATURE:
<223> OTHER INFORMATION: motif

<400> SEQUENCE: 28
tttttttttt tttttttt                                                 19

<210> SEQ ID NO 29
<211> LENGTH: 20
<212> TYPE: DNA
<213> ORGANISM: Artificial Sequence
<220> FEATURE:
<223> OTHER INFORMATION: motif

<400> SEQUENCE: 29 tattttttt ttttttttt                                                 20
```

```
<210> SEQ ID NO 30
<211> LENGTH: 20
<212> TYPE: DNA
<213> ORGANISM: Artificial Sequence
<220> FEATURE:
<223> OTHER INFORMATION: motif

<400> SEQUENCE: 30
tttttttttt tttttttttt                                              20

<210> SEQ ID NO 31
<211> LENGTH: 21
<212> TYPE: DNA
<213> ORGANISM: Artificial Sequence
<220> FEATURE:
<223> OTHER INFORMATION: motif

<400> SEQUENCE: 31
tatttttttt tttttttttt t                                            21

<210> SEQ ID NO 32
<211> LENGTH: 21
<212> TYPE: DNA
<213> ORGANISM: Artificial Sequence
<220> FEATURE:
<223> OTHER INFORMATION: motif

<400> SEQUENCE: 32
tttttttttt tttttttttt t                                            21

<210> SEQ ID NO 33
<211> LENGTH: 22
<212> TYPE: DNA
<213> ORGANISM: Artificial Sequence
<220> FEATURE:
<223> OTHER INFORMATION: motif

<400> SEQUENCE: 33
tatttttttt tttttttttt tt                                           22

<210> SEQ ID NO 34
<211> LENGTH: 22
<212> TYPE: DNA
<213> ORGANISM: Artificial Sequence
<220> FEATURE:
<223> OTHER INFORMATION: motif

<400> SEQUENCE: 34
tttttttttt tttttttttt tt                                           22

<210> SEQ ID NO 35
<211> LENGTH: 33
<212> TYPE: DNA
<213> ORGANISM: Artificial Sequence
<220> FEATURE:
<223> OTHER INFORMATION: main regulatory region

<400> SEQUENCE: 35
ataaatggac gcctgctcca tattttccg gtt                                33

<210> SEQ ID NO 36
<211> LENGTH: 9
<212> TYPE: DNA
<213> ORGANISM: Artificial Sequence
<220> FEATURE:
<223> OTHER INFORMATION: spacer core region
```

<400> SEQUENCE: 36 cgcctgctc                                                                          9

<210> SEQ ID NO 37
<211> LENGTH: 255
<212> TYPE: DNA
<213> ORGANISM: Artificial Sequence
<220> FEATURE:
<223> OTHER INFORMATION: spacer main region

<400> SEQUENCE: 37
attaccccac ctggaagtgc ccagaatttt ccggggatta cggataatac ggtggtctgg     60
attaattaat acgagatctc agggattccc actatttggt attctgatat gttttcctg     120 atatgcatca aaactctaat ctaaaacctg aatctccgct tttttttttt tttttgatga    180
ccccgttttc gtgacaaatt aatttccaac ggggtcttgt ccggataaga gaattttgtt   240
tgattatccg ttcgg                                                     255

<210> SEQ ID NO 38
<211> LENGTH: 10
<212> TYPE: DNA
<213> ORGANISM: Artificial Sequence
<220> FEATURE:
<223> OTHER INFORMATION: translation initiation site

<400> SEQUENCE: 38
ttccaccctt                                                                         10

<210> SEQ ID NO 39
<211> LENGTH: 9
<212> TYPE: DNA
<213> ORGANISM: Artificial Sequence
<220> FEATURE:
<223> OTHER INFORMATION: translation initiation site

<400> SEQUENCE: 39 ttcgaaacg                                                                          9

<210> SEQ ID NO 40
<211> LENGTH: 9
<212> TYPE: DNA
<213> ORGANISM: Artificial Sequence
<220> FEATURE:
<223> OTHER INFORMATION: translation initiation site
<220> FEATURE:
<221> NAME/KEY: misc_feature
<222> LOCATION: (7)..(7)
<223> OTHER INFORMATION: R at position 7 is A or G, preferably A

<400> SEQUENCE: 40 gccgccrcc                                                                          9

<210> SEQ ID NO 41
<211> LENGTH: 859
<212> TYPE: DNA
<213> ORGANISM: Artificial Sequence
<220> FEATURE:
<223> OTHER INFORMATION: promoter

<400> SEQUENCE: 41
ggaatctgta ttgttagaaa gaacgagagt tttttacggc gccgccatat tgggccgtgt    60
gaaaacagct tgaaaccccca ctactttcaa aggttctgtt gctatacacg aaccatgttt   120

```
aaccaacctc gcttttgact tgactgaagt catcggttaa caatcaagta ccctagtctg      180
tctgaatgct cctttccata ttcagtaggt gtttcttgca cttttgcatg cactgcggaa      240
gaattagcca atagcgcgtt tcatatgcgc ttttaccccc tcttttgtca agcgcaaaat      300
gcctgtaaga tttggtgggg gtgtgagccg ttagctgaag tacaacaggc taattccctg      360
aaaaaactgc agatagactt caagatctca gggattccca ctatttggta ttctgatatg      420
tttttcctga tatgcatcaa aactctaatc taaaacctga atctccgcta tttttttttt      480 tttttgatg accccgtttt cgtgacaaat aatttccaa cggggtcttg tccggataag       540
agaattttgt ttgattatcc gttcggataa atggacgcct gctccatatt tttccggtta     600 ttacccacc tggaagtgcc cagaattttc cggggattac ggataatacg gtggtctgga      660
ttaattaata cgccaagtct tacattttgt tgcagtctcg tgcgagtatg tgcaataata     720
aacaagatga gccaatttat tggattagtt gcagcttgac cccgccatag ctaggcatag     780
ccaagtgcta tgggtgttag atgatgcact tggatgcagt gagttttgga gtataaaaga     840
tccttaaaat tccacccctt                                                 859

<210> SEQ ID NO 42
<211> LENGTH: 664
<212> TYPE: DNA
<213> ORGANISM: Artificial Sequence
<220> FEATURE:
<223> OTHER INFORMATION: promoter

<400> SEQUENCE: 42
ccatattcag taggtgtttc ttgcactttt gcatgcactg cggaagaatt agccaatagc      60
gcgtttcata tgcgctttta ccccctcttt tgtcaagcgc aaaatgcctg taagatttgg    120
tgggggtgtg agccgttagc tgaagtacaa caggctaatt ccctgaaaaa actgcagata    180
gacttcaaga tctcagggat tcccactatt tggtattctg atatgttttt cctgatatgc    240
atcaaaactc taatctaaaa cctgaatctc cgctattttt tttttttttt tgatgacccc    300
gttttcgtga caaattaatt tccaacgggg tcttgtccgg ataagagaat ttgtttgat     360 tatccgttcg gataaatgga cgcctgctcc atattttttcc ggttattacc ccacctggaa    420
gtgcccagaa ttttccgggg attacggata atacggtggt ctggattaat taatacgcca    480
agtcttacat tttgttgcag tctcgtgcga gtatgtgcaa taataaacaa gatgagccaa    540
tttattggat tagttgcagc ttgaccccgc catagctagg catagccaag tgctatgggt    600
gttagatgat gcacttggat gcagtgagtt tggagtata aaagatccct aaaattccac    660
cctt                                                                 664

<210> SEQ ID NO 43
<211> LENGTH: 493
<212> TYPE: DNA
<213> ORGANISM: Artificial Sequence
<220> FEATURE:
<223> OTHER INFORMATION: promoter

<400> SEQUENCE: 43
ctgcagatag acttcaagat ctcagggatt cccactattt ggtattctga tatgttttc      60 ctgatatgca tcaaaactct aatctaaaac ctgaatctcc gctattttt tttttttttt    120 gatgacccg ttttcgtgac aaattaattt ccaacggggt cttgtccgga taagagaatt     180
ttgtttgatt atccgttcgg ataaatggac gcctgctcca tatttttcg gttattaccc     240 cacctggaag tgcccagaat tttccgggga ttacggataa tacggtggtc tggattaatt    300
```

```
aatacgccaa gtcttacatt ttgttgcagt ctcgtgcgag tatgtgcaat aataaacaag    360
atgagccaat ttattggatt agttgcagct tgaccccgcc atagctaggc atagccaagt    420
gctatgggtg ttagatgatg cacttggatg cagtgagttt tggagtataa aagatcctta    480
aaattccacc ctt                                                       493
```

```
<210> SEQ ID NO 44
<211> LENGTH: 370
<212> TYPE: DNA
<213> ORGANISM: Artificial Sequence
<220> FEATURE:
<223> OTHER INFORMATION: promoter

<400> SEQUENCE: 44
gaccccgttt tcgtgacaaa ttaatttcca acggggtctt gtccggataa gagaattttg     60
tttgattatc cgttcggata aatggacgcc tgctccatat ttttccggtt attacccac    120 ctggaagtgc ccagaatttt ccggggatta cggataatac ggtggtctgg attaattaat   180
acgccaagtc ttacattttg ttgcagtctc gtgcgagtat gtgcaataat aaacaagatg   240
agccaattta ttggattagt tgcagcttga ccccgccata gctaggcata gccaagtgct   300
atgggtgtta gatgatgcac ttggatgcag tgagttttgg agtataaaag atccttaaaa   360
ttccacccTT                                                          370
```

```
<210> SEQ ID NO 45
<211> LENGTH: 328
<212> TYPE: DNA
<213> ORGANISM: Artificial Sequence
<220> FEATURE:
<223> OTHER INFORMATION: promoter

<400> SEQUENCE: 45
ccggataaga gaattttgtt tgattatccg ttcggataaa tggacgcctg ctccatattt     60
ttccggttat taccccacct ggaagtgccc agaattttcc ggggattacg gataatacgg    120
tggtctggat taattaatac gccaagtctt acattttgtt gcagtctcgt gcgagtatgt    180
gcaataataa acaagatgag ccaatttatt ggattagttg cagcttgacc ccgccatagc    240
taggcatagc caagtgctat gggtgttaga tgatgcactt ggatgcagtg agttttggag    300
tataaaagat ccttaaaatt ccacccTT                                       328
```

```
<210> SEQ ID NO 46
<211> LENGTH: 1000
<212> TYPE: DNA
<213> ORGANISM: Pichia pastoris

<400> SEQUENCE: 46
ctgctactct ggtcccaagt gaaccacctt ttggacccta ttgaccggac cttaacttgc     60
caaacctaaa cgcttaatgc ctcagacgtt ttaatgcctc tcaacacctc caaggttgct    120
ttcttgagca tgcctactag gaactttaac gaactgtggg gttgcagaca gtttcaggcg    180
tgtcccgacc aatatggcct actagactct ctgaaaaatc acagttttcc agtagttccg    240
atcaaattac catcgaaatg gtcccataaa cggacatttg catccgttc ctgaattata    300 gtcttccacc gtggatcatg gtgttccttt ttttcccaaa gaatatcagc atcccttaac    360
tacgttaggt cagtgatgac aatggaccaa attgttgcaa ggttttcttt tttctttcat    420
cggcacattt cagcctcaca tgcgactatt atcgatcaat gaaatccatc aagattgaaa    480
```

```
tcttaaaatt gccccttttca cttgacagga tccttttttg tagaaatgtc ttggtgtcct    540
cgtccaatca ggtagccatc tctgaaatat ctggctccgt tgcaactccg aacgacctgc    600
tggcaacgta aaattctccg gggtaaaact taaatgtgga gtaatggaac cagaaacgtc    660
tcttcccttc tctctccttc caccgcccgt taccgtccct aggaaatttt actctgctgg    720
agagcttctt ctacggcccc cttgcagcaa tgctcttccc agcattacgt tgcgggtaaa    780
acggaggtcg tgtacccgac ctagcagccc agggatggaa aagtcccggc cgtcgctggc    840
aataatagcg ggcggacgca tgtcatgaga ttattggaaa ccaccagaat cgaatataaa    900
aggcgaacac ctttcccaat tttggtttct cctgacccaa agactttaaa tttaatttat    960
ttgtccctat ttcaatcaat tgaacaacta tcaaaacaca                         1000
```

<210> SEQ ID NO 47
<211> LENGTH: 756
<212> TYPE: PRT
<213> ORGANISM: Pichia pastoris

<400> SEQUENCE: 47

```
Met Ile Pro Thr Ile Asp Pro Lys Asp Pro Glu Leu Val Ser Glu Asp
1               5                   10                  15

Thr Ala Gln Ser Ala Ser Ala Arg Lys Arg Ser Lys Val Ser Arg Ala
            20                  25                  30

Cys Asp Glu Cys Arg Arg Lys Lys Ile Lys Cys Asp Ala Thr Phe Leu
        35                  40                  45

Ala Asn Ser Asn Thr Leu Leu Lys Pro Cys Thr Asn Cys Tyr Lys Tyr
    50                  55                  60

Asn Cys Ser Cys Ser Phe Thr Arg Val Pro Leu Lys Arg Gly Pro Ser
65                  70                  75                  80

Lys Gly Phe Ala Arg Asp Gly Ser Gly Tyr Glu Arg Arg Ser Ser
                85                  90                  95

Ser Val His Ser Val Ser Ser Gln Ser Val Thr Ser Pro Val Pro
            100                 105                 110

Ser His Ala Ser Leu Pro Ile Pro Pro Ala Asn Pro Val Ser Leu Pro
        115                 120                 125

Arg Leu Asn Val Pro Gly Asp Gly Leu Leu Ser Pro Lys Ala Val Pro
    130                 135                 140

Pro Thr Asn Leu Phe Trp Lys Val Pro Tyr Glu Leu Pro Ser Phe Ser
145                 150                 155                 160

Asp Arg Arg Ser Ser Val Ala Ser Ala Asp Ser Phe Arg Arg Pro Ser
                165                 170                 175

Ile Tyr Gln Ser Asp Ser Glu Asp Asp Phe Tyr Ser Ala Thr Gly Ser
            180                 185                 190

Gln Arg Asn Ser Ile Ser Gln Ala Pro Arg Gln Arg Asn Leu Ser Pro
        195                 200                 205

Ala Leu Ser Val Ser Ser Thr Ser Ser Leu Asn Asn Arg Ile Lys Ser
    210                 215                 220

Leu Asn Met Val Ala Ser Thr Leu Glu Ser Asn Ile His Asn Tyr Tyr
225                 230                 235                 240

Ser Gln Gly Phe Asn Ser Ser Leu Pro Ile Leu Pro Leu Asp Glu Arg
                245                 250                 255

Ile Leu Ser Thr Leu Leu Ser Asn Val Ser Asn Gly Ser Ser Ser Ala
            260                 265                 270

Ser Trp Asp Ala Ile Arg Ser Pro Ile Leu Glu Leu Phe Asp Lys Ser
        275                 280                 285
```

-continued

```
Ile Leu Met Leu Leu Arg Ser Tyr Glu Ser Gln Phe Asn Phe Asn Asp
        290                 295                 300
Leu Leu Asp His Val Thr Glu Met Gln Ser Ile Tyr Pro Arg Ile Arg
305                 310                 315                 320
Ser His Leu Leu Ser Asp Glu Leu Leu Lys Leu Ile Phe Leu Met Ser
                    325                 330                 335
Gly Val Leu Thr Asp Tyr Ala Leu Ile Leu Thr Gly Gln Pro Tyr Ser
                340                 345                 350
Thr Gly Leu Ser Ile Thr Val Ser Val Phe Asn Asp Trp Lys Thr Tyr
            355                 360                 365
Glu Asn Val Gln Arg Val Leu Val Ile Asn Arg Ala Gly Ser Leu Asp
370                 375                 380
Leu Asp Tyr Asp Ser Leu Pro Phe Leu Phe Ala Arg Cys Tyr Leu Ser
385                 390                 395                 400
Leu Ala Thr Leu Asp Leu Ile Tyr Ser Leu Ser Phe Ser Ser Pro Arg
                405                 410                 415
Leu Ile Ser Ser Phe Ala Asn Leu Pro Ile Leu Asp Ile Val Gln Lys
                420                 425                 430
Cys Gly Ile Thr Lys Asp Ala Lys Leu Asp Glu Thr Pro Leu Pro Val
            435                 440                 445
Leu Asp Gln Phe Leu Asn Cys Phe Leu Pro Gly Asp Thr Tyr Pro Thr
450                 455                 460
Ala Leu Asn Thr Leu Lys Thr Gly Leu Val Leu Leu Asp Phe Thr Asn
465                 470                 475                 480
Asn Arg Ser Thr Thr Leu Arg Phe Pro Phe Ile Asn Ile His Asp Asp
                485                 490                 495
Asn His Met Thr Gly Leu Ser His Leu Leu Ser Asn Val Ser Asp Phe
                500                 505                 510
Met Ser Gln Phe Thr Glu Val His Ser Asp Ser Lys Asp Ser Gln Leu
            515                 520                 525
Leu Phe Leu Arg Cys Ile Trp Ala Phe Trp Glu Ile Gly Ser Val Leu
530                 535                 540
Ser Glu Leu Ile Asp His Phe Ile Ser Ser Ser Ala Asn Ser Gln Val
545                 550                 555                 560
Gly Asp Lys Asp Ala Ser Phe Phe Tyr Glu His Gln Leu Lys Val Thr
                565                 570                 575
Thr Leu Leu Gly Thr Phe Ser Asn Ile Ala Ser Ala Phe Leu Thr Ser
                580                 585                 590
Ser Thr Thr Ala Ala Ser His Pro Pro Ser Ile Ser Pro Phe His
            595                 600                 605
Ile Ile Ser Met Val Glu Ser Phe Lys Met Val Gln Phe Leu Asn Lys
        610                 615                 620
Leu Ile Ala Ser Phe Ile Ser Leu Asn Glu Lys Leu Glu Lys Arg Glu
625                 630                 635                 640
Leu Glu Asp Glu Leu Ser Lys Cys Lys Glu Glu Leu Asn Asn Leu Asn
                645                 650                 655
Glu Arg Phe Gln Ala Val Ser Ser Val Gln Thr Leu Pro Val Val His
                660                 665                 670
Val Leu Phe Arg Asp Leu Val Phe Ser Ser Asn Arg Leu Asp Thr Gln
            675                 680                 685
Arg Asp Arg Ala Ser Ser Val Val Ser Ala Thr Thr Thr Thr Ser Thr
        690                 695                 700
```

```
Ala Thr Thr Thr Ala Thr Thr Lys Lys Ser Ser Phe Gly Asn Leu Leu
705                 710                 715                 720

His Ser Asp Glu Glu Asn Ile Leu Pro Thr Val Ile Asp Trp Cys Lys
            725                 730                 735

Glu Gln Lys His Ser Ala Glu Met Phe Leu Asn Lys Asn Asp Leu Asn
        740                 745                 750

Gly Trp Leu Tyr
        755

<210> SEQ ID NO 48
<211> LENGTH: 1036
<212> TYPE: PRT
<213> ORGANISM: Pichia pastoris

<400> SEQUENCE: 48

Met Met Pro Glu Glu Gln Val Thr Ser Pro Gln Arg Lys His Gln Lys
1               5                   10                  15

Ser Lys Ala Lys Thr Ile Arg Ala Pro Gly Ser Ser Ile Glu Arg Val
            20                  25                  30

Ala Gln Ala Cys Asp Arg Cys Arg Ser Lys Lys Thr Arg Cys Asp Gly
        35                  40                  45

Lys Arg Pro Gln Cys Ser Gln Cys Ala Ala Val Gly Phe Glu Cys Lys
50                  55                  60

Ile Ser Asp Lys Leu Ser Arg Arg Ala Phe Pro Arg Gly Tyr Thr Glu
65                  70                  75                  80

Thr Leu Glu Glu Arg Ile Arg Glu Leu Glu Phe Glu Asn Lys Lys Leu
                85                  90                  95

His Lys Leu Ile Asp Leu Lys Asn Glu Gln Val Glu Ile Lys Asn Arg
            100                 105                 110

Ile Asp Gln Glu Ser Thr Leu Thr Asn Glu Asn Leu Thr Leu Leu Asn
        115                 120                 125

Lys Glu Gln Glu Val Ser His Ser Gly Asn Ile His His His Ala Asp
130                 135                 140

Gly Glu Pro Cys Asn Cys Ala Asn Ser Val Ser Ala Arg Pro Val Ser
145                 150                 155                 160

Ile Ala Gly Ser Val Asp Ile Asp Thr Thr Asp Leu Ser Asp Glu Asp
                165                 170                 175

Asp Ser Leu Tyr Ser Ala Ala Ser Tyr Asn Ala Lys Tyr His Gln Thr
            180                 185                 190

Gly Thr Ser Gly Pro Glu Met Val Arg Leu Ser Gln Arg Tyr Ser Ser
        195                 200                 205

Gly Asn Phe Asn Asp Pro Leu Ser Phe Glu Gln Ser Asn Ala Pro Gly
210                 215                 220

Ala Ala Ala Ile Ser Ile Gln Asn Lys Met Arg Thr Gln Thr Phe
225                 230                 235                 240

Val Asn Leu Ala Asn Leu Val Ala Met Ser Ile Pro Arg Thr Thr Glu
                245                 250                 255

Glu Thr Leu Phe Ile Ala Ser Leu Leu Ala Lys Ile Cys Asn Val His
            260                 265                 270

Gly Phe Gln Ser Lys Ala Pro Ile Leu Thr Ala Lys Ser Ile Ala Leu
        275                 280                 285

Leu Lys Asp Lys Tyr Asn Tyr Gly Asn Asp Glu Val Phe Ala Asn Ile
290                 295                 300

Thr Leu Lys Asn Val Asn Phe Asn Lys Leu Thr Ser Gln Gln Ser Gln
305                 310                 315                 320
```

Gln Phe Phe Gln Ser Leu Asn Leu Pro Asn Gln Val Asn Leu Asp Leu
                325                 330                 335

Phe Ile Thr Thr Phe Phe Asn Thr Trp Asn Asn Phe Ile Pro Ile Ile
            340                 345                 350

Asn Arg His Ile Phe Met Ser Ser Tyr Ile Lys Phe Asn Lys Ser Arg
        355                 360                 365

Glu Thr Met Phe Thr Asp Asn Ser Met Phe Gly Asn Glu Lys Phe Gly
    370                 375                 380

Glu Ile Leu Leu Leu Ile Thr Thr Met Val Met Leu Ser Gln Glu Arg
385                 390                 395                 400

Asn Asn Asn Arg Glu Ala Val Pro Ser Ser Tyr Lys Lys Asp Ser
                405                 410                 415

Thr Pro His Pro His Arg Pro Asp Ala Ser Ser Gln Ser Asn Val Glu
            420                 425                 430

Ile Leu Gln Tyr Tyr Asp His Leu Ile His Glu Phe Ile Lys Ser Asn
        435                 440                 445

Ile Ser Asp Asp Cys Ser Leu Pro Thr Leu Glu Ser Leu Ser Leu Gln
    450                 455                 460

Leu Leu Tyr Cys Leu Ala Ile Gly Asp Leu Thr Thr Ser Tyr Glu Leu
465                 470                 475                 480

Arg Gly Lys Ile Ile Thr Met Gly Gln Gln Leu Arg Leu His Arg Cys
                485                 490                 495

Pro Ser Ala Val Leu Gly Thr Asn Gly Ser Lys Val Ser Gln Met Gln
            500                 505                 510

Gln Gly Glu Arg Arg Ile Leu Phe Trp Cys Ile Tyr Ile Leu Asp Thr
        515                 520                 525

Phe Ser Ala Leu Ile Leu Gly Val Pro Arg Leu Leu Lys Asp Tyr Glu
    530                 535                 540

Ile Glu Cys Ala Leu Pro Phe Ser Asn Glu Ser Asn Asn Ala Asn Val
545                 550                 555                 560

Lys Gly Ser Ile Glu Asn Thr Thr Asn Thr Val Ile Ile Asn Asn Ile
                565                 570                 575

Lys Leu Ser Leu Ala Gly Lys Val Ser Asp Cys Ala Leu Ala Val Met
            580                 585                 590

Arg Tyr Ser Lys Val Leu Gly Asn Ile Leu Asp Ser Ile Phe Gln Arg
        595                 600                 605

Ser Ser Ile Asn Asn Pro Ser Val Val Ser Lys Ser Thr Asn Ile Thr
    610                 615                 620

Glu Glu Thr Cys Leu Leu His Glu His Ala Leu Asp Leu Trp Arg Arg
625                 630                 635                 640

Glu Leu Ser Pro His Ile Asn Val Asp Leu Asp Lys Ser Pro Gly Gly
                645                 650                 655

Val Glu Tyr Glu Arg Leu Ser Asp Asn Gln Leu Thr Ile Leu Phe Leu
            660                 665                 670

Tyr Tyr His Ala Lys Ile Leu Ile Tyr Leu Pro Leu Met Ala Asn Glu
        675                 680                 685

Ser Ser Gln Ser Arg Ser Ser Ala Ser Tyr Ile Asn Ile Gln Gln Ser
    690                 695                 700

Thr Thr Ser Ile Leu Ala Ile Ala Asn Thr Leu Ala Thr Lys Glu Arg
705                 710                 715                 720

Asn Phe Tyr Phe Leu Pro Leu Pro Val Asn Leu Ser Arg Glu Lys Val
                725                 730                 735

-continued

Arg Leu Ala Phe Leu Ser Ala Lys Gly Ser Leu Glu Tyr Ala Arg Gly
                740                 745                 750

Gly Ala Leu Phe Gln Glu Ser Lys Ile Leu Leu Ala Ser Val Ile Asn
        755                 760                 765

Glu Leu Lys Ile Glu Thr Ser Ile Gly Met Leu Gly Cys Leu Ser Val
770                 775                 780

Pro Cys Met Glu Ala Val Asp Asn Ala Met Glu Gln Ile Met Ala Leu
785                 790                 795                 800

Pro Gly Lys Val Ser Ser Val Asn Gly Ser Asn Ser Glu Met Lys Arg
                805                 810                 815

Ser Ser Ser Lys Arg Lys Ser Ser Pro Leu Arg Gln Asp Ile Ser Gly
        820                 825                 830

Asp Glu Arg Lys Ser His Asn Ile Glu Val Ser Asp Ser Arg Thr Pro
835                 840                 845

Ser Val Gln Ser Ser Leu Tyr Pro Gln Pro Asn Gln Met His His Pro
850                 855                 860

Asn Ile Ile Lys Ser Glu Asn Glu Gln Met Ile Pro Glu Asn Asp
865                 870                 875                 880

Thr Pro Gly Ala Ile Asn Asp Ile Phe Thr Ser His Ser Pro Pro Gly
                885                 890                 895

Thr Val Thr Ser Met Lys Glu Glu Asp Leu Pro Ile Lys Val Pro Ile
        900                 905                 910

Leu Leu Gln Thr Gln Arg Gln Ile Tyr Asn Asn Pro Asn His
                915                 920                 925

Ser Leu Phe Ser Gln Gln Pro Gly Thr Gln Val Leu Ser Gly Gln Gln
        930                 935                 940

Met Pro Gly Pro Ser Ser Thr Asp Gln Gln Phe Lys Arg Ile Thr Thr
945                 950                 955                 960

Pro Asp Gly Leu Asp Ser Leu Met Met Gln Asp Phe Gly Val Asp Ala
                965                 970                 975

Ser Leu Gly Leu Pro Met Leu Asp Phe Asp Phe Asn Phe Asp Phe Glu
        980                 985                 990

Asn Val Gln Asn Asn Tyr Ser Gln Ser Asn Val Ser Pro Pro Asn Ser
        995                 1000                1005

Glu Ser Val Pro Ser Ser Ile Gln Gly Thr His Ser Asn Asp Pro
    1010                1015                1020

Lys Asp Ser Gln Val Ser Ala Gly Ser Leu Phe Gly Leu
        1025                1030                1035

<210> SEQ ID NO 49
<211> LENGTH: 887
<212> TYPE: PRT
<213> ORGANISM: Pichia pastoris

<400> SEQUENCE: 49

Met Lys Glu Asn Gln Ala Ser Asn Lys Phe Asn Leu Ile Lys Asn Pro
1               5                   10                  15

Ile Thr Gly Lys Pro Arg Ile Ser Gln Ala Cys Asp Arg Cys Arg Ile
                20                  25                  30

Lys Lys Ile Lys Cys Asp Gly Thr Leu Pro Ser Cys Thr Asn Cys Ser
        35                  40                  45

Lys Ile Gly Phe Val Cys Lys Ile Ser Asp Arg Leu Thr Arg Ser Ser
    50                  55                  60

Phe Pro Lys Gly Tyr Thr Lys Asn Leu Glu Gln Lys Leu Ile Asp Met
65                  70                  75                  80

```
Glu Leu Asp Arg Asn Arg Leu Met Leu Glu Leu Asn Arg Ile Lys Lys
                85                  90                  95
Glu Gly Phe Asp Gly Thr Asn Asn Ile Ala Met Ala Ser Ser Val
            100                 105                 110
Ser Ser Ser Glu Asn Leu Lys Ser Asp Asp Ser Glu Cys Gln Ser
            115                 120                 125
Val Thr Val Ser Leu Ser Ser Thr Ser Gly Pro Ser Leu Ser Pro Glu
    130                 135                 140
Pro Lys Gln Asp Asp Phe Arg Phe Arg Val Gly Met Asp Gly Ser Phe
145                 150                 155                 160
Val Leu Asn Gln Phe Leu Gln Ser Pro Leu Met Asp Tyr Ile Lys Ser
                165                 170                 175
Leu Asn Val Leu Gln Phe Asn Gly Cys Ala Asn Phe Asp Gln Ser Phe
            180                 185                 190
Asn Asp Asp Pro Leu Val Leu Asn Lys Tyr His Met Asn Leu Asn Arg
            195                 200                 205
Phe Leu Asn Leu Ile Phe Tyr Lys Leu Leu Leu Pro Leu Ile His Arg
210                 215                 220
Asn Ser Asn Thr Leu Asn Glu Lys Phe Ala Glu Asp Asn Asn Ser Leu
225                 230                 235                 240
Asp Ser Leu Ile Trp Lys Phe Phe Thr Asn Tyr Asn Lys Leu Ile Pro
                245                 250                 255
Ile Leu Glu Phe Asp Ser Phe Tyr Lys Asp Tyr Leu Gln Phe Ile His
            260                 265                 270
Lys Tyr Tyr Ser Asn Asn Gln Val Phe Val Asp Gly Phe Arg Lys Tyr
                275                 280                 285
Phe Glu Phe Ser Glu Phe Glu Gln Cys Phe Ile Val Lys Leu Ile Leu
            290                 295                 300
Ile Leu Lys Phe Thr Leu Pro Val Ile His Asp Thr Ser Val Pro Ser
305                 310                 315                 320
Glu Ile Tyr Arg Leu Ile Ser Met Asp Ser Leu Gln Arg Leu Phe Gly
                325                 330                 335
Asn Ile Asp Phe Leu Lys Pro Ser Thr Asp Lys Val Ser Ile Leu Leu
            340                 345                 350
Leu Val Leu His Tyr Met Val Leu Tyr Glu Ser Pro Lys Ser Leu Leu
            355                 360                 365
Asp Thr Gln Asp Glu Ala Gln Lys Tyr Asp Glu Phe Ile Gly Asn Leu
    370                 375                 380
Leu Ser Thr Ala Val His Ile Thr Ser Leu Arg Leu His Ile Asp
385                 390                 395                 400
Pro Arg Lys Leu Gln Phe Pro Arg Pro Leu Pro Ser Asn Gly Asn Arg
                405                 410                 415
Leu Arg Ile Lys Leu Ser Trp Cys Tyr Lys Leu Ile Ser Lys Leu Phe
            420                 425                 430
Arg Val Ile Tyr Asn Ile Asp Asn Asp Ser Leu Tyr Ser Leu Asp Asp
            435                 440                 445
Ser His Leu Pro Glu Leu Gln Ser Ile Ser Ile Leu His Glu Glu Leu
    450                 455                 460
Asp Val Thr Ile Gln Phe Asn Asn Leu Leu Asn Leu Ile Pro Asn Asn
465                 470                 475                 480
Phe His Ser Leu Arg Asp Lys Gln Ser Leu Ser Lys Ile Lys Thr Gln
                485                 490                 495
```

Leu Leu Glu Trp His Lys Asn Phe Asn Thr Glu Phe Val Glu His Phe
            500                 505                 510

Asn Leu Asn Asp Thr Asp Ser Asp Glu Leu Ser Ala Glu Lys Ile Asn
            515                 520                 525

Val Leu Arg Ser Lys Leu Ile Ser Leu Asn Arg Leu Asn Cys Tyr Asn
            530                 535                 540

Ser Tyr Phe Gln Leu Val Ile Glu Leu Gln Leu Lys Glu Asn Leu Asp
545                 550                 555                 560

Ser Val Val Ser Gly Ile Phe Gly Leu Ser Asn Glu Met Leu Ile Asp
                565                 570                 575

Asn Lys Ser Ser Thr Glu Leu Leu Asn Thr Leu Gln Gln Thr Pro Ile
            580                 585                 590

Ile His Gln Ser Ser Ile Leu Val Ser Leu Cys Tyr Arg Ile Gln Thr
            595                 600                 605

Gly Asn Leu Gln Asp Glu Ile Cys Ser Ile Leu Val Asn Asn Tyr Glu
            610                 615                 620

Lys Leu Leu Gln Cys Asn Asp Ala Gly Leu Pro Ile Lys Ile Leu Pro
625                 630                 635                 640

Gln Leu Val His Tyr Phe Lys Gly Lys Ile Ser Thr Asn Leu Ser Asn
                645                 650                 655

Ser Ala Ala His Glu Asp Leu Met Asn Met Phe Thr Leu Asn Asp Asn
            660                 665                 670

Leu Ser Thr Thr Thr Asp Leu Asp Ser Phe Ile Ile Pro Pro Lys
            675                 680                 685

Arg Lys Gln Asp Gln Thr Leu Pro Ile Gly Thr Lys Arg Ser Lys Ser
690                 695                 700

Ala Ser Thr Ser Ser Val Ile Ser Ser Asp Asp Cys Ser Leu Phe Ser
705                 710                 715                 720

Asn Ser Leu Ser Val Pro Thr Thr Phe Ser Gly Ser Ile Ser Val
                725                 730                 735

Gly Met Asp Asn Pro Pro Ser Ser Leu Phe Gly Ser Tyr Lys Arg Pro
            740                 745                 750

Ser Ser Ile Val Lys Gln Glu Pro Thr Ile Asn Pro Arg Ser Asn Gly
            755                 760                 765

Thr Asn Thr Asp Ser Asn Leu Phe Asp Thr Phe Asn Asp Ser Ile Lys
            770                 775                 780

Gly Ser Leu Asn Asn Gly Leu Lys Lys Leu Lys Asp Ile Arg Cys Asn
785                 790                 795                 800

Ser Val Val Glu Arg Ser His Ser Ser Gln Arg Asn Asp Phe Leu Met
                805                 810                 815

Asp Gln Glu Asp Ser Ile Thr Lys Glu Thr Ile Asn Phe Ser Glu Leu
            820                 825                 830

Phe Thr Cys Gly Thr Pro Thr Ala Ser Gln Ser Ile Asp Arg Ser Pro
            835                 840                 845

Lys Ser Leu Leu Leu Asn Asp Leu Ala Ile Ala Pro Thr Leu Val
850                 855                 860

Ile Lys Pro Asp Ala Glu Asp Leu Asp Arg Leu Lys Asn Lys Ile Arg
865                 870                 875                 880

Ser Val Lys Ser Thr Val His
                885

<210> SEQ ID NO 50
<211> LENGTH: 26
<212> TYPE: PRT

<213> ORGANISM: Komagataella phaffii

<400> SEQUENCE: 50

Leu Leu Asn Gly Tyr Ile Tyr Asp Tyr Leu Val Lys Ser Asn Met Gln
1               5                   10                  15

Asn Leu Ala Asp Gln Phe Ala Gln Glu Thr
            20                  25

<210> SEQ ID NO 51
<211> LENGTH: 25
<212> TYPE: PRT
<213> ORGANISM: Komagatella pastoris

<400> SEQUENCE: 51

Leu Asn Gly Tyr Ile His Asp Tyr Leu Val Lys Ser Asn Met Gln Asn
1               5                   10                  15

Leu Ala Asp Gln Phe Ala Gln Glu Ser
            20                  25

<210> SEQ ID NO 52
<211> LENGTH: 25
<212> TYPE: PRT
<213> ORGANISM: Saccharomyces cerevisiae

<400> SEQUENCE: 52

Leu Asn Glu Tyr Ile Phe Asp Phe Leu Thr Lys Ser Ser Leu Lys Asn
1               5                   10                  15

Thr Ala Ala Ala Phe Ala Gln Asp Ala
            20                  25

<210> SEQ ID NO 53
<211> LENGTH: 25
<212> TYPE: PRT
<213> ORGANISM: Saccharomyces cerevisiae

<400> SEQUENCE: 53

Leu Asn Glu Tyr Ile Phe Asp Phe Leu Thr Lys Ser Ser Leu Lys Asn
1               5                   10                  15

Thr Ala Ala Ala Phe Ala Gln Asp Ala
            20                  25

<210> SEQ ID NO 54
<211> LENGTH: 27
<212> TYPE: PRT
<213> ORGANISM: Yarrowia lipolytica

<400> SEQUENCE: 54

Glu Leu Leu Asn Ala Tyr Ile Tyr Asp Tyr Leu Leu Lys His Asn Met
1               5                   10                  15

His Asp Ser Ala Arg Thr Phe Gly Ala Glu Ala
            20                  25

<210> SEQ ID NO 55
<211> LENGTH: 27
<212> TYPE: PRT
<213> ORGANISM: Ogataea polymorpha

<400> SEQUENCE: 55

Glu Leu Leu Asn Ala Tyr Val Tyr Asp Phe Ile Leu Lys Ser Gly Phe
1               5                   10                  15

Thr Ala Thr Ala Ser Ala Phe Phe Lys Glu Ala
            20                  25

<210> SEQ ID NO 56
<211> LENGTH: 26
<212> TYPE: PRT
<213> ORGANISM: Aspergillus niger

<400> SEQUENCE: 56

Asn Asn Leu Asn Thr Tyr Ile Tyr Asp Tyr Phe Leu Lys Arg Gly Tyr
1               5                   10                  15

His Asp Cys Ala Arg Ala Leu Val Lys Asp
            20                  25

<210> SEQ ID NO 57
<211> LENGTH: 774
<212> TYPE: DNA
<213> ORGANISM: Artificial Sequence
<220> FEATURE:
<223> OTHER INFORMATION: scR sequence

<400> SEQUENCE: 57
caggaacaac taatggagtc tgggggtggt ttggttaccc tgggtggttc tcttaagctt      60
tcatgtaagg cctctggtat tgatttttcg cactacggta tctcctgggt tagacaagct     120
cctggaaaag gtctggaatg gatcgcttac atttacccaa attacggttc tgttgactat     180
gcctcctggg tcaatggtag gttcactatt tcccttgaca acgctcagaa acggtattc      240 ctacagatga tctccctaac cgctgctgat actgcaacct acttctgtgc tcgtgacaga     300
ggttactact ctggctctcg tggaactaga cttgacttat ggggacaagg tactctcgtt     360
accatctcta gtggtggagg tggttctgga ggaggaggtt ccggcggagg tggtagcgag     420
ctggtcatga ctcaaacccc tccatcccta tctgcatcag tcggtgaaac cgttagaatt     480
agatgccttg catctgagtt cttgttcaac ggtgtgtcct ggtatcaaca aaagcctggt     540
aagcctccaa agtttctcat ttctggtgcc tcaaacctcg aatctggagt gccaccaaga     600
ttttccggat ctggctctgg tactgactac actctgacaa ttggtggtgt tcaagctgag     660
gatgttgcta cctactattg tctcggtggt tactcaggat cttccggcct aactttcggt     720
gccggtacaa acgtcgagat caaaggtgga catcaccacc accatcacta atag            774

<210> SEQ ID NO 58
<211> LENGTH: 837
<212> TYPE: DNA
<213> ORGANISM: Artificial Sequence
<220> FEATURE:
<223> OTHER INFORMATION: vHH sequence

<400> SEQUENCE: 58
caggttcagc tgcaggagtc cggtggtggt ctggttcaag ccggtggttc attaagattg      60
tcctgtgctg cctctggtag aactttcact tctttcgcaa tgggttggtt tagacaagca     120
cctggaaaag agagagagtt tgttgcttct atctccagat ccggtacttt aactagatac     180
gctgactctg ccaagggtag attcactatt tctgttgaca acgccaagaa cactgtttct     240
ttgcaaatgg acaaccttaa cccagatgac accgcagtct attactgtgc cgctgacttg     300
cacagaccat acggtccagg aacccaaaga tccgatgagt acgattcttg gggtcaggga     360
actcaagtca ctgtctcttc aggtggtgga tctggtggtg gaggttcagg tggtggagga     420
tccggtggtg gtggttctgg tggtggtgga tctggtggag gtgaagttca acttgtcgaa     480
tccggtggtg cacttgtcca acctggtgga tctcttagac tttcttgtgc cgcctccggt     540

```
tttcctgtta accgttactc tatgcgttgg tacagacaag ccctggaaa agaacgtgaa      600 tgggttgccg gaatgtcctc agctggtgac agatcctcct acgaagattc tgtgaaggga      660
cgtttcacca tctccagaga tgacgcccgt aacaccgttt accttcaaat gaactccctt      720
aagcctgagg atactgccgt ctactattgt aacgtgaatg tcggatttga atactgggga      780
cagggaaccc aagttactgt ctcttccggt ggacatcacc accaccatca ctaatag         837
```

<210> SEQ ID NO 59
<211> LENGTH: 20
<212> TYPE: PRT
<213> ORGANISM: Artificial Sequence
<220> FEATURE:
<223> OTHER INFORMATION: signal sequence
<220> FEATURE:
<221> NAME/KEY: MISC_FEATURE
<222> LOCATION: (3)..(3)
<223> OTHER INFORMATION: X at position 3 is either F or L
<220> FEATURE:
<221> NAME/KEY: MISC_FEATURE
<222> LOCATION: (16)..(16)
<223> OTHER INFORMATION: X at position 16 is either A or T

<400> SEQUENCE: 59

```
Met Lys Xaa Ser Thr Asn Leu Ile Leu Ala Ile Ala Ala Ala Ser Xaa
 1               5                  10                  15

Val Val Ser Ala
            20
```

<210> SEQ ID NO 60
<211> LENGTH: 36
<212> TYPE: PRT
<213> ORGANISM: Artificial Sequence
<220> FEATURE:
<223> OTHER INFORMATION: leader sequence
<220> FEATURE:
<221> NAME/KEY: MISC_FEATURE
<222> LOCATION: (3)..(3)
<223> OTHER INFORMATION: X at position 3 is either F or L
<220> FEATURE:
<221> NAME/KEY: MISC_FEATURE
<222> LOCATION: (16)..(16)
<223> OTHER INFORMATION: X at position 16 is either A or T

<400> SEQUENCE: 60

```
Met Lys Xaa Ser Thr Asn Leu Ile Leu Ala Ile Ala Ala Ala Ser Xaa
 1               5                  10                  15

Val Val Ser Ala Ala Pro Val Ala Pro Ala Glu Glu Ala Ala Asn His
            20                  25                  30

Leu His Lys Arg
            35
```

<210> SEQ ID NO 61
<211> LENGTH: 85
<212> TYPE: PRT
<213> ORGANISM: Saccharomyces cerevisiae

<400> SEQUENCE: 61

```
Met Arg Phe Pro Ser Ile Phe Thr Ala Val Leu Phe Ala Ala Ser Ser
 1               5                  10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
```

```
                    50                  55                  60
Phe Ile Asn Thr Thr Ile Ala Ser Ile Ala Ala Lys Glu Glu Gly Val
 65                  70                  75                  80

Ser Leu Glu Lys Arg
                 85
```

<210> SEQ ID NO 62
<211> LENGTH: 274
<212> TYPE: PRT
<213> ORGANISM: Komagataella pastoris

<400> SEQUENCE: 62

```
Met Ser Ser Asp Ala Val Glu Gln Leu Glu Asn Phe Gln Leu Ile Lys
  1               5                  10                  15

Phe Asp Arg Phe Asp Pro Ser Thr Gln Ser Thr Ile Arg Ile Ala Arg
                 20                  25                  30

Ser Pro Lys Pro Ile Pro Val Lys Val Ile Val Gly Asp Gly Gly
                 35                  40                  45

Cys Gly Lys Thr Cys Leu Leu Asn Val Phe Ala Thr Gly Thr Phe Pro
 50                  55                  60

Glu Ala Tyr Val Pro Thr Ile Ile Glu Asn Val Val Ile Thr Leu Val
 65                  70                  75                  80

Thr Pro Thr Gly Gln Ile Ala Ala Val Thr Leu Trp Asp Thr Ala Gly
                 85                  90                  95

Gln Glu Glu Tyr Asp Arg Leu Arg Pro Leu Ser Tyr Ser Asp Val Asp
                100                 105                 110

Val Val Leu Leu Cys Tyr Ser Ile Asp Asn Leu Ser Thr Phe His Asn
                115                 120                 125

Val Ala Asp Lys Trp Tyr Pro Glu Val Ala His Phe Cys Pro Asn Thr
130                 135                 140

Pro Ile Ile Leu Val Gly Thr Lys Ser Asp Met Arg Arg His Gln Lys
145                 150                 155                 160

Ser Gln Pro His Phe Val Ser Pro Gln Asp Ser Ser Gln Leu Ala Arg
                165                 170                 175

Gln Met Gly Ala Val Met Asn Ile Glu Cys Ser Ala Lys Glu Val Ser
                180                 185                 190

Asn Val Asn Ile Val Phe Asp Ala Ala Val Ser Tyr Cys Leu Ser Asn
                195                 200                 205

Ser Arg Pro Lys Thr Arg Gly Asp Asn Asp Asn Arg Ser Asn Arg
210                 215                 220

Arg Leu Ser Arg Ala Lys Arg Ala Ser Met Phe Ile Arg Gly Lys Asp
225                 230                 235                 240

Val Ser Ser Thr Ser Gly Asn Ser Arg Glu Glu Leu Val Glu Tyr Asp
                245                 250                 255

Gln Asp Gly Leu Ala Ile Ile Pro Asp Arg Lys Lys Arg Lys Cys Ser
                260                 265                 270

Ile Ile
```

<210> SEQ ID NO 63
<211> LENGTH: 95
<212> TYPE: PRT
<213> ORGANISM: Komagataella pastoris

<400> SEQUENCE: 63

```
Met Leu Asn Lys Leu Phe Ile Ala Ile Leu Ile Val Ile Thr Ala Val
  1               5                  10                  15
```

```
Ile Gly Glu Thr Thr Thr Ser Ser Thr Ala Ser Leu Ser Glu Ser
            20                  25                  30

Pro Thr Leu Val Trp Val Thr Thr Asp Ala Ser Gly Arg Leu Ala
        35                  40                  45

Thr Thr Gln Ser Ala Tyr Thr Gln Gln Phe Ser Gln Leu Tyr Ser Ser
    50                  55                  60

Ile Ala Ser Pro Ser Ser Gly Ser Ile Gly Leu Gly Thr Ile Gln Gly
65                  70                  75                  80

Thr Val Gly Ile Val Arg Thr Tyr Glu Thr Ile Thr Leu Ala Ser
                85                  90                  95
```

<210> SEQ ID NO 64
<211> LENGTH: 86
<212> TYPE: PRT
<213> ORGANISM: Komagataella pastoris

<400> SEQUENCE: 64

```
Met Ser Thr Ala Ile Pro Gly Gly Gln Arg Thr Leu Ala Lys Arg Arg
1               5                   10                  15

Ala Ala Asn Leu Asp Lys Lys Gln Asp Glu Pro Thr Ser Ala Arg Ser
            20                  25                  30

Ala Gly Ala Gly Gly Ser Ser Thr Met Leu Lys Leu Tyr Thr Asp
        35                  40                  45

Glu Ala Gln Gly Leu Lys Val Asp Pro Leu Ile Val Leu Val Leu Ala
    50                  55                  60

Val Gly Phe Ile Phe Ser Val Ile Gly Leu His Val Ala Lys Leu
65                  70                  75                  80

Thr Gly Lys Leu Ile Asn
                85
```

<210> SEQ ID NO 65
<211> LENGTH: 361
<212> TYPE: PRT
<213> ORGANISM: Komagataella pastoris

<400> SEQUENCE: 65

```
Met Thr Pro Arg Ser His Ile Phe Phe Asp Ile Ser Ile Asn Asn Gln
1               5                   10                  15

Pro Ala Gly Arg Ile Ile Phe Glu Leu Phe Asn Asp Ile Val Pro Lys
            20                  25                  30

Thr Ala Glu Asn Phe Arg Ala Leu Ser Thr Gly Glu Lys Gly Ile Gly
        35                  40                  45

Lys Ser Gly Lys Pro Leu His Tyr Lys Gly Ser Thr Phe His Arg Ile
    50                  55                  60

Ile Lys Asp Phe Met Val Gln Gly Gly Asp Phe Thr Asn Gly Asn Gly
65                  70                  75                  80

Thr Gly Gly Glu Ser Ile Tyr Gly Glu Lys Phe Glu Asp Glu Asn Phe
                85                  90                  95

Gln Leu Thr His Asp Lys Pro Phe Leu Leu Ser Met Ala Asn Ala Gly
            100                 105                 110

Pro Gly Thr Asn Gly Ser Gln Phe Phe Ile Thr Thr Val Pro Thr Pro
        115                 120                 125

His Leu Asp Asn Lys His Val Val Phe Gly Lys Val Ile Ala Gly Lys
    130                 135                 140

Ala Thr Val Arg Lys Ile Glu Arg Asn Ser Glu Gly Glu Ala Pro Ile
145                 150                 155                 160
```

```
Glu Pro Val Val Ile Glu Asp Cys Gly Glu Leu Pro Glu Asp Ala Asp
                165                 170                 175

Leu Thr Ile Ser Asp Glu Thr Gly Asp Lys Tyr Glu Glu Val Leu Lys
            180                 185                 190

Asp Asn Glu Asn Ile Asp Ile Asp Phe Glu Gln Val Tyr Gln Ala
        195                 200                 205

Ile Thr Glu Ile Lys Glu Leu Gly Thr Lys Tyr Phe Lys Asn Gly Asp
    210                 215                 220

Thr Lys Ile Ala Phe Glu Lys Tyr Gln Lys Ala Ala Asn Tyr Leu Leu
225             230                 235                 240

Glu Tyr Ile Pro Ser Asp Leu Ser Glu Glu Gln Ser Ser Lys Leu Glu
                245                 250                 255

Leu Leu Lys Thr Ser Val Phe Ser Asn Val Ala Leu Ala Gly Leu Lys
                260                 265                 270

Val Ser Lys Phe Lys Asp Thr Ile Lys Tyr Ala Thr Leu Val Ile Glu
                275                 280                 285

Asp Glu Ser Ala Asp Ala Lys Ala Lys Ser Lys Gly Tyr Tyr Arg Arg
            290                 295                 300

Gly Ser Ala Tyr Ser Ser Leu Lys Asp Glu Asp Ser Ala Ile Ser Asp
305                 310                 315                 320

Phe Gln Lys Ala Leu Glu Leu Ser Pro Gly Asp Pro Ala Ile Ser Gln
                325                 330                 335

Ser Leu Gln Arg Thr Thr Lys Ala Arg Lys Asp Arg Leu Ala Lys Glu
                340                 345                 350

Lys Ala Ala Leu Ser Lys Phe Phe Glu
                355                 360

<210> SEQ ID NO 66
<211> LENGTH: 127
<212> TYPE: PRT
<213> ORGANISM: Komagataella pastoris

<400> SEQUENCE: 66

Met Thr Asn Trp Lys Ala Ile Leu Thr Pro Ala Gln Tyr Gln Val Leu
1               5                   10                  15

Arg Leu Gly Gly Thr Glu Arg Pro Tyr Thr Gly Gln Tyr Val Asn Phe
            20                  25                  30

Lys Lys Asn Gly Thr Tyr Leu Cys Ser Gly Cys Gln Thr Pro Leu Tyr
        35                  40                  45

Lys Ser Gly Thr Lys Phe Asp Ser Ser Cys Gly Trp Pro Ala Phe Tyr
    50                  55                  60

Glu Ala Leu Pro Gly Ala Val Lys Arg Ile Glu Asp Asn Ser Leu Gly
65                  70                  75                  80

Met Arg Arg Ile Glu Ile Arg Cys Ser Lys Cys Asp Gly His Leu Gly
                85                  90                  95

His Val Phe Glu Gly Glu Gly Phe Asp Thr Pro Thr Asp Ser Arg His
                100                 105                 110

Cys Val Asn Ser Ile Ser Leu Lys Phe Gln Gly Glu Glu Asn
            115                 120                 125

<210> SEQ ID NO 67
<211> LENGTH: 546
<212> TYPE: PRT
<213> ORGANISM: Komagataella pastoris

<400> SEQUENCE: 67
```

```
Met Ser His Leu Leu Arg Asp Ser Phe Trp Gly Arg Thr Ile Tyr
1               5                   10                  15

His Leu Ser Lys His Arg Tyr Phe Ser Phe Pro Glu Glu Lys Asp Gly
            20                  25                  30

Phe Ile Ala Pro Glu Lys Tyr Tyr Leu Asn Met Asp Gln Val Ser Ile
            35                  40                  45

His Ala Glu Ser Glu Lys Asn Ile Val Glu Gly Leu Val Asp Thr Ser
        50                  55                  60

Asn Ser Ser Leu Glu Glu Val Lys Thr Thr Arg Val Ile Val Asp Trp
65                      70                  75                  80

Asp Glu Tyr Asp Gln Lys Glu Asn Pro Gln Asn Trp Ser Ser Leu Leu
                85                  90                  95

Lys Cys Phe Val Val Phe Glu Val Gly Ile Leu Thr Val Ala Val Tyr
                100                 105                 110

Met Gly Ser Ala Ile Tyr Thr Pro Gly Ile Glu Asp Ile Met Arg Asp
            115                 120                 125

Leu Asn Val Ser Arg Thr Val Ala Thr Leu Pro Leu Thr Leu Phe Val
130                 135                 140

Ile Gly Tyr Ala Val Gly Pro Met Ile Phe Ser Pro Met Ser Glu His
145                 150                 155                 160

Pro Ala Ile Gly Arg Thr Thr Ile Tyr Val Trp Thr Leu Phe Ile Phe
                165                 170                 175

Ala Ile Leu Gln Ile Pro Thr Ala Leu Thr Thr Asn Ile Ala Gly Phe
            180                 185                 190

Cys Ile Leu Arg Phe Ile Gly Gly Phe Ala Ser Pro Ala Leu Ala
                195                 200                 205

Thr Gly Pro Ala Ser Val Gly Asp Val Ile Ala Ile Pro His Leu Pro
210                 215                 220

Val Gly Leu Gly Leu Trp Ser Ile Cys Ala Val Cys Gly Pro Ser Leu
225                 230                 235                 240

Gly Pro Leu Phe Gly Ala Ile Phe Ser Gln Leu Val Ser Trp Arg Trp
                245                 250                 255

Cys Phe Trp Phe Leu Leu Ile Thr Ser Gly Thr Leu Phe Ile Val Leu
            260                 265                 270

Gly Phe Thr Leu Pro Glu Thr Tyr Val Pro Thr Leu Leu Tyr Arg Lys
        275                 280                 285

Ala Arg Arg Leu Arg Ala Leu Thr Lys Asn Glu Leu Ile Ile Ser Lys
    290                 295                 300

Gly Glu Leu Asp Ile Gln Asp Arg Thr Ala Lys Glu Val Leu Ile Glu
305                 310                 315                 320

Cys Leu Trp Arg Pro Val Asp Ile Ser Phe Arg Asp Pro Val Val Leu
                325                 330                 335

Met Ile Asn Leu Tyr Ile Ser Met Val Tyr Ser Ile Trp Tyr Ile Trp
            340                 345                 350

Phe Glu Ala Phe Pro Ile Val Phe Leu Glu Ile Tyr Gly Phe Ser Leu
        355                 360                 365

Ile Gly Met Gly Ala Ser Phe Ala Gly Ile Leu Ile Gly Val Leu Ile
    370                 375                 380

Cys Ser Ala Cys Tyr Cys Tyr Ala Cys His Val Thr Phe Ala Arg Arg
385                 390                 395                 400

Ile Ile Ala Asn Glu Thr Ile His Pro Glu Phe Phe Val Pro Gly Ala
                405                 410                 415
```

```
Ile Ile Gly Gly Cys Ile Met Pro Thr Gly Ile Phe Ile Leu Gly Trp
            420                 425                 430

Thr Ala Thr Lys Ser Val His Trp Ile Val Pro Ile Ile Gly Ser Gly
            435                 440                 445

Leu Phe Ala Ala Gly Gly Tyr Leu Ile Phe Gln Thr Leu Phe Asn Tyr
450                 455                 460

Leu Ala Met Ser Phe Pro Arg Tyr Met Ala Ser Ala Phe Ala Gly Asn
465                 470                 475                 480

Asp Leu Phe Arg Ser Phe Ser Ala Ser Val Phe Pro Leu Phe Gly His
            485                 490                 495

Ala Leu Tyr Ala Asn Leu Gly Ser Glu Lys Phe Pro Val Gly Trp Gly
            500                 505                 510

Ser Ser Val Leu Gly Phe Ile Thr Val Ala Met Ile Ala Ile Pro Val
            515                 520                 525

Thr Phe Met Arg Tyr Gly Pro Arg Leu Arg Ala Asn Ser Arg Tyr Ala
530                 535                 540

Gly Pro
545

<210> SEQ ID NO 68
<211> LENGTH: 355
<212> TYPE: PRT
<213> ORGANISM: Komagataella pastoris

<400> SEQUENCE: 68

Met Thr Asp Tyr Val Thr Ser Lys Arg Pro Asp Asn Val Leu Asn Trp
1               5                   10                  15

Thr Ser Ile His Val Ser Ser Trp Ile Gly Glu Thr Ile Pro Glu Ile
            20                  25                  30

Asp Pro Ser Leu Leu Gln Asn Phe Leu Glu His Asp Ile Ala Gly Asp
        35                  40                  45

Val Leu Pro Tyr Leu Lys Ser Glu Asp Leu Lys Glu Ile Gly Ile Asn
    50                  55                  60

Glu Leu Lys His Arg Ile Ser Ile Lys Lys Asn Ile His Glu Leu Leu
65                  70                  75                  80

Val Ser Asn Glu Lys His Ile Asp Thr Ser Ile Leu Ser Asp Thr Ala
                85                  90                  95

Thr Glu Leu Gly Thr Leu Ile Leu Thr Asn Lys Phe Ile Thr Gln Met
            100                 105                 110

Ala Asn Arg Lys Asn Val Val Asp Asp Ser Thr His His Ser Asn Asn
        115                 120                 125

Arg Arg Leu Thr Glu Gln Phe Asn Lys Leu Arg Lys Asp Leu Leu Pro
130                 135                 140

Ile Phe Lys Trp Ile Lys Glu Thr Gln Pro Leu Pro Thr Pro Glu Asn
145                 150                 155                 160

Thr His Phe Ala Asn Met Gly Ser Val Pro Ala Ser Pro Val Glu His
                165                 170                 175

Thr Ser Gly Glu Ser Thr Leu Ser Asn Pro Ser Leu Ser Thr Ile Asn
            180                 185                 190

Ala Gly Glu Gly Val Asn Ser Ala Val Ala Gly Gln Ser Leu Gly Arg
        195                 200                 205

Lys Pro Thr Leu Ser Ser Arg Arg Gln Ser His Ala Leu Ser Pro Thr
210                 215                 220

Gly Glu His Leu Asn Val Ser Ser Ser Ser Pro Ser Thr Gly Asn Phe
225                 230                 235                 240
```

-continued

```
Glu Thr Leu Asn Gly Glu Arg Pro Asn Leu Arg Ser Ala Ser Ser Gly
                245                 250                 255

Ser Gln Glu His Thr Glu Asn Glu Leu Leu Lys Pro Leu Arg Val Lys
            260                 265                 270

Ala Asp Glu Pro Cys Tyr Lys Val Ile Gln Asn Ala Met Lys Arg His
        275                 280                 285

Gly Leu Ser Val Asp Asp Trp Arg Lys Tyr Ala Leu Val Ile Cys Tyr
    290                 295                 300

Gly Asp Glu Glu Arg Val Leu Gly Leu His Glu Lys Pro Gly Ser Ile
305                 310                 315                 320

Phe Lys Glu Leu Lys Asp Gln Lys Gln Asn Pro Ala Ile Met Leu Arg
                325                 330                 335

Gln Ile Asp Thr Asn Asn Asp Asp Gln Asn His Ile Glu Thr Pro Gly
            340                 345                 350

Gly Arg Leu
        355

<210> SEQ ID NO 69
<211> LENGTH: 1027
<212> TYPE: PRT
<213> ORGANISM: Komagataella pastoris

<400> SEQUENCE: 69

Met Thr Thr Asn Gly Gln Lys Arg Gln Lys Thr Arg Lys Pro Leu Leu
1               5                   10                  15

Ile Asn Ala Phe Val Met Gly Cys Ala Gly Leu Gln Asn Pro Gly Leu
            20                  25                  30

Trp Lys His Pro Lys Asp Ser Ser His Arg Phe Asn Gln Ile Asp His
        35                  40                  45

Trp Thr Tyr Leu Ala Lys Leu Ala Glu Lys Gly Lys Phe Asn Ala Leu
    50                  55                  60

Phe Ile Ala Asp Val Leu Gly Gly Tyr Asp Val Tyr Lys Gly Pro Glu
65                  70                  75                  80

Asn Leu Ala Thr Pro Ala Val Ala Gly Ala Gln Trp Pro Val Thr Glu
                85                  90                  95

Pro Ser Ala Val Val Ser Ala Met Ala Ala Val Thr Thr Asn Leu Ala
            100                 105                 110

Phe Gly Val Thr Phe Ser Thr Ile Ser Glu Ala Pro Tyr His Phe Ala
        115                 120                 125

Arg Arg Leu Ser Thr Leu Asp His Leu Thr Lys Gly Arg Ile Gly Trp
130                 135                 140

Asn Val Val Ser Ser Tyr Leu Glu Ser Ala Ala Arg Asn Leu Leu Asn
145                 150                 155                 160

Gly Glu Lys Leu Asp Glu His Asp Gln Arg Tyr Leu Lys Ala Glu Glu
                165                 170                 175

Tyr Ile Gln Ile Val Tyr Glu Leu Leu Leu Ser Ser Trp Arg Asp Asp
            180                 185                 190

Ala Val Val Leu Asp Lys Lys Ala Gly Val Tyr Thr Asp Pro Thr Arg
        195                 200                 205

Phe Arg Lys Ile Asn Phe Glu Gly Lys Phe Lys Val Pro Gly Pro
        210                 215                 220

His Ile Val Asp Pro Thr Pro Gln Arg Leu Pro Val Ile Leu Gln Ala
225                 230                 235                 240

Gly Thr Ser Lys Val Gly Lys Glu Phe Ala Ala Lys His Ala Glu Ile
```

-continued

```
                245                 250                 255
Val Phe Val Ile Ser Phe Ser Pro Asp Asp Leu Lys Pro Lys Ile Ala
                260                 265                 270
Glu Val Arg Gln Leu Ala Lys Glu Lys Phe Gly Arg Asn His Asp Asp
                275                 280                 285
Ile Lys Phe Val Ala Leu Ala Thr Pro Val Ile Gly Ala Thr His Glu
            290                 295                 300
Leu Ala Glu Glu Lys Tyr Gln Glu Leu Leu Ser Tyr Gly Asp Ile Glu
305                 310                 315                 320
Gly Ala Gln Ala Leu Phe Gly Gly Trp Thr Gly Ile Asp Leu Ser Gln
                325                 330                 335
Tyr Gly Glu Asp Glu Glu Leu Gly Asn Val Ser Ser Asn Ala Met Arg
            340                 345                 350
Gly Ala Val Gln Asn Trp Thr Lys Ala Ile Pro Asn Glu Lys Arg Trp
            355                 360                 365
Thr Arg Lys Val Ile Ala Lys Gln Ile Thr Val Gly Gly Leu Gly Pro
        370                 375                 380
Ala Phe Val Gly Thr Pro Glu Glu Ile Ala Asp Glu Leu Glu His Trp
385                 390                 395                 400
Ser Asp His Ala Gly Leu Asp Gly Phe Asn Phe Thr Tyr Ala Val Asn
                405                 410                 415
Pro Leu Ser Phe Glu Glu Ile Val Glu Asp Leu Ile Pro Val Leu Gln
            420                 425                 430
Arg Arg Gly Leu Ala Gln Lys Glu Tyr Pro Asn Pro Glu Thr Gly Ser
            435                 440                 445
Thr Phe Arg Lys Asn Leu Phe Gly Thr Asp Phe Val Pro Ser Thr His
        450                 455                 460
Pro Ala Tyr Asn Leu Arg Trp Arg Ala Gly Val Ser Lys Glu Glu Phe
465                 470                 475                 480
Glu Lys Ser Leu Asn Ala Thr Thr Asn Trp Tyr Ser Ser Phe Ala Arg
                485                 490                 495
Ser Gly Ala Leu Gly Glu Leu His Asn Thr Cys Arg Ile Leu Tyr Leu
            500                 505                 510
Gln Ile Val Lys Tyr Lys Tyr Arg Leu Arg Val Arg Ser Glu Gly Asn
            515                 520                 525
Ser Ile Pro Phe Ala Lys Met Thr Lys Glu Asn Glu Ala Lys Arg Gln
        530                 535                 540
Lys Thr Ser Gln Pro Lys Ala Lys Lys Gln Leu Ile Ile Asn Ala Phe
545                 550                 555                 560
Met Ser Gly Ser Ser Gly Asn Gln Ser Pro Gly Leu Trp Ser Tyr Pro
                565                 570                 575
Gly Asp Lys Ser Thr Glu Tyr Thr Thr Leu Asp Tyr Trp Val Glu Leu
            580                 585                 590
Ala Gln Lys Leu Glu Lys Ala Lys Phe His Ser Ile Phe Ile Ala Asp
            595                 600                 605
Val Leu Gly Gly Tyr Asp Val Tyr Asn Gly Pro Gly Asn Tyr Ser Ala
        610                 615                 620
Ala Ala Lys Ser Gly Ala Gln Phe Pro Met Ile Glu Pro Ser Ala Ala
625                 630                 635                 640
Val Thr Ala Met Ala Ala Ala Thr Lys Ser Ile Thr Phe Gly Val Thr
                645                 650                 655
Phe Ser Thr Ile Ser Glu Ala Pro Tyr His Phe Ala Arg Arg Leu Gly
            660                 665                 670
```

Thr Leu Asp Leu Leu Thr Asn Gly Arg Val Gly Trp Asn Ile Val Ser
    675                 680                 685

Ser Tyr Leu Asp Ser Ala Ala Arg Asn Leu Leu Asn Gly Glu Pro Leu
    690                 695                 700

Pro Leu His Ala Asp Arg Tyr Lys Arg Ala Glu Glu Phe Leu Gln Val
705                 710                 715                 720

Val Tyr Arg Leu Phe Leu Ser Ser Trp Arg Asp Asp Ala Tyr Lys Leu
                725                 730                 735

Asp Lys Lys Thr Arg Thr Phe Ala Asp Pro Lys Leu Ile Arg Thr Ile
            740                 745                 750

Asp His Val Gly Glu Phe Phe Asn Val Pro Gly Pro Gln Phe Leu Pro
        755                 760                 765

Pro Thr Pro Gln Arg Leu Pro Leu Ile Leu Gln Ala Gly Thr Ser Lys
    770                 775                 780

Val Gly Met Asp Tyr Ala Ala Lys His Ala Glu Val Val Phe Leu Ala
785                 790                 795                 800

Ser Phe Asp Pro Glu Ser Leu Gln Glu Lys Ile Lys Thr Val Arg Asp
                805                 810                 815

Ile Ala Glu Thr Lys Tyr Asn Arg Pro Arg Asp Ser Ile Lys Phe Leu
            820                 825                 830

Ile Leu Ile Thr Val Val Ile Ala Asp Thr His Glu Asp Ala Val Lys
        835                 840                 845

Arg Tyr Glu Asp Leu Ala Ser Tyr Ala Asp Leu Glu Gly Ala Gln Ala
    850                 855                 860

Leu Phe Ser Gly Trp Thr Gly Ile Asp Ile Lys Tyr Gly Glu Asp
865                 870                 875                 880

Glu Pro Leu Glu His Val Glu Ser Asn Ala Ile Lys Ser His Val Lys
                885                 890                 895

Asn Trp Thr Lys Phe Lys Asp Asn Lys Pro Arg Ala Arg Lys Asp Ile
            900                 905                 910

Ala Lys Gln Ile Gly Val Gly Gly Ser Gly Pro Leu Leu Val Gly Ser
        915                 920                 925

Val Gln Glu Ile Ala Asp Glu Leu Glu Arg Trp Ala Glu Val Ser Asp
    930                 935                 940

Leu Asp Gly Phe Asn Phe Ala Tyr Ala Asp Tyr Pro Gln Thr Phe Asp
945                 950                 955                 960

Asp Ile Ile Glu Lys Leu Leu Pro Glu Leu Asn Lys Arg Gly Val Phe
                965                 970                 975

Trp Asp Asp Tyr Lys Ile Pro Gly Gly Thr Phe Arg Glu Ser Val Phe
            980                 985                 990

Gly Arg Lys Phe Val Asp Lys Asp His Pro Ala Tyr Asp Leu Arg Trp
        995                 1000                1005

Arg Ser Asp Gln Thr Arg Glu Glu Phe Glu Lys Lys Leu Ala Glu
    1010                1015                1020

Leu Glu Lys Lys
    1025

<210> SEQ ID NO 70
<211> LENGTH: 194
<212> TYPE: PRT
<213> ORGANISM: Komagataella pastoris

<400> SEQUENCE: 70

Met Arg Phe Ser Asn Val Val Leu Thr Ala Ile Ala Ala Ala Gly Val

-continued

```
1               5                   10                  15
Gln Ala Asp Glu Ala Leu Tyr Thr Val Phe Tyr Asn Asp Val Thr Glu
                20                  25                  30

Asn Ala Gln Glu Tyr Leu Ser Tyr Ile Gln Ala Asn Thr Ala Ala Gly
                35                  40                  45

Phe Thr Asp Leu Leu Ser Leu Tyr Thr Glu Leu Ala Thr Tyr Thr Asp
 50                  55                  60

Asp Ser Tyr Thr Ser Ile Phe Thr Glu Glu Asp Phe Pro Ala Ser Glu
 65                  70                  75                  80

Leu Ser Ser Phe Val Val Asn Leu Pro Trp Tyr Ser Ser Arg Ile Glu
                85                  90                  95

Pro Gln Val Ala Ala Ala Glu Thr Gly Glu Ser Glu Glu Ser Glu
                100                 105                 110

Thr Gly Glu Ser Glu Glu Ser Glu Thr Gly Glu Glu Thr Glu Thr
                115                 120                 125

Glu Thr Gly Ser Glu Ser Glu Ser Glu Ser Glu Thr Ser Ala
                130                 135                 140

Thr Gly Thr Gly Thr Gly Thr Ser Ala Ser Glu Ser Ala Glu Thr Glu
145                 150                 155                 160

Thr Ser Thr Asp Ala Ala Val Ser Ile Asp His Pro Lys Ser Thr Leu
                165                 170                 175

Leu Met Gly Leu Thr Ala Ala Val Val Ser Ile Thr Phe Gly Val Phe
                180                 185                 190

Ala Leu
```

```
<210> SEQ ID NO 71
<211> LENGTH: 478
<212> TYPE: PRT
<213> ORGANISM: Komagataella pastoris

<400> SEQUENCE: 71
```

```
Met Ser Ser Phe Arg Val Leu Asp Leu Val Lys Pro Phe Thr Pro Phe
1               5                   10                  15

Leu Pro Glu Val Ile Ser Pro Glu Arg Lys Val Pro Phe Gln Gln Lys
                20                  25                  30

Leu Met Trp Thr Gly Val Thr Leu Leu Ile Phe Leu Val Met Ser Glu
                35                  40                  45

Ile Pro Leu Tyr Gly Ile Thr Ser Ser Asp Ser Ser Asp Pro Leu Phe
 50                  55                  60

Trp Leu Arg Met Met Leu Ala Ser Asn Arg Gly Thr Leu Met Glu Leu
 65                  70                  75                  80

Gly Ile Ser Pro Ile Val Thr Ser Gly Met Val Phe Gln Leu Leu Gln
                85                  90                  95

Gly Ile Gln Ile Leu Asp Val Asn Met Glu Asn Lys Ala Asp Arg Glu
                100                 105                 110

Leu Phe Gln Thr Ala Gln Lys Val Phe Ala Ile Leu Leu Ser Ile Gly
                115                 120                 125

Gln Ala Thr Val Tyr Val Leu Thr Gly Met Tyr Gly Pro Pro Gly Glu
                130                 135                 140

Leu Gly Val Gly Val Cys Leu Leu Leu Val Gln Leu Val Phe Ala
145                 150                 155                 160

Gly Ile Val Val Ile Leu Leu Asp Glu Leu Leu Gln Lys Gly Tyr Gly
                165                 170                 175

Leu Gly Ser Gly Ile Ser Leu Phe Met Ala Thr Asn Ile Cys Glu Gln
```

```
                180             185             190
Ile Phe Trp Lys Thr Phe Ala Pro Thr Thr Val Asn Arg Gly Arg Gly
                    195                 200                 205

Lys Glu Phe Glu Gly Ala Phe Ile Ser Phe His Leu Ile Leu Thr
    210                 215                 220

Lys Lys Asp Lys Lys Arg Ala Leu Leu Glu Ser Phe Tyr Arg Asp Asn
225                 230                 235                 240

Ala Pro Asn Met Phe Gln Val Ile Ala Thr Leu Val Val Phe Phe Thr
                245                 250                 255

Val Val Tyr Leu Gln Gly Phe Arg Leu Glu Ile Pro Val Lys Ser Thr
            260                 265                 270

Arg Gln Arg Gly Pro Tyr Gly Thr Tyr Pro Ile Arg Leu Phe Tyr Thr
        275                 280                 285

Ser Asn Met Pro Ile Met Leu Gln Ser Ala Leu Thr Ser Asn Ile Phe
    290                 295                 300

Ile Ile Ser Gln Met Leu Tyr Ser His Phe Pro Asp Asn Ala Phe Val
305                 310                 315                 320

Lys Leu Ile Gly Thr Trp Glu Ala Gln Pro Gly Ser Ala Gln Leu Phe
                325                 330                 335

Ala Ala Ser Gly Leu Ala Tyr Tyr Met Gln Pro Met Ser Leu Ser
            340                 345                 350

Gln Ala Leu Leu Asp Pro Ile Lys Thr Val Val Tyr Val Val Phe Val
        355                 360                 365

Leu Thr Thr Cys Ala Ile Phe Ser Lys Thr Trp Ile Glu Ile Ser Gly
    370                 375                 380

Ser Ser Pro Arg Asp Val Ala Lys Gln Phe Lys Asp Gln Gly Leu Val
385                 390                 395                 400

Ile Ala Gly His Arg Asp Ala Thr Val Tyr Lys Glu Leu Lys Lys Ile
                405                 410                 415

Ile Pro Thr Ala Ala Ala Phe Gly Gly Ala Thr Ile Gly Ala Leu Ser
            420                 425                 430

Val Val Ser Asp Leu Leu Gly Thr Leu Gly Ser Gly Thr Ser Ile Leu
        435                 440                 445

Leu Ala Val Thr Thr Ile Tyr Gly Tyr Tyr Glu Leu Ala Val Lys Glu
    450                 455                 460

Gly Gly Phe Ser Lys Gly Gly Pro Ser Gly Phe Val Asp Leu
465                 470                 475

<210> SEQ ID NO 72
<211> LENGTH: 22
<212> TYPE: DNA
<213> ORGANISM: Artificial Sequence
<220> FEATURE:
<223> OTHER INFORMATION: primer

<400> SEQUENCE: 72
cgaacatcca tcaccaaaac ac                                        22

<210> SEQ ID NO 73
<211> LENGTH: 37
<212> TYPE: DNA
<213> ORGANISM: Artificial Sequence
<220> FEATURE:
<223> OTHER INFORMATION: primer

<400> SEQUENCE: 73
gttgtcgacc tgcagcgtac ggtgttgccg cgaaatg                        37
```

<210> SEQ ID NO 74
<211> LENGTH: 41
<212> TYPE: DNA
<213> ORGANISM: Artificial Sequence
<220> FEATURE:
<223> OTHER INFORMATION: primer

<400> SEQUENCE: 74
taggtgatat cagatccact gatcaatttg cccaagagac g                    41

<210> SEQ ID NO 75
<211> LENGTH: 20
<212> TYPE: DNA
<213> ORGANISM: Artificial Sequence
<220> FEATURE:
<223> OTHER INFORMATION: primer

<400> SEQUENCE: 75
gactgttgcg attgctggtg                                            20

<210> SEQ ID NO 76
<211> LENGTH: 37
<212> TYPE: DNA
<213> ORGANISM: Artificial Sequence
<220> FEATURE:
<223> OTHER INFORMATION: primer

<400> SEQUENCE: 76
catttcgcgg caacaccgta cgctgcaggt cgacaac                         37

<210> SEQ ID NO 77
<211> LENGTH: 23
<212> TYPE: DNA
<213> ORGANISM: Artificial Sequence
<220> FEATURE:
<223> OTHER INFORMATION: primer

<400> SEQUENCE: 77
cggtgagaat ggcaaaagct tat                                        23

<210> SEQ ID NO 78
<211> LENGTH: 21
<212> TYPE: DNA
<213> ORGANISM: Artificial Sequence
<220> FEATURE:
<223> OTHER INFORMATION: primer

<400> SEQUENCE: 78
aagcccgatg cgccagagtt g                                          21

<210> SEQ ID NO 79
<211> LENGTH: 41
<212> TYPE: DNA
<213> ORGANISM: Artificial Sequence
<220> FEATURE:
<223> OTHER INFORMATION: primer

<400> SEQUENCE: 79
cgtctcttgg gcaaattgat cagtggatct gatatcacct a                    41

<210> SEQ ID NO 80
<211> LENGTH: 21
<212> TYPE: DNA
<213> ORGANISM: Artificial Sequence
<220> FEATURE:

```
<223> OTHER INFORMATION: primer

<400> SEQUENCE: 80
atccaggaca cgctcatcaa g                                         21

<210> SEQ ID NO 81
<211> LENGTH: 22
<212> TYPE: DNA
<213> ORGANISM: Artificial Sequence
<220> FEATURE:
<223> OTHER INFORMATION: primer

<400> SEQUENCE: 81
tgtaacgtga atgtcggatt tg                                        22

<210> SEQ ID NO 82
<211> LENGTH: 20
<212> TYPE: DNA
<213> ORGANISM: Artificial Sequence
<220> FEATURE:
<223> OTHER INFORMATION: primer

<400> SEQUENCE: 82
tagtgatggt ggtggtgatg                                           20

<210> SEQ ID NO 83
<211> LENGTH: 23
<212> TYPE: DNA
<213> ORGANISM: Artificial Sequence
<220> FEATURE:
<223> OTHER INFORMATION: primer

<400> SEQUENCE: 83
cctgaggctt tgttccaccc act                                       23

<210> SEQ ID NO 84
<211> LENGTH: 26
<212> TYPE: DNA
<213> ORGANISM: Artificial Sequence
<220> FEATURE:
<223> OTHER INFORMATION: primer

<400> SEQUENCE: 84
ggaacatagt agcaccggca taacga                                    26

<210> SEQ ID NO 85
<211> LENGTH: 10
<212> TYPE: DNA
<213> ORGANISM: Artificial Sequence
<220> FEATURE:
<223> OTHER INFORMATION: translation initiation site

<400> SEQUENCE: 85
cctgcaggcc                                                      10

<210> SEQ ID NO 86
<211> LENGTH: 9
<212> TYPE: DNA
<213> ORGANISM: Artificial Sequence
<220> FEATURE:
<223> OTHER INFORMATION: translation initiation site
<220> FEATURE:
<221> NAME/KEY: misc_feature
<222> LOCATION: (1)..(6)
<223> OTHER INFORMATION: n at positions 1-6 is any nucleic acid,
      preferably A
<220> FEATURE:
```

```
<221> NAME/KEY: misc_feature
<222> LOCATION: (8)..(9)
<223> OTHER INFORMATION: n at positions 8-9 is any nucleic acid,
      preferably A

<400> SEQUENCE: 86 nnnnnnann                                                              9
```

CARBON-SOURCE REGULATED PROTEIN PRODUCTION IN A RECOMBINANT HOST CELL

TECHNICAL FIELD

The invention refers to production of a protein of interest (POI) in a recombinant host cell comprising a heterologous expression cassette to express a gene of interest (GOI) encoding the POI, which host cell is engineered to reduce expression of a FLO8 protein.

BACKGROUND

Proteins produced in recombinant host cell culture have become increasingly important as diagnostic and therapeutic agents. For this purpose, cells are engineered and/or selected to produce unusually high levels of a recombinant or heterologous protein of interest. Optimization of cell culture conditions is important for successful commercial production of recombinant or heterologous proteins.

Successful production of proteins of interest (POI) has been accomplished both with prokaryotic and eukaryotic host cells in cell culture. Eukaryotic host cells, in particular mammalian host cells, yeasts or filamentous fungi, or bacteria are commonly used as production hosts for biopharmaceutical proteins as well as for bulk chemicals. The most prominent examples are yeasts like *Saccharomyces cerevisiae, Pichia pastoris* or *Hansenula polymorpha*, filamentous fungi like *Aspergillus awamori* or *Trichoderma reesei*, or mammalian cells like CHO cells. Methylotrophic yeast, such as *Pichia pastoris*, is well reputed for efficient secretion of heterologous proteins. *P. pastoris* has been reclassified into a new genus, *Komagataella*, and split into three species, *K. pastoris, K. phaffii*, and *K. pseudopastoris*. Strains commonly used for biotechnological applications belong to two proposed species, *K. pastoris* and *K. phaffii*. The strains GS115, X-33, CBS2612, and CBS7435 are *K. phaffii*, while the SMD series of protease deficient strains (e.g., SMD1168) is classified into the type species, *K. pastoris*, which is the reference strain for all the available *P. pastoris* strains (Kurtzman 2009, J Ind Microbiol Biotechnol. 36(11):1435-8). Mattanovich et al. (Microbial Cell Factories 2009, 8:29 doi:10.1186/1475-2859-8-29) describe the genome sequencing of the type strain DSMZ 70382 of *K. pastoris*, and analyzed its secretome and sugar transporters.

WO2015/158808A2 discloses a recombinant host cell engineered to overexpress helper proteins.

WO2015/158800A1 discloses improving a host cell's capacity to express and/or secrete a POI by engineering to underexpress certain proteins (called KO proteins) which are endogenous to the host cell and which have proven to reduce the yield of protein production when overexpressed. Such KO proteins have therefore been chosen as knock-out targets for improving the yield. In turn, underexpressing the KO proteins in *P. pastoris* host cell lines was found to increase the yield of model proteins by 1.2 to 2.4 fold. Inducible (pAOX1) or constitutive (pGAP) promoters have been used. The KO proteins have been identified as a *P. pastoris* homologue of *S. cerevisiae* FLO8 protein, a *P. pastoris* homologue of *S. cerevisiae* HCH1 protein, and KO3 a *P. pastoris* homologue of *S. cerevisiae* SCJ1 protein.

Rebnegger et al. (Applied and Environmental Microbiology 2016, 82(15):4570-4583) describe glucose-limited chemostat cultures of a *P. pastoris* flo8 deletion mutant to prevent filter clogging.

Promoters used for protein production in recombinant host cells are either regulated (e.g., induced upon addition of methanol to the medium, methanol-controlled), or constantly active (constitutive). Methanol-controlled promoters lead to technical limits, such as waste heat in the reactor, or oxygen supply.

WO20137050551A1 discloses a series of carbon-source regulatable promoter of *P. pastoris* (designated pG1-pG8), and induction of protein production upon limiting the carbon source in the cell culture.

WO2017021541A1 discloses variants of a carbon source regulatable promoter of *P. pastoris* (designated pG1), which are regulated by a carbon source other than methanol, i.e. not methanol controlled, e.g. repressed in the presence of a carbon source during a growth phase, and induced by limiting the carbon source in the production phase.

Prielhofer et al. (Microbial Cell Factories 2013; 12(5):1-10) describe *P. pastoris* promoters regulatable and induced without methanol.

Prielhofer et al. (Biotechnology and Bioengineering. 2018; 115:2479-2488) describe the glucose-regulated $P_{GTH1}$ promoter and engineered variants with greatly enhanced induction properties compared with that of the wild-type promoter.

EP2669375A1 discloses a yeast with improved protein expression by high-level expression of an MPP1 homolog.

Hye Young Kim et al. (Biochemical and Biophysical Research Communications 2014, 449:202-207) describe the role of two domains of Flo8 activator in transcriptional activation of a set of target genes, and the mode of Flo8 action by interacting with Mss11 activator.

EP2952584A1 discloses improved protein production by overexpressing certain polynucleotides.

EP2258855A1 discloses certain leader and secretion signal sequences of *P. pastoris*.

WO2010099195A1 discloses genetically modified *P. pastoris* strains and co-expression of a heterologous protein and chaperon proteins.

SUMMARY OF THE INVENTION

It is the object to improve protein production in recombinant host cells and to increase the yield of protein production. Another object of the invention is to provide a method for producing a recombinant or heterologous protein in a host cell, wherein the risk of change in morphology of the host cell during production processes is reduced.

The object is solved by the subject matter as claimed.

According to the invention, there is provided a recombinant host cell comprising an endogenous gene encoding a FLO8 protein comprising the amino acid sequence identified as SEQ ID NO:1 or a homologue thereof, which host cell is engineered by one or more genetic modifications to reduce (or abolish) expression of said polynucleotide compared to the host cell prior to said one or more genetic modifications, and which host cell comprises a heterologous expression cassette comprising a gene of interest (GOI) to express such GOI under the control of an expression cassette promoter (ECP).

Specifically, the ECP is regulatable by a non-methanol carbon source.

Specifically, the ECP is repressible by a non-methanol carbon source.

Specifically, the ECP is repressible by a repressing carbon source, e.g. a repressing carbon source that is not methanol, such as glucose or glycerol, and inducible (derepressible) by reducing the amount of the repressing carbon source.

Specifically, the ECP is not inducible by methanol.

Specifically, the non-methanol carbon source is any carbon source other than methanol that is suitably used in a host cell culture. Specifically, the non-methanol carbon source is not methanol.

Specifically, the non-methanol carbon source is a carbon source other than methanol. In particular, the ECP is not methanol-controlled. Though the cell culture or cell culture medium may or may not comprise methanol, the ECP as used herein is not regulated by any amount of methanol, in particular not inducible by methanol, thus, not methanol-controlled. Specifically, the ECP can be fully induced in a methanol free cell culture or cell culture medium.

For the purpose described herein, the term "FLO8 protein" shall refer to both, a protein comprising the amino acid sequence identified as SEQ ID NO:1, or an amino acid sequence which has a certain homology to SEQ ID NO:1. Yet, the homologous sequence is also referred to as FLO8 homologue.

Specifically, the FLO8 homologue has at least any one of 25%, 30%, or 35% sequence identity to SEQ ID NO:1 e.g., at least any one of 40%, 45%, 50%, 55%, 60%, 65%, 70%, 75%, 80%, 85%, 90%, or 95% sequence identity, or is 100% identical to SEQ ID NO:1. Specifically, sequence identity is determined as further disclosed herein, for example when comparing the full-length sequence.

Specifically, the FLO8 protein or the respective homologue comprises a LisH domain which comprises at least any one of 50%, 60%, 65%, 70%, 75%, 80%, 85%, 90%, or 95% sequence identity to SEQ ID NO:50, or is 100% identical to SEQ ID NO:50.

According to a specific aspect, the LisH domain of the FLO8 protein comprises at least any one of 80%, 85%, 90%, or 95% sequence identity to any of the naturally occurring LisH domains of a FLO8 protein of a eukaryotic organism, or a respective FLO8 orthologue, or is 100% identical to such naturally occurring LisH domain, specifically a LisH domain of yeast or fungi, in particular filamentous fungi, such as a LisH domain comprising or consisting of any one of:
  a) SEQ ID NO:50, which is a LisH domain of the FLO8 protein of *K. phaffii* (SEQ ID NO:50);
  b) SEQ ID NO:51, LisH domain of the FLO8 protein of *K. pastoris* (BLASTp: 96% identity to SEQ ID NO:50 (23/24 aa));
  c) SEQ ID NO:52, which is a LisH domain of the FLO8 ortholog of a *S. cerevisiae* strain (BLASTp: 54% identity to SEQ ID NO:50 (13/24 aa));
  d) SEQ ID NO:53, which is a LisH domain of the FLO8 ortholog of another *S. cerevisiae* strain (BLASTp: 54% identity to SEQ ID NO:50 (13/24 aa));
  e) SEQ ID NO:54, which is a LisH domain of the FLO8 ortholog of a *Yarrowia lipolytica* strain (BLASTp: 71% identity to SEQ ID NO:50 (12/17 aa));
  f) SEQ ID NO:55, which is a LisH domain of the FLO8 ortholog of *Ogataea polymorpha* (BLASTp: 62% identity to SEQ ID NO:50 (8/13 aa)); or
  g) SEQ ID NO:56, which is a LisH domain of the FLO8 ortholog of a *Aspergillus niger* strain (BLASTp: 73% identity to SEQ ID NO:50 (8/11 aa)).

Typically, the LisH domain of the FLO8 protein has a length of 25-27 amino acids and a certain sequence identity to the human protein LIS1, as described in the database Pfam, ID number PF08513, and the respective sequence. In molecular biology, the LisH domain, is a protein domain found in a large number of eukaryotic proteins that have a wide range of functions. The structure of the LisH domain in the N-terminal region of LIS1 depicted it as a dimerisation motif (The dimerization mechanism of LIS1 and its implication for proteins containing the LisH motif. Mateja A, Cierpicki T, Paduch M, Derewenda Z S, Otlewski J. 2006. J Mol Biol. 357(2):621-31).

The FLO8 homologue is particularly understood to be endogenous to the host cell that is used as recombinant host cell producing the POI as further described herein. In particular, the FLO8 protein is an ortholog that is endogenous to the species of the host cell species.

Specifically, the FLO8 protein is of *P. pastoris*, in particular *K. pastoris* or *K. phaffii* origin, if the host cell is *P. pastoris*, in particular *K. pastoris* and *K. phaffii*, respectively. Alternatively, the FLO8 protein comprises a homologous (or orthologous) sequence of such FLO8 protein of in *P. pastoris*, in particular *K. pastoris* or *K. phaffii*, origin, which homologous (orthologous) sequence is endogenous to a wild-type host cell, if of another origin or species. For example, if the host cell is *K. phaffii*, the endogenous FLO8 protein comprises or consists of the amino acid sequence identified as SEQ ID NO:1. According to another example, if the host cell is *K. pastoris*, the endogenous FLO8 protein comprises or consists of the amino acid sequence identified as SEQ ID NO:3, which is 91% identical to SEQ ID NO:1. Yet, if the host cell is of a different species (other than *K. pastoris* and/or *K. phaffii*), the FLO8 protein sequence which is endogenous to the host cell is a homologue to SEQ ID NO:1 and expression of such homologue in the host cell (the orthologous sequence of SEQ ID NO:1) is reduced for the purpose described herein.

Specifically, any or each of the homologous sequences is characterized by the same qualitative function of the FLO8 protein in the respective wild-type host cell as in *P. pastoris*, in particular *K. pastoris* or *K. phaffii* e.g., as transcription factor, in particular a DNA binding transcriptional activator involved in regulation of cell adhesion, flocculation, invasive growth, or starch catabolism, though its quantitative activity might be different when compared to the FLO8 protein in wild-type *K. pastoris* or *K. phaffii*.

Specifically, the respective homologous sequence is of a species other than *P. pastoris*, in particular *K. pastoris* or *K. phaffii* e.g., another yeast or a filamentous fungal cell, preferably yeast of the *Komagataella* or *Pichia* genus, or *Saccharomyces* genus or any methylotrophic yeast. Yet, the host cell may be an animal cell, a vertebrate cell, a mammalian cell, a human cell, a plant cell, a bacterial cell, a nematodal cell, an invertebrate cell such as an insect cell or a mollusk cell, or a stem cell, and the respective FLO8 protein and its homologue described herein is endogenous to the respective host cell, but its expression reduced or abolished as described herein.

Specifically, the FLO8 protein homologue is endogenous or originating from a *Pichia* species or endogenous or originating from any other yeast, fungi, or bacteria, and has 25% sequence identity SEQ ID NO:1 or SEQ ID NO:2, in specific cases at least any one of 35%, 40%, 45%, 50%, 55%, 60, 65%, 70%, 75%, 80%, 85%, 90%, 95%, or is 100% identical to SEQ ID NO:1 or SEQ ID NO:2. Specifically, an exogenous FLO8 protein is determined to be a FLO8 protein homologue if functional upon adding the exogenous FLO8 protein (or the gene encoding the exogenous FLO8 protein) to a culture of a flo8 knockout strain of a *Pichia* (*pastoris*) or *Saccharomyces* (*cerevisiae*) strain, which knockout strain is different from the origin of the exogenous FLO8 protein, thereby proving functional replacement of the deleted endogenous FLO8 protein.

Specifically, the FLO8 protein is of *P. pastoris* origin, in particular encoded by a gene endogenous to the host cell, wherein the host cell is *P. pastoris*.

Specifically, the FLO8 protein is of *Komagataella phaffii* origin, which comprises or consists of SEQ ID NO:1. Specifically, such FLO8 protein is encoded by a gene endogenous to the host cell, wherein the host cell is *Komagataella phaffii*. Specifically, the FLO8 protein is encoded by the nucleotide sequence identified as SEQ ID NO:2.

Specifically, the FLO8 protein is of *Komagataella* origin, which comprises at least 90% or 91% sequence identity to SEQ ID NO:1. Specifically, the FLO8 protein is of *Komagataella pastoris* origin, which comprises or consists of SEQ ID NO:3. Specifically, such FLO8 protein is encoded by a gene endogenous to the host cell, wherein the host cell is *Komagataella pastoris*.

Specifically, the FLO8 protein is of *Saccharomyces* origin, which comprises at least 35% sequence identity to SEQ ID NO:1. Specifically, the FLO8 protein is of *S. cerevisiae* origin, which comprises or consists of SEQ ID NO:5 or SEQ ID NO:6. Specifically, such FLO8 protein is encoded by a gene endogenous to the host cell, wherein the host cell is *S. cerevisiae*.

Specifically, the FLO8 protein is of *Yarrowia* origin, which comprises at least 40% or 44% sequence identity to SEQ ID NO:1. Specifically, the FLO8 protein is of *Yarrowia lipolytica* origin, which comprises or consists of SEQ ID NO:7. Specifically, such FLO8 protein is encoded by a gene endogenous to the host cell, wherein the host cell is *Yarrowia lipolytica*.

Specifically, the FLO8 protein is of *Ogataea* origin, which comprises at least 30% or 34% sequence identity to SEQ ID NO:1. Specifically, the FLO8 protein is of *Ogataea polymorpha* origin, which comprises or consists of SEQ ID NO:8. Specifically, such FLO8 protein is encoded by a gene endogenous to the host cell, wherein the host cell is *Ogataea polymorpha*.

Specifically, the FLO8 protein is of *Aspergillus* origin, which comprises at least 25% or 26% sequence identity to SEQ ID NO:1. Specifically, the FLO8 protein is of *Aspergillus niger* origin, which comprises or consists of SEQ ID NO:9. Specifically, such FLO8 protein is encoded by a gene endogenous to the host cell, wherein the host cell is *Aspergillus niger*.

Specifically, the host cell is genetically modified by one or more genetic modifications comprising genomic mutation(s) that reduce the transcription and/or translation of said polynucleotide encoding said FLO8 protein, and/or otherwise reduce expression of said polynucleotide and reduce production of said FLO8 protein, respectively.

Specifically, said one or more genetic modifications comprise a disruption, substitution, deletion or knockout of (i) one or more endogenous polynucleotides, or a part thereof; or (ii) an expression control sequence.

According to a specific aspect, said one or more genetic modifications are of one or more endogenous polynucleotides of the host cell described herein, such as coding polynucleotides, including e.g., said polynucleotide (or gene) encoding the FLO8 protein, in particular the wild-type (unmodified or native) protein, which is naturally-occurring in the host cell species, type or strain.

According to a specific aspect, said one or more genetic modifications are of an expression control sequence, including e.g., a promoter, ribosomal binding site, transcriptional or translational start and stop sequences, or of an enhancer or activator sequence.

A variety of methods of engineering a host cell can be employed to reduce expression of an endogenous polynucleotide, such as a gene encoding a FLO8 protein, including e.g., disrupting the polynucleotide encoding the FLO8 protein, disrupting the promoter which is operably linked to such polynucleotide, replacing such promoter with another promoter which has lower promoter activity, modifying or modulating (e.g., activating, up-regulating, inactivating, inhibiting, or down-regulating) regulatory sequences which modulate the expression of such polynucleotide, such as using respective transcription regulators targeted to the relevant sequences by an RNA guided ribonuclease used in a CRISPR based method of modifying a host cell, e.g., regulatory sequences selected from the group consisting of promoter, ribosomal binding sites, transcriptional start or stop sequences, translational start or stop sequences, enhancer or activator sequences, repressor or inhibitor sequences, signal or leader sequences, in particular those which control the expression and/or secretion of a protein.

Specifically, said one or more genetic modifications include one or more genomic mutations including deletion or inactivation of a gene or genomic sequence which reduces expression of a gene or part of a gene by at least 50%, 60%, 70%, 80%, 90%, or 95%, or even completely abolishes its expression, e.g., by a knockout of the gene, as compared to the respective host without such genetic modification.

Specifically, the one or more genetic modifications comprise genomic mutations which constitutively impair or otherwise reduce the expression of one or more endogenous polynucleotides.

Specifically, the one or more genetic modifications comprise genomic mutations introducing one or more inducible or repressible regulatory sequences which conditionally impair or otherwise reduce the expression of one or more endogenous polynucleotides. Such conditionally active modifications are particularly targeting those regulatory elements and genes which are active and/or expressed dependent on cell culture conditions.

Specifically, the expression of said one or more endogenous polynucleotides is reduced thereby reducing expression of the polynucleotide encoding the FLO8 protein when producing the POI. Specifically, upon genetic modification, expression of said FLO8 protein is reduced under conditions of the host cell culture during which the POI is produced.

Specifically, the host cell is genetically modified to reduce the amount (e.g., the level or concentration) of said FLO8 protein, by at least any one of 50%, 60%, 70%, 80%, 90%, or 95%, (mol/mol) compared to the host cell without said modification, or even by 100%, e.g. to a non-detectable amount, thereby completely abolishing production of the FLO8 protein, e.g., by a knockout of the gene. According to a specific embodiment, the host cell is genetically modified to comprise one or more deletions of (one or more) genomic sequences, in particular genomic sequences encoding FLO8 protein or the respective homologue thereof. Such host cell is typically provided as a deletion or knockout strain.

According to a specific embodiment, once the host cell described herein is cultured in a cell culture, the amount of total FLO8 protein in the host cell or host cell culture is reduced by at least any one of 50%, 60%, 70%, 80%, 90%, or 95%, (mol/mol), or even by 100%, e.g. to a non-detectable amount, compared to a reference amount expressed or produced by the host cell prior to or without such genetic modification, or compared to a reference amount produced in a respective host cell culture, or compared to the host cell prior to or without said modification.

When comparing the host cell described herein for the effect of said genetic modification to reduce production of said FLO8 protein, it is typically compared to the comparable host cell prior to or without such genetic modification. Comparison is typically made with the same host cell species or type without such genetic modification, which is engineered to produce the recombinant or heterologous POI, in particular when cultured under conditions to produce said POI. However, a comparison can also be made with the same host cell species or type which is not further engineered to produce the recombinant or heterologous POI.

According to a specific aspect, the reduction of said FLO8 protein or the respective homologue thereof is determined by the reduction of the amount (e.g., the level or concentration) of said FLO8 protein in the cell. Specifically, the amount of said FLO8 protein or the respective homologue thereof is determined by a suitable method, such as employing a Western Blot, immunofluorescence imaging, flow cytometry or mass spectrometry, in particular wherein mass spectrometry is liquid chromatography-mass spectrometry (LC-MS), or liquid chromatography tandem-mass spectrometry (LC-MS/MS) e.g., as described by Doneanu et al. (MAbs. 2012; 4(1): 24-44).

According to a specific aspect, the recombinant host cell comprises only one or multiple heterologous expression cassettes, e.g. multiple copies of said expression cassettes, such as at least 2, 3, 4, or 5 copies (gene copy number, GCN). For example, the recombinant host cell comprises up to 2, 3, 4, or five copies. Each of the copies may comprise or consist of the same or different sequences, yet includes the ECP operably linked to the GOI.

According to a specific aspect, the heterologous expression cassette comprises or consists of an artificial fusion of polynucleotides, including the ECP operably linked to the GOI, and optionally further sequences, such as a signal, leader, or a terminator sequence. Specifically, an expression cassette is used which is heterologous to the host cell or artificial, in particular wherein the expression cassette comprises a promoter (the ECP) and a GOI, wherein the promoter and GOI are heterologous to each other, not occurring in such combination in nature e.g., wherein either one (or only one) of the promoter and GOI is artificial or heterologous to the other and/or to the host cell described herein; the promoter is an endogenous promoter and the GOI is a heterologous GOI; or the promoter is an artificial or heterologous promoter and the GOI is an endogenous GOI; wherein both, the promoter and GOI, are artificial, heterologous or from different origin, such as from a different species or type (strain) of cells compared to the host cell described herein. Specifically, the ECP is not naturally associated with and/or not operably linked to said GOI in the cell which is used as a host cell described herein.

According to a specific aspect, the ECP is inducible in the presence of a growth-limiting amount of a non-methanol carbon source, preferably in the absence of methanol; and repressible in the presence of an excess amount of a non-methanol carbon source that is higher than the growth-limiting amount. Specifically, the GOI expression by the heterologous expression cassette is inducible by the inducible ECP.

Preferably, the ECP is carbon source regulatable, such as repressed in the presence of amounts higher than any one of 1, 1.5, 2, 2.5, or 3 g/L of a carbon source in the cell culture medium or supernatant (herein referred to as a promoter-repressing amount), and induced or de-repressed in the presence of no detectable carbon source or amounts up to any one of 0.1, 0.2, 0.3, 0.4, 0.5, 0.6, 0.7, 0.8, 0.9, or 1.0 g/L carbon source in the cell culture medium or supernatant (herein referred to as a promoter-inducing amount). Such amounts in the cell culture medium or supernatant are particularly understood as the amount which upon feeding of the host cell and consumption by the host cell may be detectable. Typically, when producing a POI under growth-limiting conditions, the cell culture is fed by adding a supplemental carbon source, yet in an amount that is immediately consumed by the cells during POI production, thus, leaving no or only a low remaining amount in the cell culture medium or supernatant, e.g. an amount up to 1.0 g/L.

Specifically, the carbon source regulating the ECP is any other than methanol, and herein referred to as a non-methanol carbon source.

Specifically, the non-methanol carbon source is a carbohydrate.

Specifically, the non-methanol carbon source is selected from saccharides, polyols, alcohols, or mixtures of any one or more of the foregoing.

Specifically, the saccharides may be any one or more of monosaccharides, such as a hexose, e.g. glucose, fructose, galactose or mannose, or a disaccharides, such as saccharose; or an alcohol or polyol e.g., ethanol, or any diol, or triol, e.g., glycerol, or a mixture of any of the foregoing. Specifically, any such non-methanol carbon source may be used in the cell culture in an amount to produce said POI under the control of the ECP.

According to a specific aspect, the ECP comprises at least one first and at least one second core regulatory region. Specifically, the ECP comprises at least two of said first and/or second core regulatory regions. Specifically, the ECP comprises a limited number of said first and second core regulatory regions, wherein the number of said first core regulatory region is only one, two or three, and the number of said second core regulatory region is only one, two or three. Specifically, the ECP comprises an equal number of said first and second core regulatory regions e.g., wherein the number of said first core regulatory region is one, and the number of said second core regulatory region is one; wherein the number of said first core regulatory region is two, and the number of said second core regulatory region is two, or wherein the number of said first core regulatory region is three, and the number of said second core regulatory region is three.

Specifically, the first core regulatory region has at least 75% sequence identity to SEQ ID NO:17, such as at least any one of at least 80%, or at least 90% sequence identity, and/or the second core regulatory region has at least 75% sequence identity to SEQ ID NO:18, such as at least any one of at least 80%, or at least 90% sequence identity.

Specifically, each of the first and second core regulatory regions has a length of 8-16 nt.

Specifically, the first core regulatory region has a length of 8 to 10 nt, in particular 9 nt. Specifically, the first core regulatory region comprises or consists of SEQ ID NO:17, or a modification of the nucleotide sequence identified as SEQ ID NO:17, wherein the modification is up to one or two point mutations, in particular wherein one point mutation is any one of substitution, insertion, or deletion of one nucleotide.

Specifically, the second core regulatory region has a length of 14 to 16 nt, in particular 15 nt. Specifically, the second core regulatory region comprises or consists of SEQ ID NO:18, or a modification of the nucleotide sequence identified as SEQ ID NO:18, wherein the modification is up to one, two or three point mutations, in particular wherein one point mutation is any one of substitution, insertion, or deletion of one nucleotide.

Specifically, the ECP comprises at least one first and at least one second core regulatory region in any order, preferably in close proximity to each other, e.g. with up to any one of 20, 19, 18, 17, 16, 15, 14, 13, 12, 11, or 10 nt between the first and second core regulatory regions which are closest.

Specifically, the ECP comprises one first and one second core regulatory region, which are linked via a spacer, in particular separated by a nucleotide sequence (herein referred to as "spacer core region") with a length of at least any one of 5, 6, 7, 8, 9, 10 nt, and/or up to any one of 20, 19, 18, 17, 16, 15, 14, 13, 12, 11, or 10. In particular, the spacer core region has at least 75% sequence identity to SEQ ID NO:36, such as at least any one of at least 80%, or at least 90% sequence identity, and/or comprises or consists of SEQ ID NO:36, or a modification of the nucleotide sequence identified as SEQ ID NO:36, wherein the modification is up to one, two, three of four point mutations, in particular wherein one point mutation is any one of substitution, insertion, or deletion of one nucleotide. Specifically, the spacer core region comprises or consists of a nucleotide sequence wherein the majority of nucleotides (at least 50% or at least 60%) are selected from G, C, or T.

Specifically, the ECP comprises at least one region consisting of a nucleotide sequence which from the 5'-end to the 3'end consists of the following three contiguous elements, (i) a first core regulatory region, (ii) a spacer core region, and (iii) the second core regulatory region, which is herein referred to as "main regulatory region".

Specifically, the ECP comprises at least one or two, or only one or two main regulatory regions, each comprising or consisting of a nucleotide sequence which has at least any one of 85%, 90%, or 95% sequence identity to SEQ ID NO:35. Such main regulatory region is preferably consisting of the first core regulatory region, the spacer core region and the second core regulatory region.

Specifically, the ECP comprises at least one polynucleotide sequence which has at least any one of 85%, 90%, or 95% sequence identity to SEQ ID NO:35.

Specifically, the ECP comprises only one, two or three main regulatory regions, as described herein, in particular wherein the number of main regulatory regions is two or three, wherein said two or three regulatory regions may be identical or differ from each other. Specifically, the ECP comprises only two main regulatory regions, which are separated by a nucleotide sequence (herein referred to as "spacer main region") with a length of at least any one of 50, 60, 70, 80, 90, 100 nt, and/or up to any one of 500, 450, 400, 350, or 300 nt, in particular ranging between 100 and 300 nt. Specifically, the spacer main region comprises a nucleotide sequence of at least any one of 50, 60, 70, 80, 90, 100 nt length which has at least 60% sequence identity to SEQ ID NO:37, such as at least any one of at least 70%, 75%, 80%, 85%, 90%, or 95% sequence identity, and/or comprises or consists of SEQ ID NO:37, or a modification of the nucleotide sequence identified as SEQ ID NO:37, wherein the modification is a number of point mutations, which is one or more, up to any one of 30, 25, 20, 15, or 10 point mutations, in particular wherein one point mutation is any one of substitution, insertion, or deletion of one nucleotide.

According to a specific aspect, the ECP comprises at least one T motif consisting of a nucleotide sequence wherein eth majority of nucleotides is a thymine (T), preferably at least any one of 50%, 60%, 70%, 80%, 90% or 100% is a T e.g., comprising or consisting of any one of SEQ ID NO:19-34, optionally without extension of said T motif by one or more further (or adjacent) thymine at either of the 5' or 3' end of said T motif.

Specifically, the ECP comprises only one or two of said T motifs, or at least two of said T motifs, up to 4, or 3 T motifs, wherein said T motifs are identical or differ from each other.

Specifically, the ECP comprises at least one of the T motifs upstream or downstream of a main regulatory region, e.g., one (or only one or two) T motifs upstream and one (or only one or two) T motif downstream of a main regulatory region. Yet, according to a specific embodiment, the ECP comprises at least one of said T motifs, in particular only one or two T motifs within the spacer main region.

Specifically, the ECP has a length of at least any one of 350, 400, 450, 500, 550, 600, 650, 700, 850, 900, 950, or 1000 bp e.g., up to 2000 bp, or up to 1500 bp.

Specifically, the ECP comprises a 3'-terminal nucleotide sequence e.g., of up to 50, 40, 30, 20, 10, 9, 8, 7, 6, or 5 nt length including the 3'-terminus, which comprises at least part of a translation initiation site, for example a sequence which is at least any one of 60%, 70%, 80%, 85% or at least 90% identical to any one of SEQ ID NO:38, SEQ ID NO:39, or SEQ ID NO:40. A translation initiation site can be a Kozak consensus sequence in eukaryotes and a suitable promoter sequence to support gene expression.

According to a specific aspect, the ECP comprises at least any one of 60%, 65%, 70%, 75%, or 80% sequence identity, in particular at least any one of 85%, 90%, or 95% sequence identity, or is 100% identical, to at least 300 (consecutive) nt, in particular at least any one of 300, 350, 400, 450, 500, 550, 600, 650, 700, 850, 900, 950, or 1000 nt, e.g., within a region comprising a transcription factor binding site (TFBS), and/or within the 3' terminal sequence including the 3' end, of any one of the sequences SEQ ID NO:10, SEQ ID NO:11, SEQ ID NO:12, SEQ ID NO:13, SEQ ID NO:14, SEQ ID NO:15, or SEQ ID NO:16, or any one of SEQ ID NO:41-45, up to the full length of any of the foregoing nucleotide sequences, in particular if the full-length is less than 1000 nt.

According to a specific aspect, the ECP comprises at least any one of 60%, 65%, 70%, 75%, or 80% sequence identity, in particular at least any one of 85%, 90%, or 95% sequence identity, or is 100% identical, to any one of the full-length sequences SEQ ID NO:10, SEQ ID NO:11, SEQ ID NO:12, SEQ ID NO:13, SEQ ID NO:14, SEQ ID NO:15, or SEQ ID NO:16, or any one of SEQ ID NO:41-45.

A specific embodiment refers to the ECP which comprises or consists of SEQ ID NO:10 or SEQ ID NO:11 or which comprises or consists of a nucleotide sequence which has at least any one of 60%, 65%, 70%, 75%, 80%, 85%, 90%, or 95% sequence identity, or is 100% identical, to any one of the full-length sequence of SEQ ID NO:10, SEQ ID NO:11, SEQ ID NO:12, SEQ ID NO:13, SEQ ID NO:14, SEQ ID NO:15, or SEQ ID NO:16, or any one of SEQ ID NO:41-45, respectively.

Specifically, the ECP promoter comprises of consists of at least a part or fragment of SEQ ID NO:10 or SEQ ID NO:11 with a length of at least any one of 300, 400, 500, 600, 700, 800, 900 or 1000 bp, in particular which includes a TFBS and/or the 3' terminus.

Specifically, any of the first and second core regulatory regions of the ECP, or the main regulatory region of the ECP, contains one or more TFBS. Specifically, each of said first and second core regulatory regions, or both of said first and second core regulatory regions together, or each of said main regulatory regions of the ECP, comprises a TFBS or at least a part thereof which is considered functional and being recognized by the respective transcription factor.

Specifically, the TFBS is recognized by any one or more of the transcription factors selected from the group consisting of Rgt1 (e.g., comprising or consisting of SEQ ID NO:47), Cat8-1 (e.g., comprising or consisting of SEQ ID NO:48) and Cat8-2 (e.g., comprising or consisting of SEQ ID NO:49).

A TFBS is characterized by certain consensus sequences, which can vary for the same factor. The specific transcription factors are identified as follows:

Rgt1 is a glucose-responsive transcriptional activator and repressor and it regulates the expression of several glucose transporter (HXT) genes. Rgt1 of P. pastoris comprises the amino acid sequence SEQ ID NO:47.

Cat8-1 and Cat8-2 are zinc cluster transcriptional activators binding to carbon source response elements, necessary for derepression of a variety of genes under non-fermentative growth conditions. Cat8-1 and Cat8-2 of P. pastoris comprise the amino acid sequences SEQ ID NO:48 and SEQ ID NO:49, respectively.

According to a specific aspect, the ECP comprises at least two, three, four, five, six, seven or eight TFBS, wherein each of the TFBS is individually recognized by any of Rgt1, Cat8-1 or Cat8-2.

Specifically, the ECP is characterized by an increased promoter strength compared to a reference promoter, wherein
the promoter strength is the same or higher than the promoter strength of the reference promoter, in particular is at least any one of 1.1-fold, 1.2-fold, 1.3-fold, 1.4-fold, 1.5-fold, 1.6-fold, 1.7-fold, 1.8-fold, 1.9-fold, 2-fold, 2.1-fold, 2.2-fold, 2.3-fold, 2.4-fold, 2.5-fold, 2.6-fold, 2.7-fold, 2.8-fold, 2.9-fold, 3-fold, 3.3-fold, 3.5-fold, 3.8-fold, 4-fold, 4.5-fold, 5-fold, 5.5-fold, or at least 6-fold increased when in the induced state.

In particular, the native pGAP promoter of the host cell, specifically a pGAP promoter which is endogenous to and naturally-occurring in the host cell that is used for recombinant POI production e.g., the native pGAP promoter of P. pastoris as used to control the expression of GAPDH in P. pastoris, which comprises or consists of SEQ ID NO:46, may serve as a reference in a P. pastoris host cell, to determine the improved ECP promoter strength. Such reference promoter may be used in parallel control experiments using the same host cell and expression system, or as internal control within the same host cell culture. Such control experiments to qualify the promoter function as compared to the reference promoter are preferably carried out in P. pastoris host cell cultures, in particular recombinant P. pastoris expressing a model protein, such as GFP or eGFP. The promoter strength as compared to the reference promoter strength can be determined by the following standard assay: P. pastoris strains expressing eGFP under the control of the promoter to be tested are screened in 24-deep well plates at 25° C. with shaking at 280 rpm with 2 mL culture per well. Glucose feed beads (6 mm, Kuhner, CH) are used to generate glucose-limiting growth conditions. Cells are analysed for eGFP expression in the induced state (YP+1 feed bead, for 20-28 hours).

According to a specific aspect, the relative promoter or transcription strength or rate of the ECP described herein is compared to the native pGAP promoter of a cell of the same species or strain that is used as a host for producing a POI.

Specifically, the reference promoter is the native pGAP promoter of the host cell. For example, a native pGAP promoter of P. pastoris which is the unmodified, endogenous promoter sequence in P. pastoris, as used to control the expression of GAPDH in P. pastoris (GS115), e.g. comprising or consisting of the sequence identified as SEQ ID NO:46 can be used as reference promoter in P. pastoris. If P. pastoris is used as a recombinant host cell for producing a POI as described herein, the transcription strength or rate of the ECP described herein is conveniently compared to such native pGAP promoter of P. pastoris.

Exemplary native pGAP promoter sequence of P. pastoris (GS115) (SEQ ID NO:46)

| # | Name | PAS* | PIPA* | GS115 description |
|---|------|------|-------|-------------------|
| pGAP | TDH3 | PAS_chr2-1_0437 | PIPA02510 | Glyceraldehyde-3-phosphate dehydrogenase |

*PAS: ORF name in P. pastoris GS115;
PIPA: ORF name in P. pastoris type strain DSMZ70382

According to another example, a native pGAP promoter of S. cerevisiae can be used as reference promoter, which is the unmodified, endogenous promoter sequence in S. cerevisiae, as used to control the expression of GAPDH in S. cerevisiae. If S. cerevisiae is used as a recombinant host cell for producing a POI as described herein, the transcription strength or rate of the ECP described herein is conveniently compared to such native pGAP promoter of S. cerevisiae.

Specifically, the promoter strength is determined by the expression level of a POI, such as a model protein (e.g., Green Fluorescence Protein, GFP, including e.g., enhanced GFP, eGFP, Gene Bank Accession no. U57607), and/or the transcription strength, as compared to the reference promoter. Preferably, the transcription analysis is quantitative or semi-quantitative, preferably employing qRT-PCR, DNA microarrays, RNA sequencing and transcriptome analysis.

Specifically, the ECP is further characterized by a promoter induction ratio which is characterized by a high transcription strength in the fully induced state, compared to a low level in the repressed state.

The promoter induction ratio, specifically refers to induction of transcription, specifically including further translation and optional expression of said POI. The transcription is typically determined as a measure of the promoter strength and specifically refers to the amount of transcripts obtained upon fully inducing said promoter. Said transcript abundance may be determined by the transcription strength in the fully induced state, which is e.g., obtained under conditions of glucose-limited chemostat cultivations and expressed relative to the transcription rate of a reference promoter.

The induction ratio is a key parameter to determine the carbon source regulation of the ECP, and sets the promoter activity or strength in the induced state in relation to the promoter activity or strength in the repressed state. For example, the expression level of a reporter protein (e.g., GFP or eGFP) and/or the transcription level in the repressed state is determined upon repression by excess glycerol, and the expression level of the model protein and/or the transcription level is determined in the induced state upon induction by limiting glucose feeding.

The ECP promoter is considered as de-repressed and fully induced, if the culture conditions provide for about maximum induction, e.g. at glucose concentrations of less than 0.4 g/L, preferably less than 0.04 g/L, specifically less than 0.02 g/L. The fully induced promoter preferably shows a transcription level/strength of at least 20%, more preferred at least 30%, 40%, 50%, 60%, 70%, 80%, 90% and at least 100% or even higher transcription level/strength of at least 150% or at least 200% as compared to the native pGAP promoter. The transcription level/strength may, for example, be determined by the amount of transcripts of a reporter gene, such as eGFP upon cultivating a clone in liquid culture. Alternatively, the transcription rate may be determined by the transcription strength of the natively controlled gene on a microarray, where microarray data show the difference of expression level between repressed and de-repressed state and a high signal intensity in the fully induced state as compared to a control.

Specifically, the induction ratio can be determined by the ratio of expression level (e.g. of a model protein such as GFP or eGFP) in the induced vs. the repressed state. The induction ratio as compared to a reference promoter can be determined by the following standard assay: *P. pastoris* strains expressing eGFP under the control of the promoter to be tested are screened in 24-deep well plates at 25° C. with shaking at 280 rpm with 2 mL culture per well. Glucose feed beads (6 mm, Kuhner, CH) are used to generate glucose-limiting growth conditions. Cells are analyzed for eGFP expression during repression (YP+1% glycerol, exponential phase) and induction (YP+1 feed bead, for 20-28 hours).

Specifically, the ECP promoter has a promoter activity or strength (e.g., transcriptional activity or transcription strength) in the de-repressed (induced) state, which is at least any one of 1.5, 2.0, 2.5, 3, 3.5, 4, 4.5, 5, 5.5, 6, 6.5, 7, 7.5, 8, 8.5, 9, 9.5, or 10 fold higher than in the repressed state. Therefore, the respective induction rate can be at least any one of 1.5, 2.0, 2.5, 3, 3.5, 4, 4.5, 5, 5.5, 6, 6.5, 7, 7.5, 8, 8.5, 9, 9.5, or 10.

It has surprisingly turned out that the transcriptional activity (or transcription strength) of an ECP described herein (when fully induced, e.g. under glucose-limiting inducing conditions) in a flo8 knockout strain as compared to a wild-type strain which comprises a flo8 locus and produces FLO8 protein is far higher, such as at least any one of 1.5-fold, 1.6-fold, 1.7-fold, 1.8-fold, 1.9-fold, 2-fold, 3-fold, 4-fold, 5-fold, 6-fold, 7-fold, 8-fold, 9-fold, or 10-fold higher. The transcription strength in the host cell described herein was found to be significantly increased allowing higher expression levels of a GOI under control of the ECP in a flo8 deletion mutant. In contrast, transcription from pGAP or pAOX is not increased in a flo8 deletion mutant (as determined in a comparable example).

According to a specific aspect, the heterologous expression cassette is comprised in an autonomously replicating vector or plasmid, or integrated within a chromosome of said host cell.

The expression cassette may be introduced into the host cell and integrated into the host cell genome (or any of its chromosomes) as intrachromosomal element e.g., at a specific site of integration or randomly integrated, whereupon a high producer host cell line is selected. Alternatively, the expression cassette may be integrated within an extrachromosomal genetic element, such as a plasmid or an artificial chromosome e.g., a yeast artificial chromosome (YAC). According to a specific example, the expression cassette is introduced into the host cell by a vector, in particular an expression vector, which is introduced into the host cell by a suitable transformation technique. For this purpose, the GOI may be ligated into an expression vector.

A preferred yeast expression vector (which is preferably used for expression in yeast) is selected from the group consisting of plasmids derived from pPICZ, pGAPZ, pPIC9, pPICZalfa, pGAPZalfa, pPIC9K, pGAPHis, pPUZZLE or GoldenPiCS.

Techniques for transfecting or transforming host cells for introducing a vector or plasmid are well known in the art. These can include electroporation, spheroplasting, lipid vesicle mediated uptake, heat shock mediated uptake, calcium phosphate mediated transfection (calcium phosphate/DNA co-precipitation), viral infection, and particularly using modified viruses such as, for example, modified adenoviruses, microinjection and electroporation.

Transformants as described herein can be obtained by introducing the expression cassette, vector or plasmid DNA into a host and selecting transformants which express the relevant protein or selection marker. Host cells can be treated to introduce heterologous or foreign DNA by methods conventionally used for transformation of host cells, such as the electric pulse method, the protoplast method, the lithium acetate method, and modified methods thereof. *P. pastoris* is preferably transformed by electroporation. Preferred methods of transformation for the uptake of the recombinant DNA fragment by the microorganism include chemical transformation, electroporation or transformation by protoplastation.

Specifically, the expression cassette comprises the ECP operably linked to the GOI encoding the POI, and optionally further comprises signal and leader sequences, as necessary to express and produce the POI as a secreted protein.

According to a specific aspect, the expression cassette further comprises a nucleotide sequence encoding a signal peptide enabling the secretion of the POI preferably wherein the nucleotide sequence encoding the signal peptide is fused adjacent to, or directly to the 5'-end of the GOI.

Specifically, the signal peptide is selected from the group consisting of signal sequences from *S. cerevisiae* alpha-mating factor prepro peptide, the signal peptides from the *P. pastoris* acid phosphatase gene (PHO1) and the extracellular protein X (EPX1) (Heiss, S., V. Puxbaum, C. Gruber, F. Altmann, D. Mattanovich & B. Gasser, Microbiology 2015; 161(7):1356-68).

Specifically, any of the signal and/or leader sequences as described in WO2014067926 A1 can be used, in particular SEQ ID NO:59 or SEQ ID NO:60.

Specifically, signal sequences as described in WO2012152823 A1 can be used, in particular the signal sequence of native alpha mating factor of *S. cerevisiae* identified as SEQ ID NO:61, or mutants thereof.

According to a specific aspect, the host cell described herein may undergo one or more further genetic modifications e.g., for improving protein production.

Specifically, the host cell is further engineered to modify one or more genes influencing proteolytic activity used to generate protease deficient strains, in particular a strain deficient in carboxypeptidase Y activity. Particular examples are described in WO1992017595A1. Further examples of a protease deficient *Pichia* strain with a functional deficiency in a vacuolar protease, such as proteinase A or proteinase B, are described in U.S. Pat. No. 6,153,424A. Further examples are *Pichia* strains which have an ade2 deletion, and/or deletions of one or both of the protease genes, PEP4 and PRB1, are provided by e.g., ThermoFisher Scientific.

Specifically, the host cell is engineered to modify at least one nucleic acid sequence encoding a functional gene product, in particular a protease, selected from the group consisting of PEP4, PRB1, YPS1, YPS2, YMP1, YMP2, YMP1, DAP2, GRHI, PRD1, YSP3, and PRB3, as disclosed in WO2010099195A1.

Overexpression or underexpression of genes encoding helper factors is specifically applied to enhance expression of a GOI, e.g. as described in WO2015158800A1.

Overexpression of the following genes was shown to increase POI secretion in *P. pastoris*: PP7435_Chr3-0607, PP7435_Chr3-0933, PP7435_Chr2-0220, PP7435_Chr3-0639, PP7435_Chr4-0108, PP7435_Chr1-1232, PP7435_Chr1-1225, PP7435_Chr1-0667, and PP7435_Chr4-0448.

Underexpression of the following genes was shown to increase POI secretion in *P. pastoris*: PP7435_Chr1-0176, PP7435_Chr3-1062, and PP7435_Chr4-0252.

In particular, the host cell can be engineered to overexpress any one or more of the helper factors and to increase the production of the respective proteins identified by any one of SEQ ID NO:62-71, thereby further increasing the POI yield. The POI can be any one of eukaryotic, prokaryotic or synthetic peptides, polypeptides, proteins, or metabolites of a host cell.

Specifically, the POI is heterologous to the host cell species.

Specifically, the POI is a secreted peptide, polypeptide, or protein, i.e. secreted from the host cell into the cell culture supernatant.

Specifically, the POI is a eukaryotic protein, preferably a mammalian derived or related protein such as a human protein or a protein comprising a human protein sequence, or a bacterial protein or bacterial derived protein Preferably, the POI is a therapeutic protein functioning in mammals.

In specific cases, the POI is a multimeric protein, specifically a dimer or tetramer.

According to a specific aspect, the POI is a peptide or protein selected from the group consisting of an antigen-binding protein, a therapeutic protein, an enzyme, a peptide, a protein antibiotic, a toxin fusion protein, a carbohydrate-protein conjugate, a structural protein, a regulatory protein, a vaccine antigen, a growth factor, a hormone, a cytokine, a process enzyme, and a metabolic enzyme.

Specifically, the antigen-binding protein is selected from the group consisting of
  a) antibodies or antibody fragments, such as any of chimeric antibodies, humanized antibodies, bi-specific antibodies, Fab, Fd, scFv, diabodies, triabodies, Fv tetramers, minibodies, single-domain antibodies like VH, VHH, IgNARs, or V-NAR;
  b) antibody mimetics, such as Adnectins, Affibodies, Affilins, Affimers, Affitins, Alphabodies, Anticalins, Avimers, DARPins, Fynomers, Kunitz domain peptides, Monobodies, or NanoCLAMPS; or
  c) fusion proteins comprising one or more immunoglobulin-fold domains, antibody domains or antibody mimetics.

A specific POI is an antigen-binding molecule such as an antibody, or a fragment thereof, in particular an antibody fragment comprising an antigen-binding domain. Among specific POIs are antibodies such as monoclonal antibodies (mAbs), immunoglobulin (Ig) or immunoglobulin class G (IgG), heavy-chain antibodies (HcAb's), or fragments thereof such as fragment-antigen binding (Fab), Fd, single-chain variable fragment (scFv), or engineered variants thereof such as for example Fv dimers (diabodies), Fv trimers (triabodies), Fv tetramers, or minibodies and single-domain antibodies like VH, VHH, IgNARs, or V-NAR, or any protein comprising an immunoglobulin-fold domain. Further antigen-binding molecules may be selected from antibody mimetics, or (alternative) scaffold proteins such as e.g., engineered Kunitz domains, Adnectins, Affibodies, Affiline, Anticalins, or DARPins.

According to a specific aspect, the POI is e.g., BOTOX, Myobloc, Neurobloc, Dysport (or other serotypes of botulinum neurotoxins), alglucosidase alpha, daptomycin, YH-16, choriogonadotropin alpha, filgrastim, cetrorelix, interleukin-2, aldesleukin, teceleulin, denileukin diftitox, interferon alpha-n3 (injection), interferon alpha-nl, DL-8234, interferon, Suntory (gamma-1a), interferon gamma, thymosin alpha 1, tasonermin, DigiFab, ViperaTAb, EchiTAb, CroFab, nesiritide, abatacept, alefacept, Rebif, eptoterminalfa, teriparatide (osteoporosis), calcitonin injectable (bone disease), calcitonin (nasal, osteoporosis), etanercept, hemoglobin glutamer 250 (bovine), drotrecogin alpha, collagenase, carperitide, recombinant human epidermal growth factor (topical gel, wound healing), DWP401, darbepoetin alpha, epoetin omega, epoetin beta, epoetin alpha, desirudin, lepirudin, bivalirudin, nonacog alpha, Mononine, eptacog alpha (activated), recombinant Factor VIII+VWF, Recombinate, recombinant Factor VIII, Factor VIII (recombinant), Alphnmate, octocog alpha, Factor VIII, palifermin, indikinase, tenecteplase, alteplase, pamiteplase, reteplase, nateplase, monteplase, follitropin alpha, rFSH, hpFSH, micafungin, pegfilgrastim, lenograstim, nartograstim, sermorelin, glucagon, exenatide, pramlintide, iniglucerase, galsulfase, Leucotropin, molgramostim, triptorelin acetate, histrelin (subcutaneous implant, Hydron), deslorelin, histrelin, nafarelin, leuprolide sustained release depot (ATRIGEL), leuprolide implant (DUROS), goserelin, Eutropin, KP-102 program, somatropin, mecasermin (growth failure), enifavirtide, Org-33408, insulin glargine, insulin glulisine, insulin (inhaled), insulin lispro, insulin detemir, insulin (buccal, RapidMist), mecasermin rinfabate, anakinra, celmoleukin, 99 mTc-apcitide injection, myelopid, Betaseron, glatiramer acetate, Gepon, sargramostim, oprelvekin, human leukocyte-derived alpha interferons, Bilive, insulin (recombinant), recombinant human insulin, insulin aspart, mecasenin, Roferon-A, interferon-alpha 2, Alfaferone, interferon alfacon-1, interferon alpha, Avonex' recombinant human luteinizing hormone, domase alpha, trafermin, ziconotide, taltirelin, diboterminalfa, atosiban, becaplermin, eptifibatide, Zemaira, CTC-111, Shanvac-B, HPV vaccine (quadrivalent), octreotide, lanreotide, ancestim, agalsidase beta, agalsidase alpha, laronidase, prezatide copper acetate (topical gel), rasburicase, ranibizumab, Actimmune, PEG-Intron, Tricomin, recombinant house dust mite allergy desensitization injection, recombinant human parathyroid hormone (PTH) 1-84 (sc, osteoporosis), epoetin delta, transgenic antithrombin III, Granditropin, Vitrase, recombinant insulin, interferon-alpha (oral lozenge), GEM-21S, vapreotide, idursulfase, omnapatrilat, recombinant serum albumin, certolizumab pegol, glucarpidase, human recombinant C1 esterase inhibitor (angioedema), lanoteplase, recombinant human growth hormone, enfuvirtide (needle-free injection, Biojector 2000), VGV-1, interferon (alpha), lucinactant, aviptadil (inhaled, pulmonary disease), icatibant, ecallantide, omiganan, Aurograb, pexigananacetate, ADI-PEG-20, LDI-200, degarelix, cintredelinbesudotox, Favld, MDX-1379, ISAtx-247, liraglutide, teriparatide (osteoporosis), tifacogin, AA4500, T4N5 liposome lotion, catumaxomab, DWP413, ART-123, Chrysalin, desmoteplase, amediplase, corifollitropinalpha, TH-9507, teduglutide, Diamyd, DWP-412, growth hormone (sustained release injection), recombinant G-CSF, insulin (inhaled, AIR), insulin (inhaled, Technosphere), insulin (inhaled, AERx), RGN-303, DiaPep277, interferon beta (hepatitis C viral infection (HCV)), interferon alpha-n3 (oral), belatacept, transdermal insulin patches, AMG-531, MBP-8298, Xerecept, opebacan, AIDSVAX, GV-1001, LymphoScan, ranpimase, Lipoxysan, lusupultide, MP52 (beta-tricalciumphosphate carrier, bone regeneration), melanoma vaccine, sipuleucel-T, CTP-37, Insegia, vitespen, human thrombin (frozen, surgical bleeding), thrombin, TransMID, alfimeprase, Puricase, terlipressin (intravenous, hepatorenal syndrome), EUR-1008M, recombinant FGF-I (injectable, vascular disease), BDM-E, rotigaptide, ETC-216, P-113, MBI-594AN, duramycin (inhaled, cystic fibrosis), SCV-07, OPI-45, Endostatin, Angiostatin, ABT-510, Bowman Birk Inhibitor Concentrate, XMP-629, 99 mTc-Hynic-Annexin V, kahalalide F, CTCE-9908, teverelix (extended release), ozarelix, romidepsin, BAY-504798, interleukin4, PRX-321, Pepscan, iboctadekin, rhlactoferrin, TRU-015, IL-21, ATN-161, cilengitide, Albuferon, Biphasix, IRX-2, omega interferon, PCK-3145, CAP-232, pasireotide, huN901-DMI, ovarian cancer immunotherapeutic vaccine, SB-249553, Oncovax-CL, OncoVax-P, BLP-25, CerVax-16, multi-epitope peptide melanoma vaccine (MART-1, gp100, tyrosinase), nemifitide, rAAT (inhaled), rAAT (dermatological), CGRP (inhaled, asthma), pegsunercept, thymosinbeta4, plitidepsin, GTP-200, ramoplanin, GRASPA, OBI-1, AC-100, salmon calcitonin (oral, eligen), calcitonin (oral, osteoporosis), examorelin, capromorelin, Cardeva, velafermin, 131I-TM-601, KK-220, T-10, ularitide, depelestat, hematide, Chrysalin (topical), rNAPc2, recombinant Factor V111 (PEGylated liposomal), bFGF, PEGylated recombinant staphylokinase variant, V-10153, SonoLysis Prolyse, NeuroVax, CZEN-002, islet cell neogenesis therapy, rGLP-1, BIM-51077, LY-548806, exenatide (controlled release, Medisorb), AVE-0010, GA-GCB, avorelin, ACM-9604, linaclotid eacetate, CETi-1, Hemospan, VAL (injectable), fast-acting insulin (injectable, Viadel), intranasal insulin, insulin (inhaled), insulin (oral, eligen), recombinant methionyl human leptin, pitrakinra subcutancous injection, eczema), pitrakinra (inhaled dry powder, asthma), Multikine, RG-1068, MM-093, NBI-6024, AT-001, PI-0824, Org-39141, Cpn10 (autoimmune diseases/inflammation), talactoferrin (topical), rEV-131 (ophthalmic), rEV-131 (respiratory disease), oral recombinant human insulin (diabetes), RPI-78M, oprelvekin (oral), CYT-99007 CTLA4-Ig, DTY-001, valategrast, interferon alpha-n3 (topical), IRX-3, RDP-58, Tauferon, bile salt stimulated lipase, Merispase, alaline phosphatase, EP-2104R, Melanotan-II, bremelanotide, ATL-104, recombinant human microplasmin, AX-200, SEMAX, ACV-1, Xen-2174, CJC-1008, dynorphin A, S1-6603, LAB GHRH, AER-002, BGC-728, malaria vaccine (virosomes, PeviPRO), ALTU-135, parvovirus B19 vaccine, influenza vaccine (recombinant neuraminidase), malaria/HBV vaccine, anthrax vaccine, Vacc-5q, Vacc-4x, HIV vaccine (oral), HPV vaccine, Tat Toxoid, YSPSL, CHS-13340, PTH(1-34) liposomal cream (Novasome), Ostabolin-C, PTH analog (topical, psoriasis), MBRI-93.02, MTB72F vaccine (tuberculosis), MVA-Ag85A vaccine (tuberculosis), FARA04, BA-210, recombinant plague FIV vaccine, AG-702, OxSODrol, rBetV1, Der-p1/Der-p2/Der-p7 allergen-targeting vaccine (dust mite allergy), PR1 peptide antigen (leukemia), mutant ras vaccine, HPV-16 E7 lipopeptide vaccine, labyrinthin vaccine (adenocarcinoma), CML vaccine, WT1-peptide vaccine (cancer), IDD-5, CDX-110, Pentrys, Norelin, CytoFab, P-9808, VT-111, icrocaptide, telbermin (dermatological, diabetic foot ulcer), rupintrivir, reticulose, rGRF, HA, alpha-galactosidase A, ACE-011, ALTU-140, CGX-1160, angiotensin therapeutic vaccine, D-4F, ETC-642, APP-018, rhMBL, SCV-07 (oral, tuberculosis), DRF-7295, ABT-828, ErbB2-specific immunotoxin (anticancer), DT3SSIL-3, TST-10088, PRO-1762, Combotox, cholecystokinin-B/gastrin-receptor binding peptides, 111In-hEGF, AE-37, trasnizumab-DM1, Antagonist G, IL-12 (recombinant), PM-02734, IMP-321, rhIGF-BP3, BLX-883, CUV-1647 (topical), L-19 based radioimmunotherapeutics (cancer), Re-188-P-2045, AMG-386, DC/1540/KLH vaccine (cancer), VX-001, AVE-9633, AC-9301, NY-ESO-1 vaccine (peptides), NA17.A2 peptides, melanoma vaccine (pulsed antigen therapeutic), prostate cancer vaccine, CBP-501, recombinant human lactoferrin (dry eye), FX-06, AP-214, WAP-8294A (injectable), ACP-HIP, SUN-11031, peptide YY [3-36] (obesity, intranasal), FGLL, atacicept, BR3-Fc, BN-003, BA-058, human parathyroid hormone 1-34 (nasal, osteoporosis), F-18-CCR1, AT-1100 (celiac disease/diabetes), JPD-003, PTH(7-34) liposomal cream (Novasome), duramycin (ophthalmic, dry eye), CAB-2, CTCE-0214, GlycoPEGylated erythropoietin, EPO-Fc, CNTO-528, AMG-114, JR-013, Factor XIII, aminocandin, PN-951, 716155, SUN-E7001, TH-0318, BAY-73-7977, teverelix (immediate release), EP-51216, hGH (controlled release, Biosphere), OGP-1, sifuvirtide, TV4710, ALG-889, Org-41259, rhCC10, F-991, thymopentin (pulmonary diseases), r(m) CRP, hepatoselective insulin, subalin, L19-IL-2 fusion protein, elafin, NMK-150, ALTU-139, EN-122004, rhTPO, thrombopoietin receptor agonist (thrombocytopenic disorders), AL-108, AL-208, nerve growth factor antagonists (pain), SLV-317, CGX-1007, INNO-105, oral teriparatide (eligen), GEM-OS1, AC-162352, PRX-302, LFn-p24 fusion vaccine (Therapore), EP-1043, *S pneumoniae* pediatric vaccine, malaria vaccine, *Neisseria meningitidis* Group B vaccine, neonatal group B streptococcal vaccine, anthrax vaccine, HCV vaccine (gpE1+gpE2+MF-59), otitis media therapy, HCV vaccine (core antigen+ISCOMATRIX), hPTH (1-34) (transdermal, ViaDerm), 768974, SYN-101, PGN-0052, aviscumnine, BIM-23190, tuberculosis vaccine, multi-epitope tyrosinase peptide, cancer vaccine, enkastim, APC-8024, GI-5005, ACC-001, TTS-CD3, vascular-targeted TNF (solid tumors), desmopressin (buccal controlled-release), onercept, or TP-9201, adalimumab (HUMIRA), infliximab (REMICADE™), rituximab (RITUXAN™/ MAB THERA™), etanercept (ENBREL™), bevacizumab (AVASTIN™), trastuzumab (HERCEPTIN™), pegrilgrastim (NEULASTA™), or any other suitable POI including biosimilars and biobetters.

According to a specific aspect, the host cell can be any animal cell, a vertebrate cell, a mammalian cell, a human cell, a plant cell, a nematodal cell, an invertebrate cell such as an insect cell or a mollusc cell, a stem cell derived of any of the foregoing, or a fungal cell or a yeast cell. Specifically the host cell is a cell of a genus selected from the group consisting of *Pichia, Hansenula, Komagataella, Saccharomyces, Kluyveromyces, Candida, Ogataea, Yarrowia,* and *Geotrichum,* specifically *Saccharomyces cerevisiae, Pichia pastoris, Ogataea minuta, Kluyveromyces lactis, Kluyveromes marxianus, Yarrowia lipolytica* or *Hansenula polymorpha,* or of filamentous fungi like *Aspergillus awamori* or *Trichoderma reesei.* Preferably, the host cell is a methylotrophic yeast, preferably *Pichia pastoris.* Herein *Pichia pastoris* is used synonymously for all, *Komagataella pastoris, Komagataella phaffii* and *Komagataella pseudopastoris.*

According to a specific aspect, the host cell is
a) a yeast cell of a genus selected from the group consisting of *Pichia, Hansenula, Komagataella, Saccharomyces, Kluyveromyces, Candida, Ogataea, Yarrowia,* and *Geotrichum,* such as of a *Pichia* genus (e.g. *Pichia pastoris, Pichia methanolica, Pichia kluyveri,* and *Pichia angusta), Komagataella* genus (e.g., *Komagataella pastoris, Komagataella pseudopastoris* or

*Komagataella phaffii*), *Saccharomyces* genus (e.g. *Saccharomyces cerevisae, Saccharomyces kluyveri, Saccharomyces uvarum*), *Kluyveromyces* genus (e.g. *Kluyveromyces lactis, Kluyveromyces marxianus*), the *Candida* genus (e.g. *Candida utilis, Candida cacaoi, Candida boidinii*), the *Geotrichum* genus (e.g. *Geotrichum fermentans*), *Hansenula polymorpha, Yarrowia lipolytica*, or *Schizosaccharomyces pombe*; or b) a cell of filamentous fungi, such as *Aspergillus awamori* or *Trichoderma reesei*.

Preferred is the species *Pichia pastoris*. Specifically, the host cell is a *Pichia pastoris* strain selected from the group consisting of CBS 704, CBS 2612, CBS 7435, CBS 9173-9189, DSMZ 70877, X-33, GS115, KM71, KM71H and SMD1168.

Sources: CBS 704 (=NRRL Y-1603=DSMZ 70382), CBS 2612 (=NRRL Y-7556), CBS 7435 (=NRRL Y-11430), CBS 9173-9189 (CBS strains: CBS-KNAW Fungal Biodiversity Centre, Centraalbureau voor Schimmelculturen, Utrecht, The Netherlands), and DSMZ 70877 (German Collection of Microorganisms and Cell Cultures); strains from Invitrogen, such as X-33, GS115, KM71, KM71H and SMD1168.

Examples of preferred *S. cerevisiae* strains include W303, CEN.PK and the BY-series (EUROSCARF collection). All of the strains described above have been successfully used to produce transformants and express heterologous genes.

According to a specific aspect, the eukaryotic host cell can be a fungal cell (e.g., *Aspergillus* (such as *A. niger, A. fumigatus, A. oryzae, A. nidulans*), *Acremonium* (such as *A. thermophilum*), *Chaetomium* (such as *C. thermophilum*), *Chrysosporium* (such as *C. thermophile*), *Cordyceps* (such as *C. militaris*), *Corynascus, Ctenomyces, Fusarium* (such as *F. oxysporum*), *Glomerella* (such as *G. graminicola*), *Hypocrea* (such as *H. jecorina*), *Magnaporthe* (such as *M. oryzae*), *Myceliophthora* (such as *M. thermophile*), *Nectria* (such as *N. haematococca*), *Neurospora* (such as *N. crassa*), *Penicillium, Sporotrichum* (such as *S. thermophile*), *Thielavia* (such as *T. terrestris, T. heterothallica*), *Trichoderma* (such as *T. reesei*), or *Verticillium* (such as *V. dahlia*)).

According to a specific aspect, the mammalian cell is a human or rodent or bovine cell, cell line or cell strain. Examples of specific mammalian cells suitable as host cells described herein are mouse myeloma (NSO)-cell lines, Chinese hamster ovary (CHO)-cell lines, HT1080, H9, HepG2, MCF7, MDBK Jurkat, MDCK, NIH3T3, PC12, BHK (baby hamster kidney cell), VERO, SP2/0, YB2/0, Y0, C127, L cell, COS, e.g., COS1 and COS7, QC1-3, HEK-293, VERO, PER.C6, HeLA, EB1, EB2, EB3, oncolytic or hybridoma-cell lines. Preferably the mammalian cells are CHO-cell lines. In one embodiment, the cell is a CHO cell. In one embodiment, the cell is a CHO-K1 cell, a CHO-K1 SV cell, a DG44 CHO cell, a DUXB11 CHO cell, a DUKX CHO cell, a CHO-S, a CHO FUT8 knock-out CHO GS knock-out cell, a CHO FUT8 GS knock-out cell, a CHOZN, or a CHO-derived cell. The CHO GS knock-out cell (e.g., GSKO cell) is, for example, a CHO-K1 SV GS knockout cell. The CHO FUT8 knockout cell is, for example, the Potelligent® CHOK1 SV (Lonza Biologics, Inc.). Eukaryotic cells also include avian cells, cell lines or cell strains, such as for example, EBx® cells, EB14, EB24, EB26, EB66, or EBvl3.

According to another specific aspect, the eukaryotic cell is an insect cell (e.g., Sf9, Mimic™ Sf9, Sf21, High Five™ (BT1-TN-5B1-4), or BT1-Ea88 cells), an algae cell (e.g., of the genus *Amphora*, Bacillariophyceae, Dunaliella, *Chlorella*, Chlamydomonas, Cyanophyta (cyanobacteria), Nannochloropsis, *Spirulina*, or Ochromonas), or a plant cell (e.g., cells from monocotyledonous plants (e.g., maize, rice, wheat, or *Setaria*), or from a dicotyledonous plants (e.g., cassava, potato, soybean, tomato, tobacco, alfalfa, *Physcomitrella patens* or *Arabidopsis*).

According to a specific aspect, the host cell is a prokaryotic cell e.g. a bacterial cell. Specifically, the host cell is a Gram-positive cell such as *Bacillus, Streptomyces Streptococcus, Staphylococcus* or *Lactobacillus*. *Bacillus* that can be used is, e.g. the *B. subtilis, B. amyloliquefaciens, B. licheniformis, B. natto*, or *B. megaterium*. In embodiments, the cell is *B. subtilis*, such as *B. subtilis* 3NA and *B. subtilis* 168. *Bacillus* is obtainable from, e.g., the *Bacillus* Genetic Stock Center, Biological Sciences 556, 484 West 12$^{th}$ Avenue, Columbus Ohio 43210-1214.

In one embodiment, the prokaryotic cell is a Gram-negative cell, such as *Salmonella* spp. or *Escherichia coli*, such as e.g., TG1, TG2, W3110, DH1, DHB4, DH5a, HMS 174, HMS174 (DE3), NM533, C600, HB101, JM109, MC4100, XL1-Blue and Origami, as well as those derived from *E. coli* B-strains, such as for example BL-21 or BL21 (DE3), all of which are commercially available.

According to a specific embodiment, the prokaryotic cell is selected from the group consisting of *E. coli, B. subtilis*, and *Pseudomonas*.

Suitable host cells are commercially available, for example, from culture collections such as the DSMZ (Deutsche Sammlung von Mikroorganismen und Zellkulturen GmbH, Braunschweig, Germany) or the American Type Culture Collection (ATCC).

According to a specific aspect, the invention provides for a method of increasing the yield of a protein of interest (POI) produced by a host cell expressing a gene of interest (GOI) encoding said POI under the control of a promoter which is regulatable or repressible by a non-methanol carbon source (in particular, the ECP described herein), by reducing in said host cell expression of a gene encoding a FLO8 protein comprising the amino acid sequence identified as SEQ ID NO:1 or a homologue thereof, in particular the gene encoding said FLO8 protein, which is endogenous to the host cell.

Specifically, the yield is increased by of at least any one of 1.2 fold, 1.3 fold, 1.4 fold, 1.5 fold, 1.6 fold, 1.7 fold, 1.8 fold, 1.9 fold, 2.0 fold, 2.1 fold, 2.2 fold, 2.3 fold, 2.4 fold, 2.5 fold, 2.6 fold, 2.7 fold, 2.8 fold, 2.9 fold, 3 fold, 3.5 fold, 4 fold, 5 fold, 5.5 fold, 6 fold, 6.5 fold, 7 fold, 7.5 fold, 8 fold, 8.5 fold, 9 fold, 9.5 fold, 10 fold, 10.5 fold, 11 fold, 11.5 fold, or 12 fold, as compared to the comparable host cell expressing said GOI, a) which is not engineered to reduce the expression of said gene encoding the endogenous FLO8 protein, or wherein the expression of said gene encoding the endogenous FLO8 protein is not modified; and optionally b) wherein the promoter controlling the expression of said GOI is a constitutive promoter, in particular a GAP promoter, or a methanol-inducible promoter, in particular an AOX1 promoter.

Specifically, the method of increasing the yield of the POI production described herein employs a recombinant host cell as further described herein.

According to a further specific aspect, the invention provides for a method for producing a protein of interest (POI) encoded by a gene of interest (GOI) by culturing the recombinant host cell as further described herein under conditions to produce said POI.

According to a further specific embodiment, the invention provides for the use of the host cell described herein for the production of a POI.

Specifically, the host cell is a cell line cultured in a cell culture, in particular a production host cell line.

According to a specific embodiment, the cell line is cultured under batch, fed-batch or continuous culture conditions. The culture may be performed in microtiter plates, shake-flasks, or a bioreactor, and optionally starting with a batch phase as the first step, followed by a fed-batch phase or a continuous culture phase as the second step.

Specifically, the method comprises the steps:
a) culturing the host cell under growing conditions; and a further step
b) culturing the host cell under growth-limiting conditions in the presence of up to 1 g/L of a second non-methanol carbon source, resulting in expression of said GOI to produce said POI.

Specifically, the second step b) follows the first step a).

Specifically, the first carbon source is a non-methanol carbon source herein referred to as basal carbon source.

Specifically, the host cell is cultured in the first step under growing conditions in a cell culture medium comprising the first carbon source, e.g. in an amount sufficient to enable growth of the host cell in cell culture, optionally until the amount of the carbon source is consumed, and further culturing can be under growth-limiting conditions.

Specifically, the second carbon source is a non-methanol carbon source herein referred to as supplemental carbon source.

Specifically, said first and/or second carbon source is selected from saccharides, polyols, alcohols, or mixtures of any one or more of the foregoing, as further described herein.

According to a specific embodiment, the basal carbon source is different from the supplemental carbon source, e.g. quantitatively and/or qualitatively different. The quantitative difference typically provides for the different conditions to repress or de-repress the promoter activity.

According to a further specific embodiment the basal and the supplemental carbon sources comprise the same type of molecules or carbohydrates, preferably in different concentrations. According to a further specific embodiment, the carbon source is a mixture of two or more different carbon sources.

Any type of organic carbon source may be used, in particular those typically used for host cell culture, in particular for eukaryotic host cell culture. According to a specific embodiment, the carbon source is a hexose, such as glucose, fructose, galactose or mannose, a disaccharide, such as saccharose, an alcohol, such as glycerol or ethanol, or a mixture thereof.

According to a specifically preferred embodiment, the basal carbon source is selected from the group consisting of glucose, glycerol, ethanol, or mixtures thereof. According to a preferred embodiment, the basal carbon source is glycerol.

According to a further specific embodiment, the supplemental carbon source is a hexose such as glucose, fructose, galactose and mannose, a disaccharide, such as saccharose, an alcohol, such as glycerol or ethanol, or a mixture thereof. According to a preferred embodiment, the supplemental carbon source is glucose.

Specifically,
a) the basal carbon source is selected from the group consisting of glucose, glycerol, ethanol, a mixture thereof; and
b) the supplemental carbon source is a hexose such as glucose, fructose, galactose or mannose, a disaccharide, such as saccharose, an alcohol, such as glycerol or ethanol, or a mixture of any of the foregoing.

Both of said culturing steps specifically comprise cultivating the cell line in the presence of said carbon sources. For example, said culturing the host cell under growing conditions (step a) is carried out using a basal carbon source; and said culturing the host cell under growth-limiting conditions (step b) is carried out using a supplemental carbon source, e.g. in a limited amount such that the cell culture medium comprises up to 1 g/L or even no detectable amount of the supplemental carbon source in the cell culture medium or supernatant during the culturing (step b).

The de-repressing (or inducing) conditions suitably may be achieved by specific means. The second step b) optionally employs a feed medium that provides for no or the supplemental carbon source in a limited amount in the cell culture medium or supernatant. Specifically, the feed medium is chemically defined and methanol-free.

Specifically, the second step b) employs a feed medium that provides for the supplemental carbon source in a growth limiting amount to keep the specific growth rate within the range of $0.0001\ h^{-1}$ to $0.2\ h^{-1}$, preferably $0.005\ h^{-1}$ to $0.15\ h^{-1}$.

The feed medium may be added to the culture medium in the liquid form or else in an alternative form, such as a solid, e.g. as a tablet or other sustained release means, or a gas. Yet, according to a preferred embodiment the limited amount of a supplemental carbon source added to the cell culture medium, may even be zero. Preferably, under conditions of a limited carbon substrate, the detectable concentration of a supplemental carbon source in the culture medium is 0-1 g/L, preferably less than any one of 0.9, 0.8, 0.7, 0.6, 0.5, 0.4, 0.3, 0.2, 0.1 g/L, preferably less than any one of 90, 80, 70, 60, 50, 40, 30, 20, or 10 mg/L, or even less than 9, 8, 7, 6, 5, 4, 3, 2, or 1 mg/L, or specifically 1-50 mg/L, or 1-10 mg/L, specifically preferred 1 mg/L or even below, such as below the detection limit as measured with a suitable standard assay, e.g. determined as a residual concentration in the culture medium upon consumption by the growing cell culture.

In a preferred method, the limited amount of the supplemental source provides for a residual amount in the cell culture which is below the detection limit as determined in the fermentation broth at the end of a production phase or in the output of a fermentation process, preferably upon harvesting the fermentation product.

Specifically, said step a) culturing is performed in a batch phase; and said step b) culturing is performed in fed-batch or a continuous cultivation phase.

Specifically, the host cells are grown in a carbon source rich medium comprising a basal carbon source during the phase of high growth rate (under growing conditions), step a) (e.g. at least 50%, or at least 60%, at least 70%, at least 80%, at least 90%, at least 95%, at least 98%, at least 99%, or up to the maximum growth rate) and producing the POI during a phase of low growth rate (under growth-limiting conditions), step b) (e.g. less than 90%, preferably less than 80%, less than 70%, less than 60%, less than 50%, or less than 40%, less than 30%, less than 20%, less than 10%, less than 5%, less than 3%, less than 2%, less than 1%, less than 0.5%, less than 0.4%, less than 0.3%, or less than 0.2% of the maximum growth rate) while limiting the carbon source, in particular by feeding a defined minimal medium comprising only the amount of carbon source which is completely consumed when maintaining the cell culture in the production phase.

Specifically, the POI is expressed under said growth-limiting conditions, e.g. by cultivating the cell line at a growth rate of less than the maximal growth rate, typically less than 90%, preferably less than 80%, less than 70%, less than 60%, less than 50%, less than 40%, less than 30%, less than 20%, less than 10%, less than 5%, less than 3%, less than 2%, less than 1%, less than 0.5%, less than 0.4%, less than 0.3%, or less than 0.2% of the maximum growth rate of the cells. Typically the maximum growth rate is individually determined for each type of host cell.

Specifically, the batch phase is performed until a basal carbon source that is initially added to the cell culture is consumed by the cell line. The dissolved oxygen (DO) spike method can be used to determine basal carbon source consumption during batch phase.

According to a specific embodiment, the batch phase is characterized by a continuous decrease in oxygen partial pressure (pO2) signal and wherein the end of the batch phase is characterized by an increase of pO2. Typically, while consuming the basal carbon source during the batch phase and without adding further carbon sources as typical for batch phases, the oxygen partial pressure (pO2) signal will continuously decrease until for example below 65% such as for example 30%. Upon consumption of the basal carbon source, the pO2 may increase to e.g. above 30% such as for example above 65%, or more indicating the appropriate time point to switch to the fed-batch system using feed medium to add further carbon source under carbon source limited conditions.

Specifically, the pO2 is decreased to less than 65% or less saturation during batch phase followed by an increase of above 65% or more saturation at the end of the batch. Specifically, the batch phase is performed until an increase of the oxygen partial pressure (pO2) signal above 65% saturation, specifically above any of 70%, 75%, 80%, or 85%.

Specifically, the batch phase is performed for around 10 to 36 h.

The term "around" with respect to cultivation time shall mean +/−5% or +/−10%.

For example, the specific batch performance time of around 10 to 36 h may be 18 to 39.6 h, specifically 19 to 37.8 h.

According to a specific embodiment, the batch phase is performed using 40 to 50 g/L glycerol, specifically 45 g/L glycerol as a basal carbon source in batch media, and cultivation is performed at 25° C. for around 27 to 30 h, or at 30° C. for around 23 to 36 h, or at any temperature between 25° C. and 30° C. during a cultivation time of 23 to 36 h. Lowering the glycerol concentration in the batch medium would decrease the length of the batch phase, while increasing the glycerol in the batch medium would even prolong the batch phase. As an alternative to glycerol, glucose can be used, e.g. in about the same amounts.

In a typical system of cell culture and POI expression, wherein a batch phase is followed by a fed-batch phase, specifically, the cultivation in the fed-batch phase is performed for any one of around 15 to 80 h, around 15 to 70 h, around 15 to 60 h, around 15 to 50 h, around 15 to 45 h, around 15 to 40 h, around 15 to 35 h, around 15 to 30 h, around 15 to 35 h, around 15 to 25 h, or around 15 to 20 h; preferably around 20 to 40 h. Specifically, the cultivation in the fed-batch phase is performed for any one of around 80 h, around 70 h, around 60 h, around 55 h, around 50 h, around 45 h, around 40 h, around 35 h, around 33 h, around 30 h, around 25 h, around 20 h, or around 15 h.

Any fed-batch cultivation of less than 120 h or less than 100 h or up to 80 h, which results in a successful POI production thereby obtaining a high yield is herein referred to as "speed fermentation". Specifically, the volume specific product formation rate (rP) is the amount of product (mg) formed per Unit Volume (L) and Unit time (h) (mg (L h)$^{-1}$). Volume specific product formation rate is also called space time yield (STY) or volumetric productivity.

Specifically, the fed-batch cultivation of the method described herein is performed such that a space time yield of around 30 mg (L h)$^{-1}$ (meaning 30 mg (L h)$^{-1}$+/−5% or +/−10%). Specifically a space time yield of around 30 mg (L h)$^{-1}$ is achieved within around 30 h fed batch, specifically at least any of 27, 28, 29, 30, 31, 32, or 33 mg (L h)$^{-1}$ within less than any one of 33 h, 32 h, 31 h, 30 h, 29 h, 28 h, 27 h, 26 h, or 25 h fed batch time can be achieved.

Specifically, the batch phase is performed as a first step a), and the fed-batch phase is performed as a second step b).

Specifically, the second step b) employs a feed medium in a fed-batch phase that provides for a supplemental carbon source in a growth limiting amount to keep the specific growth rate within the range of 0.0001 h$^{-1}$ to 0.2 h$^{-1}$, preferably less than any of 0.2, 0.15, 0.1 h$^{-1}$ or 0.15 h$^{-1}$.

Specifically, the culturing method including both, batch and fed-batch cultivation steps, may particularly employ a yeast host cell, e.g. a yeast of any of the *Saccharomyces* genus or *Pichia* genus or *Komagataella* genus, or yeast from a genus other than *Pichia*, such as *K. lactis, Z. rouxii, P. stipitis, H. polymorpha,* or *Y. lipolytica*, preferably *Pichia pastoris* or *Komagataella pastoris*.

According to a further specific aspect, the invention provides for a method for producing a protein of interest (POI) in a host cell, comprising the steps:

a) genetically engineering the host cell to reduce expression of a an endogenous gene encoding a FLO8 protein comprising the amino acid sequence identified as SEQ ID NO:1 or a homologue thereof;

b) introducing into the host cell a heterologous expression cassette comprising a gene of interest (GOI) encoding or expressing said POI under the control of an expression cassette promoter (ECP) that is operably linked to the GOI, which ECP is regulatable or repressible by a non-methanol carbon source;

c) culturing said host cell under conditions to produce said POI;

d) optionally isolating said POI from the cell culture; and e) optionally purifying said POI.

Specifically, step a) of the method described herein is carried out before, or after, or concomitantly with step b).

According to a specific aspect, the host cell is first genetically modified to reduce expression of said FLO8 protein or the respective homologue thereof before being engineered for producing the POI. According to a specific example, a wild-type host cell is genetically modified according to step a) of the method described herein. Specifically, the host cell is provided upon introducing said one or more genetic modifications into a wild-type host cell strain for reduction of said FLO8 protein or the respective homologue thereof.

According to a further aspect, the host cell is first engineered for producing the heterologous or recombinant POI, before being further genetically modified to reduce said FLO8 protein or the respective homologue thereof. According to a specific example, a wild-type host cell may first be engineered to comprise the expression cassette for POI production. Such engineered host cell may then be further modified to reduce said FLO8 protein or the respective homologue thereof as described herein.

According to a further aspect, the host cell is undergoing both, the engineering for POI production and genetically modifying for reduction of said FLO8 protein or the respective homologue thereof in one method step, e.g., employing the respective expression cassette, reagents and tools in one or more reaction mixtures.

Specifically, the method employs method steps to produce the recombinant host cell as further described herein.

Specifically, the heterologous expression cassette comprises the ECP as further described herein.

Specifically, the POI can be produced by culturing the host cell in an appropriate medium, isolating the expressed POI from the cell culture, in particular from the cell culture supernatant or medium upon separating the cells, and purifying it by a method appropriate for the expressed product, in particular upon separating the POI from the cell and purifying by suitable means. Thereby, a purified POI preparation can be produced.

FIGURES

FIG. 1: Sequences referred to herein

DETAILED DESCRIPTION OF THE INVENTION

Specific terms as used throughout the specification have the following meaning.

The term "carbon source" also referred as "carbon substrate" as used herein shall mean a fermentable carbon substrate, typically a source carbohydrate, suitable as an energy source for microorganisms, such as those capable of being metabolized by host organisms or production cell lines, in particular sources selected from the group consisting of monosaccharides, oligosaccharides, polysaccharides, alcohols including glycerol, in the purified form, in minimal media or provided in raw materials, such as a complex nutrient material. The carbon source may be used as described herein as a single carbon source or as a mixture of different carbon sources.

A non-methanol carbon source is herein understood as an amount of a carbon source which is any other than methanol, in particular a methanol-free carbon source.

A "basal carbon source" such as used as described herein typically is a carbon source suitable for cell growth, such as a nutrient for host cells, in particular for eukaryotic cells. The basal carbon source may be provided in a medium, such as a basal medium or complex medium, but also in a chemically defined medium containing a purified carbon source. The basal carbon source typically is provided in an amount to provide for cell growth, in particular during the growth phase in a cultivation process, for example to obtain cell densities of at least 5 g/L cell dry mass, preferably at least 10 g/L cell dry mass, or at least 15 g/L cell dry mass, e.g. exhibiting viabilities of more than 90% during standard sub-culture steps, preferably more than 95%.

The basal carbon source is typically used in an excess or surplus amount, which is understood as an excess providing energy to increase the biomass, e.g. during the cultivation of a cell line with a high specific growth rate, such as during the growth phase of a cell line in a batch or fed-batch cultivation process. This surplus amount is particularly in excess of the limited amount of a supplemental carbon source (as used under growth-limited conditions) to achieve a residual concentration in the fermentation broth that is measurable and typically at least 10 fold higher, preferably at least 50 fold or at least 100 fold higher than during feeding the limited amount of the supplemental carbon source.

A "supplemental carbon source" such as described herein typically is a supplemental substrate facilitating the production of fermentation products by production cell lines, in particular in the production phase of a cultivation process. The production phase specifically follows a growth phase, e.g. in batch, fed-batch and continuous cultivation process. The supplemental carbon source specifically may be contained in the feed of a fed-batch process. The supplemental carbon source is typically employed in a cell culture under carbon substrate limited conditions, i.e. using the carbon source in a limited amount.

A "limited amount" of a carbon source or a "limited carbon source" is herein understood to specifically refer to the type and amount of a carbon substrate facilitating the production of fermentation products by production cell lines, in particular in a cultivation process with controlled growth rates of less than the maximum growth rate. The production phase specifically follows a growth phase, e.g. in batch, fed-batch and continuous cultivation process. Cell culture processes may employ batch culture, continuous culture, and fed-batch culture. Batch culture is a culture process by which a small amount of a seed culture solution is added to a medium and cells are grown without adding an additional medium or discharging a culture solution during culture. Continuous culture is a culture process by which a medium is continuously added and discharged during culture. The continuous culture also includes perfusion culture. Fed-batch culture, which is an intermediate between the batch culture and the continuous culture and also referred to as semi-batch culture, is a culture process by which a medium is continuously or sequentially added during culture but, unlike the continuous culture, a culture solution is not continuously discharged.

Specifically preferred is a fed-batch process which is based on feeding of a growth limiting nutrient substrate to a culture. The fed-batch strategy, including single fed-batch or repeated fed-batch fermentation, is typically used in bio-industrial processes to reach a high cell density in the bioreactor. The controlled addition of the carbon substrate directly affects the growth rate of the culture and helps to avoid overflow metabolism or the formation of unwanted metabolic byproducts. Under carbon source limited conditions, the carbon source specifically may be contained in the feed of a fed-batch process. Thereby, the carbon substrate is provided in a limited amount.

Also in chemostat or continuous culture as described herein, the growth rate can be tightly controlled.

The limited amount of a carbon source is herein particularly understood as the amount of a carbon source necessary to keep a production cell line under growth-limited conditions, e.g. in a production phase or production mode. Such a limited amount may be employed in a fed-batch process, where the carbon source is contained in a feed medium and supplied to the culture at low feed rates for sustained energy delivery, e.g. to produce a POI, while keeping the biomass at low specific growth rates. A feed medium is typically added to a fermentation broth during the production phase of a cell culture.

The limited amount of a carbon source may, for example, be determined by the residual amount of the carbon source in the cell culture broth, which is below a predetermined threshold or even below the detection limit as measured in a standard (carbohydrate) assay. The residual amount typically would be determined in the fermentation broth upon harvesting a fermentation product.

The limited amount of a carbon source may as well be determined by defining the average feed rate of the carbon source to the fermenter, e.g. as determined by the amount added over the full cultivation process, e.g. the fed-batch phase, per cultivation time, to determine a calculated average amount per time. This average feed rate is kept low to ensure complete usage of the supplemental carbon source by the cell culture, e.g. between 0.6 g $L^{-1}$ $h^{-1}$ (g carbon source per L initial fermentation volume and h time) and 25 g $L^{-1}$ $h^{-1}$, preferably between 1.6 g $L^{-1}$ $h^{-1}$ and 20 g $L^{-1}$ $h^{-1}$.

The limited amount of a carbon source may also be determined by measuring the specific growth rate, which specific growth rate is kept low, e.g. lower than the maximum specific growth rate, during the production phase, e.g. within a predetermined range, such as in the range of 0.001 $h^{-1}$ to 0.20 $h^{-1}$, or 0.005 $h^{-1}$ to 0.20 $h^{-1}$, preferably between 0.01 $h^{-1}$ and 0.15 $h^{-1}$.

Specifically, a feed medium is used which is chemically defined and methanol-free.

The term "chemically defined" with respect to cell culture medium, such as a minimal medium or feed medium in a fed-batch process, shall mean a cultivation medium suitable for the in vitro cell culture of a production cell line, in which all of the chemical components and (poly)peptides are known. Typically, a chemically defined medium is entirely free of animal-derived components and represents a pure and consistent cell culture environment.

The term "host cell" as used herein shall refer to a single cell, a single cell clone, or a cell line of a host cell.

The term "cell line" as used herein refers to an established clone of a particular cell type that has acquired the ability to proliferate over a prolonged period of time. A cell line is typically used for expressing an endogenous or recombinant gene, or products of a metabolic pathway to produce polypeptides or cell metabolites mediated by such polypeptides. A "production host cell line" or "production cell line" is commonly understood to be a cell line ready-to-use for cell culture in a bioreactor to obtain the product of a production process, such as a POI.

The host cell producing the POI as described herein is also referred to as "production host cell", and a respective cell line a "production cell line".

Specific embodiments described herein refer to a production host cell line which is engineered to underexpress an endogenous gene encoding a FLO8 protein, and/or has a reduced expression of such gene, and is characterized by a high yield of POI production under the control of a carbon source regulatable promoter (such as an ECP described herein), in particular a promoter which can be induced without the need to add methanol to the cell culture. Such host cell turned out to be stably expressing the POI without significantly changing morphology.

The term "host cell" shall particularly apply to any eukaryotic or prokaryotic cell or organism, which is suitably used for recombination purposes to produce a POI or a host cell metabolite. It is well understood that the term "host cell" does not include human beings. Specifically, host cells as described herein are artificial organisms and derivatives of native (wild-type) host cells. It is well understood that the host cells, methods and uses described herein, e.g., specifically referring to those comprising one or more genetic modifications, said heterologous expression cassettes or constructs, said transfected or transformed host cells and recombinant proteins, are non-naturally occurring, "manmade" or synthetic, and are therefore not considered as a result of "law of nature".

The term "cell culture" or "culturing" or "cultivation" as used herein with respect to a host cell refers to the maintenance of cells in an artificial, e.g., an in vitro environment, under conditions favoring growth, differentiation or continued viability, in an active or quiescent state, of the cells, specifically in a controlled bioreactor according to methods known in the industry.

When culturing a cell culture using appropriate culture media, the cells are brought into contact with the media in a culture vessel or with substrate under conditions suitable to support culturing the cells in the cell culture. As described herein, a culture medium is provided that can be used for the growth of host cells e.g., eukaryotic cells, specifically yeast or filamentous fungi. Standard cell culture techniques are well-known in the art.

The cell cultures as described herein particularly employ techniques which provide for the production of a secreted POI, such as to obtain the POI in the cell culture medium, which is separable from the cellular biomass, herein referred to as "cell culture supernatant", and may be purified to obtain the POI at a higher degree of purity. When a protein (such as e.g., a POI) is produced and secreted by the host cell in a cell culture, it is herein understood that such proteins are secreted into the cell culture supernatant, and can be obtained by separating the cell culture supernatant from the host cell biomass, and optionally further purifying the protein to produce a purified protein preparation.

Cell culture media provide the nutrients necessary to maintain and grow cells in a controlled, artificial and in vitro environment. Characteristics and compositions of the cell culture media vary depending on the particular cellular requirements. Important parameters include osmolality, pH, and nutrient formulations. Feeding of nutrients may be done in a continuous or discontinuous mode according to methods known in the art.

Whereas a batch process is a cell culture mode in which all the nutrients necessary for culturing the cells are contained in the initial culture medium, without additional supply of further nutrients during fermentation, in a fed-batch process, after a batch phase, a feeding phase takes place in which one or more nutrients are supplied to the culture by feeding. Although in most processes the mode of feeding is critical and important, the host cell and methods described herein are not restricted with regard to a certain mode of cell culture.

A recombinant POI can be produced using the host cell and the respective cell line described herein, by culturing in an appropriate medium, isolating the expressed product or metabolite from the culture, and optionally purifying it by a suitable method.

Several different approaches for the production of the POI as described herein are preferred. A POI may be expressed, processed and optionally secreted by transfecting or transforming a host cell with an expression vector harboring recombinant DNA encoding the relevant protein, preparing a culture of the transfected or transformed cell, growing the culture, inducing transcription and POI production, and recovering the POI.

In certain embodiments, the cell culture process is a fed-batch process. Specifically, a host cell transformed with a nucleic acid construct encoding a desired recombinant POI, is cultured in a growth phase and transitioned to a production phase in order to produce a desired recombinant POI.

In another embodiment, host cells described herein are cultured in a continuous mode, e.g., employing a chemostat. A continuous fermentation process is characterized by a defined, constant and continuous rate of feeding of fresh culture medium into a bioreactor, whereby culture broth is at the same time removed from the bioreactor at the same defined, constant and continuous removal rate. By keeping culture medium, feeding rate and removal rate at the same constant level, the cell culture parameters and conditions in the bioreactor remain constant.

A stable cell culture as described herein is specifically understood to refer to a cell culture maintaining the genetic properties, specifically keeping the POI production level high, e.g. at least at a µg level, even after about 20 generations of cultivation, preferably at least 30 generations, more preferably at least 40 generations, most preferred of at least 50 generations. Specifically, a stable recombinant host cell line is provided which is considered a great advantage when used for industrial scale production.

The cell culture described herein is particularly advantageous for methods on an industrial manufacturing scale, e.g. with respect to both the volume and the technical system, in combination with a cultivation mode that is based on feeding of nutrients, in particular a fed-batch or batch process, or a continuous or semi-continuous process (e.g. chemostat).

The host cell described herein is typically tested for its capacity to express the GOI for POI production, tested for the POI yield by any of the following tests: ELISA, activity assay, HPLC, or other suitable tests, such as SDS-PAGE and Western Blotting techniques, or mass spectrometry.

To determine the effect of a genetic modification on the underexpression or reduction of the gene encoding the FLO8 protein or its homologue in the respective cell culture and e.g., on its effect on POI production, the host cell line may be cultured in microtiter plates, shake flask, or bioreactor using fed-batch or chemostat fermentations in comparison with strains without such genetic modification in the respective cell.

The production method described herein specifically allows for the fermentation on a pilot or industrial scale. The industrial process scale would preferably employ volumes of at least 10 L, specifically at least 50 L, preferably at least 1 m$^3$, preferably at least 10 m$^3$, most preferably at least 100 m$^3$.

Production conditions in industrial scale are preferred, which refer to e.g., fed batch culture in reactor volumes of 100 L to 10 m$^3$ or larger, employing typical process times of several days, or continuous processes in fermenter volumes of approximately 50-1000 L or larger, with dilution rates of approximately 0.02-0.15 h$^{-1}$.

The devices, facilities and methods used for the purpose described herein are specifically suitable for use in and with culturing any desired cell line including prokaryotic and/or eukaryotic cell lines. Further, in embodiments, the devices, facilities and methods are suitable for culturing any cell type including suspension cells or anchorage-dependent (adherent) cells and are suitable for production operations configured for production of pharmaceutical and biopharmaceutical products—such as polypeptide products (POI), nucleic acid products (for example DNA or RNA), or cells and/or viruses such as those used in cellular and/or viral therapies.

In certain embodiments, the cells express or produce a product, such as a recombinant therapeutic or diagnostic product. As described in more detail herein, examples of products produced by cells include, but are not limited to, POIs such as exemplified herein including antibody molecules (e.g., monoclonal antibodies, bispecific antibodies), antibody mimetics (polypeptide molecules that bind specifically to antigens but that are not structurally related to antibodies such as e.g. DARPins, affibodies, adnectins, or IgNARs), fusion proteins (e.g., Fc fusion proteins, chimeric cytokines), other recombinant proteins (e.g., glycosylated proteins, enzymes, hormones), or viral therapeutics (e.g., anti-cancer oncolytic viruses, viral vectors for gene therapy and viral immunotherapy), cell therapeutics (e.g., pluripotent stem cells, mesenchymal stem cells and adult stem cells), vaccines or lipid-encapsulated particles (e.g., exosomes, virus-like particles), RNA (such as e.g. siRNA) or DNA (such as e.g. plasmid DNA), antibiotics or amino acids. In embodiments, the devices, facilities and methods can be used for producing biosimilars.

As mentioned, in certain embodiments, devices, facilities and methods allow for the production of eukaryotic cells, e.g., mammalian cells or lower eukaryotic cells such as for example yeast cells or filamentous fungi cells, or prokaryotic cells such as Gram-positive or Gram-negative cells and/or products of the eukaryotic or prokaryotic cells, e.g., POIs including proteins, peptides, or antibiotics, amino acids, nucleic acids (such as DNA or RNA), synthesized by said cells in a large-scale manner. Unless stated otherwise herein, the devices, facilities, and methods can include any desired volume or production capacity including but not limited to bench-scale, pilot-scale, and full production scale capacities.

Moreover, and unless stated otherwise herein, the devices, facilities, and methods can include any suitable reactor(s) including but not limited to stirred tank, airlift, fiber, microfiber, hollow fiber, ceramic matrix, fluidized bed, fixed bed, and/or spouted bed bioreactors. As used herein, "reactor" can include a fermentor or fermentation unit, or any other reaction vessel and the term "reactor" is used interchangeably with "fermentor." For example, in some aspects, an example bioreactor unit can perform one or more, or all, of the following: feeding of nutrients and/or carbon sources, injection of suitable gas (e.g., oxygen), inlet and outlet flow of fermentation or cell culture medium, separation of gas and liquid phases, maintenance of temperature, maintenance of oxygen and $CO_2$ levels, maintenance of pH level, agitation (e.g., stirring), and/or cleaning/sterilizing. Example reactor units, such as a fermentation unit, may contain multiple reactors within the unit, for example the unit can have 1, 2, 3, 4, 5, 10, 15, 20, 25, 30, 35, 40, 45, 50, 60, 70, 80, 90, or 100, or more bioreactors in each unit and/or a facility may contain multiple units having a single or multiple reactors within the facility. In various embodiments, the bioreactor can be suitable for batch, semi fed-batch, fed-batch, perfusion, and/or a continuous fermentation processes. Any suitable reactor diameter can be used. In embodiments, the bioreactor can have a volume between about 100 mL and about 50,000 L. Non-limiting examples include a volume of 100 mL, 250 mL, 500 mL, 750 mL, 1 liter, 2 liters, 3 liters, 4 liters, 5 liters, 6 liters, 7 liters, 8 liters, 9 liters, 10 liters, 15 liters, 20 liters, 25 liters, 30 liters, 40 liters, 50 liters, 60 liters, 70 liters, 80 liters, 90 liters, 100 liters, 150 liters, 200 liters, 250 liters, 300 liters, 350 liters, 400 liters, 450 liters, 500 liters, 550 liters, 600 liters, 650 liters, 700 liters, 750 liters, 800 liters, 850 liters, 900 liters, 950 liters, 1000 liters, 1500 liters, 2000 liters, 2500 liters, 3000 liters, 3500 liters, 4000 liters, 4500 liters, 5000 liters, 6000 liters, 7000 liters, 8000 liters, 9000 liters, 10,000 liters, 15,000 liters, 20,000 liters, and/or 50,000 liters. Additionally, suitable reactors can be multi-use, single-use, disposable, or non-disposable and can be formed of any suitable material including metal alloys such as stainless steel (e.g., 316L or any other suitable stainless steel) and Inconel, plastics, and/or glass.

In embodiments and unless stated otherwise herein, the devices, facilities, and methods described herein can also include any suitable unit operation and/or equipment not otherwise mentioned, such as operations and/or equipment for separation, purification, and isolation of such products.

Any suitable facility and environment can be used, such as traditional stick-built facilities, modular, mobile and temporary facilities, or any other suitable construction, facility, and/or layout. For example, in some embodiments modular clean-rooms can be used. Additionally, and unless otherwise stated, the devices, systems, and methods described herein can be housed and/or performed in a single location or facility or alternatively be housed and/or performed at separate or multiple locations and/or facilities.

Suitable techniques may encompass culturing in a bioreactor starting with a batch phase, followed by a short exponential fed batch phase at high specific growth rate, further followed by a fed batch phase at a low specific growth rate. Another suitable culture technique may encompass a batch phase followed by a fed-batch phase at any suitable specific growth rate or combinations of specific growth rate such as going from high to low growth rate over POI production time, or from low to high growth rate over POI production time. Another suitable culture technique may encompass a batch phase followed by a continuous culturing phase at a low dilution rate.

A preferred embodiment includes a batch culture to provide biomass followed by a fed-batch culture for high yields POI production.

It is preferred to culture a host cell as described herein in a bioreactor under growth conditions to obtain a cell density of at least 1 g/L cell dry weight, more preferably at least 10 g/L cell dry weight, preferably at least 20 g/L cell dry weight, preferably at least any one of 30, 40, 50, 60, 70, or 80 g/L cell dry weight. It is advantageous to provide for such yields of biomass production on a pilot or industrial scale.

A growth medium allowing the accumulation of biomass, specifically a basal growth medium, typically comprises a carbon source, a nitrogen source, a source for sulphur and a source for phosphate. Typically, such a medium comprises furthermore trace elements and vitamins, and may further comprise amino acids, peptone or yeast extract.

Preferred nitrogen sources include $NH_4H_2PO_4$, or $NH_3$ or $(NH_4)_2SO_4$;

Preferred sulphur sources include $MgSO_4$, or $(NH_4)_2SO_4$ or $K_2SO_4$;

Preferred phosphate sources include $NH_4H_2PO_4$, or $H_3PO_4$, or $NaH_2PO_4$, $KH_2PO_4$, $Na_2HPO_4$ or $K_2HPO_4$;

Further typical medium components include KCl, $CaCl_2$, and Trace elements such as: Fe, Co, Cu, Ni, Zn, Mo, Mn, I, B;

Preferably the medium is supplemented with vitamin $B_7$;

A typical growth medium for *P. pastoris* comprises glycerol, sorbitol or glucose, $NH_4H_2PO_4$, $MgSO_4$, KCl, $CaCl_2$, biotin, and trace elements.

In the production phase a production medium is specifically used with only a limited amount of a supplemental carbon source.

Preferably the host cell line is cultured in a mineral medium with a suitable carbon source, thereby further simplifying the isolation process significantly. An example of a preferred mineral medium is one containing an utilizable carbon source (e.g., glucose, glycerol, or sorbitol), salts containing the macro elements (potassium, magnesium, calcium, ammonium, chloride, sulphate, phosphate) and trace elements (copper, iodide, manganese, molybdate, cobalt, zinc, and iron salts, and boric acid), and optionally vitamins or amino acids, e.g., to complement auxotrophies.

Specifically, the cells are cultured under conditions suitable to effect expression of the desired POI, which can be purified from the cells or culture medium, depending on the nature of the expression system and the expressed protein, e.g., whether the protein is fused to a signal peptide and whether the protein is soluble or membrane-bound. As will be understood by the skilled artisan, culture conditions will vary according to factors that include the type of host cell and particular expression vector employed.

A typical production medium comprises a supplemental carbon source, and further $NH_4H_2PO_4$, $MgSO_4$, KCl, $CaCl_2$, biotin, and trace elements.

For example the feed of the supplemental carbon source added to the fermentation may comprise a carbon source with up to 50 wt % utilizable sugars.

The fermentation preferably is carried out at a pH ranging from 3 to 8.

Typical fermentation times are about 24 to 120 hours with temperatures in the range of 20° C. to 35° C., preferably 22-30° C.

The POI is preferably expressed employing conditions to produce yields of at least 1 mg/L, preferably at least 10 mg/L, preferably at least 100 mg/L, most preferred at least 1 g/L.

The term "expression" or "expression cassette" as used herein refers to nucleic acid molecules containing a desired coding sequence and control sequences in operable linkage, so that hosts transformed or transfected with these sequences are capable of producing the encoded proteins or host cell metabolites. In order to effect transformation, the expression system may be included in a vector; however, the relevant DNA may also be integrated into a host cell chromosome. Expression may refer to secreted or non-secreted expression products, including polypeptides or metabolites.

Expression cassettes are conveniently provided as expression constructs e.g., in the form of "vectors" or "plasmids", which are typically DNA sequences that are required for the transcription of cloned recombinant nucleotide sequences, i.e. of recombinant genes and the translation of their mRNA in a suitable host organism. Expression vectors or plasmids usually comprise an origin for autonomous replication or a locus for genome integration in the host cells, selectable markers (e.g., an amino acid synthesis gene or a gene conferring resistance to antibiotics such as zeocin, kanamycin, G418 or hygromycin, nourseothricin), a number of restriction enzyme cleavage sites, a suitable promoter sequence and a transcription terminator, which components are operably linked together. The terms "plasmid" and "vector" as used herein include autonomously replicating nucleotide sequences as well as genome integrating nucleotide sequences, such as artificial chromosomes e.g., a yeast artificial chromosome (YAC).

Expression vectors may include but are not limited to cloning vectors, modified cloning vectors and specifically designed plasmids. Preferred expression vectors described herein are expression vectors suitable for expressing of a recombinant gene in a eukaryotic host cell and are selected depending on the host organism. Appropriate expression vectors typically comprise regulatory sequences suitable for expressing DNA encoding a POI in a eukaryotic host cell. Examples of regulatory sequences include promoter, operators, enhancers, ribosomal binding sites, and sequences that control transcription and translation initiation and termination. The regulatory sequences are typically operably linked to the DNA sequence to be expressed.

To allow expression of a recombinant nucleotide sequence in a host cell, the expression cassette or vector described herein comprises an ECP, typically a promoter nucleotide sequence which is adjacent to the 5' end of the coding sequence, e.g., upstream from and adjacent to a gene of interest (GOI), or if a signal or leader sequence is used, upstream from and adjacent to said signal and leader sequence, respectively, to facilitate expression and secretion of the POI. The promoter sequence is typically regulating and initiating transcription of the downstream nucleotide sequence, with which it is operably linked, including in particular the GOI.

Specific expression constructs described herein comprise a promoter operably linked to a nucleotide sequence encoding a POI under the transcriptional control of said promoter. Specifically, the promoter is not natively associated with the coding sequence of the POI.

Specific expression constructs described herein comprise a polynucleotide encoding the POI linked with a leader sequence which causes secretion of the POI from the host cell. The presence of such a secretion leader sequence in the expression vector is typically required when the POI intended for recombinant expression and secretion is a protein which is not naturally secreted and therefore lacks a natural secretion leader sequence, or its nucleotide sequence has been cloned without its natural secretion leader sequence. In general, any secretion leader sequence effective to cause secretion of the POI from the host cell may be used. The secretion leader sequence may originate from yeast source, e.g. from yeast α-factor such as MFa of *Saccharomyces cerevisiae*, or yeast phosphatase, from mammalian or plant source, or others.

In specific embodiments, multicloning vectors may be used, which are vectors having a multicloning site. Specifically, a desired heterologous gene can be integrated or incorporated at a multicloning site to prepare an expression vector. In the case of multicloning vectors, a promoter is typically placed upstream of the multicloning site.

The recombinant host cell described herein is specifically engineered to reduce the amount of the host cell's endogenous FLO8 protein or the respective homologue or orthologue in the host cell, in particular by lowering the expression of the respective coding gene sequence, thus to underexpress the gene.

The term "gene expression", or "expressing a polynucleotide" as used herein, is meant to encompass at least one step selected from the group consisting of DNA transcription into mRNA, mRNA processing, mRNA maturation, mRNA export, translation, protein folding and/or protein transport.

The term "reduce expression" typically refers to "underexpressing" and generally refers to any amount less than an expression level exhibited by a reference standard, which is the host cell prior to the engineering to reduce expression of a certain polynucleotide, or which is otherwise expressed in a host cell of the same type or species which is not engineered to lower expression of said polynucleotide. Reduction of expression as described herein specifically refers to a polynucleotide or gene encoding a defined FLO8 protein, in particular a gene that is endogenous to the host cell prior to engineering. In particular, the respective gene product is the defined FLO8 protein as described herein. Upon engineering the host cell by genetic modification to reduce expression of said gene the expression of said gene product or polypeptide is at a level which is less than the expression of the same gene product or polypeptide prior to a genetic modification of the host cell or in a comparable host which has not been genetically modified. "Less than" includes, e.g., 10%, 20%, 30%, 40%, 50%, 60%, 70%, 80, 90% or more. No expression of the gene product or a polypeptide is also encompassed by the term "reduction of expression" or "underexpression."

According to specific embodiments described herein, the host cell is engineered to knock-down or knockout (for inactivation or deletion of a gene or a part thereof) the endogenous host cell gene encoding the FLO8 protein (as defined herein, including e.g. the respective homologue or orthologue), or other (coding or non-coding) nucleotide sequences which confer the host cell's ability to express or produce said FLO8 protein.

Specifically, a deletion strain is provided, wherein a nucleotide sequence is disrupted.

The term "disrupt" as used herein refers to the significant reduction to complete removal of the expression of one or more endogenous proteins in a host cell, such as by knockdown or knockout. This may be measured as presence of this one or more endogenous proteins in a cell culture or culture medium of the host cell, such as by mass spectrometry wherein the total content of a endogenous protein may be less than a threshold or non-detectable.

The term "disrupted" specifically refers to a result of genetic engineering by at least one step selected from the group consisting of gene silencing, gene knock-down, gene knockout, delivery of a dominant negative construct, conditional gene knockout, and/or by gene alteration with respect to a specific gene.

The term "knock-down", "reduction" or "depletion" in the context of gene expression as used herein refers to experimental approaches leading to reduced expression of a given gene compared to expression in a control cell. Knockdown of a gene can be achieved by various experimental means such as introducing nucleic acid molecules into the cell which hybridize with parts of the gene's mRNA leading to its degradation (e.g., shRNAs, RNAi, miRNAs) or altering the sequence of the gene in a way that leads to reduced transcription, reduced mRNA stability or diminished mRNA translation.

A complete inhibition of expression of a given gene is referred to as "knockout". Knockout of a gene means that no functional transcripts are synthesized from said gene leading to a loss of function normally provided by this gene. Gene knockout is achieved by altering the DNA sequence leading to disruption or deletion of the gene or its regulatory sequences, or part of such gene or regulatory sequences. Knockout technologies include the use of homologous recombination techniques to replace, interrupt or delete crucial parts or the entire gene sequence or the use of DNA-modifying enzymes such as zinc-finger or meganucleases to introduce double strand breaks into DNA of the target gene e.g., described by Gaj et al. (Trends Biotechnol. 2013; 31(7):397-405).

Specific embodiments employ one or more knockout plasmids or cassettes which are transformed or transfected into the host cells. By homologous recombination the target gene in the host cells can be disrupted. This procedure is typically repeated until all alleles of the target gene are stably removed.

One specific method for knocking out a specific gene as described herein is the CRISPR-Cas9 methods as described in e.g., Weninger et al. (J. Biotechnol. 2016, 235:139-49). Another method includes the split marker approach as described by e.g. Heiss et al. 2013 (Appl Microbiol Biotechnol. 97(3):1241-9.)

Another embodiment refers to target mRNA degradation by using small interfering RNA (siRNA) to transfect the host cell and targeting a mRNA encoding the target protein expressed endogenously by said host cell.

Expression of a gene may be inhibited or reduced by methods which directly interfere with gene expression, encompassing, but not restricted to, inhibition or reduction of DNA transcription, e.g., by use of specific promoter-related repressors, by site specific mutagenesis of a given promoter, by promoter exchange, or inhibition or reduction of translation, e.g., by RNAi or non-coding RNA induced post-transcriptional gene silencing. The expression of a dysfunctional, or inactive gene product with reduced activity, can, for example, be achieved by site specific or random mutagenesis, insertions or deletions within the coding gene.

The inhibition or reduction of the activity of gene product can, for example, be achieved by administration of, or incubation with, an inhibitor to the respective enzyme, prior to or simultaneously with protein expression. Examples for such inhibitors include, but are not limited to, an inhibitory peptide, an antibody, an aptamer, a fusion protein or an antibody mimetic against said enzyme, or a ligand or receptor thereof, or an inhibitory peptide or nucleic acid, or a small molecule with similar binding activity.

Gene silencing, gene knock-down and gene knockout refers to techniques by which the expression of a gene is reduced, either through genetic modification or by treatment with an oligonucleotide with a sequence complementary to either an mRNA transcript or a gene. If genetic modification of DNA is done, the result is a knock-down or knockout organism. If the change in gene expression is caused by an oligonucleotide binding to an mRNA or temporarily binding to a gene, this results in a temporary change in gene expression without modification of the chromosomal DNA and is referred to as a transient knock-down.

In a transient knock-down, which is also encompassed by the above term, the binding of this oligonucleotide to the active gene or its transcripts causes decreased expression through blocking of transcription (in the case of gene-binding), degradation of the mRNA transcript (e.g., by small interfering RNA (siRNA) or antisense RNA) or blocking mRNA translation.

Other approaches to carry out gene silencing, knock-down or knockout are known to the skilled person from the respective literature, and their application in the context of the present invention is considered as routine. Gene knockout refers to techniques by which the expression of a gene is fully blocked, i.e. the respective gene is inoperative, or even removed. Methodological approaches to achieve this goal are manifold and known to the skilled person. Examples are the production of a mutant which is dominantly negative for the given gene. Such mutant can be produced by site directed mutagenesis (e.g., deletion, partial deletion, insertion or nucleic acid substitution), by use of suitable transposons, or by other approaches which are known to the skilled person from the respective literature, the application of which in the context of the present invention is thus considered as routine. One example is knockout by use of targeted Zinc Finger Nucleases. A respective Kit is provided by Sigma Aldrich as "CompoZR knockout ZFN". Another approach encompasses the use of Transcription activator-like effector nucleases (TALENs).

The delivery of a dominant negative construct involves the introduction of a sequence coding for a dysfunctional gene expression product, e.g., by transfection. Said coding sequence is functionally coupled to a strong promoter, in such way that the gene expression of the dysfunctional enzyme overrules the natural expression of the gene expression product, which, in turn, leads to an effective physiological defect of the respective activity of said gene expression product.

A conditional gene knockout allows blocking gene expression in a tissue- or time-specific manner. This is done, for example, by introducing short sequences called loxP sites around the gene of interest. Again, other approaches are known to the skilled person from the respective literature, and their application in the context of the present invention is considered as routine.

One other approach is gene alteration which may lead to a dysfunctional gene product or to a gene product with reduced activity. This approach involves the introduction of frame shift mutations, nonsense mutations (i.e., introduction of a premature stop codon) or mutations which lead to an amino acid substitution which renders the whole gene product dysfunctional, or causing a reduced activity. Such gene alteration can for example be produced by mutagenesis (e.g., deletion, partial deletion, insertion or nucleic acid substitution), either unspecific (random) mutagenesis or site directed mutagenesis. Protocols describing the practical application of gene silencing, gene knock-down, gene knockout, delivery of a dominant negative construct, conditional gene knockout, and/or gene alteration are commonly available to the skilled artisan, and are within his routine. The technical teaching provided herein is thus entirely enabled with respect to all conceivable methods leading to an inhibition or reduction of gene expression of a gene product, or to the expression of a dysfunctional, or inactive gene product, or with reduced activity.

Genetic modifications described herein may employ tools, methods and techniques known in the art, such as described by J. Sambrook et al., Molecular Cloning: A Laboratory Manual (3rd edition), Cold Spring Harbor Laboratory, Cold Spring Harbor Laboratory Press, New York (2001).

The term "endogenous" as used herein is meant to include those molecules and sequences, in particular endogenous genes or proteins, which are present in the wild-type (native) host cell, prior to its modification to reduce expression of the respective endogenous genes and/or reduce the production of the endogenous proteins. In particular, an endogenous nucleic acid molecule (e.g., a gene) or protein that does occur in (and can be obtained from) a particular host cell as it is found in nature, is understood to be "host cell endogenous" or "endogenous to the host cell". Moreover, a cell "endogenously expressing" a nucleic acid or protein expresses that nucleic acid or protein as does a host of the same particular type as it is found in nature. Moreover, a host cell "endogenously producing" or that "endogenously produces" a nucleic acid, protein, or other compound produces that nucleic acid, protein, or compound as does a host cell of the same particular type as it is found in nature.

Thus, even if an endogenous protein is no more produced by a host cell, such as in a knockout mutant of the host cell, where the protein encoding gene is inactivated or deleted, the protein is herein still referred to as "endogenous".

The term "heterologous" as used herein with respect to a nucleotide sequence, construct such as an expression cassette, amino acid sequence or protein, refers to a compound which is either foreign to a given host cell, i.e. "exogenous", such as not found in nature in said host cell; or that is naturally found in a given host cell, e.g., is "endogenous", however, in the context of a heterologous construct or integrated in such heterologous construct, e.g., employing a heterologous nucleic acid fused or in conjunction with an endogenous nucleic acid, thereby rendering the construct heterologous. The heterologous nucleotide sequence as found endogenously may also be produced in an unnatural, e.g., greater than expected or greater than naturally found, amount in the cell. The heterologous nucleotide sequence, or a nucleic acid comprising the heterologous nucleotide sequence, possibly differs in sequence from the endogenous nucleotide sequence but encodes the same protein as found endogenously. Specifically, heterologous nucleotide sequences are those not found in the same relationship to a host cell in nature. Any recombinant or artificial nucleotide sequence is understood to be heterologous. An example of a heterologous polynucleotide is a nucleotide sequence not natively associated with a promoter, e.g., to obtain a hybrid promoter, or operably linked to a coding sequence, as described herein. As a result, a hybrid or chimeric polynucleotide may be obtained. A further example of a heterologous compound is a POI encoding polynucleotide operably linked to a transcriptional control element, e.g., a promoter, to which an endogenous, naturally-occurring POI coding sequence is not normally operably linked.

The term "operably linked" as used herein refers to the association of nucleotide sequences on a single nucleic acid molecule, e.g., a vector, or an expression cassette, in a way such that the function of one or more nucleotide sequences is affected by at least one other nucleotide sequence present on said nucleic acid molecule. By operably linking, a nucleic acid sequence is placed into a functional relationship with another nucleic acid sequence on the same nucleic acid molecule. For example, a promoter is operably linked with a coding sequence of a recombinant gene, when it is capable of effecting the expression of that coding sequence. As a further example, a nucleic acid encoding a signal peptide is operably linked to a nucleic acid sequence encoding a POI, when it is capable of expressing a protein in the secreted form, such as a preform of a mature protein or the mature protein. Specifically, such nucleic acids operably linked to each other may be immediately linked, i.e. without further elements or nucleic acid sequences in between the nucleic acid encoding the signal peptide and the nucleic acid sequence encoding a POI.

A "promoter" sequence is typically understood to be operably linked to a coding sequence, if the promoter controls the transcription of the coding sequence. If a promoter sequence is not natively associated with the coding sequence, its transcription is either not controlled by the promoter in native (wild-type) cells or the sequences are recombined with different contiguous sequences.

The promoter which is regulatable, in particular repressible, by a non-methanol carbon source and used for the purpose described herein, is herein referred to as "ECP". Therefore, the present disclosure regarding the "ECP" shall also refer to the "promoter which is regulatable (or repressible) by a non-methanol carbon source", and vice versa.

The ECP as described herein in particular initiates, regulates, or otherwise mediates or controls the expression of a POI coding DNA. Promoter DNA and coding DNA may be from the same gene or from different genes, and may be from the same or different organisms.

The ECP as described herein is specifically understood as a regulatable promoter, in particular a carbon source regulatable promoter with different promoter strength in the repressed and induced state, in particular a non-methanol carbon source regulatable promoter, such as the ECP which is repressible by a non-methanol carbon source, and particularly not inducible by methanol. Specifically, by using the ECP which has transcriptional activity in the absence of methanol, there is no need to add methanol to the host cell culture for POI production under the transcriptional control of the ECP.

The strength of the ECP specifically refers to its transcription strength, represented by the efficiency of initiation of transcription occurring at that promoter with high or low frequency. The higher transcription strength, the more frequently transcription will occur at that promoter. Promoter strength is a typical feature of a promoter, because it determines how often a given mRNA sequence is transcribed, effectively giving higher priority for transcription to some genes over others, leading to a higher concentration of the transcript. A gene that codes for a protein that is required in large quantities, for example, typically has a relatively strong promoter. The RNA polymerase can only perform one transcription task at a time and so must prioritize its work to be efficient. Differences in promoter strength are selected to allow for this prioritization.

The ECP used herein is relatively strong in the fully induced state, which is typically understood as the state of about maximal activity. The relative strength is commonly determined with respect to a comparable promoter, herein referred to as a reference promoter, which can be a standard promoter, such as the respective pGAP promoter of the cell as used as the host cell.

The frequency of transcription is commonly understood as the transcription rate, e.g. as determined by the amount of a transcript in a suitable assay, e.g. RT-PCR or Northern blotting. For example, the transcription strength of a promoter according to the invention is determined in the host cell which is *P. pastoris* and compared to the native pGAP promoter of *P. pastoris*.

The strength of a promoter to express a gene of interest is commonly understood as the expression strength or the capability of support a high expression level/rate. For example, the expression and/or transcription strength of a promoter of the invention is determined in the host cell which is *P. pastoris* and compared to the native pGAP promoter of *P. pastoris*.

The comparative transcription strength compared to a reference promoter may be determined by standard methods, such as by measuring the quantity of transcripts, e.g. employing a microarray, or else in a cell culture, such as by measuring the quantity of respective gene expression products in recombinant cells. In particular, the transcription rate may be determined by the transcription strength on a microarray, Northern blot or with quantitative real time PCR (qRT-PCR) or with RNA sequencing (RNA-seq) where the data show the difference of expression level between conditions with high growth rate and conditions with low growth rate, or conditions employing different media composition, and a high signal intensity as compared to the reference promoter.

The expression rate may, for example, be determined by the amount of expression of a reporter gene, such as eGFP.

ECP as described herein exerts a relatively high transcription strength, e.g., reflected by a transcription rate or transcription strength of at least 15% as compared to the native pGAP promoter in the host cell, also called "homologous pGAP promoter". Preferably the transcription rate or strength is at least any one of 20%, 30%, 40%, 50%, 60%, 70%, 80%, 90% or 100%, or even higher, such as at least any one of 110%, 120%, 130%, 140%, 150%, 160%, 170%, 180%, 190%, or 200% as compared to the native pGAP promoter, such as determined in the (e.g. eukaryotic) host cell selected as a host cell for recombination purpose to produce the POI.

The native pGAP promoter typically initiates expression of the gap gene encoding glyceraldehyde-3-phosphate dehydrogenase (GAPDH), which is a constitutive promoter present in most living organisms. GAPDH (EC 1\2\1\12), a key enzyme of glycolysis and gluconeogenesis, plays a crucial role in catabolic and anabolic carbohydrate metabolism.

The native pGAP promoter specifically is active in a recombinant eukaryotic cell in a similar way as in a native eukaryotic cell of the same species or strain, including the unmodified (non-recombinant) or recombinant eukaryotic cell. Such native pGAP promoter is commonly understood to be an endogenous promoter, thus, homologous to the host cell, and may serve as a standard or reference promoter for comparison purposes. The relative expression or transcription strength of a promoter as described herein is usually compared to the native pGAP promoter of a cell of the same species or strain that is used as a host for producing a POI.

The term "regulatable" with respect to an inducible or repressible regulatory element, such as a promoter described herein shall refer to an element that is repressed in a host cell in the presence of an excess amount of a substance (such as a nutrient in the cell culture medium) e.g., in the growth phase of a batch culture, and de-repressed to induce strong activity e.g., in the production phase (such as upon reducing the amount of a nutrient, or upon feeding of a supplemental substrate), according to a fed-batch strategy. A regulatory element can as well be designed to be regulatable, such that the element is inactive without addition of a cell culture additive, and active in the presence of such additive. Thus, expression of a POI under the control of such regulatory element can be induced upon addition of such additive.

The ECP as described herein is a relatively strong regulatable promoter that is typically silenced or repressed under cell growth conditions (growth phase), and activated or de-repressed under production condition (production phase), and therefore suitable for inducing POI production in a production cell line by limiting the carbon source.

Specifically, the promoter as described herein is carbon source regulatable with a differential promoter strength as determined in a test comparing its strength in the presence of glucose and glucose limitation, showing that it is still repressed at relatively high glucose concentrations, preferably at concentrations of at least 10 g/L, preferably at least 20 g/L. Specifically the promoter described herein is fully induced at limited glucose concentrations, considering glucose threshold concentrations fully inducing the promoter, which threshold is typically less than 20 g/L, preferably less than 10 g/L, less than or up to 1 g/L, even less than 0.1 g/L or less than 50 mg/L, preferably with a full transcription strength of e.g. at least 50% of the native, homologous pGAP promoter, at glucose concentrations of less than 40 mg/L.

The term "repression," or "repressed," as used herein within the context of the present disclosure, e.g., to characterize a carbon-source regulatable promoter described herein, refers to the interference of transcription of a gene of interest (encoding a protein of interest) that is under the transcriptional control of a promoter that is understood to be repressible, resulting in decreased expression of the protein of interest by the cell(s).

Repression of the ECP described herein is specifically occurring when a repressing agent is in the cell culture medium. A repressing agent can be a certain carbon-source or a repressing amount of a carbon-source e.g. above a certain threshold amount. Expression of a gene of interest or of a protein of interest is said to be "derepressed," when, the repressing agent is removed from the medium, or reduced to below a threshold amount that is no more repressing. Upon derepressing, the ECP is understood to be fully induced, and expression of the protein of interest is typically at least 1.5-fold over the basal levels of expression by the cell(s) under promoter-repressing conditions.

Specifically, transcription of a gene of interest under the control of the ECP described herein may be repressed by at least any one of 30, 40, 50, 60, 70, 80, 85%, 90%, or 95%, or completely repressed (100% repressed) compared to transcription of said gene upon de-repressing or fully inducing the ECP.

The differential promoter strength comparing the promoter strength under repressed and derepressed condition, determines the regulatable properties of a promoter and the respective induction ratio. According to certain embodiments, the induction ratio is understood as a differential promoter strength which is determined by the initiation of POI production upon switching to inducing conditions below a predetermined carbon source threshold, and compared to the strength in the repressed state. The transcription strength commonly is understood as the strength in the fully induced state, i.e. showing about maximum activities under de-repressing conditions. The differential promoter strength is, e.g. determined according to the efficiency or yield of POI production in a recombinant host cell line under de-repressing conditions as compared to repressing conditions, or else by the amount of a transcript. The regulatable promoter as described herein has a preferred differential promoter strength (induction ratio), which is at least 1.5 fold or at least 2 fold, more preferably at least 5 fold, even more preferred at least 10 fold, more preferred at least 20 fold, more preferably at least 30, 40, 50, or 100 fold in the de-repressed (fully induced) state compared to the repressed state, also understood as fold induction.

The term "mutagenesis" as used herein shall refer to a method of providing mutants of a nucleotide sequence, e.g. through insertion, deletion and/or substitution of one or more nucleotides, so to obtain variants thereof with at least one change in the non-coding or coding region. Mutagenesis may be through random, semi-random or site directed mutation. Specific ECP described herein and respective nucleotide sequences may be used to produce variants, which are likewise regulatable promoters which may be used for the purpose as described herein. Such variants can be produced by a suitable mutagenesis method using the ECP nucleotide sequences provided herein as a parent sequence. Such mutagenesis method encompass those methods of engineering the nucleic acid or de novo synthesizing a nucleotide sequence using the respective parent promoter sequence information as a template. Specific mutagenesis methods apply rational promoter engineering.

The exemplary ECP described herein may e.g. be modified to generate promoter variants with altered expression levels and regulatory properties. For instance, a promoter library may be prepared by mutagenesis of selected promoter sequences, which may be used as parent molecules, e.g. to fine-tune the gene expression in eukaryotic cells by analyzing variants for their expression under different fermentation strategies and selecting suitable variants. A synthetic library of variants may be used, e.g. to select a promoter matching the requirements for producing a selected POI. Such variants may have increased expression efficiency in (e.g., eukaryotic) host cells and differential expression under carbon source rich and limiting conditions. Typically large randomized gene libraries are produced with a high gene diversity, which may be selected according to a specifically desired genotype or phenotype.

Certain ECP variants may be size variants of the ECP nucleotide sequences provided herein and/or comprise more than one of the elements or regions of the promoter described herein, such as the core regulatory regions, the main regulatory regions, or the T motifs, and/or comprise one or more (of the same or different) fragments of the ECP nucleotide sequences.

Specific mutagenesis methods provide for point mutations of one or more nucleotides in a sequence, in particular tandem point mutations, such as to change at least 2, 3, 4, 5, 6, 7, 8, 9, 10, or even more continuous nucleotides within the nucleotide sequence of the promoter. A point mutation is typically at least one of a deletion, insertion, and/or substitution of one or more nucleotides. The promoter sequence may be mutated at the distal ends, in particular within the 5'-region which amounts to up to 50% of the full-length promoter sequence, which 5'-region can be highly variable without substantially losing the promoter activity. The promoter sequence may specifically be mutated within the main regulatory region, yet, it may be preferred that the sequence identity to the exemplary main regulatory region and in particular to the exemplary core regulatory region is high, such as e.g. at least any one of 80%, 85%, 90%, or 95%. Outside any of the core or main regulatory regions, the variability of the sequence may be higher and the ECP still be functional e.g., with a sequence identity of less than 80% or less than 85%.

Any mutation within the core or main regulatory regions is typically conservative, i.e. such as to maintain (or even improve) the recognition by a certain transcription factor.

Specifically, the ECP described herein may comprise a hybrid nucleotide sequence e.g. comprising the core or main regulatory regions described herein and in addition one or more regions or alternative (native or artificial) promoter sequences, such as an translation initiation site at the 3'-region (specifically the 3'-end which comprises at least 10 or 15 3'-terminal nucleotide sequence including the 3'-terminus, (e.g., up to 20, 25, or 30 nt) of a different promoter, e.g. of any constitutive or regulatable (or otherwise inducible) promoter, thereby substituting the translation initiation site of the ECP promoter.

The term "nucleotide sequence" or "nucleic acid sequence" used herein refers to either DNA or RNA. "Nucleic acid sequence" or "polynucleotide sequence" or simply "polynucleotide" refers to a single or double-stranded polymer of deoxyribonucleotide or ribonucleotide bases read from the 5' to the 3' end. It includes expression cassettes, self-replicating plasmids, infectious polymers of DNA or RNA, and non-functional DNA or RNA.

The term "protein of interest (POI)" as used herein refers to a polypeptide or a protein that is produced by means of recombinant technology in a host cell. More specifically, the protein may either be a polypeptide not naturally occurring in the host cell, i.e. a heterologous protein, or else may be native to the host cell, i.e. a homologous protein to the host cell, but is produced, for example, by transformation with a self-replicating vector containing the nucleic acid sequence encoding the POI, or upon integration by recombinant techniques of one or more copies of the nucleic acid sequence encoding the POI into the genome of the host cell, or by recombinant modification of one or more regulatory sequences controlling the expression of the gene encoding the POI, e.g., of the promoter sequence. In some cases the term POI as used herein also refers to any metabolite product by the host cell as mediated by the recombinantly expressed protein.

The term "scaffold" as used herein describes a multifaceted group of compact and stably folded proteins—differing in size, structure, and origin—that serve as a starting point for the generation of antigen-binding molecules. Inspired by the structure-function relationships of antibodies (immunoglobulins), such an alternative protein scaffold provides a robust, conserved structural framework that supports an interaction site which can be reshaped for the tight and specific recognition of a given (bio)molecular target.

The term "sequence identity" of a variant, homologue or orthologue as compared to a parent nucleotide or amino acid sequence indicates the degree of identity of two or more sequences. Two or more amino acid sequences may have the same or conserved amino acid residues at a corresponding position, to a certain degree, up to 100%. Two or more nucleotide sequences may have the same or conserved base pairs at a corresponding position, to a certain degree, up to 100%.

Sequence similarity searching is an effective and reliable strategy for identifying homologs with excess (e.g., at least 50%) sequence identity. Sequence similarity search tools frequently used are e.g., BLAST, FASTA, and HMMER.

Sequence similarity searches can identify such homologous proteins or genes by detecting excess similarity, and statistically significant similarity that reflects common ancestry. Homologues may encompass orthologues, which are herein understood as the same protein in different organisms, e.g., variants of such protein in different different organisms or species.

An orthologous sequence of the same protein in different organisms or species is typically homologous to the protein sequence, specifically of orthologs originating from the same genus. Typically, orthologs have at least about any one of 25%, 30%, 35%, 40%, 50%, 60%, 70%, 80%, 85%, 90%, or 95% identity, up to 100% sequence identity. Specifically, orthologs can be determined upon replacement of the FLO8 protein or the gene encoding FLO8 protein by the orthologous sequences in a host cell, which is modified to knockout the endogenous FLO8 protein. For example, if a putative FLO8 protein is functional in a *P. pastoris* or *S. cerevisiae* host cell replacing the endogenous FLO8 protein that is encoded by a gene which has been knocked out in such *P. pastoris* and *S. cerevisiae* host cell, respectively, such putative FLO8 protein can be considered a FLO8 protein homologue for the purpose described herein.

The FLO8 protein comprising or consisting of the amino acid sequence identified as SEQ ID NO:1 is of *K. phaffii* origin. It is well understood that there are homologous sequences present in other eukaryotic or prokaryotic host cells. For example, yeast cells comprise the respective homologous sequences, in particular in yeast of *Pichia pastoris*, which has been reclassified into a new genus, *Komagataella*, and split into three species, *K. pastoris, K. phaffii*, and *K. pseudopastoris*. Specific homologous sequences are e.g., found in *K. pastoris* (e.g., SEQ ID NO:3, such as encoded by the nucleotide sequence comprising or consisting of SEQ ID NO:4), *Saccharomyces cerevisiae* (e.g., SEQ ID NO:5 or SEQ ID NO:6), *Yarrowia lipolytica* (e.g., SEQ ID NO:7), *Ogataea polymorpha* (e.g., SEQ ID NO:8), or *Aspergillus niger* (e.g., SEQ ID NO:9).

Any homologous sequence of the FLO8 protein with a certain sequence identity described herein, in particular any FLO8 protein which is an ortholog of the *P. pastoris* FLO8 protein, is included in the definition of a FLO8 protein described herein.

"Percent (%) amino acid sequence identity" with respect to an amino acid sequence, homologs and orthologues described herein is defined as the percentage of amino acid residues in a candidate sequence that are identical with the amino acid residues in the specific polypeptide sequence, after aligning the sequence and introducing gaps, if necessary, to achieve the maximum percent sequence identity, and not considering any conservative substitutions as part of the sequence identity. Those skilled in the art can determine appropriate parameters for measuring alignment, including any algorithms needed to achieve maximal alignment over the full length of the sequences being compared.

For purposes described herein, the sequence identity between two amino acid sequences is determined using the NCBI BLAST program version BLASTP 2.8.1 with the following exemplary parameters: Program: blastp, Word size: 6, Expect value: 10, Hitlist size: 100, Gapcosts: 11.1, Matrix: BLOSUM62, Filter string: F, Compositional adjustment: Conditional compositional score matrix adjustment.

"Percent (%) identity" with respect to a nucleotide sequence e.g., of a promoter or a gene, is defined as the percentage of nucleotides in a candidate DNA sequence that is identical with the nucleotides in the DNA sequence, after aligning the sequence and introducing gaps, if necessary, to achieve the maximum percent sequence identity, and not considering any conservative substitutions as part of the sequence identity. Alignment for purposes of determining percent nucleotide sequence identity can be achieved in various ways that are within the skill in the art, for instance, using publicly available computer software. Those skilled in the art can determine appropriate parameters for measuring alignment, including any algorithms needed to achieve maximal alignment over the full length of the sequences being compared.

The term "isolated" or "isolation" as used herein with respect to a POI shall refer to such compound that has been sufficiently separated from the environment with which it would naturally be associated, in particular a cell culture supernatant, so as to exist in "purified" or "substantially pure" form. Yet, "isolated" does not necessarily mean the exclusion of artificial or synthetic mixtures with other compounds or materials, or the presence of impurities that do not interfere with the fundamental activity, and that may be present, for example, due to incomplete purification. Isolated compounds can be further formulated to produce preparations thereof, and still for practical purposes be isolated—for example, a POI can be mixed with pharmaceutically acceptable carriers or excipients when used in diagnosis or therapy.

The term "purified" as used herein shall refer to a preparation comprising at least 50% (mol/mol), preferably at least 60%, 70%, 80%, 90% or 95% of a compound (e.g., a POI). Purity is measured by methods appropriate for the compound (e.g., chromatographic methods, polyacrylamide gel electrophoresis, HPLC analysis, and the like). An isolated, purified POI as described herein may be obtained by purifying the cell culture supernatants to reduce impurities.

As isolation and purification methods for obtaining a recombinant polypeptide or protein product, methods, such as methods utilizing difference in solubility, such as salting out and solvent precipitation, methods utilizing difference in molecular weight, such as ultrafiltration and gel electrophoresis, methods utilizing difference in electric charge, such as ion-exchange chromatography, methods utilizing specific affinity, such as affinity chromatography, methods utilizing difference in hydrophobicity, such as reverse phase high performance liquid chromatography, and methods utilizing difference in isoelectric point, such as isoelectric focusing may be used.

The following standard methods are preferred: cell (debris) separation and wash by Microfiltration or Tangential Flow Filter (TFF) or centrifugation, POI purification by precipitation or heat treatment, POI activation by enzymatic digest, POI purification by chromatography, such as ion exchange (IEX), hydrophobic interaction chromatography (HIC), Affinity chromatography, size exclusion (SEC) or HPLC Chromatography, POI precipitation of concentration and washing by ultrafiltration steps.

A highly purified product is essentially free from contaminating proteins, and preferably has a purity of at least 90%, more preferred at least 95%, or even at least 98%, up to 100%. The purified products may be obtained by purification of the cell culture supernatant or else from cellular debris.

An isolated and purified POI can be identified by conventional methods such as Western blot, HPLC, activity assay, or ELISA.

The term "recombinant" as used herein shall mean "being prepared by or the result of genetic engineering. A recombinant host may be engineered to delete and/or inactivate one or more nucleotides or nucleotide sequences, and may specifically comprise an expression vector or cloning vector containing a recombinant nucleic acid sequence, in particular employing nucleotide sequence foreign to the host. A recombinant protein is produced by expressing a respective recombinant nucleic acid in a host. The term "recombinant" with respect to a POI as used herein, includes a POI that is prepared, expressed, created or isolated by recombinant means, such as a POI isolated from a host cell transformed to express the POI. In accordance with the present invention conventional molecular biology, microbiology, and recombinant DNA techniques within the skill of the art may be employed. Such techniques are explained fully in the literature. See, e.g., Maniatis, Fritsch & Sambrook, "Molecular Cloning: A Laboratory Manual, Cold Spring Harbor, (1982).

Certain recombinant host cells are "engineered" host cells which are understood as host cells which have been manipulated using genetic engineering, i.e. by human intervention. When a host cell is engineered to reduce expression or to underexpress a given gene or the respective protein, the host cell is manipulated such that the host cell has no longer the capability to express such gene and protein, respectively, compared to the host cell under the same condition prior to manipulation, or compared to the host cells which are not engineered such that said gene or protein is underexpressed.

According to specific examples, it has surprisingly been found that the reduction of a FLO8 encoding gene expression in a host cell, in particular the deletion of such gene, had a positive influence on the expression levels of genes controlled by non-methanol controlled inducible promoters (ECPs), thus allowing for higher expression levels without losing the carbon-source promoter regulation. Therefore, cells with and without deletion of the respective endogenous gene encoding the FLO8 protein (flo8 gene) were generated and the strength and regulation of genes under control of an ECP were tested. For several exemplary POIs, which are either intracellular or secreted model proteins, it was shown that expression was increased in cells with deletion of the respective flo8 gene, which was traceable to increased transcript levels. The increased expression could be shown both in small scale screening cultivations and in controlled production processes in a bioreactor. Thus, a new expression system has been developed that allows much higher product formation in methanol-free media e.g. in yeast such as *Pichia*, compared to previously existing expression systems.

According to specific examples, the effect of FLO8 disruption on the expression strength of the non-methanol carbon source regulated promoters pG1, pG3, pG4, pG6 (which are regulated by a carbon source other than methanol) was compared to the constitutive promoter pGAP or the methanol-induced promoter pAOX1. All non-methanol carbon source regulated promoters were found to have a statistically significant higher transcription in the dFLO8 strain, which is surprising and indicates an increased expression under the control of such promoters. In contrast, the methanol-inducible pAOX1 did not show a significantly increased transcription strength in the dFLO8 mutant compared to the wild type, and there was also no significant effect on the transcription strength of pGAP. Thus, it is concluded that the pGAP or pAOX1 promoter activity is not affected by the underexpression of FLO8.

It was surprisingly found that expression of a heterologous gene of interest to produce a protein of interest in a cell culture has been effectively increased upon a knockout or disruption of FLO8, when using carbon source repressable promoters which are not inducible by methanol, compared to the standard pGAP promoter. For example, an increase in eGFP fluorescence for each of the promoter pG1, pG1-3, pG3, pG4, pG6, pG7, and pG8, was found in the dFLO8 strains, which was ranging from 1.2 to 3.9 fold increase compared to expression in the wild-type host cell (without FLO8 disruption).

The following items are embodiments described herein:

1. A recombinant host cell comprising an endogenous gene encoding a FLO8 protein comprising the amino acid sequence identified as SEQ ID NO:1 or a homologue thereof, which host cell is engineered by one or more genetic modifications to reduce expression of said gene compared to the host cell prior to said one or more genetic modifications, and which host cell comprises a heterologous expression cassette comprising a gene of interest (GOI) under the control of an expression cassette promoter (ECP) which ECP is regulatable by a non-methanol carbon source.

2. The host cell of item 1, wherein the homologue has at least 25% sequence identity to SEQ ID NO:1.

3. The host cell of any one of items 1 to 2, wherein said one or more genetic modifications comprises a disruption, substitution, deletion or knockout of (i) one or more endogenous polynucleotides, or a part thereof; or (ii) an expression control sequence.

4. The host cell of item 3, wherein said endogenous polynucleotide is a gene encoding said FLO8 protein or said homologue.

5. The host cell of item 4, wherein the expression control sequence comprises any one of a promoter, a ribosomal binding site, transcriptional or translational start and stop sequences, or an enhancer or activator sequence.

6. The host cell of any one of items 1 to 4, wherein the ECP is inducible in the presence of a growth-limiting amount of a non-methanol carbon source, preferably in the absence of methanol; and repressible in the presence of an excess amount of a non-methanol carbon source that is higher than the growth-limiting amount.

7. The host cell of item 6, wherein the growth-limiting amount of the non-methanol carbon source is up to 1 g/L cell culture medium.

8. The host cell of any one of items 1 to 7, wherein the ECP comprises at least one first and at least one second core regulatory region, wherein the first core regulatory region has at least 75% sequence identity to SEQ ID NO:17, and the second core regulatory region has at least 75% sequence identity to SEQ ID NO:18.

9. The host cell of any one of items 1 to 8, wherein the ECP comprises at least one regulatory region which has at least 85% sequence identity to SEQ ID NO:35.

10. The host cell of item 8 or 9, wherein the ECP comprises at least two of said first and/or second core regulatory regions.

11. The host cell of any one of items 1 to 10, wherein the ECP comprises at least one T motif consisting of any one of SEQ ID NO:19-34, optionally without extension of said T motif by one or more thymine at either of the 5' or 3' end of said T motif.

12. The host cell of item 11, wherein the ECP comprises at least two of said T motifs.

13. The host cell of any one of items 1 to 7, wherein the ECP comprises at least 60% sequence identity to at least 300 nt of any one of the sequences SEQ ID NO:10-16, or any one of SEQ ID NO:41-45.

14. The host cell of item 13, wherein the ECP comprises at least 60% sequence identity to any one of the full-length sequences SEQ ID NO:10-16, or any one of SEQ ID NO:41-45.

15. The host cell of item 13 or 14, wherein the ECP comprises or consists of SEQ ID NO:10 or SEQ ID NO:11.

16. The host cell of any one of items 1 to 15, wherein the expression cassette is comprised in an autonomously replicating vector or plasmid, or within a chromosome of said host cell.

17. The host cell of any one of items 1 to 16, wherein the expression cassette further comprises a nucleotide sequence encoding a signal peptide enabling the secretion of a protein of interest (POI) which is encoded by the GOI, preferably wherein the nucleotide sequence encoding the signal peptide is fused adjacent to the 5'-end of the GOI.

18. The host cell of any one of items 1 to 17, wherein the GOI encodes a protein of interest (POI) which is a peptide or protein selected from the group consisting of an antigen-binding protein, a therapeutic protein, an enzyme, a peptide, a protein antibiotic, a toxin fusion protein, a carbohydrate-protein conjugate, a structural protein, a regulatory protein, a vaccine antigen, a growth factor, a hormone, a cytokine, a process enzyme, and a metabolic enzyme.

19. The host cell of any one of items 1 to 18, wherein the antigen-binding protein is selected from the group consisting of
a) antibodies or antibody fragments, such as any of chimeric antibodies, humanized antibodies, bi-specific antibodies, Fab, Fd, scFv, diabodies, triabodies, Fv tetramers, minibodies, single-domain antibodies like VH, VHH, IgNARs, or V-NAR;
b) antibody mimetics, such as Adnectins, Affibodies, Affilins, Affimers, Affitins, Alphabodies, Anticalins, Avimers, DARPins, Fynomers, Kunitz domain peptides, Monobodies, or NanoCLAMPS; or
c) fusion proteins comprising one or more immunoglobulin-fold domains, antibody domains or antibody mimetics.

20. The host cell of any one of items 1 to 19, which is
a) a yeast cell of a genus selected from the group consisting of *Pichia, Hansenula, Komagataella, Saccharomyces, Kluyveromyces, Candida, Ogataea, Yarrowia*, and *Geotrichum*, such as *Pichia pastoris, Komagataella phaffii, Komagataella pastoris, Komagataella pseudopastoris, Saccharomyces cerevisiae, Ogataea minuta, Kluyveromyces lactis, Kluyveromes marxianus, Yarrowia lipolytica* or *Hansenula polymorpha*; or
b) a cell of filamentous fungi, such as *Aspergillus awamori* or *Trichoderma reesei*.

21. A method of increasing the yield of a protein of interest (POI) produced by a host cell expressing a gene of interest (GOI) encoding said POI under the control of a promoter which is regulatable or repressible by a non-methanol carbon source, by reducing in said host cell expression of a gene encoding a FLO8 protein comprising the amino acid sequence identified as SEQ ID NO:1 or a homologue thereof.

22. A method for producing a protein of interest (POI) encoded by a gene of interest (GOI) by culturing the host cell of any one of items 1 to 20 under conditions to produce said POI.

23. The method of item 21 or 22, comprising the steps:
   a) culturing the host cell under growing conditions; and a further step
   b) culturing the host cell under growth-limiting conditions in the presence of up to 1 g/L of a second non-methanol carbon source, resulting in expression of said GOI to produce said POI.

24. The method of item 23, wherein said first or second carbon source is selected from saccharides, polyols, alcohols, or mixtures of any one or more of the foregoing.

25. The method of item 23 or 24, wherein said step a) culturing is performed in a batch phase; and said step b) culturing is performed in fed-batch or a continuous cultivation phase.

26. A method for producing a protein of interest (POI) in a host cell, comprising the steps:
   a) genetically engineering the host cell to reduce expression of a an endogenous gene encoding a FLO8 protein comprising the amino acid sequence identified as SEQ ID NO:1 or a homologue thereof;
   b) introducing into the host cell a heterologous expression cassette comprising a non-methanol carbon source regulatable promoter (in particular an ECP described herein) that is operably linked to a gene of interest (GOI) encoding said POI;
   c) culturing said host cell under conditions to produce said POI;
   d) optionally isolating said POI from the cell culture; and
   e) optionally purifying said POI.

The foregoing description will be more fully understood with reference to the following examples. Such examples are, however, merely representative of methods of practicing one or more embodiments of the present invention and should not be read as limiting the scope of invention.

EXAMPLES

The examples below will demonstrate that disruption of the transcriptional regulator FLO8 leads to a higher transcriptional activity of carbon regulated promoters such as pG1, pG3, pG4, pG6, and pG8, and engineered variants thereof enabling increased productivity of recombinant proteins under carbon limited cultivation conditions.

Example 1: Construction of *P. pastoris* dFLO8 Strains

*P. pastoris* wild type strain CBS7435 or CBS2612 (CBS-KNAW Fungal Biodiversity Centre, Centraalbureau voor Schimmelcultures, Utrecht, The Netherlands) were used as a host strain.

To generate the dFLO8 mutant strains the gene PP7435_Chr4-0252 (FLO8) was disrupted with the split-marker cassette method as adapted for *P. pastoris* (Gasser et al., 2013) and described in WO2015158800A1. Briefly, two 1.5 kb regions located approximately 200 bp up- and downstream of the translation start of the ORF were amplified using primers A_fw and A_bw as well as D_fw and D_bw, respectively (Table 1). The resulting fragments A and B were used to flank two ca. 1 kb long and overlapping parts (435 bps) of the KanMX marker cassette (primers B_fw, B_bw, C_fw and C_bw) by fusion PCR, using overhangs on the primers A_bw and D_fw that were homologous to the 5' and 3' end of the respective parts B and C of the resistance marker cassette. The two fused fragments AB and CD were simultaneously transformed into electrocompetent *P. pastoris* cells as described in (Gasser et al., 2013). Successful integration requires three different recombination events, which resulted in replacement of a 0.4 kb fragment at the 5' end of PP7435_Chr4-0252 and its promoter by the KanMX cassette.

Selection of positive transformants was done on selective YPD-agar plates (per liter 10 g yeast extract, 20 g peptone, 20 g glucose, 20 g agar-agar) containing 500 μg mL$^{-1}$ Geneticin. Correct deletion mutants were verified by PCR with primers located outside of the split marker cassette (Det_fw and Det_bw, Table 1) and gel electrophoresis.

TABLE 1

Primers for splitmarker cassette construction

| Primer | Sequence |
|---|---|
| A_fw | CGAACATCCATCACCAAAACAC (SEQ ID NO: 72) |
| A_bw | GTTGTCGACCTGCAGCGTACGGTGTTGCCGCGAAATG (SEQ ID NO: 73) |
| D_fw | TAGGTGATATCAGATCCACTGATCAATTTGCCCAAGAGACG (SEQ ID NO: 74) |
| D_bw | GACTGTTGCGATTGCTGGTG (SEQ ID NO: 75) |
| B_fw | CATTTCGCGGCAACACCGTACGCTGCAGGTCGACAAC (SEQ ID NO: 76) |
| B_bw | CGGTGAGAATGGCAAAAGCTTAT (SEQ ID NO: 77) |
| C_fw | AAGCCCGATGCGCCAGAGTTG (SEQ ID NO: 78) |
| C_bw | CGTCTCTTGGGCAAATTGATCAGTGGATCTGATATCACCTA (SEQ ID NO: 79) |
| Det_fw | ATCCAGGACACGCTCATCAAG (SEQ ID NO: 80) |

Example 2: Effect of FLO8 Disruption on pG1 and pG1-3 Driven Intracellular eGFP Productivity a) Construction of *P. pastoris* dFLO8 Strains

*P. pastoris* CBS2612_pG1_eGFP #8 (described in WO2013050551A1) and CBS2612_pG1-3_eGFP #1 (described in WO2017021541A1 and Prielhofer et al., 2018 as CBS2612_pGTH1-D1240) were used as host strains. These strains have been demonstrated to have integrated a single copy of a Zeocin resistance cassette together with the eGFP expression cassette comprised of the glucose-regulated promotor pG1 (SEQ ID NO:12) or an engineered variant thereof (pG1-3, SEQ ID NO:10), the GOI and the *S. cerevisiae* CYC1 transcription terminator. Corresponding dFLO8 mutant strains were constructed as described in Example 1.

b) Screening of eGFP Productivity

For expression screenings, single colonies of the dFLO8 strains as well as their respective parental strains and a non-producing wild type strain were inoculated in 2 mL liquid YP medium (per liter: 20 g peptone, 10 g yeast extract) containing 25 μg mL$^{-1}$ Zeocin and 500 μg mL$^{-1}$ Geneticin (if appropriate). Pre-cultures were grown for ca.

24 h at 25° C. and 280 rpm in 24-DWP and subsequently used to inoculate 2 mL of synthetic screening medium ASMv6 (media composition is given below) containing 50 g L$^{-1}$ polysaccharide and 1.5% of glucose-releasing enzyme (enabling a glucose release rate of ca. 0.8 mg mL$^{-1}$ h$^{-1}$; m2p media development kit) to a starting-OD$_{600}$ of 5 (inducing conditions). For repressing conditions, ASMv6 containing 2% glycerol were used. Main cultures were then incubated for another 48 h at 25° C. and 280 rpm. To measure eGFP-expression, cells were diluted to an OD$_{600}$ of 0.1 in phosphate-buffered saline (PBS) and were analyzed by flow cytometry as described in Stadlmayr et al., 2010. For each sample 15 000 cells were analyzed. Auto-fluorescence of *P. pastoris* was measured using *P. pastoris* wild type cells and subtracted from the signal. Normalized eGFP expression levels (fluorescence intensity related to cell size) are given as percentage of pGAP-controlled expression (Table 2).

Synthetic screening medium ASMv6 contained per liter: 22.0 g citric acid monohydrate, 6.30 g (NH$_4$)$_2$HPO$_4$, 0.49 g MgSO$_4$*7H$_2$O, 2.64 g KCl, 0.0535 g CaCl$_2$*2H$_2$O, 1.470 mL PTM0 trace salts stock solution, 0.4 mg Biotin; pH was set to 6.5 with KOH (solid).

PTM0 trace salts stock solution contained per liter: 6.0 g CuSO$_4$*5H$_2$O, 0.08 g NaI, 3.36 g MnSO$_4$*H$_2$O, 0.2 g Na$_2$MoO$_4$*2H$_2$O, 0.02 g H$_3$BO$_3$, 0.82 g CoCl$_2$*6H$_2$O, 20.0 g ZnCl$_2$, 65.0 g FeSO$_4$*7H$_2$O and 5.0 ml H$_2$SO$_4$ (95%-98%).

TABLE 2

Impact of dFLO8 on expression of eGFP under control of pG1 or pG1-3. Shown are eGFP expression levels relative to pGAP after 48 h cultivation in 2% glycerol (repression) or limiting-glucose (induction) as well as the increase in eGFP fluorescence in the dFLO8 strain under inducing conditions compared to pG1 or pG1-3 in the wild type.

| Promoter | Host Cell | Repression (glycerol) | Induction (limiting glucose) | fold change pG1+ dFLO8 vs pG1 + wt | fold change pG1-3 + dFLO8 vs pG1-3 + wt |
|---|---|---|---|---|---|
| pGAP | Wild type | 100 | 100 | — | — |
| pG1 | wild type | 12.31 ± 1.13 | 250.17 ± 8.73 | 1.0 | — |
| pG1 | dFLO8 | 24.84 ± 3.28 | 950.92 ± 4.64 | 3.8 | — |
| pG1 | dFLO8_loxP | 23.14 ± 0.22 | 983.49 ± 8.48 | 3.9 | — |
| pG1-3 | wild type | 8.71 ± 0.46 | 519.94 ± 53.88 | 2.1 | 1.0 |
| pG1-3 | dFLO8 | 17.50 ± 0.37 | 1448.20 ± 20.62 | 5.8 | 2.8 |
| pG1-3 | dFLO8_loxP* | 17.86 ± 1.14 | 1507.22 ± 9.80 | 6.0 | 2.9 |

*produced by a method as described in Example 2.

Deletion of FLO8 had a positive influence on pG1-driven expression, leading to nearly 4-fold higher eGFP levels in inducing (glucose-limiting) conditions (Table 2). Thus, the effect of disrupting FLO8 was also studied for the promoter variant pG1-3, which has higher intrinsic expression per se. The positive impact was also shown for the promoter variant, again enabling 2.5 to 3-fold higher eGFP levels in the dFLO8 strain compared to expression from the same promoter in the wild type background (Table 2).

Example 3: Effect of FLO8 Disruption on P$_{G1-3}$ Driven Productivity of Secreted Recombinant Proteins Next, the impact of the dFLO8 mutation on pG1-3 driven expression of secretory model proteins was evaluated. For this purpose the expression cassette for vHH or scR was transformed into CBS2612 and CBS2612_dFLO8.

a) Construction of *P. pastoris* dFLO8 Strains and Selection Marker Recycling

*P. pastoris* wild type strain CBS2612 (CBS-KNAW Fungal Biodiversity Centre, Centraalbureau voor Schimmelcultures, Utrecht, The Netherlands) was used as a host strain.

CBS2612_KanR_dFLO8 #2 was constructed as described in Example 1. To excise the KanMX selection marker cassette from the genome based on Cre-loxP recombination, CBS2612_KanR_dFLO8 #2 was transformed transiently with plasmid pTAC_Cre_hphMX4 by electroporation as described in Gasser et al., 2013. pTAC_Cre_hphMX4 is a derivate of plasmid pYX022 (R&D Systems) and comprised of an origin of replication for *E. coli*, an expression cassette for the Cre-recombinase gene, a Hygromycin resistance cassette as well as an ARS/CEN element. For its construction pTAC_Cre_kanMX (Marx et al., 2008) was digested with EcoR91I to remove the kanamycin resistance cassette. Plasmid pGA26_hphMX4 was digested with the same enzymes to excise the hygromycin resistance cassette and the appropriate fragments were fused by ligation.

Selection of positive transformants was done on YPD-agar containing 100 µg mL$^{-1}$ Hygromycin. Hygromycin resistant clones were subsequently restreaked in parallel on YPD-agar (without Hygromycin to promote loss of pKTAC-CRE_hygR) as well as YPD-agar containing 500 µg mL$^{-1}$ Geneticin. Strains that had lost their resistance to Geneticin were further checked by PCR and gel electrophoresis employing primers Det_bw and Det_fw (Table 1) to confirm excision of the KanMX resistance cassette from the genome. From the corresponding strains, CBS2612_L_dFLO8 #2_4 was chosen for further use.

b) Construction of *P. pastoris* Strains Secreting Antibody Fragments scFv (scR) & vHH Under Transcriptional Control of P$_{G1-3}$ Expression plasmids pPM2d_pAOX_scR and pPM2d_pAOX_vHH are derivatives of the pPUZZLE plasmid backbone (Stadlmayr et al. 2010). They are comprised of an origin of replication for *E. coli* (pUC19), a Zeocin resistance cassette, the *S. cerevisiae* alpha-mating factor pre-pro leader, the genes of interest (vHH or scR) and the *S. cerevisiae* CYC1 transcription terminator, as well as a locus for integration into the *P. pastoris* genome (3'AOX1 region). For their construction the genes encoding the scFv (scR) and vHH were codon-optimized by DNA2.0 and obtained as synthetic DNA (sequence stated below). A His6-tag was fused C-terminally to the genes for detection. After restriction digest with XhoI and BamHI (for scR) or EcoRV (for vHH), each gene was ligated into pPM2d_pAOX digested with XhoI and BamHI or EcoRV. Replacement of $P_{AOX1}$ by $P_{G1-3}$ was done by restriction digestion of these plasmids as well as the expression plasmid pPM1aZ10_pG1-3_eGFP (also a pPUZZLE derivative described in WO2017021541A1) with AlwNI and SbfI and fusion of the appropriate plasmid fragments. The fragment derived from pPM1aZ10_pG1-3_eGFP contained also the sequence for the AOX-terminator enabling targeted integration to this locus.

The resulting expression plasmids pPM1aZ30_pG1-3_scR and pPM1aZ30_pG1-3_vHH were linearized with AscI and transformed into CBS2612 (short name wt), CBS2612_KanR_dFLO8 #2 (short name dFLO8) or CBS2612_L_dFLO8 #2_4 (short name dFLO8L) by electroporation using a standard protocol as described in Gasser et al., 2013.

Selection of positive transformants was done on selective YPD-agar containing 50 μg mL$^{-1}$ of Zeocin and 500 μg mL$^{-1}$ Geneticin (if appropriate).

c) Screening of Antibody Fragment Productivity

For expression screenings, single colonies of the respective transformants were inoculated in 2 mL liquid YP medium (per liter: 20 g peptone, 10 g yeast extract) containing 25 μg mL$^{-1}$ Zeocin and 500 μg mL$^{-1}$ Geneticin (if appropriate) and grown for ca. 24 h at 25° C. in 24-DWP at 280 rpm. These cultures were used to inoculate 2 mL of synthetic screening medium ASMv6 (for composition see Example 2) containing 50 g L$^{-1}$ polysaccharide and 1.5% of glucose-releasing enzyme (enabling a glucose release rate of ca. 0.8 mg h$^{-1}$ mL$^{-1}$; m2p media development kit) to a starting-$OD_{600}$ of 8. Cultivation conditions were similar to pre-culture conditions. After 48 hours, 1 mL of cell suspension was transferred to a pre-weighted 1.5 mL centrifugation tube and centrifuged at 16100 g for 5 min at room temperature. Supernatants were carefully transferred to a new vial and stored at −20° C. until further use. Centrifugation tubes containing the pellets were weighted again to determine the wet cell weight (WCW). Quantification of the recombinant secreted protein in the supernatant was done by microfluidic capillary electrophoresis as described below.

d) Quantification by Microfluidic Capillary Electrophoresis (mCE)

The 'LabChip GX/GXII System' (PerkinElmer) was used for quantitative analysis of secreted protein titer in culture supernatants. The consumables 'Protein Express Lab Chip' (760499, PerkinElmer) and 'Protein Express Reagent Kit' (CLS960008, PerkinElmer) were used. Chip and sample preparation were done according to the manufacturer's recommendations. A brief description of the procedure is given below.

Chip preparation: After reagents have come to room temperature 520 and 280 μL of Protein Express Gel Matrix were transferred to spin filters. 20 μL of Protein Express Dye solution was added to the 520 μL Gel Matrix containing spin filter. After briefly vortexing the dye containing spin filter in the inverted orientation, both spin filters were centrifuged at 9300 g for 10 minutes. To wash the chip, 120 μL Milli-Q® water were added to all active chip wells and the chip is subjected to the instruments washing program. After two further rinsing steps with Milli-Q® water, remaining fluids were fully aspirated and appropriate amounts of the filtered Gel Matrix solutions as well as the Protein Express Lower Marker solution were added to the appropriate chip wells.

Sample and ladder preparation: For sample preparation 6 μL sample were mixed with 21 μL of sample buffer in a 96-microtiter plate. Samples were denatured at 100° C. for 5 minutes and centrifuged at 1200 g for 2 minutes. Subsequently, 105 μL of Milli-Q® water were added. Sample solutions were briefly mixed by pipetting and centrifuged again at 1200 g for 2 minutes before measurement. To prepare the ladder 12 μL of Protein Express Ladder were denatured at 100° C. for 5 minutes in a PCR tube. Subsequently, 120 μL of Milli-Q® water were added and the ladder solution was briefly vortexed before spinning the tube for 15 seconds in a minicentrifuge.

Quantitation was done by employing the LabChip software provided by the manufacturer and comparison against BSA standards.

Table 3 shows that average scR-titers are 1.8-fold higher in the supernatant of dFLO8 strains compared to the wild type, while biomass concentration was not differing, leading to 1.86-fold higher scR yields in the supernatant of dFLO8 strains. A similar increase in average titers and vHH yield (1.7-fold) upon the dFLO8 mutation was also observed in case of the vHH-expressing strains (Table 4).

TABLE 3

Average WCW, product titers and yields of a 24-DWP screening of CBS2612 and CB2612_L_dFLO8 #2_4 transformed with pPM1aZ30_pG1-3_scR. 20 clones per construct were screened.

| Strains | WCW ± SD [g L$^{-1}$] | Titer ± SD [mg L$^{-1}$] | Yield ± SD [mg g$^{-1}$] |
|---|---|---|---|
| wt + pG1-3_scR #1-20 | 80.8 ± 3.64 | 29.3 ± 8.99 | 0.36 ± 0.107 |
| dFLO8L + pG1-3_scR #1-20 | 79.3 ± 2.40 | 53.0 ± 4.53 | 0.67 ± 0.057 |

TABLE 4

Average WCW, product titers and yields of a 24-DWP screening of CBS2612 and CB2612_KanR_dFLO8 #2 transformed with pPM1aZ30_pG1-3_vHH. 20 clones per construct were screened.

| Strains | WCW ± SD [g L$^{-1}$] | Titer ± SD [mg L$^{-1}$] | Yield ± SD [mg g$^{-1}$] |
|---|---|---|---|
| wt + pG1-3_vHH #1-20 | 92.4 ± 3.21 | 56.2 ± 32.70 | 0.61 ± 0.351 |
| dFLO8 + pG1-3_vHH #1-20 | 90.7 ± 4.48 | 97.0 ± 31.70 | 1.04 ± 0.360 |

Next, FLO8 was disrupted in four different vHH-expressing clones selected from the screening above (CBS2612_pG1-3_vHH #4, #5, #13 and #15) by using the split-marker cassette approach as described in Example 1. Subsequently, dFLO8 mutant clones as well as the corresponding FLO8 parental clones were screened for their productivity applying the 24-DWP-screening regime. Table 5 shows that vHH titers and product yield were 2- to 3-fold higher in the dFLO8 clones. To verify that increased production levels were based on higher transcriptional expression, vHH transcript levels were quantified by qPCR at different time-points. On average 2-fold higher vHH expression levels were observed in the dFLO8 clones, indicating that the improved vHH titers are indeed based on higher transcriptional activity of pG1-3 (see Example 4).

TABLE 5

Average WCW and titers of 4 different vHH-expressing strains as well as their corresponding dFLO8 strains. Four replicates of each parental strain as well as six corresponding dFLO8 strains were screened. (FC: fold change).

| Strains | WCW ± SD [g L$^{-1}$] | Titer ± SD [mg L$^{-1}$] | FC |
|---|---|---|---|
| pG1-3_vHH #4 | 81.8 ± 1.25 | 81.4 ± 6.42 | |
| pG1-3_vHH #4_dFLO8 #1-6 | 78.9 ± 0.94 | 171.9 ± 3.90 | 2.11 |
| pG1-3_vHH #5 | 86.6 ± 1.23 | 37.9 ± 2.22 | |
| pG1-3_vHH #5_dFLO8 #1-6 | 79.8 ± 1.51 | 91.2 ± 4.17 | 2.41 |
| pG1-3_vHH #13 | 77.6 ± 1.81 | 33.6 ± 1.30 | |
| pG1-3_vHH #13_dFLO8 #1-6 | 78.9 ± 1.52 | 101.7 ± 2.05 | 3.03 |
| pG1-3_vHH #15 | 80.1 ± 1.23 | 37.7 ± 2.05 | |
| pG1-3_vHH #15_dFLO8 #1-6 | 78.7 ± 3.70 | 101.1 ± 4.21 | 2.68 |

Example 4: Effect of FLO8 Disruption on pG1-3 Controlled vHH-Transcription

To test if disruption of FLO8 leads to an increased transcriptional activity of genes under control of pG1-3, 6 technical replicates of CBS2612_pG1-3_vHH #4 and #13 as well as the corresponding dFLO8 mutant strains CBS2612_pG1-3_vHH #4_dFLO8_1 and #13_dFLO8_2 (Table 5; Example 3) were cultivated in the 24-DWP format as described in Example 3. After 2, 19 and 26 hours, 1 mL of culture from 2 replicates was harvested and centrifuged for 1 minute at 16100 g and 4° C. and the supernatant discarded. Subsequently, the cell pellet was resuspended in 1 mL TRI reagent (Sigma-Aldrich) and stored at −80° C. until further processing.

RNA isolation was done as described in Example 6. To remove residual DNA, the RNA samples were treated with the DNA-free™-kit (Ambion) according to the manufacturers' manual. Subsequently, RNA quality, purity and concentration were analysed by gel electrophoresis as well as spectrophotometric analysis using a NanoDrop 2000 (Thermo Scientific).

Synthesis of cDNA was done with the Biozym cDNA Synthesis Kit according to the manufacturers' manual. Briefly, 500 ng of total RNA were added to the master mix containing reverse transcriptase, dNTPs, RNase inhibitor and synthesis buffer. For priming oligo d(T)$_{23}$ VN (NEB) was used. Incubation of the reaction mix was done for 60 minutes at 55° C. Subsequently, inactivation of the enzymes was achieved by incubation of the reaction mix at 99° C. for 5 minutes.

For quantitative real-time PCR (qPCR) vHH-specific primers were used (Table 6). Normalization was done by comparing to ACT1 expression levels (Table 6). For analysis 1 µL of cDNA, water and primers were mixed with Sensi-Mix SYBR 2× Master Mix (Bioline) and analyzed in a real-time PCR cycler (Rotor-Gene, Qiagen).

TABLE 6

Quantitative real-time PCR primers for vHH-transcript analysis

| Primer | Sequence |
|---|---|
| vHH_fw | TGTAACGTGAATGTCGGATTTG (SEQ ID NO: 81) |
| vHH_bw | TAGTGATGGTGGTGGTGATG (SEQ ID NO: 82) |
| Act1_fw | CCTGAGGCTTTGTTCCACCCACT (SEQ ID NO: 83) |
| Act1_bw | GGAACATAGTAGCAC CGGCATAACGA (SEQ ID NO: 84) |

All samples were measured in technical triplicates. Data analysis was performed with the Rotor-Gene software employing the Comparative Quantitation (QC) method.

Table 7 shows that in the dFLO8 strains average vHH-transcript levels were increased across all analyzed culture time-points.

TABLE 7

Average relative vHH-transcript levels at different screening-culture time-points

| Strain | Relative Transcript 2 h | 19 h | 26 h |
|---|---|---|---|
| pG1-3 vHH #4 | 1.00* | 1.56 | 1.65 |
| pG1-3 vHH #4 dFLO8_1 | 1.76 | 2.14 | 2.87 |
| pG1-3 vHH #13 | 1.00* | 2.97 | 2.90 |
| pG1-3 vHH #13 dFLO8_2 | 2.21 | 3.93 | 5.10 |

*set to 1

Example 5: Impact of FLO8 Disruption on pG1-3-Driven Secreted Antibody Fragment Productivity in Lab-Scale Bioreactor Fed-Batch Cultures Before fed-batch cultivations were carried out, the Geneticin resistance marker cassette was excised from the genome of strain CBS2612_pG1-3_vHH #4_dFLO8_4 (short name dFLO8_pG1-3_vHH #4_4) (Table 5, Example 3) by Cre-mediated recombination as described in Example 3. Productivity of three replicates of the resulting strain CBS2612_pG1-3_vHH #4_dFLO8_4 #L1 (short name L_dFLO8_pG1-3_vHH #4_4_1) was compared to product levels of three replicates of its parental strain in the 24-DPW screening format as described in Example 3 (Table 8). Average productivities of CBS2612_pG1-3_vHH #4_dFLO8_4 #L1 remained similar to its parental strain (p-value of 0.096).

TABLE 8

WCW and titer of CBS2612_dFLO8_pG1-3_vHH #4_4 and CBS2612_L_dFLO8_pG1-3_vHH #4_4_1 in 24-DWP screening.

| Strains | WCW ± SD [g L$^{-1}$] | Titer ± SD [mg L$^{-1}$] |
|---|---|---|
| dFLO8_pG1-3_vHH #4_4 | 80.87 ± 1.91 | 306.34 ± 12.85 |
| L_dFLO8_pG1-3_vHH #4_4_1 | 80.40 ± 0.57 | 329.92 ± 8.48 |

Fed-batch cultivations were done with strain CBS2612_pG1-3_vHH #4 and the corresponding loxed dFLO8 mutant CBS2612_L_dFLO8_pG1-3_vHH #4_4_1 in 1 L benchtop bioreactors (SR0700ODLS; Dasgip, Germany). For pre-cultures 100 mL YPG media containing 50 µg mL Zeocin in a 1 L shake flask were inoculated with a 1.0 mL cryostock and incubated for ca. 24 h at 180 rpm and 25° C. Batch cultures were operated at a working volume of 0.25 L and were inoculated to a starting $OD_{600}$ of 1.5. Glycerol batch media composition is given below. During the entire process the temperature was controlled at 30° C., the DO was kept at 30% by automated adjustment of stirrer speed (between 400 and 1200 rpm) and air flow (between 9.5 and 30 sL $h^{-1}$) and the pH was regulated at 5.0 by automated addition of 12.5% $NH_4OH$. After a sudden spike in DO indicating batch-end, a linear incremental glucose feed (media composition detailed below) resulting in fast initial growth rates followed by an extended phase of gradually decreasing μ was applied that has been specifically optimized for $P_{G1-3}$-based $q_P$ to μ kinetics (Prielhofer et al., 2018).

Glycerol Batch medium contained per liter:
2 g Citric acid monohydrate ($C_8H_8O_7*H_2O$), 45 g Glycerol, 12.6 g $(NH_4)_2HPO_4$, 0.5 g $MgSO_4*7H_2O$, 0.9 g KCl, 0.022 g $CaCl_2*2H_2O$, 6.6 mL Biotin stock solution (0.2 g $L^{-1}$) and 4.6 mL PTM0 trace salts stock solution (described in Example 2). HCl (conc.) was added to set the pH to 5.

Glucose feed media contained per liter:
495 g glucose monohydrate, 5.2 g $MgSO_4*7H_2O$, 8.4 g KCl, 0.28 g $CaCl_2*2H_2O$, 11.8 mL biotin stock solution (0.2 g $L^{-1}$) and 10.1 mL PTM0 trace salts stock solution (described in Example 2).

YDM and secreted recombinant protein were analysed at various time points throughout the process (Table 9). For YDM analysis 1 mL of culture broth was transferred to a 2 mL pre-dried (at 105° C. for at least 24 h) and pre-weighted centrifugation tube. After centrifugation at 16100 g for 5 minutes the supernatant was carefully transferred to a fresh vial and stored at −20° C. until further use. Cell pellets were washed twice with deionized water and dried at 105° C. for at least 24 h before the weight was measured again.

Supernatants were analyzed by microfluidic capillary electrophoresis (GXII, Perkin-Elmer) as described in Example 3.

TABLE 9

YDM and vHH-titers during bioreactor fed-batch cultivation of CBS2612_pG1-3_vHH #4 and L_CBS2612_dFLO8_pG1-3_vHH #4_4_1

| | pG1-3_vHH #4 | | L_dFLO8_pG1-3_vHH #4_4_1 | |
|---|---|---|---|---|
| Time [h] | YDM ± SD [g $L^{-1}$] | Titer ± SD [mg $L^{-1}$] | YDM ± SD [g $L^{-1}$] | Titer ± SD [mg $L^{-1}$] |
| 0* | 22.1 ± 0.06 | — | 22.8 ± 0.10 | — |
| 4 | 34.3 ± 0.21 | 31.6 ± 4.85 | 36.7 ± 0.18 | 48.8 ± 1.30 |
| 8 | 51.9 ± 0.10 | 98.7 ± 26.27 | 57.0 ± 0.99 | 167.5 ± 18.17 |
| 11 | 63.7 ± 0.50 | 158.2 ± 35.89 | 72.7 ± 1.26 | 275.4 ± 27.80 |
| 24 | 112.2 ± 0.25 | 203.4 ± 38.20 | 123.4 ± 1.28 | 817.2 ± 9.64 |
| 28 | 122.5 ± 0.49 | 214.0 ± 46.04 | 136.7 ± 0.71 | 991.7 ± 76.97 |
| 32 | 134.6 ± 0.64 | 177.0 ± 32.98 | 141.8 ± 0.72 | 1,006.7 ± 25.20 |

*glucose-feed start

From Table 9 it can be seen that throughout the process product titers for the dFLO8 strain were consistently higher than for the wt-background strain. At the end of the process a 5.7-fold increase in productivity was observed. Also in the fed batch cultivation, increased vHH transcript levels were observed in the dFLO8 strain over the whole time course.

Example 6: Effect of FLO8 Disruption on the Expression Strength and Regulatory Behavior of Non-Methanol Carbon Regulated Promoters In the next step, the impact of disruption of FLO8 on the transcription strength of other carbon regulated promoters (described in WO2013050551A1 and Prielhofer et al. 2013) in inducing conditions was studied. For transcriptome analysis under glucose-limiting conditions, CBS7435 wild type and CBS7436_KanR_dFLO8 #2 were used. Pre- and main-cultures were cultivated in 24-deep-well-plates (24-DWP). For the first pre-culture 2 mL YPD (per liter: 10 g yeast extract, 20 g peptone, 20 g glucose) containing 500 μg $mL^{-1}$ Geneticin (if appropriate) were inoculated with a single colony of CBS7435 and CBS7435_KanR_dFLO8 #2, respectively, and grown for ca. 24 h at 25° C. and 280 rpm. For the second pre-culture 2 mL M2(D) media (composition described below) inoculated to a starting $OD_{600}$ of 4 was used. Glucose-releasing polymer beads (12 mm feed beads, Kuhner, CH), liberating glucose at a non-linear rate of 1.63 $t^{0.74}$ mg per disc (t=time [h]) were added and cultures were incubated for ca. 24 h at 25° C. and 280 rpm. For main-cultures 2 mL of M2 medium (M2(D) without glucose) was used. Cultures were shaken at 280 rpm and 25° C. Slow release of glucose ensured glucose limited growth. Samples were taken after 3 h of main culture (estimated specific growth rate: 0.1 $h^{-1}$), immediately mixed in a 2:1 ratio with a precooled fixing solution (5% [vo/vol] phenol in ethanol [absolute]), aliquoted into sealed tubes and centrifuged at 16100 g for 1 min. Pellets were stored at −80° C. until further use.

M2(D) contained per liter: 22.0 g glucose monohydrate, 22.0 g Citric acid monohydrate, 3.15 g $(NH_4)_2HPO_4$, 0.49 g $MgSO_4*7H_2O$, 0.80 g KCl, 0.0268 g $CaCl_2*2H_2O$, 1.47 mL of PTM0 trace salts stock solution (described in Example 1) and 0.4 mg Biotin; The pH was set to 5 with KOH (solid).

For RNA isolation 1 mL of TRI Reagent (Sigma-Aldrich) and 500 μL acid washed glass beads were added and cells were disruption in a FastPrep-24 (mpbio) at speed 5.5 m/s for 40 seconds. Afterwards, 200 μL of chloroform were added. Subsequently, samples were shaken vigorously and then allowed to stand for 5-10 minutes at room temperature. After centrifugation for 10 minutes at 16100 g and 4° C. to promote phase separation, the upper colourless aqueous phase containing the RNA was transferred into a fresh tube and 500 μL of isopropanol were added to precipitate the RNA. After 10 minutes of incubation samples were centrifuged for 10 minutes at 16100 g and 4° C. and the supernatant was discarded. The RNA pellet was washed once with 70% ethanol, air-dried and re-suspended in RNAse free water.

For transcriptome analysis, in-house-designed *P. pastoris*-specific oligonucleotide arrays (AMAD-ID 034821, 8×15K custom arrays; Agilent, USA) were used (Graf et al.; BMC Genomics. 2008; 9:390). Synthesis of cRNA, hybridization, as well as scanning were carried out according to the Agilent protocol for 2-color expression arrays. Samples were labeled with Cy3 and Cy5 in triplicates and hybridized against a reference pool generated from cells grown under various culture conditions. For all samples, dye swap experiments were carried out.

Normalization steps and statistical analysis of microarray data included removal of color bias using locally weighted MA-scatterplot smoothing (LOESS), followed by between array normalization using the "Aquantile" method. For identifying differentially expressed genes and calculating p-values a linear model fit with an eBayes correction was used. P-values were adjusted for multiple testing with the false discovery method (FDR) by Benjamini & Yekutieli, 2001. Genes with adjusted p-values <0.05 are considered to have a statistically significant differential expression. For identifying differentially expressed genes, additionally a fold change cut-off of at least 0.58>log 2 FC<−0.58 was applied.

All steps were done using the R software (Robinson M D, McCarthy D J, Smyth G K. edgeR: a Bioconductor package for differential expression analysis of digital gene expression data. 2010. Bioinformatics. 26:139-40) and the limma package. Fold-changes for a selection of carbon-regulated genes (genes under control of carbon-source regulated promoters) are shown in Table 10. The expression of the native FLO8 gene is clearly and significantly reduced in the dFLO8 mutant compared to the wild type. For all the carbon-source regulated genes, increased transcript levels in the dFLO8 mutant can be seen, reaching from 3.7 to 11.4-fold higher transcription strength in the inducing conditions. All these genes have a statistically significant higher transcription (adjusted p-values <0.05) in the dFLO8 mutant strain. This strongly indicates that the potential for production of all non-methanol carbon regulated promoters as described in Prielhofer et al. 2013 and Prielhofer et al. 2018 is enhanced by the disruption of FLO8. In contrast, expression strength of the GAP promoter is not affected by disruption of FLO8.

Glycerol fed batch solution was then fed at a constant rate of 5 mL/h for 5 hours. Then, a methanol pulse (2 g) and a salt shot (10 mL) were given to the culture. After methanol pulse consumption had been indicated by an increase in dissolved oxygen concentration in the culture, a constant feed with methanol fed batch solution was started with a feed rate of 1.0 g/h. Salt shots of 10 mL are given every 10 g of newly formed biomass, that corresponds to ~43 g methanol feed medium. With increasing biomass concentrations, the methanol feed rate was increased appropriately when methanol accumulation could be ruled out due to a sudden increase in dissolved oxygen in the culture when turning off the methanol feed for a short period of time. The final methanol feed rate was 2.5 g/h.

Samples were taken frequently. The cultivation was harvested after approximately 100 hours when cell densities had reached more than 100 g/L cell dry weight.

The media were as follows:

Batch medium (per liter) contained: 2.0 g citric acid, 12.4 g $(NH_4)_2HPO_4$, 0.022 g $CaCl_2 \cdot 2H_2O$, 0.9 g KCl, 0.5 g $MgSO_4 \cdot 7H_2O$, 40 g glycerol, 4.6 mL PTM1 trace salts stock solution. The pH is set to 5.0 with 25% HCl.

TABLE 10

Effect of dFLO8 mutant on transcription strength of the FLO8 gene and genes controlled under carbon-regulated promoters in glucose-limiting inducing conditions. Fold changes (FC) between the dFLO8 mutant strain compared to the wild type strain are shown. Expression changes with adjusted p-value < 0.05 are showing a statistically significant difference.

| Gene ID GS115 | Gene ID CBS7435 | Promoter sequence | Promoter*/ gene name | FC expression dFLO8 vs wt | Adjusted p-value dFLO8 vs wt |
|---|---|---|---|---|---|
| PAS_chr1-3_0011 | PP7435_Chr1-0007 | SEQ ID NO: 12 | G1* | 11.09 | 7.59E−06 |
| PAS_chr4_0550 | PP7435_Chr4-0424 | SEQ ID NO: 13 | G3* | 3.66 | 4.96E−06 |
| PAS_chr4_0043 | PP7435_Chr4-0972 | SEQ ID NO: 14 | G4* | 11.43 | 4.40E−07 |
| PAS_chr2-1_0853 | PP7435_Chr2-0787 | SEQ ID NO: 15 | G6* | 8.82 | 1.11E−07 |
| PAS_chr2-1_0437 | PP7435_Chr2-0858 | SEQ ID NO: 46 | GAP* | 1.08 | 0.786 |
| PAS_chr4_0711 | PP7435_Chr4-0252 | — | FLO8 | <0.29 | 8.61E−05 |

*Promotor nomenclature as described in Prielhofer et al. 2013

Example 7: Effect of FLO8 Disruption on the Transcription Strength of the Methanol Regulated Promoter pAOX1

The impact of disruption of FLO8 on the transcription strength was also determined for *P. pastoris* standard promoters such as pAOX1 and pGAP under methanol-inducing conditions. Therefore the strains CBS7435 expressing a recombinant Fab fragment under control of pAOX1 and the respective dFLO8 mutant strain dFLO8 #2 were cultivated in methanol-based fed batch cultivation.

The fed batches were carried out in 1.4 L DASGIP reactors (Eppendorf, Germany) with a maximum working volume of 1.0 L. Cultivation temperature was controlled at 25° C., pH was controlled at 5.0 by addition of 25% ammonium hydroxide and the dissolved oxygen concentration was maintained above 20% saturation by controlling the stirrer speed between 400 and 1200 rpm, and the airflow between 24 and 72 sL/h.

The inoculum for the fed batch cultivation was cultivated in shaking flasks containing 100 mL of YP medium containing 20 g/L glycerol and 50 μg/mL Zeocin, and incubated at 28° C. and 180 rpm for approximately 24 hours. The cultures were used to inoculate the starting volume of 0.4 L in the bioreactor to a starting optical density (600 nm) of 1.0. The batch was finished after approximately 24 h and the first (10 mL) salt shot was given.

Glycerol fed batch solution (per liter) contained: 623 g glycerol, 12 mL PTM0 trace salts stock solution and 40 mg biotin. PTM0 composition is given in Example 2.

Methanol fed batch solution (per liter) of pure methanol contained: 12 m L PTM0 trace salts stock solution and 40 mg biotin.

Salt shot solution (per liter) contained: 20.8 g $MgSO_4 \cdot 7H_2O$, 41.6 KCl, 1.04 g $CaCl_2 \cdot 2H_2O$.

Quantification of intact Fab by ELISA was done using anti-human IgG antibody (ab7497, Abcam) as coating antibody and a goat anti-human IgG (Fab specific)-alkaline phosphatase conjugated antibody (Sigma A8542) as detection antibody. Human Fab/Kappa, IgG fragment (Bethyl P80-115) was used as standard with a starting concentration of 100 ng/mL, supernatant samples are diluted accordingly. Detection was done with pNPP (Sigma S0942). Coating-, Dilution- and Washing buffer were based on PBS (2 mM $KH_2PO_4$, 10 mM $Na_2HPO_4 \cdot 2 H_2O$, 2.7 mM g KCl, 8 mM NaCl, pH 7.4) and completed with BSA (1% (w/v)) and/or Tween20 (0.1% (v/v)) accordingly.

Regarding the product titer, the increase in Fab production under control of pAOX1 in the dFLO8 mutant was maximum 1.45-fold at the end of the methanol fed batch cultivation (after 119 h, as described in WO2015/158800A1), while the biomass formation was slightly decreased (by 10-14%).

Microarray samples were taken after 53.5 h (25 h methanol feed) and processed as described in Example 6. Fold-changes for a selection of genes between the dFLO8 mutant strain compared to the wild type strain are shown in Table 11. Again, FLO8 transcript levels are significantly lower in the dFLO8 mutant compared to the wild type. Contrary to the non-methanol carbon regulated genes and promoters shown in Table 10, the methanol-inducible pAOX1 does not show a significantly increased transcription strength in the dFLO8 mutant compared to the wild type in its fully induced conditions (as the adjusted p-value is larger 0.05). There is also no significant effect on pGAP in the methanol-grown cells. Thus, transcription of these standard promoters in *P. pastoris* is not affected by the underexpression of FLO8.

TABLE 11

Effect of dFLO8 mutant on transcription strength of the FLO8 gene and the gene controlled under the methanol-inducible AOX1 promoter in in methanol inducing fed batch conditions. Fold changes (FC) between the dFLO8 mutant strain compared to the wild type strain are shown. Expression changes with adjusted p-value <0.05 are showing a statistically significant difference.

| Gene ID GS115 | Gene ID CBS7435 | Promoter sequence | Promoter*/ gene name | FC expression dFLO8 vs wt | Adjusted p-value dFLO8 vs wt |
|---|---|---|---|---|---|
| PAS_chr4_0821 | PP7435_Chr4-0130 | — | AOX1* | 1.36 | 0.186 |
| PAS_chr2-1_0437 | PP7435_Chr2-0858 | SEQ ID NO: 46 | GAP* | 1.24 | 0.400 |
| PAS_chr4_0711 | PP7435_Chr4-0252 | — | FLO8 | <0.3 | 3.71E−08 |

Example 8: Effect of FLO8 Disruption on Intracellular eGFP Expression Driven by Non-Methanol Carbon Regulated Promoters As native gene expression driven by most non-methanol carbon regulated promoters (WO2013050551A1; Prielhofer et al. 2013) was significantly upregulated under inducing conditions in the dFLO8 strain (see Example 6) disruption of FLO8 was also tested in the respective eGFP-reporter strains described in WO2013050551A1 and Prielhofer et al (2013). For each non-methanol inducible promoter one strain harboring the pPM1aZ10_pG #_eGFP expression vector (CBS2612_pG3_eGFP #1; CBS2612_pG4_eGFP #6; CBS2612_pG6_eGFP #53; X33_pG7_eGFP #1; CBS2612_pG8_eGFP #8) was selected and FLO8 disrupted by employing the split-marker cassette method described in Example 1. Screening-cultivations under inducing (glucose-limiting) conditions were done as described in Example 2 with the exception that the polysaccharide and glucose-releasing enzyme were obtained from a different supplier (EnPump 200, Enpresso). As the properties of the new glucose-releasing enzyme differed, the concentration was adapted to 0.4% corresponding to a constant glucose-release rate of ca. 0.6 mg mL$^{-1}$ h$^{-1}$. In each case two replicates of the respective parent as well as at least 7 corresponding dFLO8 strains were screened. eGFP-productivity was determined as described in Example 2 with the exception that values were not normalized for cell size. Table 12 shows that disruption of FLO8 lead to an increase in eGFP fluorescence for each promoter reaching from 1.7- and 1.2-fold in case of pG3 and pG8, respectively, as well as 2.3-fold in case of pG4 and pG7 and 2.2-fold in case of pG6. This further underlines the potential of FLO8 disruption for enhancement of other non-methanol carbon regulated promoters besides pG1 and pG1 derivates.

These results confirm the increased eGFP expression under control of pG1 or a pG1 derivative (pG1-3) in dFLO8 host cells compared to such expression in wild-type host cells. Table 2 shows that disruption of FLO8 leads to an increase in eGFP fluorescence which is 3.8 (or 3.9) and 2.8 (or 2.9)-fold in case of pG1 and pG1-3, respectively.

TABLE 12

Impact of dFLO8 on expression of eGFP under control of non-methanol carbon regulated promoters. Shown are eGFP expression levels as percentages of pGAP expression as well as fold-changes of the respective dFLO8_pG#_eGFP strains compared to the parental wild-type strain after 48 h cultivation in limiting-glucose (induction) conditions.

| Promoter | Host cell | eGFP expression relative to pGAP ± SD | FC dFLO8/wt |
|---|---|---|---|
| pGAP | wt | 100 ± 2.2% | |
| pG3 | wt | 20 ± 0.7% | |
| pG3 | dFLO8 | 33 ± 4.5% | 1.7 |
| pG4 | wt | 42 ± 1.1% | |
| pG4 | dFLO8 | 96 ± 9.0% | 2.3 |
| pG6 | wt | 76 ± 0.0% | |
| pG6 | dFLO8 | 164 ± 1.4% | 2.2 |
| pG7 | wt | 697 ± 1.0% | |
| pG7 | dFLO8 | 1591 ± 2% | 2.3 |
| pG8 | wt | 20 ± 3.1% | |
| pG8 | dFLO8 | 24 ± 3.4% | 1.2 |

REFERENCES

Benjamini Y & Yekutieli D (2001) The Control of the False Discovery Rate in Multiple Testing under Dependency. *The Annals of Statistics* 29: 1165-1188.

Gasser B, Prielhofer R, Marx H, Maurer M, Nocon J, Steiger M, Puxbaum V, Sauer M & Mattanovich D (2013) *Pichia pastoris*: protein production host and model organism for biomedical research. *Future Microbiol* 8: 191-208.

Marx H, Mattanovich D & Sauer M (2008) Overexpression of the riboflavin biosynthetic pathway in *Pichia pastoris*. *Microb Cell Fact* 7: 23.

Prielhofer R, Reichinger M, Wagner N, Claes K, Kiziak C, Gasser B & Mattanovich D (2018) Superior protein titers in half the fermentation time: Promoter and process engineering for the glucose-regulated GTH1 promoter of *Pichia pastoris*. *Biotechnol Bioeng*.

Stadlmayr G, Mecklenbrauker A, Rothmuller M, Maurer M, Sauer M, Mattanovich D & Gasser B (2010) Identification and characterisation of novel *Pichia pastoris* promoters for heterologous protein production. *J Biotechnol* 150: 519-529.

What is claimed is:

1. A recombinant host cell wherein expression of an endogenous FLO8 protein is reduced compared to an endogenous expression of said FLO8 protein in a corresponding wild-type host cell, the host cell comprising a heterologous expression cassette comprising a gene of interest (GOI) under control of an expression cassette promoter (ECP), wherein the ECP is repressible by a non-methanol carbon source and comprises:
   (i) any one of SEQ ID NO:10-16, or
   (ii) any one of SEQ ID NO:41-45, or
   (iii) at least 85% sequence identity to a region of at least 300 nt including the 3' end of any one of SEQ ID NO:10-16, or SEQ ID NO:41-45;
wherein said expression of the endogenous FLO8 protein is reduced through one or more genetic modifications comprising a disruption, substitution, deletion or knockout of (i) one or more endogenous polynucleotides encoding the FLO8 protein, or a part thereof; or (ii) an expression control sequence operably linked to an endogenous polynucleotide encoding the FLO8 protein, wherein said expression control sequence is selected from the group consisting of a promoter, a ribosomal binding site, transcriptional or translational start and stop sequences, an enhancer and activator sequence and wherein:
   a) the recombinant host cell is a *Komagataella phaffii* host cell and the FLO8 protein comprises the amino acid sequence of SEQ ID NO:1;
   b) the recombinant host cell is a *Komagataella pastoris* host cell and the FLO8 protein comprises the amino acid sequence of SEQ ID NO:3;
   c) the recombinant host cell is a *Saccharomyces cerevisiae* host cell and the FLO8 protein comprises the amino acid sequence of SEQ ID NO:5 or SEQ ID NO:6;
   d) the recombinant host cell is a *Yarrowia lipolytica* host cell and the FLO8 protein comprises the amino acid sequence of SEQ ID NO:7;
   e) the recombinant host cell is an *Ogataea polymorpha* host cell and the FLO8 protein comprises the amino acid sequence of SEQ ID NO:8; or
   f) the recombinant host cell is an *Aspergillus niger* host cell and the FLO8 protein comprises the amino acid sequence of SEQ ID NO:9.

2. The recombinant host cell of claim 1, wherein an endogenous gene encoding said FLO8 protein is knocked out.

3. The recombinant host cell of claim 1, wherein the ECP is inducible in the presence of a growth-limiting amount of a non-methanol carbon source and repressible in the presence of an excess amount of a non-methanol carbon source that is higher than the growth-limiting amount.

4. The recombinant host cell of claim 3, wherein the ECP comprises the SEQ ID NO:10 or the SEQ ID NO:11.

5. The recombinant host cell of claim 1, wherein the expression cassette further comprises a nucleotide sequence encoding a signal peptide enabling the secretion of a protein of interest (POI) which is encoded by the GOI, wherein the nucleotide sequence encoding the signal peptide is fused adjacent to the 5'-end of the GOI.

6. The recombinant host cell of claim 1, wherein the GOI encodes a protein of interest (POI) which is a peptide or protein selected from the group consisting of an antigen-binding protein, a therapeutic protein, an enzyme, a peptide, a protein antibiotic, a toxin fusion protein, a carbohydrate-protein conjugate, a structural protein, a regulatory protein, a vaccine antigen, a growth factor, a hormone, a cytokine, a process enzyme, and a metabolic enzyme.

7. The recombinant host cell of claim 1, which is the *Komagataella phaffii* or the *Komagataella pastoris*.

8. A method of increasing the yield of a protein of interest (POI) produced by a recombinant host cell expressing a gene of interest (GOI) encoding said POI under the control of an expression cassette promoter (ECP), which is repressible by a non-methanol carbon source (first), by reducing in said recombinant host cell expression of an endogenous gene encoding a FLO8 protein compared to an endogenous expression of said FLO8 protein in a corresponding wild-type host cell,
wherein the ECP is repressible by a non-methanol carbon source and comprises:
   (i) any one of SEQ ID NO:10-16, or
   (ii) any one of SEQ ID NO:41-45, or
   (iii) at least 85% sequence identity to a region of at least 300 nt including the 3' end of any one of SEQ ID NO:10-16, or SEQ ID NO:41-45;
wherein said expression of the endogenous FLO8 protein is reduced through one or more genetic modifications comprising a disruption, substitution, deletion or knockout of (i) one or more endogenous polynucleotides encoding the FLO8 protein, or a part thereof; or (ii) an expression control sequence operably linked to an endogenous polynucleotide encoding the FLO8 protein, wherein said expression control sequence is selected from the group consisting of a promoter, a ribosomal binding site, transcriptional or translational start and stop sequences, an enhancer and activator sequence and wherein:
   a) the recombinant host cell is a *Komagataella phaffii* host cell and the FLO8 protein comprises the amino acid sequence of SEQ ID NO:1;
   b) the recombinant host cell is a *Komagataella pastoris* host cell and the FLO8 protein comprises the amino acid sequence of SEQ ID NO:3;
   c) the recombinant host cell is a *Saccharomyces cerevisiae* host cell and the FLO8 protein comprises the amino acid sequence of SEQ ID NO:5 or SEQ ID NO:6;
   d) the recombinant host cell is a *Yarrowia lipolytica* host cell and the FLO8 protein comprises the amino acid sequence of SEQ ID NO:7;

e) the recombinant host cell is an *Ogataea polymorpha* host cell and the FLO8 protein comprises the amino acid sequence of SEQ ID NO:8; or f) the recombinant host cell is an *Aspergillus niger* host cell and the FLO8 protein comprises the amino acid sequence of SEQ ID NO:9.

9. A method for producing a protein of interest (POI) encoded by a gene of interest (GOI) by culturing the recombinant host cell of claim 1 under conditions to produce said POI.

10. The method of claim 8, comprising the steps:
a) culturing the recombinant host cell under growing conditions; and
b) culturing the recombinant host cell under growth-limiting conditions in the presence of up to 1 g/L of a second non-methanol carbon source, resulting in expression of said GOI to produce said POI, wherein said step a) culturing is performed in a batch phase; and said step b) culturing is performed in fed-batch or a continuous cultivation phase.

11. The method of claim 10, wherein said first non-methanol carbon source or said second non-methanol carbon source is selected from saccharides, polyols, alcohols, or mixtures of any one or more of the foregoing.

12. A method for producing a protein of interest (POI) in a recombinant host cell, comprising the steps:
a) genetically engineering the recombinant host cell to reduce expression of an endogenous gene encoding a FLO8 protein compared to an endogenous expression of said FLO8 protein in a corresponding wild-type host cell and introducing into the recombinant host cell a heterologous expression cassette comprising a gene of interest (GOI) expressing said POI under the control of an expression cassette promoter (ECP) that is operably linked to the GOI, which ECP is repressible by a non-methanol carbon source and comprises:
(i) any one of SEQ ID NO:10-16, or
(ii) any one of SEQ ID NO:41-45, or
(iii) at least 85% sequence identity to a region of at least 300 nt including the 3'end of any one of SEQ ID NO:10-16, or SEQ ID NO:41-45;
b) culturing said recombinant host cell under conditions to produce said POI;
c) isolating said POI from the cell culture; and
d) purifying said POI;
wherein said expression of the endogenous FLO8 protein is reduced through one or more genetic modifications comprising a disruption, substitution, deletion or knockout of (i) one or more endogenous polynucleotides encoding the FLO8 protein, or a part thereof; or (ii) an expression control sequence operably linked to an endogenous polynucleotide encoding the FLO8 protein, wherein said expression control sequence is selected from the group consisting of a promoter, a ribosomal binding site, transcriptional or translational start and stop sequences, an enhancer and activator sequence and wherein:
a) the recombinant host cell is a *Komagataella phaffii* host cell and the FLO8 protein comprises the amino acid sequence of SEQ ID NO:1;
b) the recombinant host cell is a *Komagataella pastoris* host cell and the FLO8 protein comprises the amino acid sequence of SEQ ID NO:3;
c) the recombinant host cell is a *Saccharomyces cerevisiae* host cell and the FLO8 protein comprises the amino acid sequence of SEQ ID NO:5 or SEQ ID NO:6;

d) the recombinant host cell is a *Yarrowia lipolytica* host cell and the FLO8 protein comprises the amino acid sequence of SEQ ID NO:7;
e) the recombinant host cell is an *Ogataea polymorpha* host cell and the FLO8 protein comprises the amino acid sequence of SEQ ID NO:8; or f) the recombinant host cell is an *Aspergillus niger* host cell and the FLO8 protein comprises the amino acid sequence of SEQ ID NO:9.

13. The recombinant host cell of claim 1, wherein the ECP comprises at least 90% sequence identity to a region of at least 300 nt including the 3'end of any one of SEQ ID NO:10-16, or SEQ ID NO:41-45.

14. The recombinant host cell of claim 1, wherein the ECP comprises at least 95% sequence identity to a region of at least 300 nt including the 3'end of any one of SEQ ID NO:10-16, or SEQ ID NO:41-45.

15. The recombinant host cell of claim 1, wherein the non-methanol carbon source is selected from glycerol, glucose, or a combination thereof.

16. The recombinant host cell of claim 1, wherein the ECP is inducible in the absence of methanol.

17. The method of claim 8, wherein the non-methanol carbon source is selected from glycerol, glucose, or a combination thereof.

18. The method of claim 8, wherein the ECP is inducible in the absence of methanol.

19. The method of claim 12, wherein the non-methanol carbon source is selected from glycerol, glucose, or a combination thereof.

20. The method of claim 12, wherein the promoter is inducible in the absence of methanol.

21. The method of claim 8, wherein the promoter comprises at least 90% sequence identity to a region of at least 300 nt including the 3'end of any one of SEQ ID NO:10-16, or SEQ ID NO:41-45.

22. The method of claim 8, wherein the promoter comprises at least 95% sequence identity to a region of at least 300 nt including the 3'end of any one of SEQ ID NO:10-16, or SEQ ID NO:41-45.

23. The method of claim 9, wherein the non-methanol carbon source is selected from glycerol, glucose, or a combination thereof.

24. The method of claim 9, wherein the ECP is inducible in the absence of methanol.

25. The method of claim 9, wherein the promoter comprises at least 90% sequence identity to a region of at least 300 nt including the 3'end of any one of SEQ ID NO:10-16, or SEQ ID NO:41-45.

26. The method of claim 9, wherein the promoter comprises at least 95% sequence identity to a region of at least 300 nt including the 3'end of any one of SEQ ID NO:10-16, or SEQ ID NO:41-45.

27. The method of claim 12, wherein the non-methanol carbon source is selected from glycerol, glucose, or a combination thereof.

28. The method of claim 12, wherein the ECP is inducible in the absence of methanol.

29. The method of claim 12, wherein the ECP comprises at least 90% sequence identity to a region of at least 300 nt including the 3'end of any one of SEQ ID NO:10-16, or SEQ ID NO:41-45.

30. The method of claim 12, wherein the ECP comprises at least 95% sequence identity to a region of at least 300 nt including the 3'end of any one of SEQ ID NO:10-16, or SEQ ID NO:41-45.

* * * * *